United States Patent
Oslob et al.

(10) Patent No.: US 9,663,516 B2
(45) Date of Patent: May 30, 2017

(54) BICYCLIC-PYRIMIDINEDIONE COMPOUNDS

(71) Applicant: MyoKardia, Inc., South San Francisco, CA (US)

(72) Inventors: Johan Oslob, Sunnyvale, CA (US); Danielle Aubele, San Mateo, CA (US); Marc Evanchik, San Jose, CA (US); Jonathan Charles Fox, San Francisco, CA (US); Mark Grillo, San Francisco, CA (US); Brian Kane, Oakland, CA (US); Robert McDowell, San Francisco, CA (US); Yonghong Song, Foster City, CA (US); Min Zhong, Palo Alto, CA (US)

(73) Assignee: MYOKARDIA, INC., South San Francisco, CA (US)

( * ) Notice: Subject to any disclaimer, the term of this patent is extended or adjusted under 35 U.S.C. 154(b) by 0 days.

(21) Appl. No.: 14/973,132

(22) Filed: Dec. 17, 2015

(65) Prior Publication Data
US 2016/0176868 A1 Jun. 23, 2016

Related U.S. Application Data

(60) Provisional application No. 62/093,820, filed on Dec. 18, 2014.

(51) Int. Cl.
| | | |
|---|---|---|
| *C07D 471/04* | (2006.01) | |
| *C07D 487/04* | (2006.01) | |
| *A61K 31/519* | (2006.01) | |
| *A61K 31/55* | (2006.01) | |
| *A61K 45/06* | (2006.01) | |

(52) U.S. Cl.
CPC .......... *C07D 471/04* (2013.01); *A61K 31/519* (2013.01); *A61K 31/55* (2013.01); *A61K 45/06* (2013.01); *C07D 487/04* (2013.01)

(58) Field of Classification Search
CPC ............................ C07D 471/04; C07D 487/04
See application file for complete search history.

*Primary Examiner* — Bruck Kifle
(74) *Attorney, Agent, or Firm* — Mintz, Levin, Cohn, Ferris, Glovsky & Popeo, PC

(57) ABSTRACT

The present invention provides novel bicyclic pyrimidinedione compounds that are useful for the treatment of hypertrophic cardiomyopathy (HCM) and conditions associated with left ventricular hypertrophy or diastolic dysfunction. The synthesis and characterization of the compounds is described, as well as methods for treating HCM and other forms of heart disease.

31 Claims, 7 Drawing Sheets

BICYCLIC-PYRIMIDINEDIONE COMPOUNDS

CROSS-REFERENCES TO RELATED APPLICATIONS

This application claims the benefit of priority to U.S. Provisional Application No. 62/093,820, filed Dec. 18, 2014, the entire content of which is incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Genetic (heritable) hypertrophic cardiomyopathy (HCM) comprises a group of highly penetrant, monogenic, autosomal dominant myocardial diseases. HCM is caused by one or more of over 1,000 known point mutations in any one of the structural protein genes contributing to the functional unit of myocardium, the sarcomere. About 1 in 500 individuals in the general population are found to have left ventricular hypertrophy unexplained by other known causes (e.g., hypertension or valvular disease), and many of these can be shown to have HCM, once other heritable (e.g., lysosomal storage diseases), metabolic, or infiltrative causes have been excluded.

Sarcomere gene mutations that cause HCM are highly penetrant, but there is wide variability in clinical severity and clinical course. Some genotypes are associated with a more malignant course, but there is considerable variability between and even within families carrying the same mutation. Sex differences have also been noted, with male patients generally more severely affected than female patients. While many patients with HCM report minimal or no symptoms for extended periods of time, HCM is a progressive disease with a significant cumulative burden of morbidity. Symptoms of effort intolerance predominate, and can be exacerbated by exercise and other maneuvers that increase heart rate and/or decrease preload. As with many other disorders, symptoms tend to worsen with age. By far the most prevalent clinical burden for patients with HCM is exertional dyspnea, which limits their activities of daily living and can be debilitating.

Patients with HCM are often symptomatic in the absence of documented hemodynamic abnormalities like left ventricular outflow tract obstruction (with or without mitral regurgitation). Patients' symptoms of exertional dyspnea can rapidly worsen with the onset of atrial fibrillation, a common complication of HCM that can precipitate acute pulmonary edema and increases the risk of systemic arterial thromboembolic disease, including stroke. Other adverse events associated with HCM include intolerance of hypovolemia or hypervolemia, and syncope. Concomitant coronary artery disease may confer a higher risk of acute coronary syndromes than in patients without HCM. Sudden cardiac death (SCD) in patients with HCM is both uncommon and difficult to predict but is a leading cause of non-traumatic death in young adults. For survivors of SCD, ICD placement is standard practice, and in other HCM patients risk profiling, while imprecise, is used to identify those for whom ICD placement for primary prevention is deemed prudent.

Medical therapy for HCM is limited to the treatment of symptoms and does not address the fundamental, underlying cause of disease—disruptions in normal sarcomere function. Currently available therapies are variably effective in alleviating symptoms but typically show decreased efficacy with increasing disease duration. Patients are thus empirically managed with beta-blockers, non-dihydropyridine calcium channel blockers, and/or disopyramide. None of these agents carry labeled indications for treating HCM, and essentially no rigorous clinical trial evidence is available to guide their use. Compounding this unfortunate situation is the fact that no new medical therapies for HCM have been identified for many years. For patients with hemodynamically significant outflow tract obstruction (resting gradient >30 mmHg), in appropriately selected patients surgical myectomy or alcohol septal ablation is usually required to alleviate the hemodynamic obstruction. The present invention provides new therapeutic agents and methods that remedy the long-felt need for improved treatment of HCM and related cardiac disorders.

BRIEF SUMMARY OF THE INVENTION

In one aspect, provided is a compound having the formula:

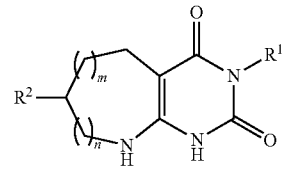

or a pharmaceutically acceptable salt thereof, wherein
the subscript m is an integer of from 0 to 2;
the subscript n is 0 or 1; and the sum of n+m is no more than 2;
$R^1$ is a member selected from the group consisting of $C_1$-$C_8$ alkyl, $C_3$-$C_8$ cycloalkyl, $C_3$-$C_8$ cycloalkyl-$C_1$-$C_3$ alkyl, 4- to 7-membered heterocycloalkyl, 4- to 7-membered heterocycloalkyl-$C_1$-$C_3$ alkyl, phenyl, phenyl-$C_1$-$C_3$ alkyl, 5- to 6-membered heteroaryl and 5- to 6-membered heteroaryl-$C_1$-$C_3$ alkyl, wherein each $R^1$ is optionally substituted with from 1-5 $R^a$;
$R^2$ is a member selected from the group consisting of $C_2$-$C_8$ alkyl, $C_3$-$C_8$ cycloalkyl, $C_3$-$C_8$ cycloalkyl-$C_1$-$C_3$ alkyl, phenyl, phenyl-$C_1$-$C_3$ alkyl, 4- to 7-membered heterocycloalkyl, 4- to 7-membered heterocycloalkyl-$C_1$-$C_3$ alkyl, 5- to 6-membered heteroaryl and 5- to 6-membered heteroaryl-$C_1$-$C_3$ alkyl, wherein each $R^2$ is optionally substituted with from 1-5 $R^b$;
each $R^a$ is independently selected from the group consisting of halo, CN, hydroxyl, $C_1$-$C_4$ alkyl, $C_1$-$C_4$ haloalkyl, $C_1$-$C_4$ alkoxy and —$CO_2$—$C_1$-$C_8$ alkyl;
each $R^b$ is independently selected from the group consisting of halo, CN, hydroxyl, $C_1$-$C_4$ alkyl, $C_1$-$C_4$ haloalkyl, $C_1$-$C_4$ alkoxy, —$COR^{b1}$, —$CO_2R^{b1}$, —$SO_2R^{b1}$, —$SO_2NR^{b1}R^{b2}$, and —$CONR^{b1}R^{b2}$, wherein each $R^{b1}$ and $R^{b2}$ is independently selected from the group consisting of H and $C_1$-$C_4$ alkyl or optionally $R^{b1}$ and $R^{b2}$ when attached to a nitrogen atom are combined to form a 4- to 6-membered ring; and optionally two $R^b$ groups on the same carbon atom are combined to form oxo;
and wherein the ring bearing $R^2$ is optionally further substituted with from one to five $R^c$, each of which is independently selected from the group consisting of halo, CN, hydroxyl, $C_1$-$C_4$ alkyl, $C_1$-$C_4$ haloalkyl and $C_1$-$C_4$ alkoxy, or optionally two $R^1$ groups on the same carbon atom are combined to form oxo.

In another aspect, the invention provides a pharmaceutical composition containing a compound or a pharmaceutically acceptable salt thereof as described herein and a pharmaceutically acceptable excipient.

In another aspect, the invention provides a method of treating hypertrophic cardiomyopathy. The method includes administering to a subject in need thereof an effective amount of a compound or pharmaceutically acceptable salt thereof as described herein.

In another aspect, the invention is intended to include all isotopically labeled analogs of the compounds of invention. Isotopes include those atoms having the same atomic number but difference mass. For example, isotopes of hydrogen include $^2$H(D) and $^3$H(T) and isotopes of carbon include $^{13}$C and $^{14}$C. Isotopically labeled compounds of the invention can be prepared according to methods commonly known in the art. Such compounds have various uses as, but not limit to, standards and reagents in determining biological/pharmacological activities. For those stable isotopically labeled compounds of the invention, they can also favorably modulate biological, pharmacological, or pharmacokinetic properties.

DETAILED DESCRIPTION OF THE INVENTION

I. General

Figure 1:
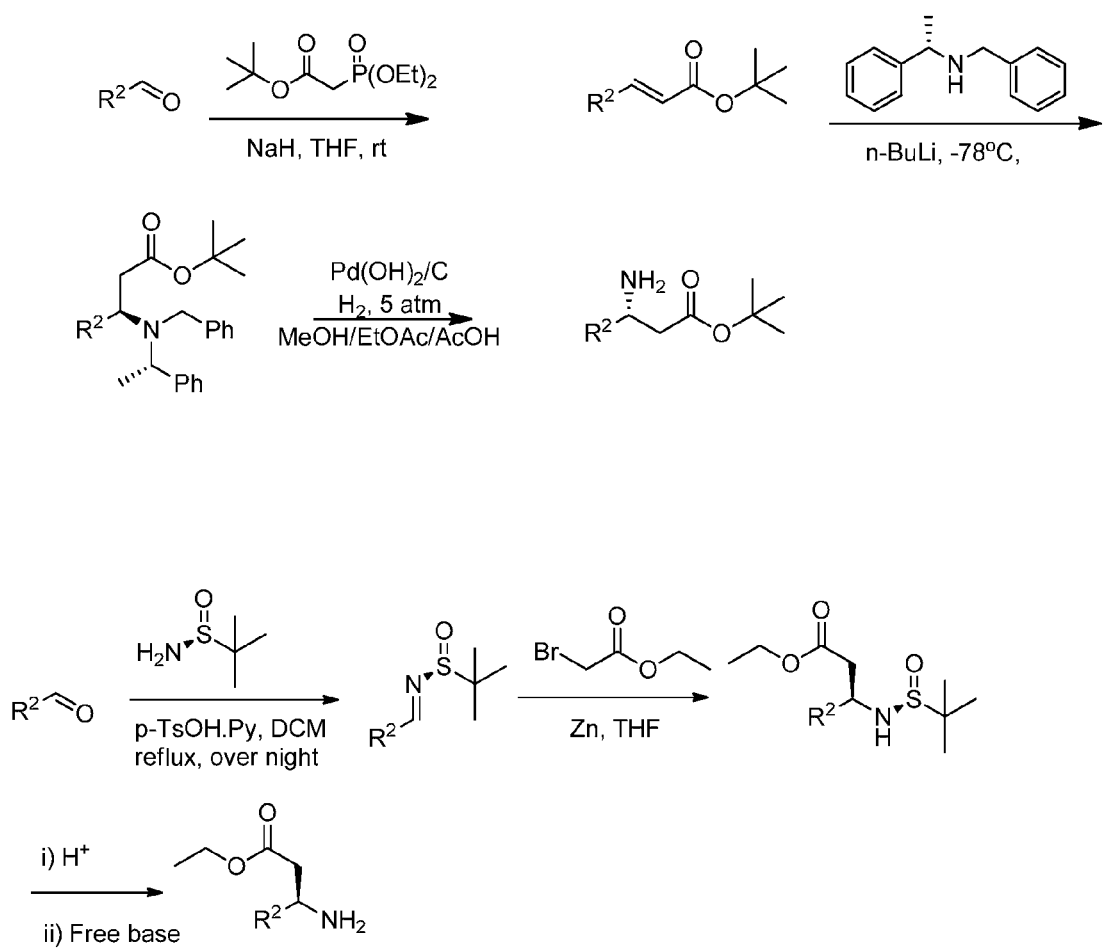
FIGS. 1-7 show general schematic routes for the synthesis of the compounds or pharmaceutically acceptable salts described herein.

A series of bicyclic pyrimidinedione compounds has been found to reduce excess contractility in hypercontractile states and/or promote cardiac relaxation in hearts with diastolic dysfunction by stabilizing the conformation of beta cardiac myosin post-ATP hydrolysis but prior to strongly binding the actin filament and releasing phosphate, thus reducing the proportion of myosin molecules that are available to participate in the "powerstroke" portion of the muscle contraction cycle. As such, the compounds can improve cardiac elasticity, reduce dynamic and/or static left ventricular outflow obstruction, improve diastolic left ventricular relaxation, reduce left ventricular diastolic (filling) pressures, reduce functional mitral regurgitation, and/or reduce left atrial and pulmonary capillary wedge pressures in patients with HCM helping overcome the debilitating exertional dyspnea and/or symptoms referable to left ventricular outflow obstruction (presyncope or syncope) that often accompanies the disease. The compounds can also be used to treat other cardiac disorders.

II. Definitions

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Unless stated otherwise, alkyl groups are unsubstituted. A "substituted alkyl" group can be substituted with one or more moieties selected from halo, hydroxy, amino, alkylamino, nitro, cyano, and alkoxy.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Unless otherwise stated, cycloalkyl groups are unsubstituted. A "substituted cycloalkyl" group can be substituted with one or more moieties selected from halo, hydroxy, amino, alkylamino, nitro, cyano, and alkoxy.

As used herein, the term "heterocycloalkyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocycloalkyl groups can include any number of ring atoms, such as, 3 to 6, 4 to 6, 5 to 6, or 4 to 7 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Examples of heterocycloalkyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocycloalkyl groups are unsubstituted, but can be described, in some embodiments as substituted. "Substituted heterocycloalkyl" groups can be substituted with one or more moieties selected from halo, hydroxy, amino, alkylamino, nitro, cyano, and alkoxy.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 5 to 6, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2, 3-, 1,2,4- and 1,3,5-isomers), thiophene, furan, thiazole, isothiazole, oxazole, and isoxazole. Heteroaryl groups are unsubstituted, but can be described, in some embodiments as substituted. "Substituted heteroaryl" groups can be substituted with one or more moieties selected from halo, hydroxy, amino, alkylamino, nitro, cyano, and alkoxy.

As used herein, the term "alkoxy" refers to an alkyl group having an oxygen atom that connects the alkyl group to the point of attachment: i.e., alkyl-O—. As for the alkyl portions, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups are unsubstituted, but can be described, in some embodiments as substituted. "Substituted alkoxy" groups can be substituted with one or more moieties selected from halo, hydroxy, amino, alkylamino, nitro, cyano, and alkoxy.

As used herein, the terms "halo" and "halogen" refer to fluorine, chlorine, bromine and iodine.

As used herein, the term "pharmaceutically acceptable" refers to a substance that is compatible with a compound of the invention, as well as with any other ingredients with which the compound is formulated. Furthermore, a pharmaceutically acceptable substance is not deleterious to the recipient of the substance.

As used herein, the term "salt" refers to an acid or base salt of a compound of the invention. Pharmaceutically acceptable salts can be derived, for example, from mineral acids (hydrochloric acid, hydrobromic acid, phosphoric acid, and the like), organic acids (acetic acid, propionic acid, glutamic acid, citric acid and the like), and quaternary ammonium ions. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The neutral form of a compound may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

As used herein, the term "pharmaceutical composition" refers to a product comprising a compound of the invention, an excipient as defined herein, and other optional ingredients in specified amounts, as well as any product which results directly or indirectly from combination of the specified ingredients in the specified amounts.

As used herein, the term "excipient" refers to a substance that aids the administration of an active agent to a subject. Pharmaceutical excipients useful in the present invention include, but are not limited to, binders, fillers, disintegrants, lubricants, coatings, sweeteners, flavors and colors. One of skill in the art will recognize that other excipients can be useful in the present invention.

As used herein, the terms "treat," "treating" and "treatment" refer to any indicia of success in the treatment or amelioration of a pathology, injury, condition, or symptom related to hypertrophic cardiomyopathy, including any objective or subjective parameter such as abatement; remission; diminishing of symptoms; making the pathology, injury, condition, or symptom more tolerable to the patient; decreasing the frequency or duration of the pathology, injury, condition, or symptom; or, in some situations, preventing the onset of the pathology, injury, condition, or symptom. Treatment or amelioration can be based on any objective or subjective parameter; including, e.g., the result of a physical examination.

III. Compounds

In one aspect, provided herein are compounds having formula (I):

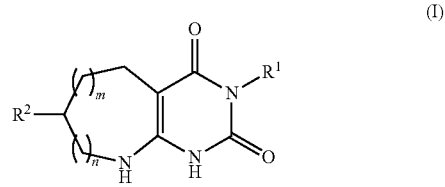

or a pharmaceutically acceptable salt thereof, wherein the subscript m is an integer of from 0 to 2;

the subscript n is 0 or 1; and the sum of n+m is no more than 2;

$R^1$ is a member selected from the group consisting of $C_1$-$C_8$ alkyl, $C_3$-$C_8$ cycloalkyl, $C_3$-$C_8$ cycloalkyl-$C_1$-$C_3$ alkyl, 4- to 7-membered heterocycloalkyl, 4- to 7-membered heterocycloalkyl-$C_1$-$C_3$ alkyl, phenyl, phenyl-$C_1$-$C_3$ alkyl, 5- to 6-membered heteroaryl and 5- to 6-membered heteroaryl-$C_1$-$C_3$ alkyl, wherein each $R^1$ is optionally substituted with from 1-5 $R^a$;

$R^2$ is a member selected from the group consisting of $C_2$-$C_8$ alkyl, $C_3$-$C_8$ cycloalkyl, $C_3$-$C_8$ cycloalkyl-$C_1$-$C_3$ alkyl, phenyl, phenyl-$C_1$-$C_3$ alkyl, 4- to 7-membered heterocycloalkyl, 4- to 7-membered heterocycloalkyl-$C_1$-$C_3$ alkyl, 5- to 6-membered heteroaryl and 5- to 6-membered heteroaryl-$C_1$-$C_3$ alkyl, wherein each $R^2$ is optionally substituted with from 1-5 $R^b$;

each $R^a$ is independently selected from the group consisting of halo, CN, hydroxyl, $C_1$-$C_4$ alkyl, $C_1$-$C_4$ haloalkyl, $C_1$-$C_4$ alkoxy and —$CO_2$—$C_1$-$C_8$ alkyl;

each $R^b$ is independently selected from the group consisting of halo, CN, hydroxyl, $C_1$-$C_4$ alkyl, $C_1$-$C_4$ haloalkyl, $C_1$-$C_4$ alkoxy, —$COR^{b1}$, —$CO_2R^{b1}$, —$SO_2R^{b1}$, —$SO_2NR^{b1}R^{b2}$, and $CONR^{b1}R^{b2}$, wherein each $R^{b1}$ and $R^{b2}$ is independently selected from the group consisting of H and $C_1$-$C_4$ alkyl or optionally $R^{b1}$ and $R^{b2}$ when attached to a nitrogen atom are combined to form a 4- to 6-membered ring; and optionally two $R^b$ groups on the same carbon atom are combined to form oxo;

and wherein the ring bearing $R^2$ is optionally further substituted with from one to five $R^c$, each of which is independently selected from the group consisting of halo, CN, hydroxyl, $C_1$-$C_4$ alkyl, $C_1$-$C_4$ haloalkyl and $C_1$-$C_4$ alkoxy, or optionally two $R^c$ groups on the same carbon atom are combined to form oxo.

In some embodiments, compounds are provided wherein $R^1$ is a member selected from the group consisting of $C_1$-$C_8$ alkyl, $C_3$-$C_8$ cycloalkyl and $C_3$-$C_8$ cycloalkyl-$C_1$-$C_3$ alkyl, each of which is optionally substituted with from 1-3 $R^a$. In other embodiments, compounds are provided wherein $R^2$ is $C_3$-$C_8$ cycloalkyl, which is optionally substituted with from 1-3 $R^b$. In still other embodiments, compounds are provided wherein $R^2$ is phenyl, which is optionally substituted with from 1-3 $R^b$.

In some embodiments, compounds of formula (I) or their pharmaceutically acceptable salts are provided wherein n is 0. In some embodiments, compounds of formula (I) or their pharmaceutically acceptable salts are provided wherein n is 1. In some embodiments, compounds of formula (I) or their pharmaceutically acceptable salts are provided wherein m is 0. In some embodiments, compounds of formula (I) or their pharmaceutically acceptable salts are provided wherein m is 1. In some embodiments, compounds of formula (I) or their pharmaceutically acceptable salts are provided wherein m is 2.

In still other embodiments, compounds of formula (I) or their pharmaceutically acceptable salts are provided wherein n is 0 and m is 0. In still other embodiments, compounds of formula (I) or their pharmaceutically acceptable salts are provided wherein n is 0 and m is 1. In still other embodiments, compounds of formula (I) or their pharmaceutically acceptable salts are provided wherein n is 0 and m is 2.

In some embodiments, compounds of formula (I) or their pharmaceutically acceptable salts are provided having formula (Ia):

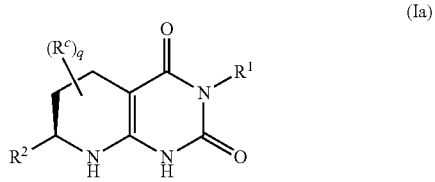

wherein $R^1$ is a member selected from the group consisting of $C_1$-$C_8$ alkyl, $C_3$-$C_8$ cycloalkyl and $C_3$-$C_8$ cycloalkyl-$C_1$-$C_3$ alkyl, each of which is optionally substituted with from 1-3 $R^a$;

$R^2$ is a member selected from the group consisting of $C_5$-$C_6$ cycloalkyl and phenyl, each of which is optionally substituted with from 1-3 $R^b$;

each $R^a$ is independently selected from the group consisting of halo, CN, $C_1$-$C_4$ alkyl, $C_1$-$C_4$ and haloalkyl;

each $R^b$ is independently selected from the group consisting of halo, CN, hydroxyl, $C_1$-$C_4$ alkyl, $C_1$-$C_4$ haloalkyl and $C_1$-$C_4$ alkoxy;

the subscript q is 0 to 2;

each $R^c$ is independently selected from the group consisting of halo, $C_1$-$C_4$ alkyl and $C_1$-$C_4$ haloalkyl; and wherein the compound is substantially free of other isomers at the carbon atom bearing $R^2$.

In some embodiments, compounds of formula (I) or their pharmaceutically acceptable salts are provided having formula (Ia):

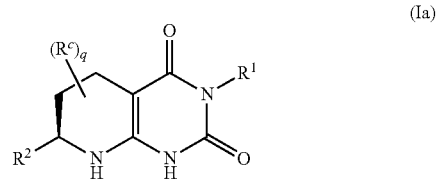

wherein $R^1$ is a member selected from the group consisting of $C_1$-$C_8$ alkyl, $C_3$-$C_8$ cycloalkyl and $C_3$-$C_8$ cycloalkyl-$C_1$-$C_3$ alkyl, each of which is optionally substituted with from 1-3 $R^a$;

$R^2$ is a member selected from the group consisting of $C_5$-$C_6$ cycloalkyl and phenyl, each of which is optionally substituted with from 1-3 $R^b$;

each $R^a$ is independently selected from the group consisting of halo, —CN, $C_1$-$C_4$ alkyl, $C_1$-$C_4$ and haloalkyl;

each $R^b$ is independently selected from the group consisting of halo, —CN, hydroxyl, $C_1$-$C_4$ alkyl, $C_1$-$C_4$ haloalkyl and $C_1$-$C_4$ alkoxy;

the subscript q is 2 to 5;

each $R^c$ is independently selected from the group consisting of halo, $C_1$-$C_4$ alkyl and $C_1$-$C_4$ haloalkyl; and wherein the compound is substantially free of other isomers at the carbon atom bearing $R^2$.

In some embodiments, compounds of formula (Ia), or their pharmaceutically acceptable salts are provided wherein $R^1$ is $C_2$-$C_6$ alkyl, which is optionally substituted with from 1-4 halo. In other embodiments, compounds of formula (Ia), or their pharmaceutically acceptable salts are provided wherein $R^1$ is $C_2$-$C_6$ alkyl. In some embodiments, compounds of formula (Ia), or their pharmaceutically acceptable salts are provided wherein $R^2$ is phenyl, which is optionally substituted with from 1-2 $R^b$. In other embodiments, compounds of formula (Ia), or their pharmaceutically acceptable salts are provided wherein $R^2$ is $C_5$-$C_6$ cycloalkyl, which is optionally substituted with from 1-2 $R^b$. In some embodiments, compounds of formula (Ia), or their pharmaceutically acceptable salts are provided wherein the subscript q is 0.

In some embodiments, compounds of formula (I) or their pharmaceutically acceptable salts are provided having a formula selected from:

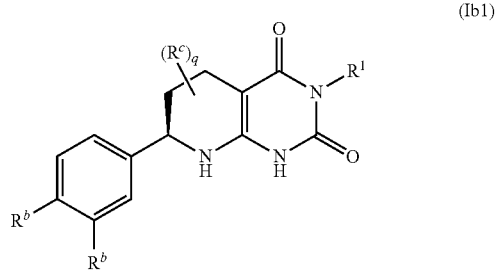

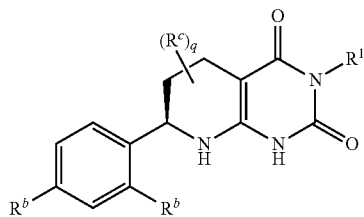
(Ib2)

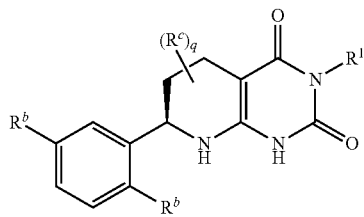
(Ib3)

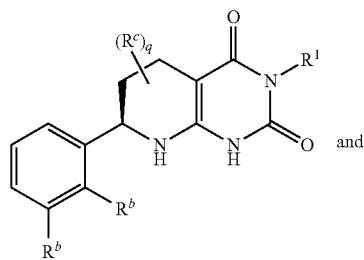
(Ib4)
and

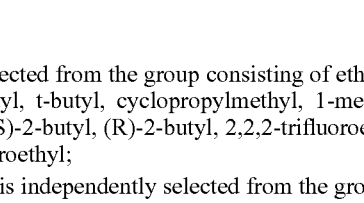
(Ib5)

wherein

R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl and 2,2-difluoroethyl;

each $R^b$ is independently selected from the group consisting of halo, $C_1$-$C_4$ alkyl, and $C_1$-$C_4$ haloalkyl;

q is an integer of from 0 to 2; and each $R^c$ is independently selected from the group consisting of halo, $C_1$-$C_4$ alkyl and $C_1$-$C_4$ haloalkyl.

In some embodiments, compounds of formula (I) or their pharmaceutically acceptable salts are provided having a formula selected from:

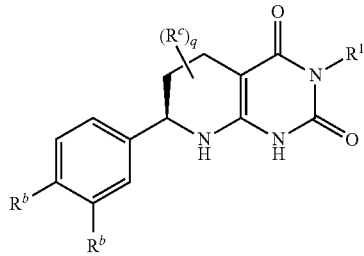
(Ib1)

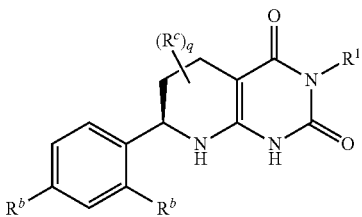
(Ib2)

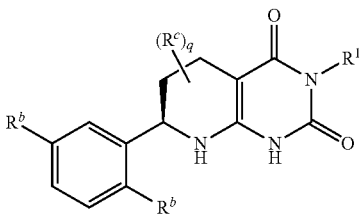
(Ib3)

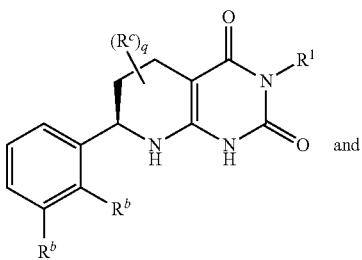
(Ib4)
and

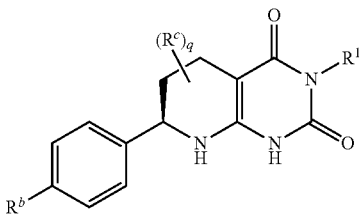
(Ib5)

wherein

R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl and 2,2-difluoroethyl;

each $R^b$ is independently selected from the group consisting of halo, $C_1$-$C_4$ alkyl, and $C_1$-$C_4$ haloalkyl;

q is an integer of from 3 to 5; and each $R^c$ is independently selected from the group consisting of halo, $C_1$-$C_4$ alkyl and $C_1$-$C_4$ haloalkyl.

In some embodiments, compounds of formula (I) or their pharmaceutically acceptable salts are provided having a formula selected from:

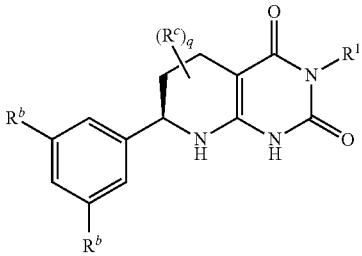
(Ib6)

-continued

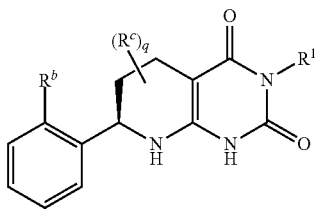
(Ib7)

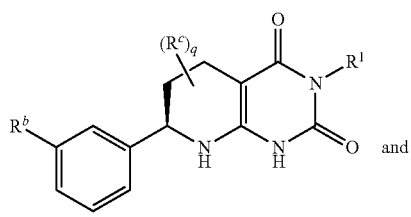
(Ib8) and

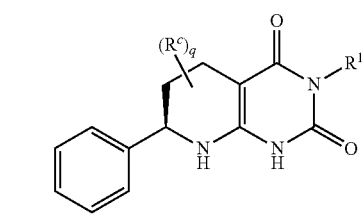
(Ib9)

wherein
R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl and 2,2-difluoroethyl;
each $R^b$ is independently selected from the group consisting of halo, $C_1$-$C_4$ alkyl, and $C_1$-$C_4$ haloalkyl;
q is an integer of from 0 to 5; and
each $R^c$ is independently selected from the group consisting of halo, $C_1$-$C_4$ alkyl and $C_1$-$C_4$ haloalkyl.

In some embodiments, compounds of formula (I) or their pharmaceutically acceptable salts are provided having a formula selected from:

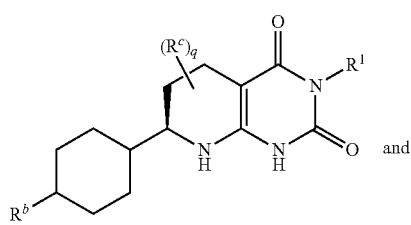
(Ic1) and

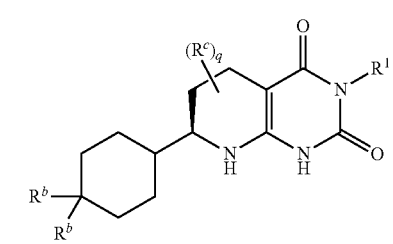
(Ic2)

wherein
R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl, and 2,2-difluoroethyl;
each $R^b$ is independently selected from the group consisting of halo, $C_1$-$C_4$ alkyl, and $C_1$-$C_4$ haloalkyl;
q is an integer of from 0 to 2; and
each $R^c$ is independently selected from the group consisting of halo, $C_1$-$C_4$ alkyl and $C_1$-$C_4$ haloalkyl.

In some embodiments, compounds of formula (I) or their pharmaceutically acceptable salts are provided having a formula selected from:

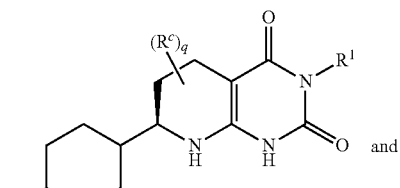
(Ic1) and

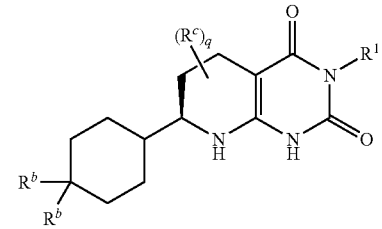
(Ic2)

wherein
R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl, and 2,2-difluoroethyl;
each $R^b$ is independently selected from the group consisting of halo, $C_1$-$C_4$ alkyl, and $C_1$-$C_4$ haloalkyl;
q is an integer of from 3 to 5; and
each $R^c$ is independently selected from the group consisting of halo, $C_1$-$C_4$ alkyl and $C_1$-$C_4$ haloalkyl.

In some embodiments, compounds of formula (I) or their pharmaceutically acceptable salts are provided having a formula selected from:

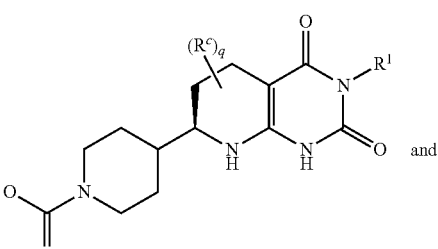
(Ic3)

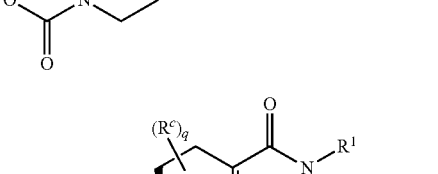
and

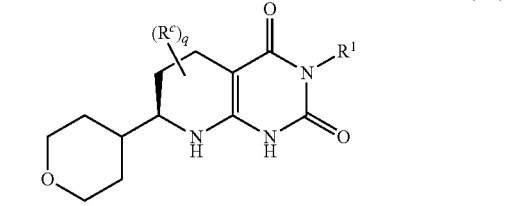
(Ic4)

wherein
R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl, and 2,2-difluoroethyl;

R^{b1} C₁-C₄ alkyl;

q is an integer of from 0 to 5; and each R^c is independently selected from the group consisting of halo, C₁-C₄ alkyl and C₁-C₄ haloalkyl.

In some embodiments, compounds of formula (I) or their pharmaceutically acceptable salts are provided having a formula selected from:

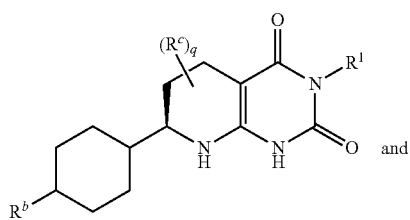
(Ic1)

and

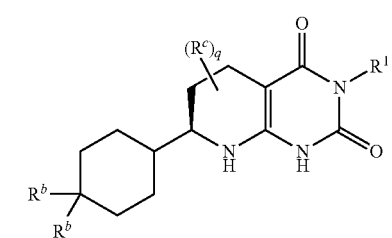
(Ic2)

wherein
R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl and 2,2-difluoroethyl;

each R^b is independently selected from the group consisting of halo, C₁-C₄ alkyl, and C₁-C₄ haloalkyl;

q is an integer of from 0 to 2; and each R^c is independently selected from the group consisting of halo, C₁-C₄ alkyl and C₁-C₄ haloalkyl.

In some embodiments, compounds of formula (I) or their pharmaceutically acceptable salts are provided having a formula selected from:

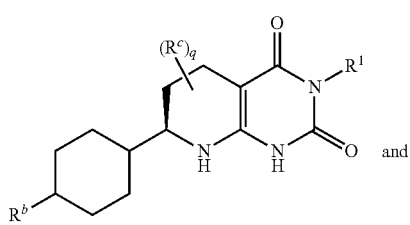
(Ic1)

and

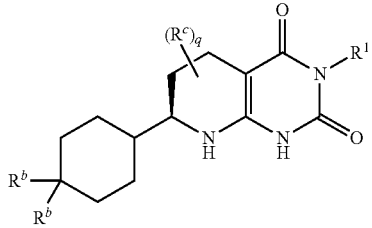
(Ic2)

wherein
R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl, and 2,2-difluoroethyl;

each R^b is independently selected from the group consisting of halo, C₁-C₄ alkyl, and C₁-C₄ haloalkyl;

q is an integer of from 3 to 5; and each R¹ is independently selected from the group consisting of halo, C₁-C₄ alkyl and C₁-C₄

In some embodiments, compounds of formula (I) or their pharmaceutically acceptable salts are provided having a formula selected from:

(Ic3)

and (Ic4)

wherein
R¹ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl, and 2,2-difluoroethyl;

R^{b1} is C₁-C₄ alkyl;

q is an integer of from 0 to 5; and each R¹ is independently selected from the group consisting of halo, C₁-C₄ alkyl and C₁-C₄ haloalkyl.

In selected embodiments of the compounds described herein, the 0-5 R^c substituents are separately identified as R^{c1}, R^{c2}, R^{c3}, R^{c4} and R^{c5}.

The compounds or their pharmaceutically acceptable salts provided herein can have any combination of the selected embodiments for R¹, R², R^a, R^b, R^{b1}, R^{b2} and R^c groups recited herein. Selected embodiments recited for R², for example, can be combined with any of the selected embodiments recited for R¹.

In certain selected embodiments $R^2$ is cyclohexyl, 4,4-difluorocyclohexyl, or (4,4-difluorocyclohexyl)methyl.

In some embodiments, $R^1$ is isopropyl; $R^2$ is $C_4$-$C_6$ cycloalkyl, $C_4$-$C_6$ cycloalkyl $C_1$-$C_2$ alkyl, or a 5- to 6-membered heterocycloalkyl, wherein each $R^2$ is optionally substituted with from 1-2 $R^b$.

In some embodiments, the compound has the formula:

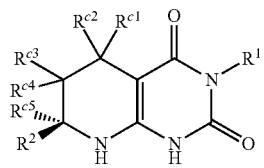

(II)

or a pharmaceutically acceptable salt thereof, wherein
$R^1$ is selected from the group consisting of methyl, ethyl, 2,2,2-trifluoroethyl, 2,2-difluoroethyl, propyl, isopropyl, cyclopropyl, n-butyl, isobutyl, (S)-2-butyl, (R)-2-butyl, cyclopropylmethyl, 1-methylcyclopropyl, cyclobutyl, 3,3-difluorocyclobut-1-yl, oxetan-3-yl, N-methoxycarbonylazetidin-3-yl, cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, pyrid-2-yl, 3-fluoropyrid-2-yl, 4-fluoropyrid-2-yl, 5-fluoropyrid-2-yl, 6-fluoropyrid-2-yl, and 6-methylpyrid-2-yl;
$R^2$ is selected from the group consisting of cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 3-methylphenyl, 4-methylphenyl, 2-chlorophenyl, 3-chlorophenyl, 4-chlorophenyl, 2-trifluoromethylphenyl, 3-trifluoromethylphenyl, 4-trifluoromethylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, 3-chloro-2-fluorophenyl, 5-chloro-2-fluorophenyl, 3-chloro-5-fluorophenyl, 2-fluoro-3-trifluoromethylphenyl, 2-fluoro-4-trifluoromethylphenyl, 2-fluoro-5-trifluoromethylphenyl, 3-fluoro-4-trifluoromethylphenyl, 3-fluoro-5-trifluoromethylphenyl, pyrid-2-yl, 3-fluoropyrid-2-yl, 4-fluoropyrid-2-yl, 5-fluoropyrid-2-yl, 6-fluoropyrid-2-yl, 6-methylpyrid-2-yl, phenylmethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, (S)-1-phenylethyl, (R)-1-phenylethyl, and phenyldifluoromethyl;
$R^{c5}$ is selected from the group consisting of hydrogen, deuterium, methyl, difluoromethyl, trifluoromethyl, ethyl, 2,2,2-trifluoroethyl, 2,2-difluoroethyl, propyl, isopropyl, n-butyl, isobutyl, (S)-2-butyl, (R)-2-butyl, and tert-butyl; and
$R^{c1}$, $R^{c2}$, $R^{c3}$, $R^{c4}$ are independently selected from the group consisting of hydrogen, deuterium, fluoro, methyl, difluoromethyl, and trifluoromethyl.

In some embodiments, the compound has the formula:

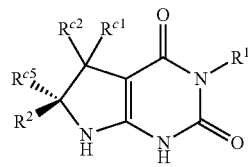

(III)

or a pharmaceutically acceptable salt thereof, wherein
$R^1$ is selected from the group consisting of methyl, ethyl, 2,2,2-trifluoroethyl, 2,2-difluoroethyl, propyl, isopropyl, cyclopropyl, n-butyl, isobutyl, (S)-2-butyl, (R)-2-butyl, cyclopropylmethyl, 1-methylcyclopropyl, cyclobutyl, 3,3-difluorocyclobut-1-yl, oxetan-3-yl, N-methoxycarbonylazetidin-3-yl, cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, pyrid-2-yl, 3-fluoropyrid-2-yl, 4-fluoropyrid-2-yl, 5-fluoropyrid-2-yl, 6-fluoropyrid-2-yl, and 6-methylpyrid-2-yl;
$R^2$ is selected from the group consisting of cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 3-methylphenyl, 4-methylphenyl, 2-chlorophenyl, 3-chlorophenyl, 4-chlorophenyl, 2-trifluoromethylphenyl, 3-trifluoromethylphenyl, 4-trifluoromethylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, 3-chloro-2-fluorophenyl, 5-chloro-2-fluorophenyl, 3-chloro-5-fluorophenyl, 2-fluoro-3-trifluoromethylphenyl, 2-fluoro-4-trifluoromethylphenyl, 2-fluoro-5-trifluoromethylphenyl, 3-fluoro-4-trifluoromethylphenyl, 3-fluoro-5-trifluoromethylphenyl, pyrid-2-yl, 3-fluoropyrid-2-yl, 4-fluoropyrid-2-yl, 5-fluoropyrid- 2-yl, 6-fluoropyrid-2-yl, 6-methylpyrid-2-yl, phenylmethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, (S)-1-phenylethyl, (R)-1-phenylethyl, and phenyldifluoromethyl;

$R^{c5}$ is selected from the group consisting of hydrogen, deuterium, methyl, difluoromethyl, trifluoromethyl, ethyl, 2,2,2-trifluoroethyl, 2,2-difluoroethyl, propyl, isopropyl, n-butyl, isobutyl, (S)-2-butyl, (R)-2-butyl, and tert-butyl;

$R^{c1}$ and $R^{c2}$ are independently selected from the group consisting of hydrogen, deuterium, fluoro, methyl, difluoromethyl, and trifluoromethyl.

In some embodiments, the compound is selected from

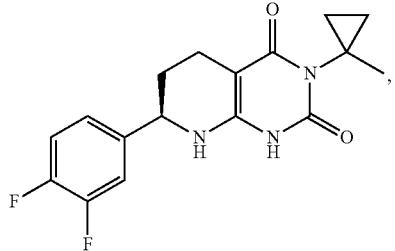

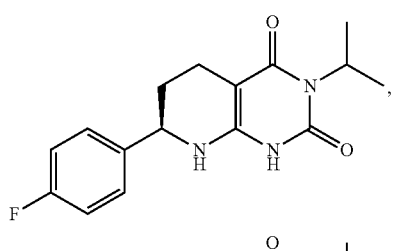

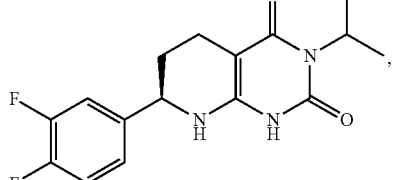

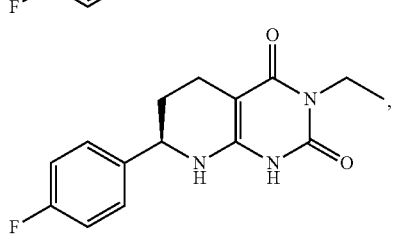

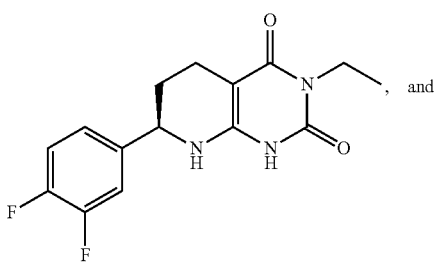, and

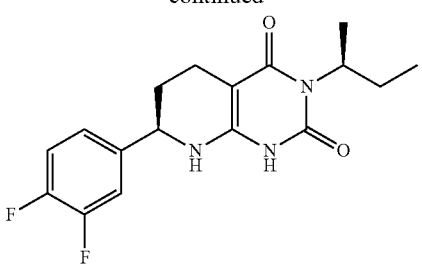

or a pharmaceutically acceptable salt thereof.

In some embodiments, the compound is selected from

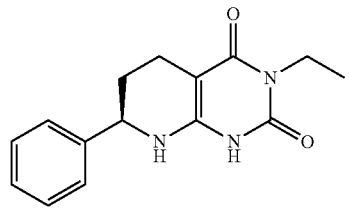

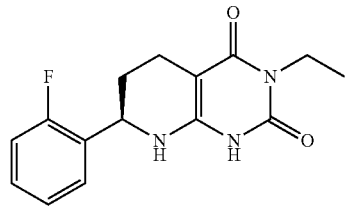

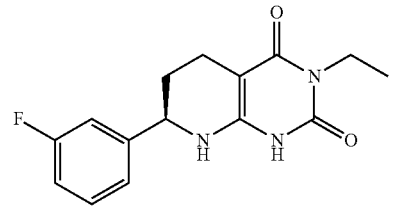

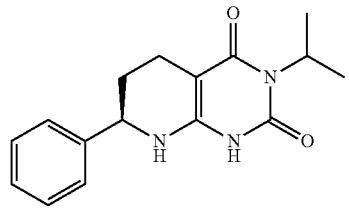

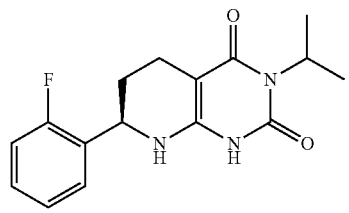

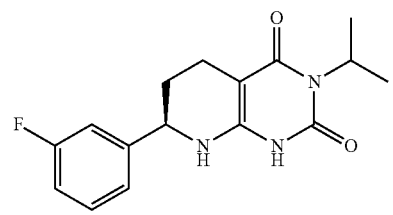

-continued

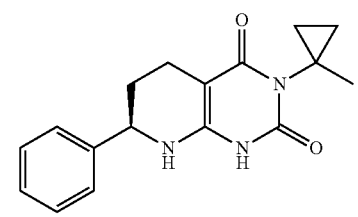

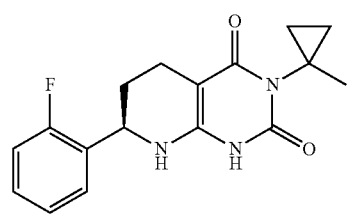

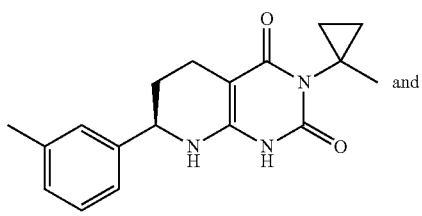

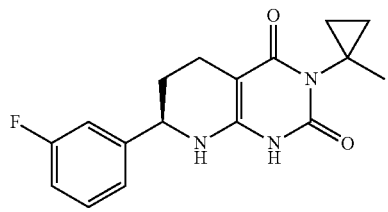

or a pharmaceutically acceptable salt thereof.

In some embodiments, the compound is selected from

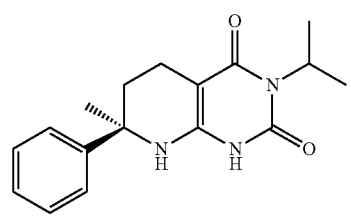

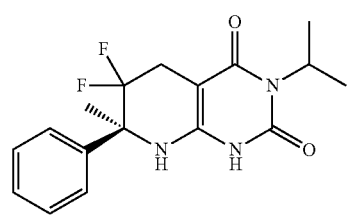

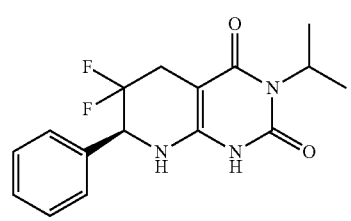

-continued

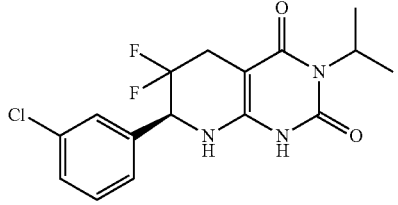

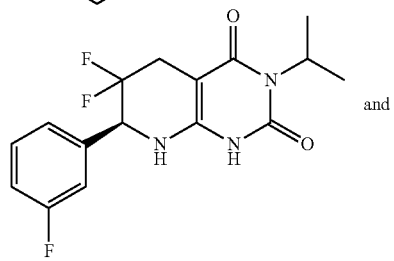

and

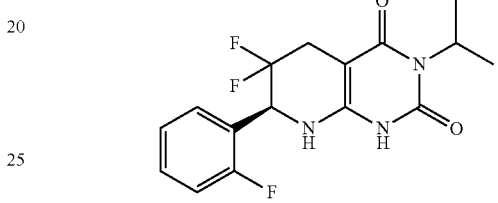

or a pharmaceutically acceptable salt thereof.

IV. Compound Preparation

Figure 2:
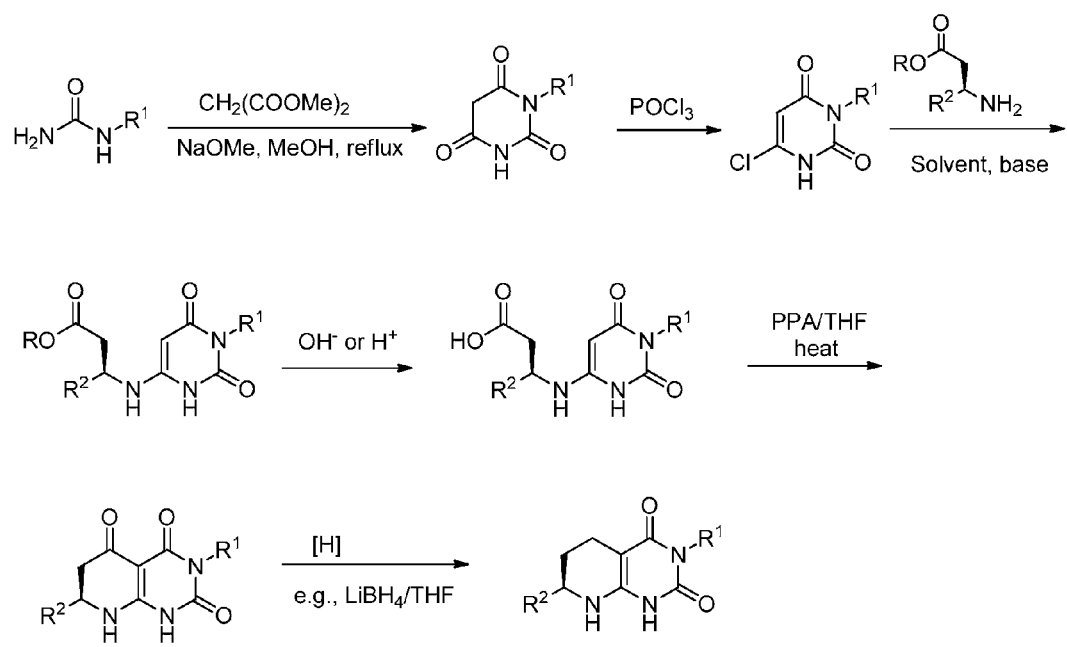
Figure 3:
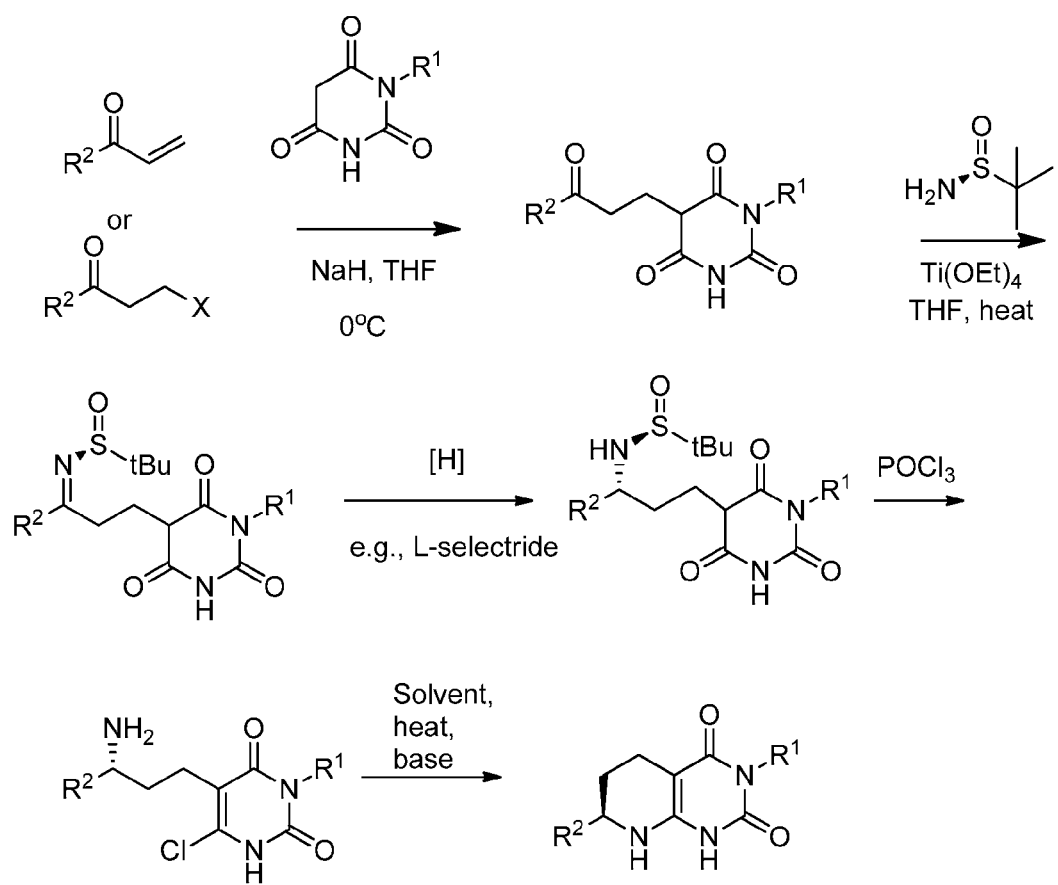
Figure 4:
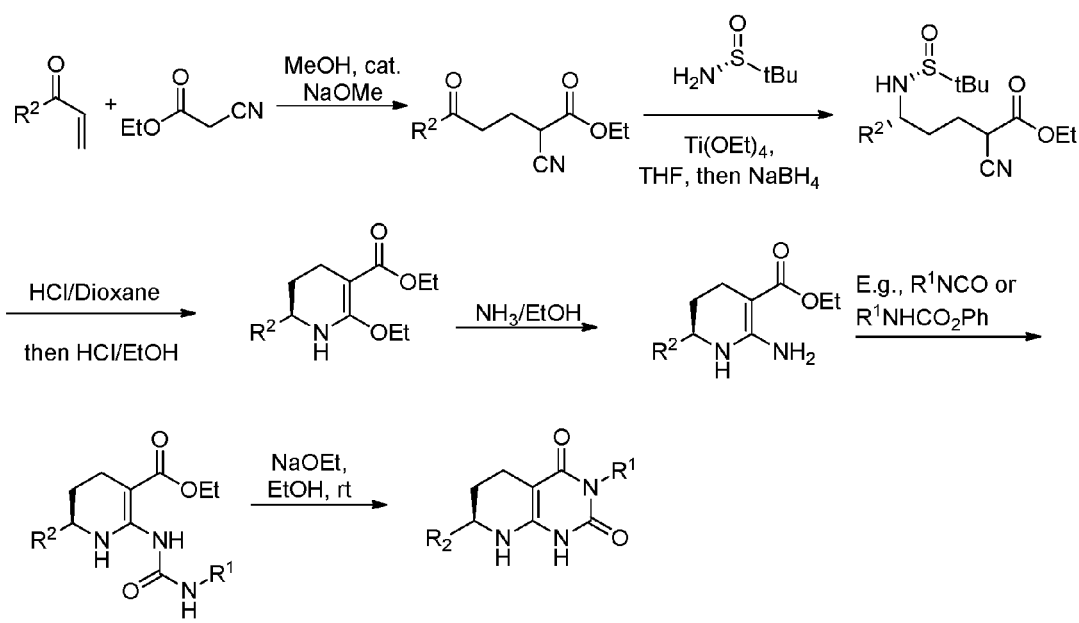
Figure 5:
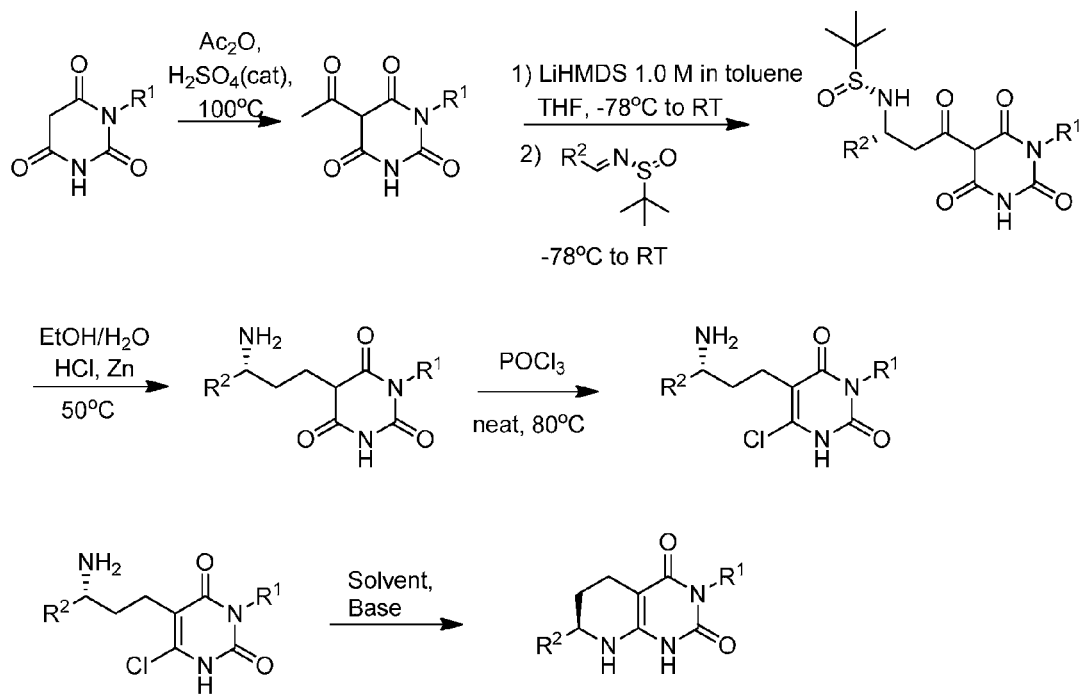
Figure 6:
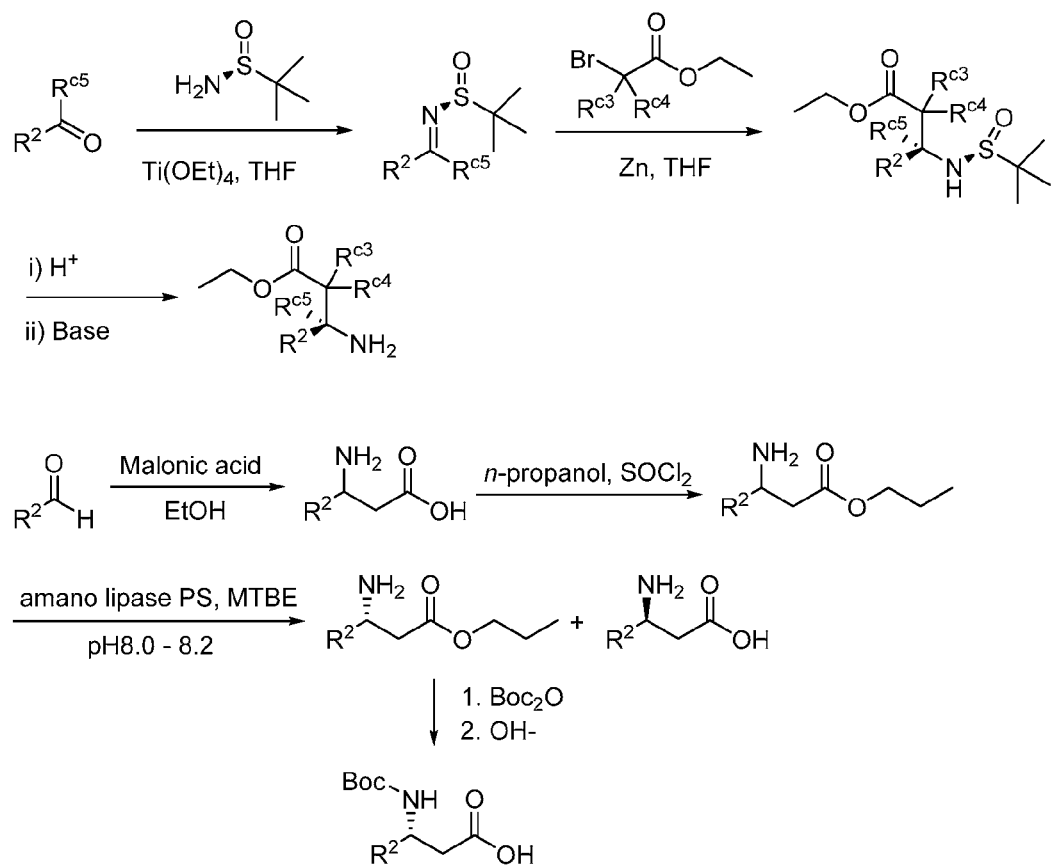
Figure 7:
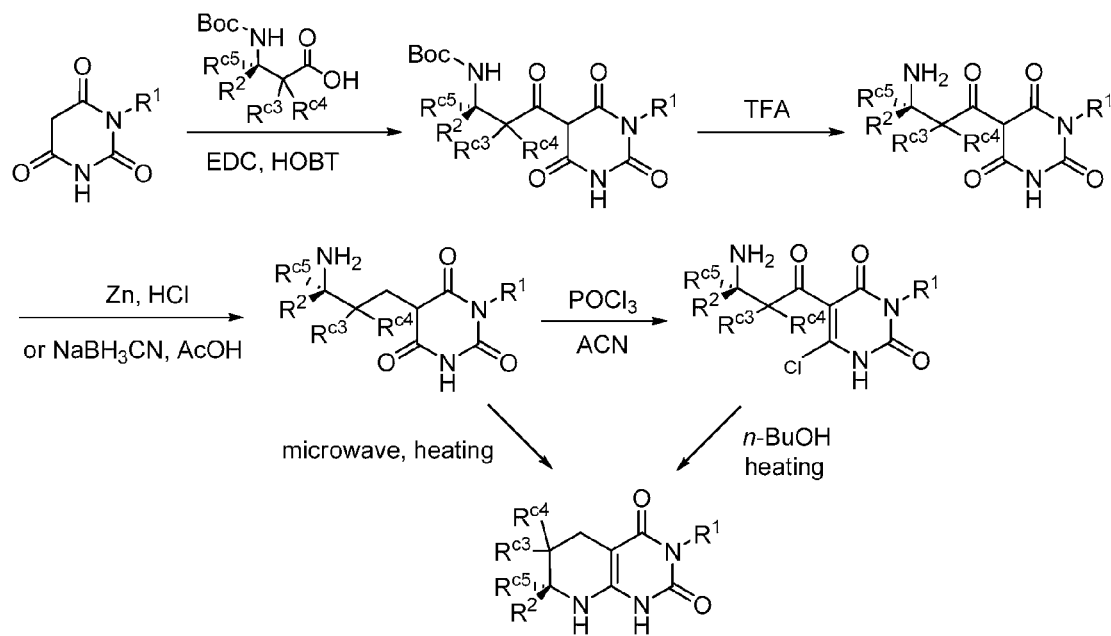

The compounds of formula (I) can be prepared via any suitable method. Compounds can be prepared, for example, by the route outlined in FIGS. 1-7, as well as in the Examples below. One of skill in the art will appreciate that the compounds of invention can be prepared using other synthetic methods, including transformations as described in, for example, LaRock (*Comprehensive Organic Transformations: A Guide to Functional Group Preparations*, Wiley, 1999).

V. Compositions

In another aspect, provided herein is a pharmaceutical composition containing a compound of formula I or a pharmaceutically acceptable salt thereof and a pharmaceutically acceptable excipient. The compositions are useful for treating hypertrophic cardiomyopathy in humans and other subjects.

The pharmaceutical compositions for the administration of the compounds or their pharmaceutically acceptable salts provided herein may conveniently be presented in unit dosage form and may be prepared by any of the methods known in the art of pharmacy and drug delivery. All methods include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active agent is generally included in an amount sufficient to produce the desired effect upon myocardial contractility (i.e. to decrease the often supranormal systolic contractility in HCM) and to improve left ventricular relaxation in diastole. Such improved relaxation can alleviate symptoms in hypertrophic cardiomyopathy and other etiologies of diastolic dysfunction. It can also ameliorate the effects of diastolic dysfunction causing impairment of coronary blood flow, improving the latter as an adjunctive agent in angina pectoris and ischemic heart disease. It can also confer benefits on salutary left ventricular remodeling in HCM and other causes of left ventricular hypertrophy due to chronic volume or pressure overload from, e.g., valvular heart disease or systemic hypertension The pharmaceutical compositions containing the active ingredient may be in a form suitable for oral use, for example, as tablets, troches, lozenges, aqueous or oily suspensions, dispersible powders or granules, emulsions, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions provided herein may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds or their pharmaceutically acceptable salts provided herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds or their pharmaceutically acceptable salts provided herein are employed. As used herein, topical application is also meant to include the use of mouth washes and gargles.

The compounds of this invention may also be coupled to a carrier that is a suitable polymer for targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds or their pharmaceutically acceptable salts provided herein may be coupled to a carrier that is a biodegradable polymer useful in achieving controlled release of a drug, such as polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, sterts, tubing, prostheses and the like.

VI. Methods of Treating Cardiac Disorders

The mutations that lead to HCM cause significant perturbations in myosin mechanics. These mutations exert their effects via distinct mechanisms depending on their locations in the myosin gene. The well-studied HCM mutations, R403Q and R453C, are located in different sections of the motor domain and cause distinct mechanistic perturbations that lead to the common outcome of increased force production. Without wishing to be bound by any particular theory, it is believed that the compounds or their pharmaceutically acceptable salts provided herein can bind directly to the mutant sarcomeric proteins and correct for their aberrant function, either in cis (by affecting the same specific function) or in trans (by altering a complementary function). As such, they can provide therapeutic benefit for HCM patients by counteracting the hypercontractile and/or impaired relaxation associated with this disease.

Accordingly, the invention provides a method of treating hypertrophic cardiomyopathy (HCM) or a cardiac disorder having one or more pathophysiological features associated with HCM. The method includes administering to a subject in need thereof an effective amount of a compound provided herein.

The compounds of the invention or their pharmaceutically acceptable salts can alter the natural history of HCM and other diseases rather than merely palliating symptoms. The mechanisms conferring clinical benefit to HCM patients can extend to patients with other forms of heart disease sharing similar pathophysiology, with or without demonstrable genetic influence. For example, an effective treatment for HCM, by improving ventricular relaxation during diastole, can also be effective in a broader population characterized by diastolic dysfunction. The compounds of the invention or their pharmaceutically acceptable salts can specifically target the root causes of the conditions or act upon other downstream pathways. Accordingly, the compounds of the invention or their pharmaceutically acceptable salts can also confer benefit to patients suffering from diastolic heart failure with preserved ejection fraction, ischemic heart disease, angina pectoris, or restrictive cardiomyopathy. Compounds of the invention or their pharmaceutically acceptable salts can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). By reducing left ventricular filling pressures the compounds could reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. Reducing or eliminating either dynamic and/or static left ventricular outflow obstruction may reduce the likelihood of requiring septal reduction therapy, either surgical or percutaneous, with their attendant risks of short and long term complications. The compounds or their pharmaceutically acceptable salts may reduce the severity of the chronic ischemic state associated with HCM and thereby reduce the risk of Sudden Cardiac Death (SCD) or its equivalent in patients with implantable cardioverter-defibrillators (frequent and/or repeated ICD discharges) and/or the need for potertially toxic antiarrhythmic medications. The compounds or their pharmaceutically acceptable salts could be valuable in reducing or eliminating the need for concomitant medications with their attendant potertial toxicities, drug-drug interactions, and/or side effects. The compounds or their pharmaceutically acceptable salts may reduce interstitial myocardial fibrosis and/or slow the progression, arrest, or reverse left ventricular hypertrophy.

Depending on the disease to be treated and the subject's condition, the compounds or their pharmaceutically acceptable salts provided herein may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require improved ventricular relaxation during diastole, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Compounds and compositions provided herein may be used in combination with other drugs that are used in the treatment, prevention, suppression or amelioration of the diseases or conditions for which compounds and compositions provided herein are useful. Such other drugs may be administered, by a route and in an amount commonly used therefor, contemporaneously or sequentially with a compound or composition provided herein. When a compound or composition provided herein is used contemporaneously with one or more other drugs, a pharmaceutical composition containing such other drugs in addition to the compound or composition provided herein is preferred. Accordingly, the pharmaceutical compositions provided herein include those that also contain one or more other active ingredients or therapeutic agents, in addition to a compound or composition provided herein. Suitable additional active agents include, for example: therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The weight ratio of the compound provided herein to the second active ingredient may be varied and will depend upon the effective dose of each ingredient. Generally, an effective dose of each will be used.

VII. Examples

Abbreviations: AcCl: acetyl chloride; aq: aqueous; CH$_2$Cl$_2$: dichloromethane; CH$_3$CN: acetonitrile; CH$_3$OH: methanol; DIEA: diisopropyl ethylamine; DMF: dimethyl formamide; DMSO: dimethyl sulfoxide; equiv.: equivalent (s); Et$_3$N: triethylamine; Et$_2$O: diethyl ether; EtOH: ethanol; h or hr: hour(s); HCl: hydrogen chloride; H$_2$O: water; IPA: isopropyl alcohol; iPrMgCl: isopropyl magnesium chloride; K$_2$CO$_3$: potassium carbonate; LiBH$_4$: lithium borohydride; LiHMDS: lithium hexamethyldisilazane; MeOH: methanol; MgSO$_4$: magnesium sulfate; min: minutes; mL: milliliter; MW or microwave (reaction done in microwave reactor); NaBH$_4$: sodium borohydride; NaCl: sodium chloride; NaH: sodium hydride; NaHCO$_3$: sodium bicarbonate; NaOEt: sodium ethoxide; NaOH: sodium hydroxide; NaOMe: sodium methoxide; Na$_2$SO$_4$: sodium sulfate; n-BuLi: n-butyl lithium; n-BuOH: n-butanol; NH$_4$Cl: ammonium chloride; NMP: N-methyl pyrrolidine; Pd/C: palladium on carbon; Pd(OH)$_2$: palladium hydroxide; pH: −log [H$^+$]; POCl$_3$: phosphoryl trichloride; PPA: polyphosphoric acid; PPTS: pyridinium p-toluenesulfonate; RT: room temperature; TEBAC: triethylbenzylammonium chloride; TFA: trifluoroacetic acid; THF: tetrahydrofuran; and Ti(OEt)$_4$: titanium (IV) ethoxide. All of the experiments were carried out in fume hoods with specific safety precautions and necessary personal protective equipment.

Example 1

Preparation of (R)-3-isopropyl-7-phenyl-7,8-dihydropyrido[2,3-d]pyrimidine-2,4,5(1H,3H,6H)-trione

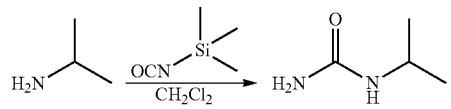

Compound 1.1. Isopropylurea

To a stirred solution of isopropylamine (15.3 g, 259 mmol, 1.00 equiv) in CH$_2$Cl$_2$ (200 mL) under argon at 0° C. was added dropwise trimethylsilyl isocyanate (30 g, 260 mmol, 1.0 equiv). The resulting mixture was allowed to reach ambient temperature and stirred overnight. After cooling to 0° C., MeOH (100 mL) was added dropwise. The resulting solution was stirred 2 h at room temperature and then concentrated under reduced pressure. The crude residue was recrystallized from MeOH/Et$_2$O=1/20 (v/v) to yield 15.4 g (58%) of the title compound as a white solid. $^1$H NMR (400 MHz, DMSO-d$_6$): δ 5.72 (d, J=7.4 Hz, 1H), 5.25 (br s, 2H), 3.59 (dq, J=13.9, 6.7 Hz, 1H), 0.99 (d, J=6.7 Hz, 6H) ppm.

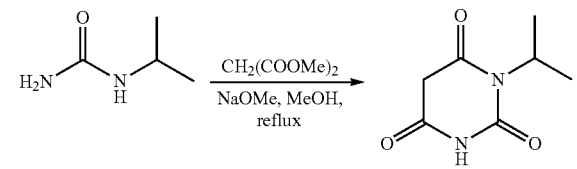

Compound 1.2.
1-Isopropylpyrimidine-2,4,6(1H,3H,5H)-trione

To a stirred solution of isopropylurea ((compound 1.1), 14.4 g, 0.14 mol, 1.00 equiv) in MeOH (500 mL) were added dimethyl malonate (19.55 g, 0.148 mol, 1.05 equiv) and sodium methoxide (18.9 g, 0.35 mol, 2.50 equiv). The resulting mixture was stirred overnight at 65° C. After cooling to ambient temperature and then to 0° C., the pH was carefully adjusted to 3 using concentrated HCl. The resulting mixture was concentrated under reduced pressure. The resulting residue was taken up in EtOH (200 mL) and was filtered. The filtrate was concentrated under reduced pressure and the resulting residue was purified by silica gel column chromatography eluting with CH$_2$Cl$_2$/MeOH=20/1 (v/v). The fractions containing pure compound were combined and concentrated in vacuo to yield 16.8 g (71%) of the title compound as a white solid. LC-MS (ES, m/z): [M−H]$^−$= 169. $^1$H-NMR (300 MHz, DMSO-d$_6$,): δ 11.19 (s, 1H), 4.83 (m, 1H), 3.58 (s, 2H), 1.32 (d, J=6.0 Hz, 6H) ppm.

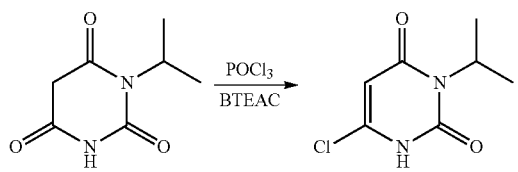

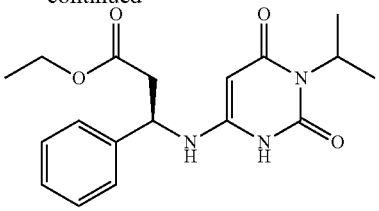

Compound 1.3.
6-Chloro-3-isopropylpyrimidine-2,4(1H,3H)-dione

To a 100-mL round-bottom flask containing 1-isopropylpyrimidine-2,4,6(1H,3H,5H)-trione ((compound 1.2), 11.4 g, 66.99 mmol, 1.00 equiv) under argon were added benzyltriethylammonium chloride (BTEAC) (21.3 g, 93.5 mmol, 1.40 equiv) and phosphoroyl trichloride (30 mL). The resulting mixture was stirred overnight at 50° C. After cooling to room temperature, the mixture was concentrated under reduced pressure. The residue was dissolved in $CH_2Cl_2$ (150 mL) followed by slow addition of $H_2O$ (100 mL). The layers were separated and the organic layer was washed with $H_2O$ (100 mL), dried over anhydrous $Na_2SO_4$ and concentrated in vacuo. The resulting residue was purified by silica gel column chromatography eluting with EtOAc/petroleum ether=1/1 (v/v). The fractions containing pure compound were combined and concentrated in vacuo to yield 5.12 g (41%) of the title compound as a light yellow solid. LC-MS (ES, m/z): $[M+H]^+=189$. $^1$H-NMR (DMSO-$d_6$, 300 MHz): δ 12.22 (s, 1H), 5.88 (s, 1H), 4.95 (m, 1H), 1.34 (d, J=6.0 Hz, 6H) ppm.

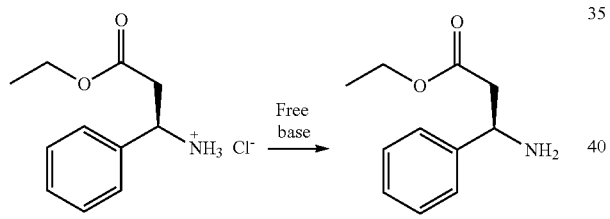

Compound 1.4. Ethyl (3R)-3-amino-3-phenylpropanoate

To commercially available ethyl (3R)-3-amino-3-phenylpropanoate hydrochloride (506 mg, 2.21 mmol) in 5% $Na_2CO_{3(aq)}$ (30 mL) was added $Et_2O$ (40 mL). The two layers were separated and the organic layer was dried over anhydrous $MgSO_4$ and concentrated to yield 361 mg (85%) of the title compound as a clear oil. LC-MS (ES, m/z): $[M+H]^+=194$.

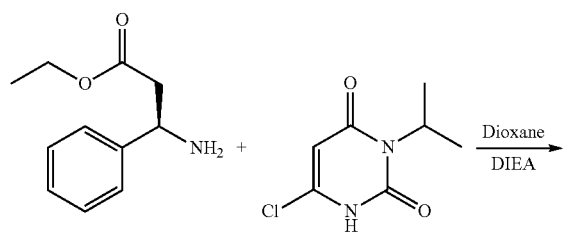

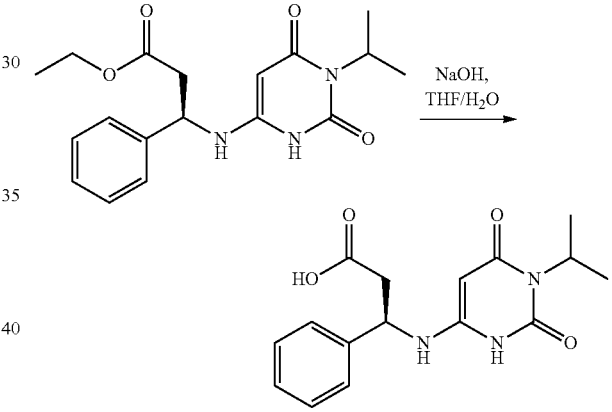

Compound 1.5. Ethyl (R)-3-((1-isopropyl-2,6-dioxo-1,2,3,6-tetrahydropyrimidin-4-yl)amino)-3-phenylpropanoate To a stirring solution of ethyl (3R)-3-amino-3-phenylpropanoate ((compound 1.4), 361 mg, 1.87 mmol) in 1,4-dioxane (3 mL) was added DIEA (0.6 mL) and 6-chloro-3-isopropylpyrimidine-2,4(1H,3H)-dione ((compound 1.3), 460 mg, 2.45 mmol, 1.3 equiv). The reaction mixture was heated in a microwave reactor (Biotage® Initiator$^+$) at 150° C. for 30 minutes. The reaction was cooled and the dioxane was removed in vacuo. The crude material was used in the next step without further purification. LC-MS (ES, m/z): $[M+H]^+=346$.

Compound 1.6. (R)-3-((1-Isopropyl-2,6-dioxo-1,2,3,6-tetrahydropyrimidin-4-yl)amino)-3-phenylpropanoic acid To a stirring solution of crude ethyl (R)-3-((1-isopropyl-2,6-dioxo-1,2,3,6-tetrahydropyrimidin-4-yl)amino)-3-phenylpropanoate ((compound 1.5), in THF (5 mL) was added 1 M NaOH (5 mL). The reaction mixture was stirred at room temperature for 30 min and was concentrated to 5 mL under reduced pressure. The pH of the resulting mixture was adjusted to 3 with 1 N $HCl_{(aq)}$. A solid (containing product by UPLC) precipitated and was isolated by filtration. To the filtrate, which also contained appreciable product by UPLC, was added with EtOAc (50 mL). The filtered solid was added back into the filtrate and the two layers were separated. The organic layer was concentrated in vacuo to give a white solid that was suspended in $H_2O/CH_3CN$ (0.1% TFA) (15 mL) and filtered. The resulting filtrate was purified by reverse phase HPLC ((Shimadzu, Prominence LC-20AP system equipped with a Phenomenex Gemini-NX C18 column) Mobile phase A: $H_2O$ (0.1% TFA), phase B: $CH_3CN$ (0.1% TFA)=70:30 (v/v) for 3 min, up to 55% over 2.5 min, held at 55% for 1.5 min). The fractions containing pure compound were combined and lyophilized to yield 45 mg (8% over two steps) of the title compound as a white solid. LC-MS (ES, m/z): [M+H]$^+$=318.

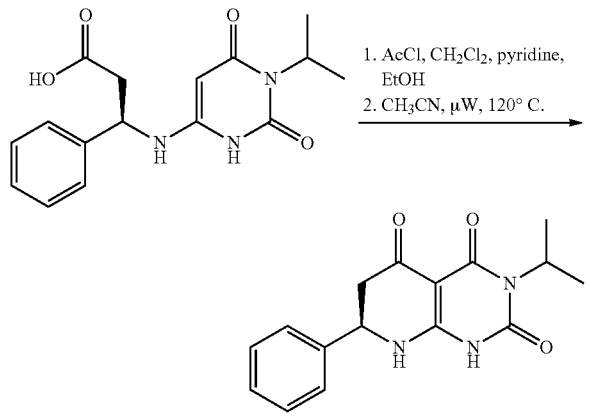

Compound 1.7. (R)-3-Isopropyl-7-phenyl-7,8-dihydropyrido[2,3-d]pyrimidine-2,4,5(1H,3H,6H)-trione To a stirring solution of (R)-3-((1-isopropyl-2,6-dioxo-1,2,3,6-tetrahydropyrimidin-4-yl)amino)-3-phenylpropanoic acid ((compound 1.6), 45 mg, 0.14 mmol) in CH$_2$Cl$_2$ (5 mL) at 0° C. was added pyridine (0.05 mL) and acetyl chloride (1 mL of 0.1 mL AcCl in 10 mL CH$_2$Cl$_2$). The reaction mixture was stirred at 0° C. for 30 minutes and a second portion of the acetyl chloride in CH$_2$Cl$_2$ solution was added (1 mL). The reaction was stirred for 30 minutes, was quenched with EtOH and was concentrated. The crude material was dissolved in CH$_3$CN (5 mL), transferred to a microwave vial and heated in a microwave reactor (Biotage® Initiator$^+$) at 120° C. for 30 minutes. The volatiles were removed and the crude product was used in the next step without further purification. LC-MS (ES, m/z): [M+H]$^+$=300.

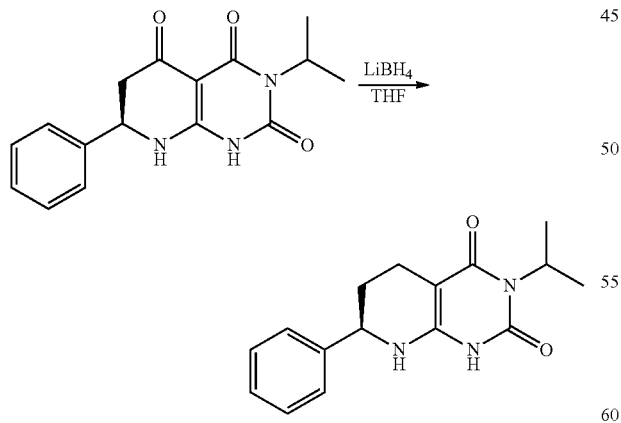

Compound 1. (R)-3-Isopropyl-7-phenyl-7,8-dihydropyrido[2,3-d]pyrimidine-2,4,5(1H,3H,6H)-trione To crude (R)-3-isopropyl-7-phenyl-7,8-dihydropyrido[2,3-d]pyrimidine-2,4,5(1H,3H,6H)-trione (compound 1.7) in THF (8 mL) at 0° C. was added LiBH$_4$ (50 mg, 2.3 mmol, equiv.). The reaction was stirred at 0° C. for 30 minutes before another portion of LiBH$_4$ (50 mg) was added. The reaction was stirred for an additional 30 minutes at 0° C. and was carefully quenched with saturated NH$_4$Cl$_{(aq)}$. Ethyl acetate (20 mL) was added and the two layers were separated. The aqueous layer was further extracted with EtOAc (20 mL). The combined organics were concentrated and the resulting white solid was suspended in H$_2$O/CH$_3$CN (0.1% TFA (v/v)) and filtered. The filtrate was subjected to reverse phase HPLC ((Shimadzu, Prominence LC-20AP system equipped with a Phenomenex Gemini-NX C18 column) Mobile phase A: H$_2$O (0.1% TFA), phase B: CH$_3$CN (0.1% TFA)=70/30 for 1 min, up to 65% B over 4.5 min, held at 65% for 1.5 min, up to 75% over 0.5 min).

The fractions containing pure compound were combined and lyophilized to yield 11.1 mg (27% over two steps) of the title compound as a white solid. LC-MS (ES, m/z): [M+H]$^+$=286. $^1$H-NMR (400 MHz, DMSO-d$_6$,): δ 10.00 (br s, 1H), 7.38-7.33 (m, 2H), 7.29-7.25 (m, 3H), 6.25 (br s, 1H), 5.04-4.95 (m, 1H), 4.51-4.47 (m, 1H), 2.33-2.21 (m, 1H), 2.08-2.01 (m, 1H), 1.96-1.84 (m, 1H), 1.82-1.72 (m, 1H), 1.31 (dd, J=7.0, 1.6 Hz, 6H) ppm.

The following are representative compounds that were synthesized using the methodology outlined in example 1:

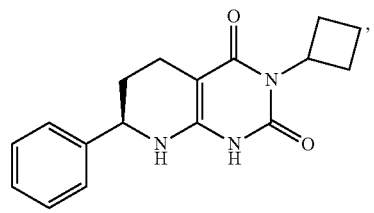

28

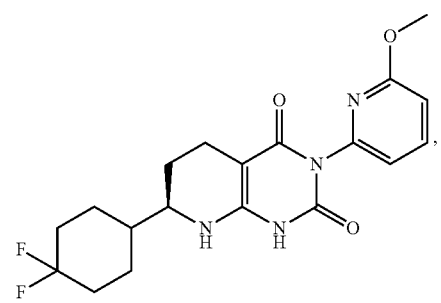

39

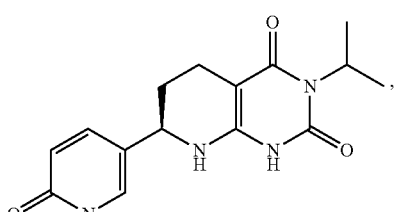

54

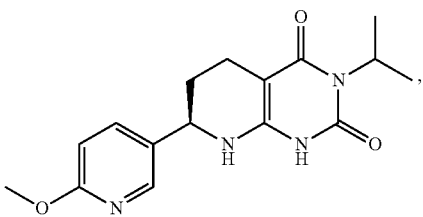

59

31
-continued
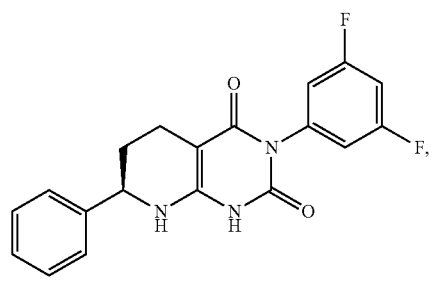
65
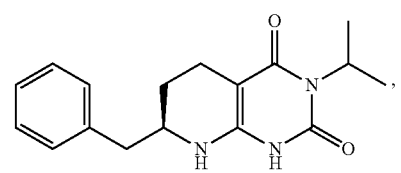
66
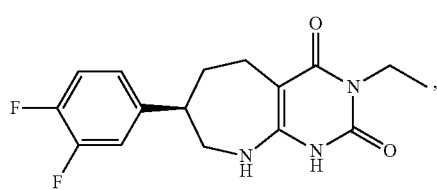
84
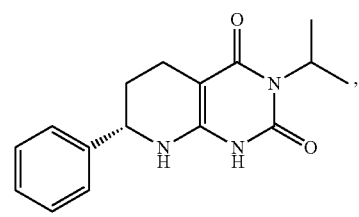
89
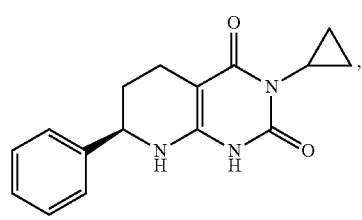
90
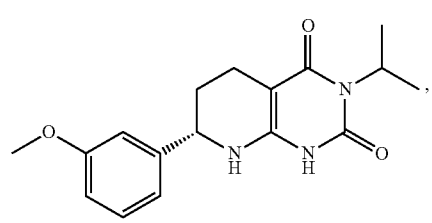
93
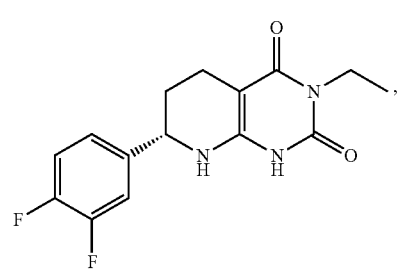
94
32
-continued
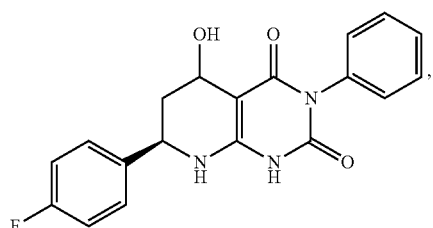
95
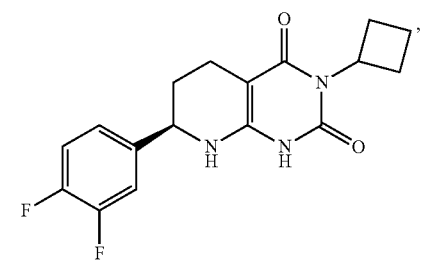
96
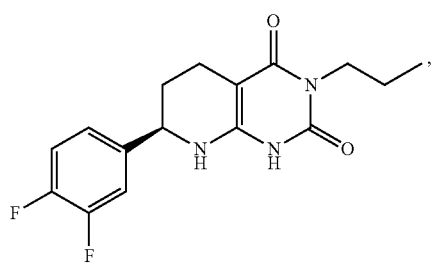
97
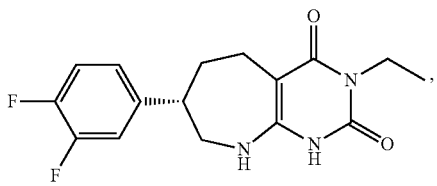
98
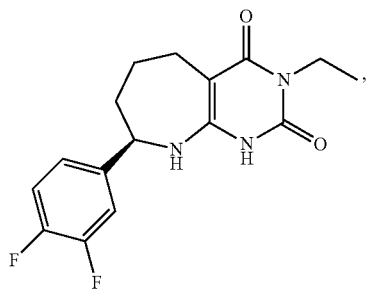
99
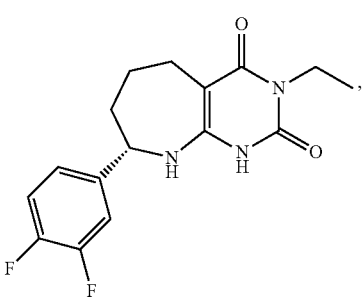
100

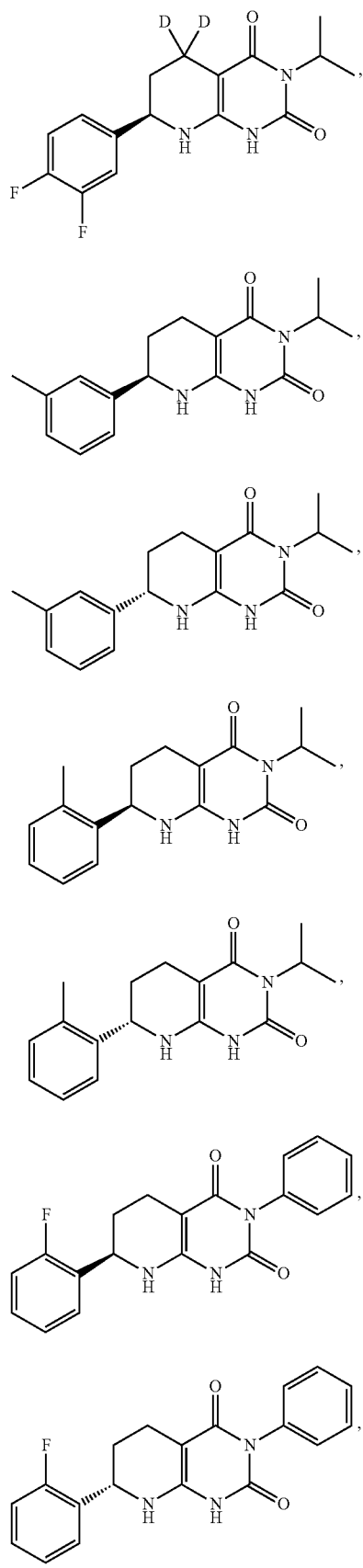
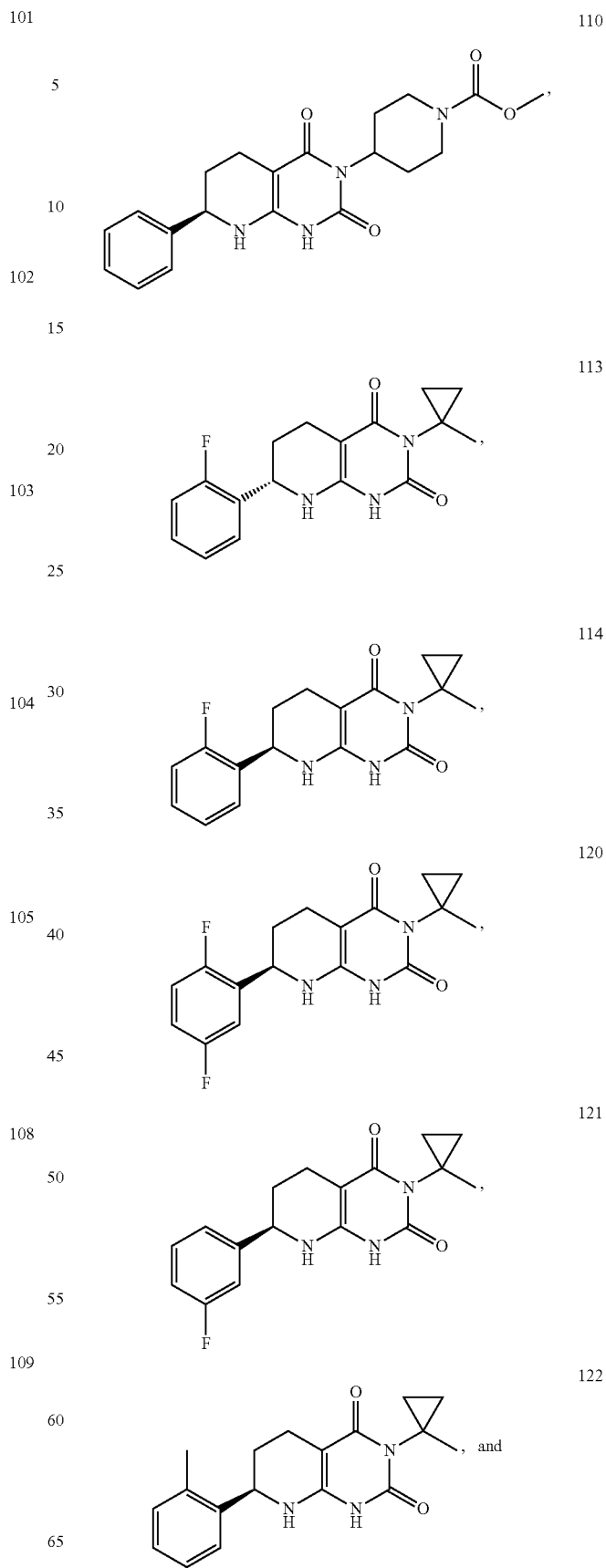

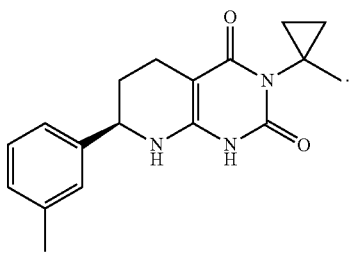

124

Example 2

Preparation of (R)-7-(4,4-difluorocyclohexyl)-3-(3,5-difluorophenyl)-5,6,7,8-tetrahydropyrido[2,3-d]pyrimidine-2,4(1H,3H)-dione

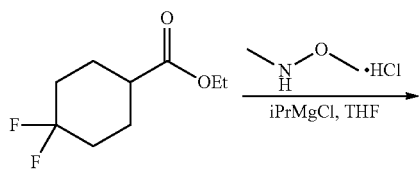

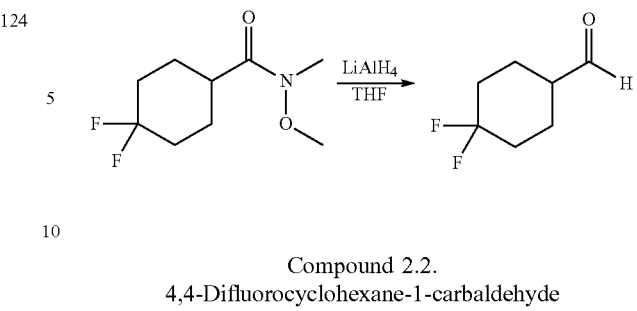

Compound 2.2. 4,4-Difluorocyclohexane-1-carbaldehyde

To a stirring solution of 4,4-difluoro-N-methoxy-N-methylcyclohexane-1-carboxamide ((compound 2.1), 11.6 g, 56.0 mmol, 1.00 equiv) in THF (120 mL) under an inert atmosphere of argon at 0° C. was added LiAlH$_4$ (4.26 g, 112.25 mmol, 2.00 equiv) batch-wise (CAUTION! Exothermic step). The resulting solution was warmed to room temperature and stirred for 3 h. The reaction was cooled back to 0° C. and was carefully quenched by the slow addition of H$_2$O (5 mL, dropwise), 15% NaOH$_{(aq)}$ (5 mL and H$_2$O (15 mL). The resulting mixture was stirred for 30 min at 25° C. and was filtered. The filtrate was dried over anhydrous MgSO$_4$ and concentrated in vacuo to yield 8 g (crude) of the title compound as light yellow oil.

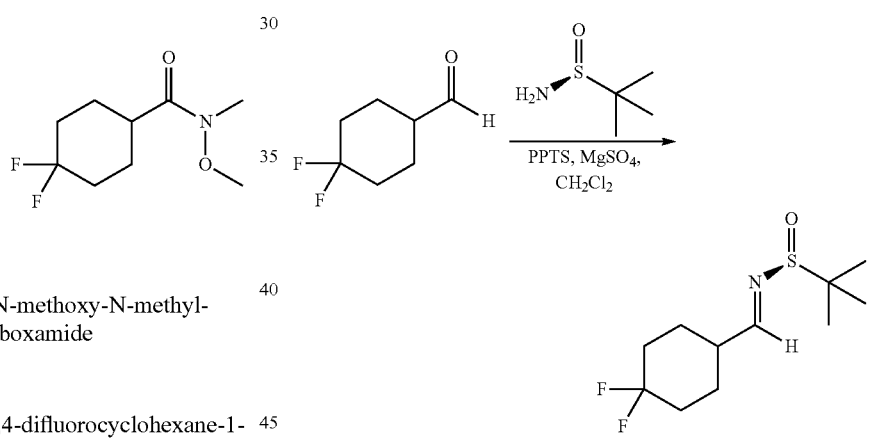

Compound 2.3. (S)—N-[(1E)-(4,4-Difluorocyclohexyl)methylidene]-2-methylpropane-2-sulfinamide Compound 2.1. 4,4-Difluoro-N-methoxy-N-methyl-cyclohexane-1-carboxamide To a stirring solution of ethyl 4,4-difluorocyclohexane-1-carboxylate (16 g, 83.25 mmol, 1.00 equiv) and methoxy(methyl)amine hydrochloride (12.125 g, 125.00 mmol, 1.50 equiv) in THF (120 mL) under an inert atmosphere of argon at −20° C. was added isopropyl magnesium chloride (2M in THF, 125 mL, 3.00 equiv) dropwise over 30 min. The resulting solution was warmed to room temperature and stirred for 3 h. The reaction was cooled to 0° C. and was carefully quenched by the addition saturated NH$_4$Cl$_{(aq)}$ (100 mL). The resulting mixture was extracted with EtOAc (3×100 mL). The organic layers were combined, washed with brine (2×100 mL), dried over anhydrous MgSO$_4$ and concentrated in vacuo. The resulting residue was purified by silica gel column chromatography eluting with EtOAc/petroleum ether=1/2 (v/v). The fractions containing pure compound were combined and concentrated to yield 11.6 g (67%) of the title compound as light yellow oil. LC-MS (ES, m/z): [M+H]$^+$=208. $^1$H-NMR (300 MHz, CDCl$_3$): δ 3.71 (s, 3H), 3.18 (s, 3H), 2.74 (m, 1H), 2.24-2.14 (m, 2H), 1.94-1.65 (m, 6H) ppm.

To a stirring solution of 4,4-difluorocyclohexane-1-carbaldehyde ((compound 2.2), 16.0 g, 108 mmol, 1.00 equiv) in CH$_2$Cl$_2$ (250 mL) under an argon atmosphere was added (S)-2-methylpropane-2-sulfinamide (19.62 g, 161.9 mmol, 1.50 equiv), PPTS (1.36 g, 5.41 mmol, 0.05 equiv) and anhydrous MgSO$_4$ (64.86 g, 540.5 mmol, 5.00 equiv). The resulting mixture was stirred overnight at 25° C. and filtered. The filtrate was concentrated in vacuo and the resulting residue was purified by silica gel column chromatography eluting with EtOAc/petroleum ether=1/4 (v/v). The fractions containing pure compound were combined and concentrated in vacuo to yield 17 g (63%) of the title compound as a light yellow oil. LC-MS (ES, m/z): [M+H]$^+$=252. $^1$H-NMR (400 MHz, CDCl$_3$): δ 8.03 (m, 1H), 2.58 (m, 1H), 2.15 (m, 2H), 2.05 (m, 2H), 1.90-1.75 (m, 4H), 1.22 (s, 9H) ppm.

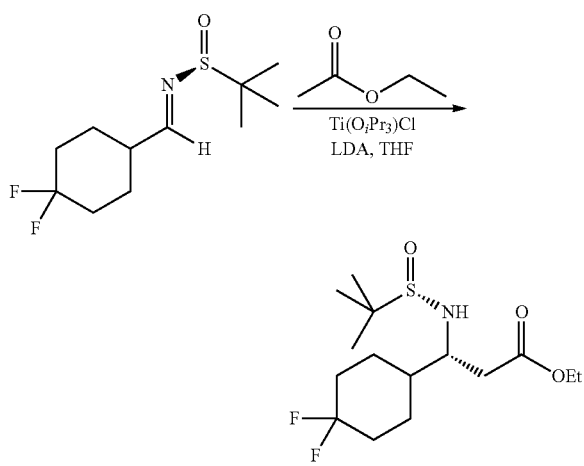

Compound 2.4. Ethyl (3R)-3-(4,4-difluorocyclohexyl)-3-[[(S)-2-methylpropane-2-sulfinyl]amino]propanoate To a stirring solution of EtOAc (5.61 g, 63.7 mmol, 2.00 equiv) in THF (60 mL) under an argon atmosphere at −78° C. was added lithium diisopropylamide (2M in THF, 33.7 mL, 67.4 mmol, 2.10 equiv, dropwise). The solution was stirred for 30 min at −78° C. and then a solution of Ti(Oi-Pr)₃Cl (34.8 g, 134. mmol, 4.20 equiv) in THF (20 mL) was added. The reaction mixture was stirred for 30 min at −78° C. and (S)-N-[(1E)-(4,4-difluorocyclohexyl)methylidene]-2-methylpropane-2-sulfinamide ((compound 2.3), 8.0 g, 32. mmol, 1.00 equiv) in THF (10 mL) was added. The resulting solution was stirred for 3 h at −78° C. and quenched by the addition of saturated NH₄Cl$_{(aq)}$ (100 mL). The mixture was filtered and the filtrate was extracted with of EtOAc (3×150 mL). The organic layers were combined, washed with brine (3×150 mL), dried over anhydrous MgSO₄ and concentrated in vacuo. The resulting residue was purified by silica gel column chromatography eluting with EtOAc/petroleum ether=1/1 (v/v). The fractions containing pure compound were combined and concentrated in vacuo to yield 9.0 g (83%) of the title compound as orange oil. LC-MS (ES, m/z): [M+H]⁺=340. ¹H-NMR (300 MHz, CDCl₃): δ 4.32 (d, J=8.4 Hz, 1H), 4.17 (q, J=7.2 Hz, 2H), 3.41-3.32 (m, 1H), 2.85 (m, 1H), 2.66 (m, 1H), 2.09 (m, 2H), 1.98 (m, 1H), 1.73 (m, 3H), 1.66 (m, 1H), 1.55-1.30 (m, 2H), 1.30-1.18 (m, 12H) ppm.

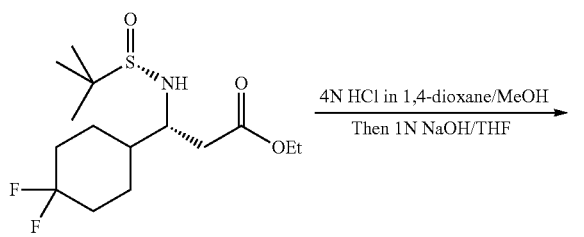

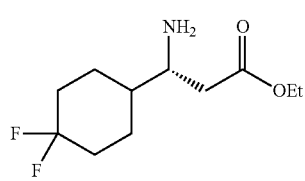

Compound 2.5. Ethyl (3R)-3-amino-3-(4,4-difluorocyclohexyl)propanoate

To a stirring solution of ethyl (3R)-3-(4,4-difluorocyclohexyl)-3-[[(S)-2-methylpropane-2-sulfinyl]amino]propanoate ((compound 2.4), 9.0 g, 27 mmol, 1.0 equiv) in MeOH (40 mL) under argon was added 4N HCl in 1,4-dioxane (5 mL). The resulting solution was stirred for 5 h at 25° C. and then concentrated in vacuo. The resulting residue was diluted with THF (40 mL) and 1N NaOH (30 mL, added at 0° C.). After stirring for 30 min at 0° C., the resulting mixture was concentrated in vacuo. The residue was diluted with CH₂Cl₂/EtOH=5/1 (v/v) (200 mL). The solid was filtered and the filtrate was concentrated in vacuo. This resulted in 3.7 g (59%) of the title compound as an orange oil. LC-MS (ES, m/z): [M+H]⁺=236. ¹H-NMR (400 MHz, CDCl₃): δ 4.18 (m, 2H), 3.13 (m, 1H), 2.53 (m, 1H), 2.34 (m, 1H), 2.30-2.14 (m, 2H), 1.84 (m, 3H), 1.79-1.65 (m, 3H), 1.41 (m, 3H), 1.26 (m, 3H) ppm.

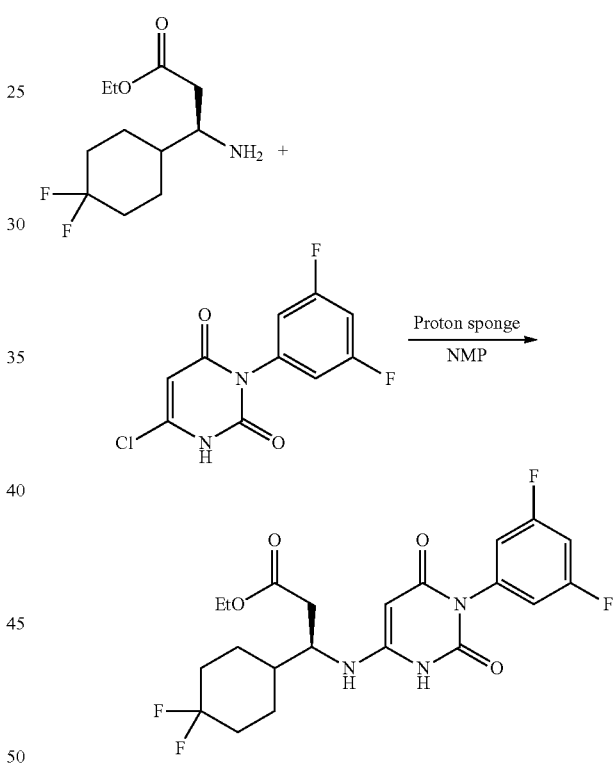

Compound 2.6. Ethyl (3R)-3-(4,4-difluorocyclohexyl)-3-[[1-(3,5-difluorophenyl)-2,6-dioxo-1,2,3,6-tetrahydropyrimidin-4-yl]amino]propanoate To a stirring solution of ethyl (3R)-3-amino-3-(4,4-difluorocyclohexyl)propanoate ((compound 2.5), 3.0 g, 13 mmol, 1.20 equiv) in NMP (12 mL) under argon were added proton sponge (3.41 g, 15.9 mmol, 1.5 equiv) and 6-chloro-3-(3,5-difluorophenyl)-1,2,3,4-tetrahydropyrimidine-2,4-dione (2.75 g, 10.6 mmol, 1.00 equiv). The resulting solution was stirred for 4 h at 120° C. The reaction mixture was directly purified by preparative HPLC ((IntelFlash): Column, C18; mobile phase, H₂O with 0.5% TFA (v/v) and CH₃CN (5% CH₃CN up to 95% (v/v) in 40 min)) to yield 2.25 g (46%) of the title compound as a brown solid. LC-MS (ES, m/z): [M+H]⁺=458. ¹H-NMR (400 MHz, CDCl₃): δ 10.45 (br, 1H), 6.94-6.85 (m, 3H), 5.91 (br, 1H), 5.19 (s, 1H), 4.16 (m, 2H), 3.64 (s, 1H), 2.55 (m, 1H), 2.37 (m, 1H), 2.07 (m, 2H), 1.71-1.60 (m, 5H), 1.28 (m, 5H) ppm.

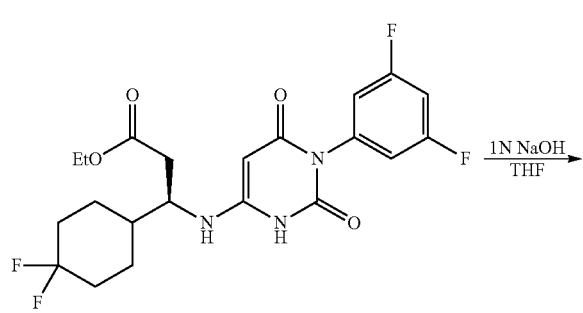

Compound 2.7. (3R)-3-(4,4-Difluorocyclohexyl)-3-[[1-(3,5-difluorophenyl)-2,6-dioxo-1,2,3,6-tetrahydropyrimidin-4-yl]amino]propanoic acid To a stirring solution of ethyl (3R)-3-(4,4-difluorocyclohexyl)-3-[[1-(3,5-difluorophenyl)-2,6-dioxo-1,2,3,6-tetrahydropyrimidin-4-yl]amino]propanoate ((compound 2.6), 1.2 g, 2.6 mmol, 1.0 equiv) in THF (15 mL) was added 1N NaOH$_{(aq)}$ (10 mL). The resulting solution was stirred for 2 h at 25° C. and then concentrated in vacuo. The residue was diluted with THF (20 mL). The pH value of the solution was adjusted to 6 with ion exchange resin (Dowex, 50WX8 (H) Fine Mesh Resin, 100-200 Mesh). The solid was filtered and the filtrate was concentrated in vacuo to yield 800 mg (71%) of the title compound as a brown solid. LC-MS (ES, m/z): [M+H]⁻=430. ¹H-NMR (400 MHz, DMSO-d₆): δ 12.44 (br, 1H), 10.35 (br, 1H), 7.28 (m, 1H), 7.07 (m, 2H), 4.81 (s, 1H), 3.76-3.65 (m, 1H), 2.64 (m, 2H), 2.54 (m, 1H), 2.06 (m, 2H), 1.83-1.70 (m, 5H), 1.33-1.21 (m, 2H) ppm.

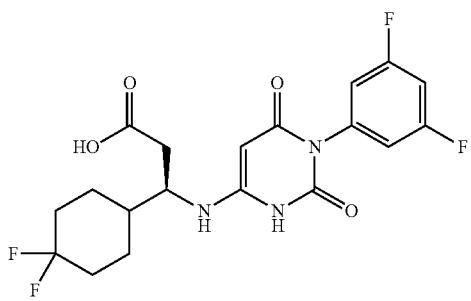

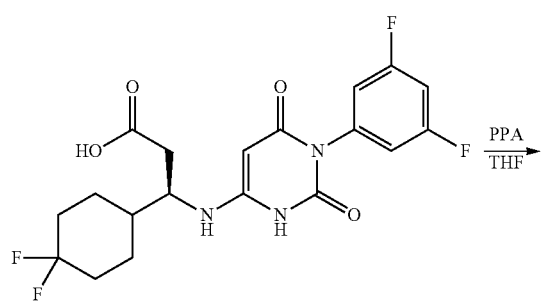

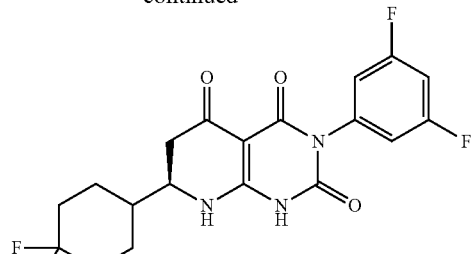

Compound 2.8 (R)-7-(4,4-Difluorocyclohexyl)-3-(3,5-difluorophenyl)-7,8-dihydropyrido[2,3-d]pyrimidine-2,4,5(1H,3H,6H)-trione To a 25-mL round-bottom flask purged and maintained with an inert atmosphere of argon, was added (3R)-3-(4,4-difluorocyclohexyl)-3-[[1-(3,5-difluorophenyl)-2,6-dioxo-1,2,3,6-tetrahydropyrimidin-4-yl]amino]propanoic acid ((compound 2.7), 100 mg, 0.23 mmol, 1.00 equiv) and THF (0.5 mL) in PPA (10 mL). The resulting solution was stirred for 15 min at 80° C. The reaction was cooled and quenched by the slow and careful addition of H₂O/ice (10 mL). The pH of the solution was adjusted to 7 with saturated NaHCO₃$_{(aq)}$. The solid was collected by filtration to yield 25 mg (26%) of the title compound as an off-white solid. LC-MS (ES, m/z): [M+H]⁺=412.

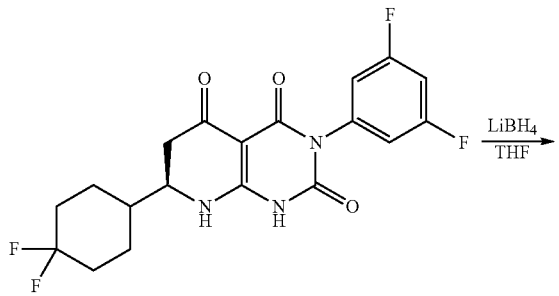

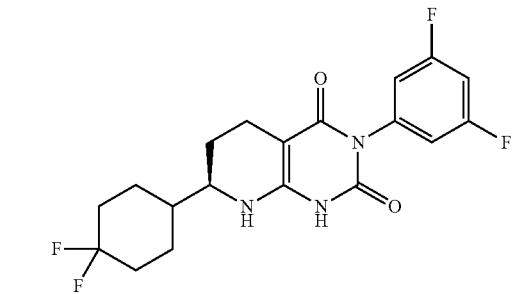

Compound 2. (R)-7-(4,4-Difluorocyclohexyl)-3-(3,5-difluorophenyl)-5,6,7,8-tetrahydropyrido[2,3-d]pyrimidine-2,4(1H,3H)-dione To a stirring solution of (R)-7-(4,4-difluorocyclohexyl)-3-(3,5-difluorophenyl)-7,8-dihydropyrido[2,3-d]pyrimidine-2,4,5(1H,3H,6H)-trione ((compound 2.8), 55 mg, 0.13 mmol, 1.00 equiv) in THF (3 mL) under argon at 0° C. was added LiBH₄ (2M in THF, 0.67 mL, 1.3 mmol, 10 equiv). The resulting solution was stirred overnight at 25° C. The reaction was cooled to 0° C. and quenched by the addition of saturated NH$_4$Cl$_{(aq)}$ (15 mL). The resulting mixture was extracted with EtOAc (3×15 mL). The organic layers were combined, washed with brine (2×20 mL), dried over anhydrous MgSO$_4$ and concentrated in vacuo. The resulting residue was purified by preparative HPLC (XBridge Prep C18 OBD Column, 19×150 mm 5 um 13 nm; mobile phase, H$_2$O with 10 mmol NH$_4$HCO$_3$ and CH$_3$CN (28.0% CH$_3$CN up to 64.0% over 7 min, up to 95.0% over the next 1 min and down to 28.0% (v/v) in final 2 min) to yield 32.1 mg (60%) of the title compound as a white solid. LC-MS (ES, m/z): [M+H]$^+$=398. $^1$H-NMR (300 MHz, CD$_3$OD): δ 7.03-6.96 (m, 1H), 6.90-6.84 (m, 2H), 3.33-3.26 (obscured m, 1H), 2.49-2.27 (m, 2H), 2.16-2.03 (m, 2H), 1.95-1.52 (m, 7H), 1.46-1.32 (m, 2H) ppm.

The following are representative compounds that were synthesized using the methodology outlined in example 2:

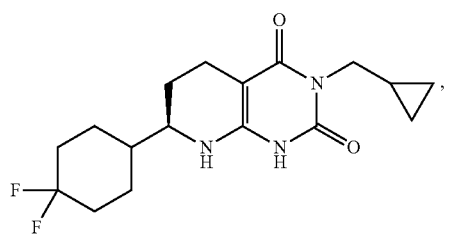
19

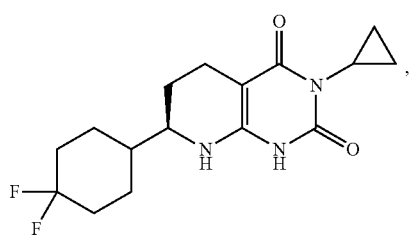
21

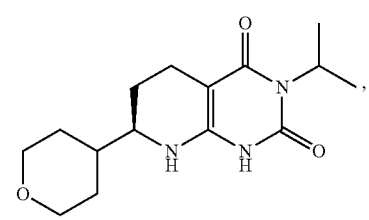
27

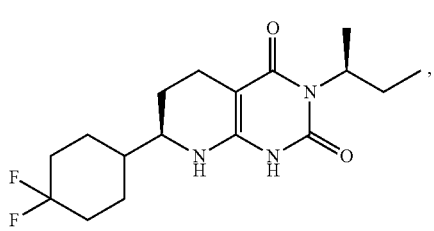
29

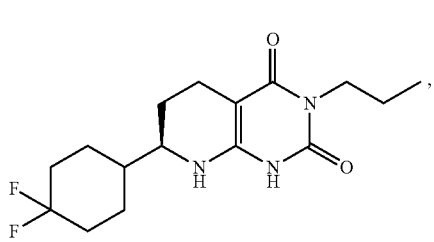
30

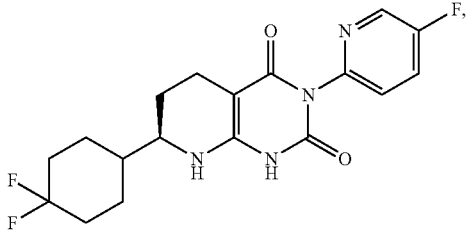
33

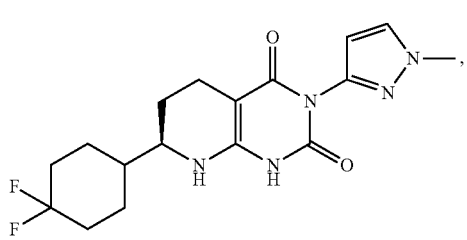
36

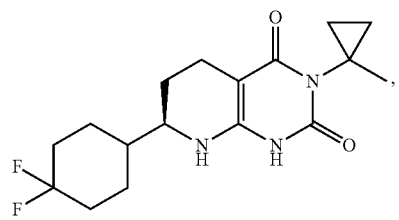
37

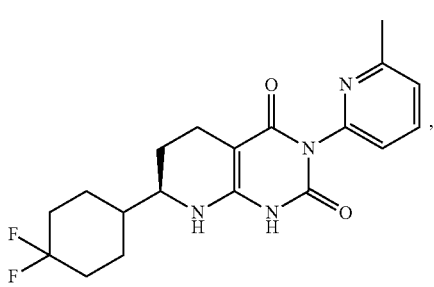
38

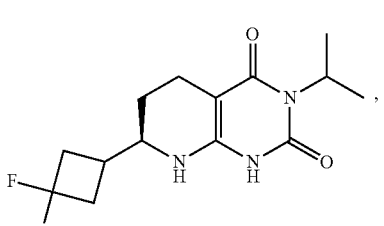
41

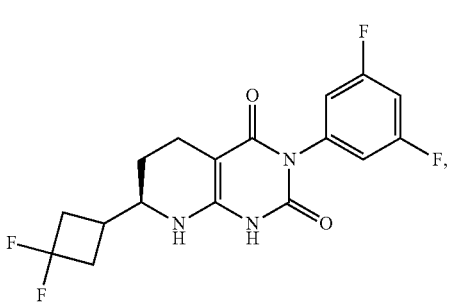
42

43

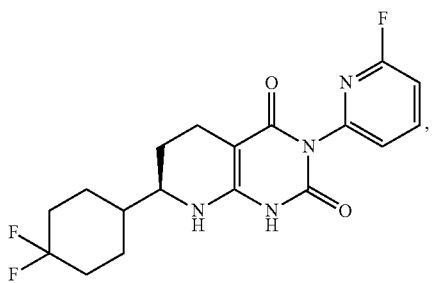

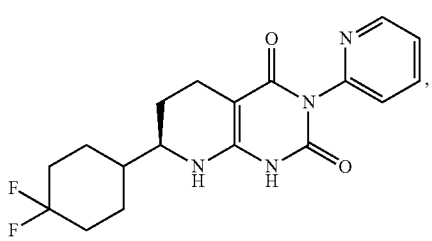

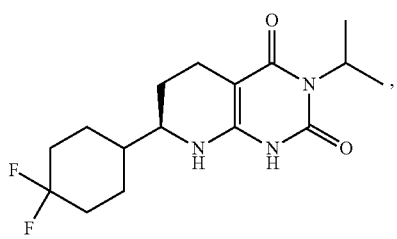

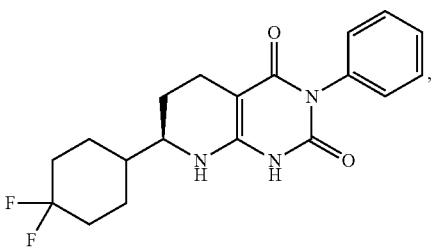

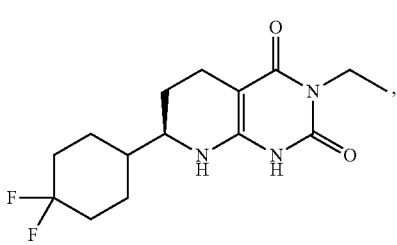

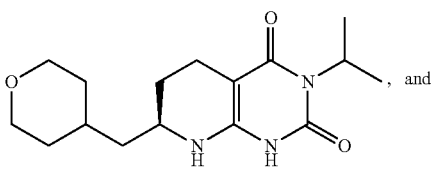, and

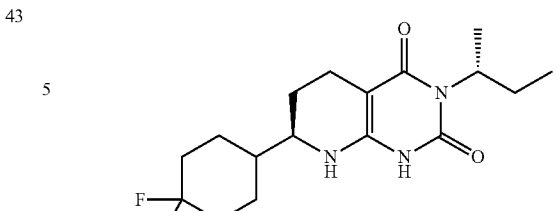

Example 3

Preparation of (R)-7-(4-fluorophenyl)-3-phenyl-5,6,7,8-tetrahydropyrido[2,3-d]pyrimidine-2,4(1H,3H)-dione

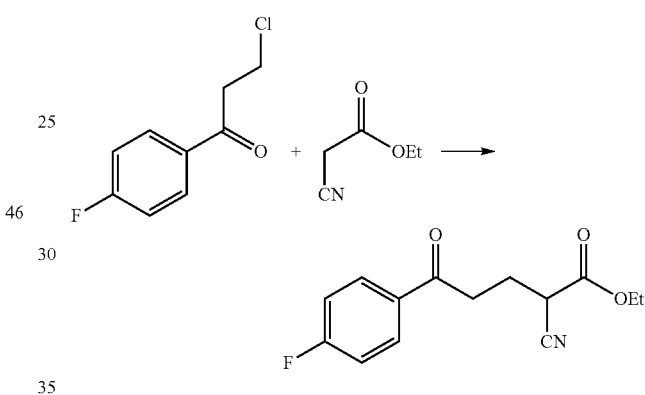

Compound 3.1. Ethyl 2-cyano-5-(4-fluorophenyl)-5-oxopentanoate

To a stirring solution of ethyl 2-cyanoacetate (18.23 g, 161.2 mmol, 6.0 equiv) in THF (100 mL) at 0° C. was added K$_2$CO$_3$ (7.4 g, 54. mmol, 2.0 equiv). After stirring for 10 min at 0° C., 3-chloro-1-(4-fluorophenyl)propan-1-one (5.0 g, 27. mmol, 1.0 equiv) was added portionwise. The resulting mixture was warmed to room temperature, stirred for 3 h and concentrated in vacuo. The residue was diluted with EtOAc (200 mL) and washed with H$_2$O (2×100 mL). The organic layer was dried over Na$_2$SO$_4$ and concentrated in vacuo. The crude product was purified by preparative HPLC (IntelFlash): Column, C18; mobile phase, H$_2$O/CH$_3$CN=100/0 (v/v) increasing to H$_2$O/CH$_3$CN=0/100 (v/v) over 45 min). The fractions containing pure compound were combined and concentrated in vacuo to yield 4.0 g (57%) of the title compound as yellow oil. LC-MS (ES, m/z): [M+H]=264. $^1$H-NMR (300 MHz, DMSO-d$_6$): δ 8.05 (m, 2H), 7.37 (m, 2H), 4.22 (m, 3H), 3.23 (m, 2H), 2.20 (m, 2H), 1.24 (m, 3H) ppm.

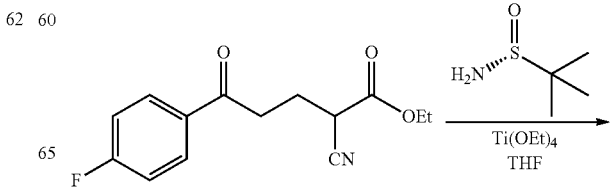

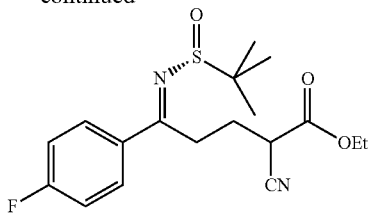

Compound 3.2. Ethyl (5E)-2-cyano-5-(4-fluorophenyl)-5-[[(R)-2-methylpropane-2-sulfinyl]imino]pentanoate To a stirring solution of ethyl 2-cyano-5-(4-fluorophenyl)-5-oxopentanoate ((compound 3.1), 773 mg, 2.94 mmol, 1.00 equiv) and (R)-2-methylpropane-2-sulfinamide (711 mg, 5.87 mmol, 2.00 equiv) in THF (10 mL) was added and titanium (IV) ethoxide (3.34 g, 14.6 mmol, 5.0 equiv). The resulting mixture was stirred overnight at 65° C. Upon cooling, the reaction was quenched by the addition of ice water (50 mL). The reaction mixture was filtered and the filtrate was extracted with EtOAc (2×50 mL). The organic layers were combined, dried over anhydrous $Na_2SO_4$ and concentrated in vacuo. The resulting residue was purified by silica gel column chromatography eluting with EtOAc/petroleum ether=1/10 (v/v). The fractions containing pure compound were combined and concentrated in vacuo to yield 620 mg (58%) of the title compound as clear oil. LC-MS (ES, m/z): [M+H]$^+$=367. $^1$H-NMR (300 MHz, DMSO-$d_6$): δ 7.93 (m, 2H), 7.36 (m, 2H), 4.43 (m, 1H), 4.21 (m, 2H), 3.30-3.20 (m, 2H), 2.12 (m, 2H), 1.20 (m, 12H) ppm.

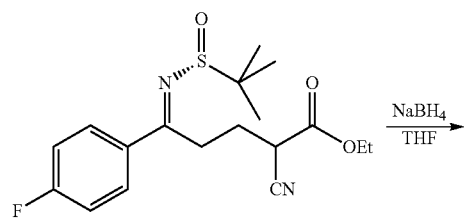

Compound 3.3. Ethyl (5R)-2-cyano-5-(4-fluorophenyl)-5-[[(R)-2-methylpropane-2-sulfinyl]amino]pentanoate To a stirring solution of ethyl (5E)-2-cyano-5-(4-fluorophenyl)-5-[[(R)-2-methylpropane-2-sulfinyl]imino]pentanoate ((compound 3.2), 2.2 g, 6.0 mmol, 1.0 equiv) in THF (25 mL) under argon at 0° C. was added sodium borohydride (341 mg, 9.01 mmol, 1.50 equiv) portion-wise. The resulting solution was stirred for 2 h at 25° C. The reaction was quenched with saturated $NH_4Cl_{(aq)}$ (5 mL) and diluted with $H_2O$ (40 mL). The resulting mixture was extracted with EtOAc (3×40 mL) and the organic layers were combined. The organic layer was washed with brine (50 mL), dried over anhydrous $Na_2SO_4$ and concentrated in vacuo. The resulting residue was purified by silica gel column chromatography eluting with EtOAc/petroleum ether=1/3 (v/v). The fractions containing pure compound were combined and concentrated in vacuo to yield 1.0 g (45%) of the title compound as a yellow oil. LC-MS (ES, m/z): [M+H]$^+$=369. $^1$H-NMR (300 MHz, DMSO-$d_6$): δ 7.44-7.13 (m, 2H), 7.16 (m, 2H), 5.73 (s, 1H), 4.27-4.12 (m, 4H), 2.07-1.70 (m, 4H), 1.20 (m, 3H), 1.11 (s, 9H) ppm.

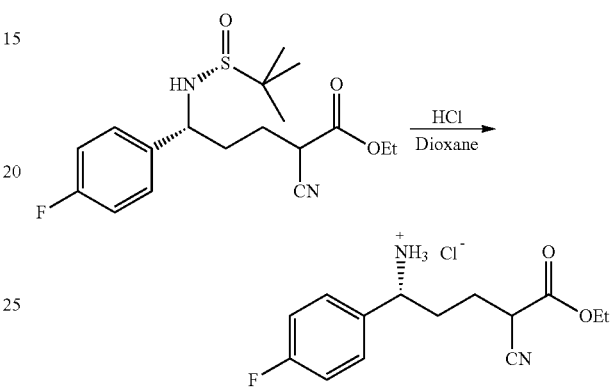

Compound 3.4. Ethyl (5R)-5-amino-2-cyano-5-(4-fluorophenyl)pentanoate hydrochloride To a stirring solution of ethyl (5R)-2-cyano-5-(4-fluorophenyl)-5-[[(R)-2-methylpropane-2-sulfinyl]amino]pentanoate ((compound 3.3), 3.0 g, 8.1 mmol, 1.0 equiv) in $CH_3CN$ (30 mL) at 0° C. was added 4N HCl in 1,4-dioxane (10 mL). The resulting solution was stirred for 1 h at 0° C. and then was diluted with $Et_2O$ (40 mL). The precipitated solid was isolated by filtration to give 2.2 g (crude) of the title compound as a white solid. LC-MS (ES, m/z): [M+H]$^+$=265.

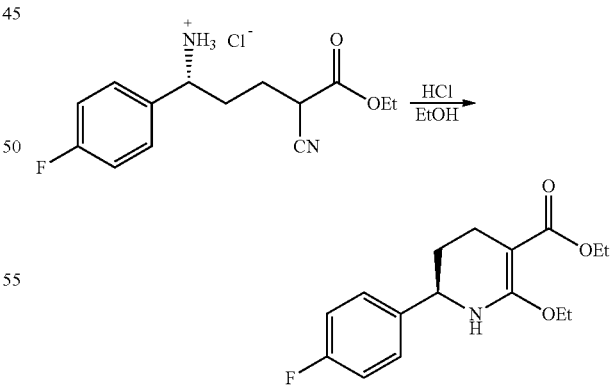

Compound 3.5. Ethyl (6R)-2-ethoxy-6-(4-fluorophenyl)-1,4,5,6-tetrahydropyridine-3-carboxylate To a 50-mL 3-necked round-bottom flask purged and maintained with argon was added ethyl (5R)-5-amino-2-cyano-5-(4-fluorophenyl)pentanoate hydrochloride ((compound 3.4), 2.2 g, 7.3 mmol, 1.0 equiv) in EtOH (20 mL). Dry HCl$_{(g)}$ was bubbled through the solution at 0° C. for 5 minutes and the resulting mixture was stirred for 4 h. The reaction mixture was concentrated in vacuo to yield 2.2 g (crude) of the title compound as clear oil. This crude intermediate was used in next step without purification. LC-MS (ES, m/z): [M+H]$^+$=294.

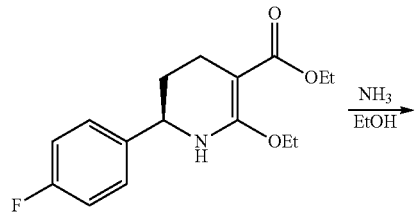

Compound 3.6. Ethyl (6R)-2-amino-6-(4-fluorophenyl)-1,4,5,6-tetrahydropyridine-3-carboxylate To a 10-mL round-bottom flask, was added ethyl (6R)-2-ethoxy-6-(4-fluorophenyl)-1,4,5,6-tetrahydropyridine-3-carboxylate ((compound 3.5), 250 mg, 0.85 mmol, 1.00 equiv) and saturated NH$_3$ in EtOH (5 mL). The resulting solution was stirred for 1 h at 0° C. The resulting mixture was concentrated in vacuo. The residue was purified by silica gel column chromatography eluting with EtOAc/petroleum ether=1/2 (v/v). The fractions containing pure compound were combined and concentrated in vacuo to yield 66 mg (29%) of the title compound as a white solid. LC-MS (ES, m/z): [M+H]$^+$=265. $^1$H-NMR (300 MHz, DMSO-d$_6$): δ 7.50-7.28 (m, 2H), 7.27-7.14 (m, 2H), 6.78 (s, 2H), 6.44 (s, 1H), 4.39-4.02 (m, 1H), 3.95 (m, 2H), 2.26-2.13 (m, 1H), 2.10 (m, 1H), 2.06-1.90 (m, 1H), 1.87-1.68 (m, 1H), 1.23-1.13 (m, 3H) ppm.

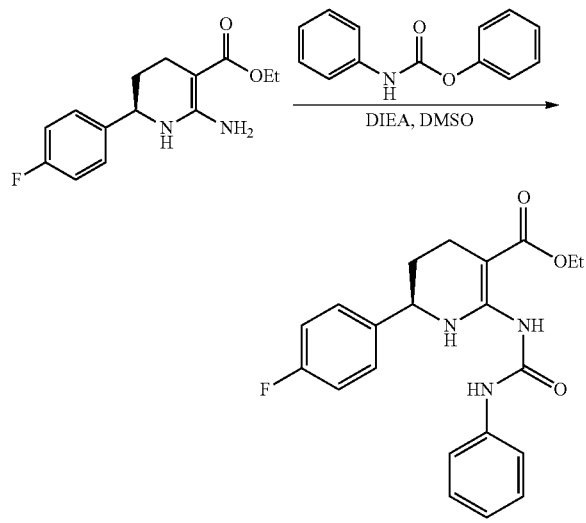

Compound 3.7. Ethyl (6R)-6-(4-fluorophenyl)-2-[(phenylcarbamoyl)amino]-1,4,5,6-tetrahydropyridine-3-carboxylate To a stirring solution of ethyl (6R)-2-amino-6-(4-fluorophenyl)-1,4,5,6-tetrahydropyridine-3-carboxylate ((compound 3.6), 260 mg, 0.98 mmol, 1.00 equiv) in DMSO (5 mL) was added DIEA (388 mg, 3.00 mmol, 3.00 equiv) and phenyl N-phenylcarbamate (234 mg, 1.10 mmol, 1.10 equiv). The resulting solution was stirred for 2 h at 65° C. The reaction was quenched by the addition of H$_2$O (10 mL) and the resulting mixture was extracted with CH$_2$Cl$_2$ (3×10 mL). The organic layers were combined, washed with brine (2×10 mL), dried over anhydrous MgSO$_4$ and concentrated in vacuo to yield 290 mg (77%) of the title compound (crude) as a white solid. LC-MS (ES, m/z): [M+H]$^+$=384.

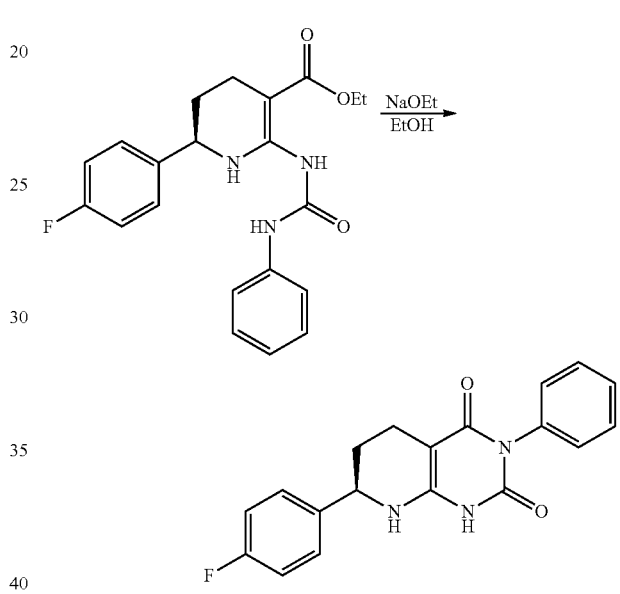

Compound 3. (R)-7-(4-Fluorophenyl)-3-phenyl-5,6,7,8-tetrahydropyrido[2,3-d]pyrimidine-2,4(1H,3H)-dione To a stirring solution of ethyl (6R)-6-(4-fluorophenyl)-2-[(phenylcarbamoyl)amino]-1,4,5,6-tetrahydropyridine-3-carboxylate ((compound 3.7), 290 mg, 0.76 mmol, 1.00 equiv) in EtOH (3 mL) was added NaOEt (76 mg, 1.50 equiv). The resulting solution was stirred at 25° C. for 16 h and then quenched with ice water (30 mL). The mixture was extracted with EtOAc (2×25 mL). The organic layers were combined, washed with brine (20 mL), dried over anhydrous Na$_2$SO$_4$ and concentrated in vacuo. The crude product was purified by preparative HPLC ((IntelFlash): Column, C18; mobile phase, H$_2$O:CH$_3$CN=100/0 (v/v) increasing to H$_2$O:CH$_3$CN=0/100 (v/v) over 45 min). The fractions containing product were combined and lyophilized to yield 100 mg of enantiomerically impure product (as determined by chiral HPLC). This material (100 mg) was purified by preparative chiral HPLC (Column, Chiralpak IB, 2*25 cm, 5 um; mobile phase, hexanes (0.2% diethylamine) and EtOH (held at 30.0% EtOH over 46 min)). The fractions containing enantiomerically pure product were combined and lyophilized to yield 13.7 mg (5%) of the title compound as a white solid. LC-MS (ES, m/z): [M+H]$^+$=338. $^1$H-NMR (300 MHz, DMSO-$d_6$): δ 9.23-9.11 (m, 1H), 7.43-7.31 (m, 5H), 7.24-7.15 (m, 4H), 6.69 (br s, 1H), 4.68-4.61 (m, 1H), 2.36-2.27 (m, 1H), 2.11-1.92 (m, 2H), 1.85-1.77 (m, 1H) ppm.

Example 4

Preparation of (7R)-7-(3,4-difluorophenyl)-3-isopropyl-5,6,7,8-tetrahydropyrido[2,3-d]pyrimidine-2,4 (1H,3H)-dione

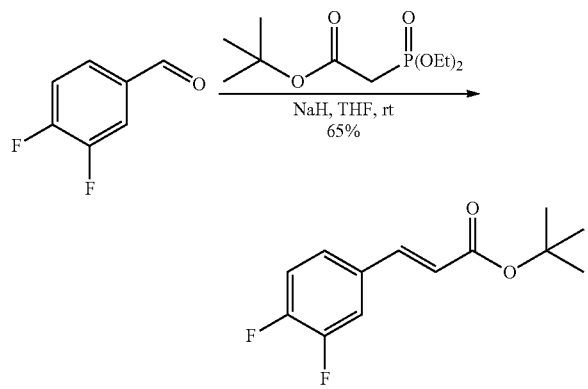

Compound 4.1. tert-Butyl (2E)-3-(3,4-difluorophenyl)prop-2-enoate

To a stirred solution of tert-butyl 2-(diethoxyphosphoryl) acetate (8.8 g, 34.89 mmol, 1.00 equiv) in THF (30 mL) under argon at 0° C. was added 60% sodium hydride (1.4 g, 58.33 mmol, 1.10 equiv) batch wise. The mixture was stirred for 30 min at 0° C. and 3,4-difluorobenzaldehyde (5.0 g, 35 mmol, 1.0 equiv) was added. The resulting solution was warmed to room temperature, stirred for 1 hour, quenched with ice water (60 mL) and extracted with EtOAc (3×50 mL). The organic layers were combined and concentrated in vacuo to yield 8 g (crude) of the title compound as oil. $^1$H-NMR (400 MHz, CDCl$_3$): δ 7.49 (m, 1H), 7.36-7.14 (m, 3H), 6.30 (m, 1H), 1.53 (s, 9H) ppm.

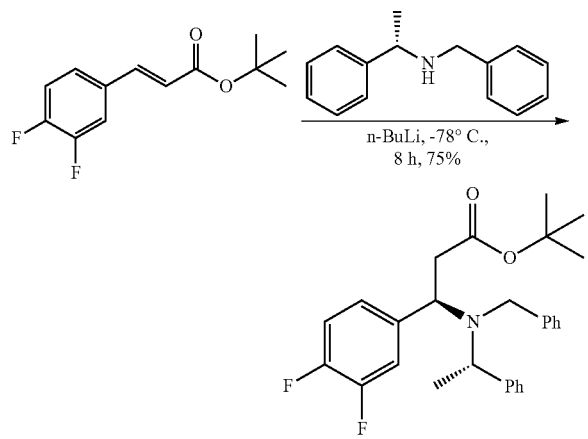

Compound 4.2. tert-Butyl (3R)-3-[benzyl[(1S)-1-phenylethyl]amino]-3-(3,4-difluorophenyl)propanoate To a stirring solution of tert-butyl (2E)-3-(3,4-difluorophenyl)prop-2-enoate ((compound 4.1), 4.0 g, 17 mmol, 1.0 equiv) in THF (100 mL) under argon at −78° C. was added n-BuLi (2.5M in hexanes, 10 mL, 1.55 equiv) dropwise. The reaction mixture was stirred at −78° C. for 1 h and benzyl [(1S)-1-phenylethyl]amine (5.63 g, 26.64 mmol, 1.60 equiv) was added dropwise over 10 minutes. The resulting solution was stirred for 5 h at −78° C. The reaction was quenched by the addition of saturated NH$_4$Cl$_{(aq)}$ (20 mL). The resulting mixture was extracted with EtOAc (3×30 mL) and the organic layers were combined and concentrated in vacuo. The resulting residue was purified by silica gel column chromatography eluting with EtOAc/petroleum ether=1/20 (v/v). The fractions containing pure compound were combined and concentrated in vacuo to yield 6.8 g (90%) of the title compound as a yellow oil. $^1$H-NMR (400 MHz, CDCl$_3$): δ 7.42 (m, 6H), 7.38-7.11 (m, 7H), 4.39 (m, 1H), 3.96 (m, 1H), 3.66 (m, 2H), 2.53-2.41 (m, 2H), 1.34 (m, 12H) ppm.

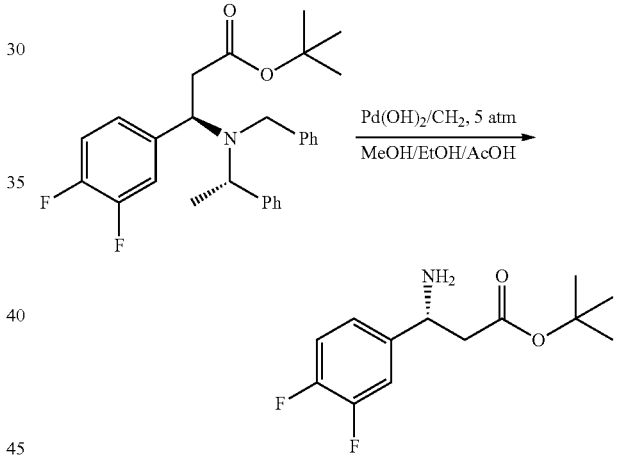

Compound 4.3. tert-Butyl (R)-3-amino-3-(3,4-difluorophenyl)propanoate

Into a 250-mL pressure tank reactor was added tert-butyl (3R)-3-[benzyl[(1S)-1-phenylethyl]amino]-3-(3,4-difluorophenyl) propanoate ((compound 4.2), 5.35 g, 1.18 mmol) and 20% Pd(OH)$_2$/C (50% water, 1.0 g) in MeOH/EtOAc/acetic acid (40/4/1, 200 mL). The reactor was purged and maintained with atmosphere of hydrogen (5 atm). The resulting solution was stirred for 5 h at 30° C. The reaction mixture was filtered and the filtrate was concentrated in vacuo. To the crude residue was added EtOAc/petroleum ether=1/50 (v/v). Solid precipitated and was isolated by filtration to yield 2 g (crude) of the title compound as a white solid. LC-MS (ES, m/z): [M+H]$^-$=258. $^1$H-NMR (400 MHz, CD$_3$OD): δ 7.47-7.28 (m, 3H), 4.55 (m, 1H), 2.87 (m, 2H), 1.41 (s, 9H) ppm.

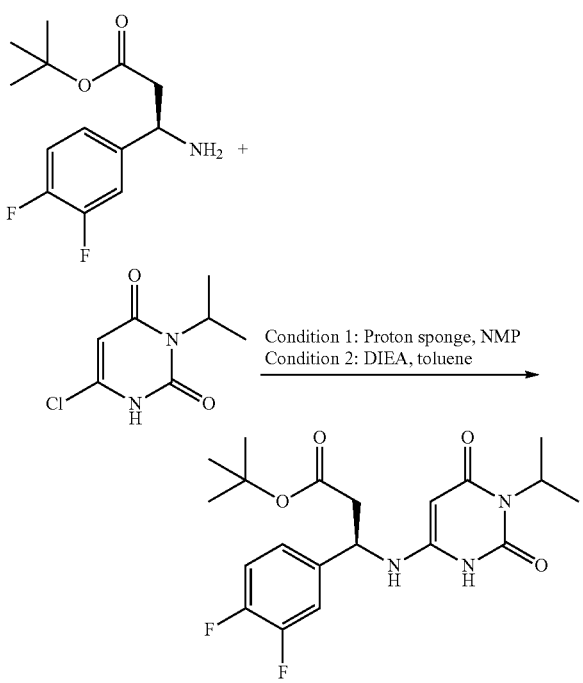

Compound 4.4. tert-Butyl (R)-3-(3,4-difluorophenyl)-3-((1-isopropyl-2,6-dioxo-1,2,3,6-tetrahydropyrimidin-4-yl)amino)propanoate Condition 1: To a stirring solution of tert-butyl (R)-3-amino-3-(3,4-difluorophenyl)propanoate ((compound 4.3), 1.09 g, 4.24 mmol, 2.00 equiv) in NMP (5 mL) under argon were added proton sponge (500 mg, 2.34 mmol, 1.50 equiv) and 6-chloro-3-isopropylpyrimidine-2,4(1H,3H)-dione ((compound 1.3), 400 mg, 2.12 mmol, 1.00 equiv). The reaction mixture was heated at 120° C. for 2 hours. The reaction mixture was cooled and purified by preparative HPLC ((Combiflash): Column, C18; mobile phase, H$_2$O with 0.5% TFA and CH$_3$CN (5% CH$_3$CN up to 95% over 25 min)). The fractions containing pure compound were combined and lyophilized to yield 300 mg (35%) of the title compound as a brown solid. LC-MS (ES, m/z): [M+H]$^+$=410. $^1$H-NMR (400 MHz, DMSO-d$_6$): δ 10.11 (br s, 1H), 7.53-7.39 (m, 2H), 7.25 (m, 1H), 6.68 (m, 1H), 4.91 (m, 1H), 4.76 (m, 1H), 4.48 (s, 1H), 2.73 (m, 2H), 1.32 (s, 9H), 1.26 (m, 6H) ppm.

Condition 2: 6-Chloro-3-isopropylpyrimidine-2,4(1H,3H)-dione ((compound 4.3), 200 g, 1.06 mol, 1.2 eq.) was added to a 3.0 L round-bottom flask with an inert atmosphere of nitrogen, followed by xylene (1200 mL) and DIPEA (165 g, 1.28 mol, 1.5 eq.) at ambient temperature. The reaction mass temperature was raised to 130° C. Subsequently, a solution of tert-butyl (3R)-3-amino-3-(3,4-difluorophenyl)propanoate (228 g, 0.89 mol, 1.0 eq.) in xylene (800 mL) was added to the reaction mixture at 130° C. over a period of 2 h. The reaction progress was monitored by HPLC until the content of tert-butyl (3R)-3-amino-3-(3,4-difluorophenyl)propanoate was not more than 1.0% (UV at 210 nm). The solvent was distilled off under reduced pressure at 40-50° C. and the residue was dissolved in EtOAc (1600 mL). The resulting organic solution was washed with water (1000 mL×4). The organic layer was concentrated under reduced pressure at 30-40° C. to a volume of 400 mL. The suspension was filtered at 20-25° C. Next, the filtered cake was slurred with EtOAc (300 mL) and filtered. The solid was separated and the combined mother liquid was concentrated under reduced pressure at 30-40° C. and the residue was slurred with EtOAc (300 mL). This process of filtering, concentrating, and re-slurring was repeated three times. The solid collected was dried with flow nitrogen to give the title compound (213 g, 59% yield with a purity of 98%) as a white solid.

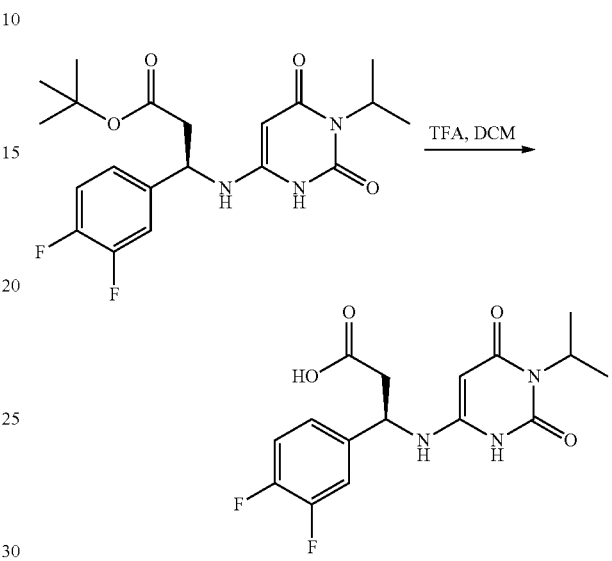

Compound 4.5. (R)-3-(3,4-Difluorophenyl)-3-[[1-isopropyl-2,6-dioxo-1,2,3,6-tetrahydropyrimidin-4-yl]amino]propanoic acid To a stirring solution of tert-butyl (R)-3-(3,4-difluorophenyl)-3-((1-isopropyl-2,6-dioxo-1,2,3,6-tetrahydropyrimidin-4-yl)amino)propanoate ((compound 4.4), 300 mg, 0.73 mmol, 1.00 equiv) in CH$_2$Cl$_2$ (3 mL) under argon was added and trifluoroacetic acid (1 mL). The resulting solution was stirred for 2 h at 25° C. and concentrated in vacuo. This resulted in 250 mg (crude) the title compound as a black solid. LC-MS (ES, m/z): [M+H]$^+$=354.

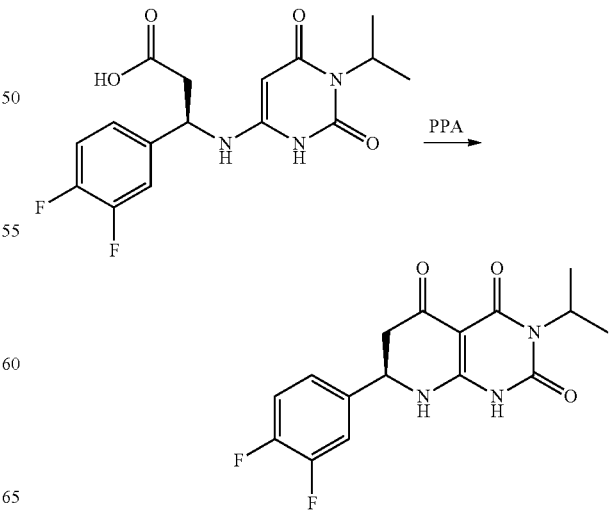

Compound 4.6. (R)-7-(3,4-Difluorophenyl)-3-isopropyl-7,8-dihydropyrido[2,3-d]pyrimidine-2,4,5(1H,3H,6H)-trione To (R)-3-(3,4-difluorophenyl)-3-[[1-isopropyl-2,6-dioxo-1,2,3,6-tetrahydropyrimidin-4-yl]amino]propanoic acid ((compound 4.5), 250 mg, 0.71 mmol, 1.00 equiv) was added PPA (4 mL). The resulting solution was stirred for 3 h at 80° C. The reaction was cooled and quenched with ice/$H_2O$ (15 mL). The resulting solid was filtered and dried under reduced pressure to yield 150 mg (63%) of the title compound as a brown solid. LC-MS (ES, m/z): [M+H]$^+$=336.

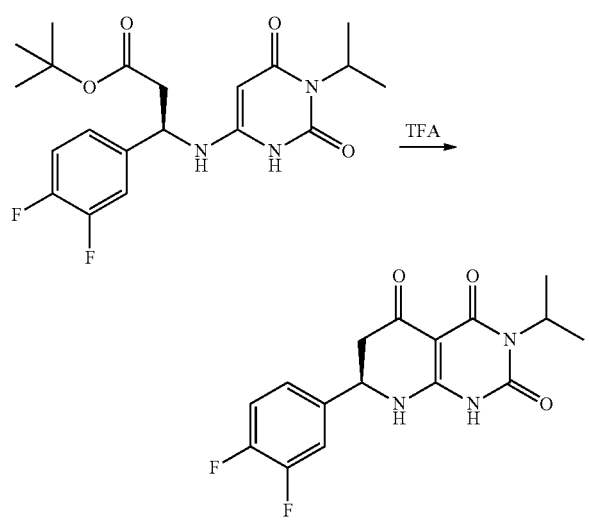

Compound 4.6. (R)-7-(3,4-Difluorophenyl)-3-isopropyl-7,8-dihydropyrido[2,3-d]pyrimidine-2,4,5(1H,3H,6H)-trione tert-Butyl (R)-3-(3,4-difluorophenyl)-3-((1-isopropyl-2,6-dioxo-1,2,3,6-tetrahydropyrimidin-4-yl)amino)propanoate ((compound 4.4), 120.0 g, 0.293 mol, 1.0 eq.) was added to a 2.0 L jacketed reactor maintaining with an inert atmosphere of nitrogen, followed by toluene (1800 mL) and TFA (167 g, 1.47 mol, 5.0 eq.) at 25° C. The reaction mass was heated to 75° C. and the reaction was monitored with HPLC (UV at 278 nm) to attain <1% of (R)-3-(3,4-difluorophenyl)-3-[[1-isopropyl-2,6-dioxo-1,2,3,6-tetrahydropyrimidin-4-yl]amino]propanoic acid (compound 4.5). After stirring at 72-75° C. for 22 h, an additional TFA (1.0 eq.) was added to complete cyclization at 72-75° C. Subsequently, the reaction mixture was concentrated at 40-45° C. under vacuum. The resulting mass was treated with EtOAc (1000 mL) and the solvent was distilled off at 40-45° C. under reduced pressure. This procedure was repeated twice to get solid suspension. After stirring the solid mass in EtOAc (1000 mL) for 30 min at 20-25° C., the mixture was filtered under reduced pressure at 20-25° C. This slurring and filtration procedure was repeated twice by switching EtOAc to water (2000 mL) and MTBE (2000 mL), respectively. The solid material was dried under reduced pressure at 30° C. for 12 h to give the title compound (80 g, 99.2% yield with a purity of >99%) as a light yellow solid.

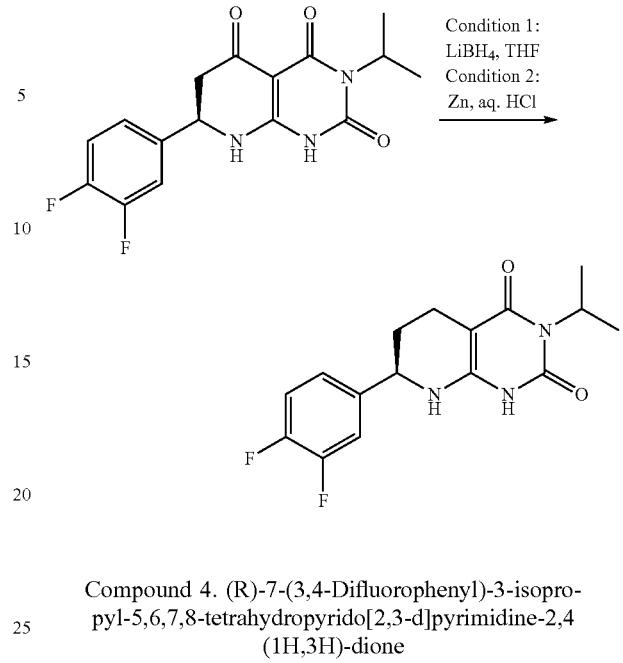

Compound 4. (R)-7-(3,4-Difluorophenyl)-3-isopropyl-5,6,7,8-tetrahydropyrido[2,3-d]pyrimidine-2,4(1H,3H)-dione Condition 1: To a stirring solution of (R)-7-(3,4-difluorophenyl)-3-isopropyl-7,8-dihydropyrido[2,3-d]pyrimidine-2,4,5(1H,3H,6H)-trione ((compound 4.6), 150 mg, 0.45 mmol, 1.00 equiv) in THF (3 mL) under argon at 0° C. was added LiBH$_4$ (2M in THF, 2.2 mL, 10.00 equiv). The resulting solution was warmed to room temperature, stirred for 16 h and carefully quenched with saturated NH$_4$Cl$_{(aq)}$ (15 mL, dropwise) at 0° C. The resulting mixture was extracted with EtOAc (3×15 mL) and the organic layers were combined. The organic layer was washed with brine (2×20 mL), dried over anhydrous MgSO$_4$ and concentrated in vacuo. The resulting residue was purified by preparative HPLC (XBridge Prep C18 OBD Column, 19×150 mm 5 um 13 nm; mobile phase, H$_2$O with 10 mmol NH$_4$HCO$_3$ and CH$_3$CN (25.0% CH$_3$CN up to 51.0% (v/v) over 9 min)). The fractions containing pure compound were combined and lyophilized to yield 38.3 mg (27%) of the title compound as a white solid. LC-MS (ES, m/z): [M+H]$^+$=322. $^1$H-NMR (300 MHz, DMSO-d$_6$): δ 10.11 (br s, 1H), 7.48-7.33 (m, 2H), 7.14-7.10 (m, 1H), 6.33 (br s 1H), 5.05-4.96 (m, 1H), 4.54-4.52 (m, 1H), 2.32-2.22 (m, 1H), 2.04-1.74 (m, 3H), 1.33-1.30 (m, 6H) ppm.

Condition 2: of (R)-7-(3,4-difluorophenyl)-3-isopropyl-7,8-dihydropyrido[2,3-d]pyrimidine-2,4,5(1H,3H,6H)-trione (compound 4.6, 80 g, 238.8 mmol, 1.0 eq.) was added to a cleaned reactor, followed by 155 g of Zn (238.8 mmol, 10 eq.) and EtOH (1000 mL) at 25° C. Subsequently, 1.0 M aq. HCl (1000 mL) solution was added drop-wise to the reaction mixture at 70° C. The reaction mixture was stirred at 70° C. for 1 h and the reaction progress was monitored by HPLC. Next, 12 M aq. HCl solution (100 mL×4) to the reaction mixture was added drop-wise at 70° C. and the resulting mixture was stirred for about 6 h until the starting material attains below 1.0% (UV at 210 nm). The mixture was cooled to rt and diluted with EtOH (1500 mL). The suspension was filtered and filtered cake was washed with EtOH (200 mL). The mother liquid was concentrated to a volume of 1000 mL at 30-40° C. under reduced pressure. The suspension was filtered and the combined solid was slurred with water (1000 mL) and filtered. This procedure was repeated by replacing water with petroleum ether (1000 mL). The solid material was dried in vacuo to give the title compound (57 g, 74% yield with a chemical purity of >99% yield and chiral purity of 98.7%) as a white solid.

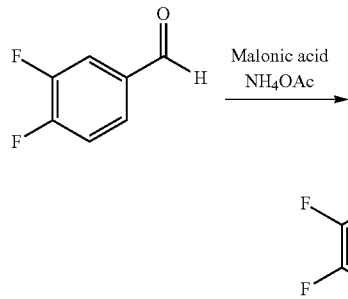

Compound 4.7.
3-Amino-3-(3,4-difluorophenyl)propanoic acid

Malonic acid (65.2 g, 627 mmol) and ammonium acetate (80.6 g, 1045 mmol) were dissolved in ethanol (350 mL) and then 3,4-difluorobenzaldehyde (59.46 g, 418 mmol) was added. The mixture was stirred and heated to 90° C. at which time a homogeneous solution was achieved. The mixture was heated at 90-94° C. overnight. The mixture was cooled and diluted with cold water (150 mL). The precipitate was collected and washed with water (50 mL) followed by ethanol (50 mL). The solid was dried overnight in vacuo to afford the title compound (51.54 g, 61.3% yield). LC-MS (ES, m/z): [M+H]$^+$=202.

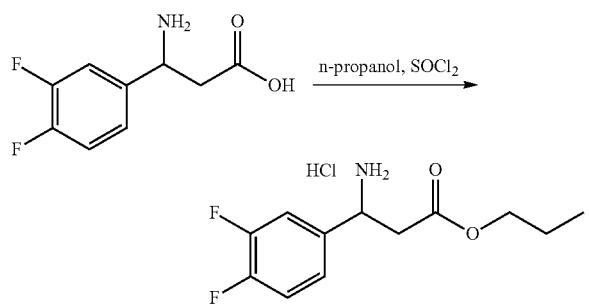

Compound 4.8.
3-Amino-3-(3,4-difluorophenyl)propanoate hydrochloride

3-Amino-3-(3,4-difluorophenyl)propanoic acid ((Compound 4.7), 335.7 g, 1669 mmol) was added to n-propanol (1250 mL). Thionyl chloride (135 mL, 1836 mmol) was added in portions. The temperature was slowly raised and kept at about 50° C. for 6 h at which time a clear solution was observed. The reaction mixture was concentrated under reduced pressure and the residue was triturated with ether and stirred overnight. The solid was filtered and rinsed well with ether and then thoroughly dried overnight in vacuo to afford the title compound (471.2 g, 90% yield). LC-MS (ES, m/z): [M+H]$^+$=244.

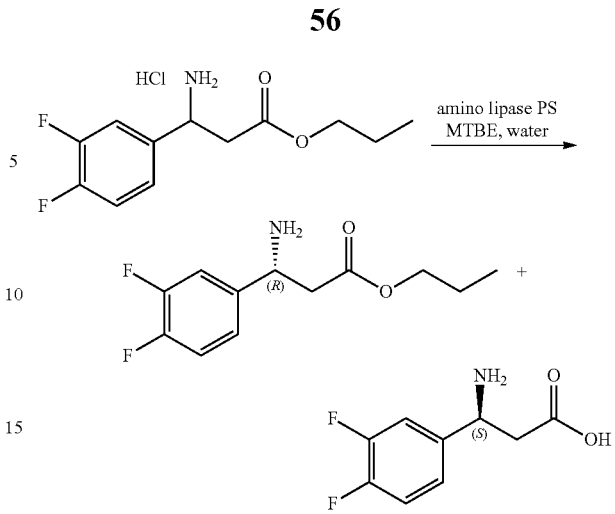

Compound 4.9. Propyl
(R)-3-amino-3-(3,4-difluorophenyl)propanoate (±)-3-Amino-3-(3,4-difluoro-phenyl)-propionic acid propyl ester hydrochloride salt ((Compound 4.8), 240 g, 0.857 mmol) was dissolved in 400 mL of water. The resulting solution was cooled to 5-10° C. and the pH was adjusted to 8.0-8.2 with 25% NaOH$_{(aq)}$ (95 mL). Then MTBE (500 mL) was added followed by amano lipase PS (12 g, 5%). The resulting mixture was stirred at 33-34° C. overnight. During this period, the (S)-β-amino acid was crystallized from the reaction mixture. The reaction was cooled to 10° C. A white precipitate was collected by filtration through a glass frit. The solid was washed with MTBE (150 mL×3) and with ice-water (500 mL), respectively. The combined two-layer filtrate was transferred to the separation funnel and washed with aqueous NaHCO$_3$ (400 mL×3). The organic phase was separated and washed with brine (400 mL), dried over anhydrous Na$_2$SO$_4$, and evaporated under reduced pressure to provide the title compound. Additional amount of the title compound was recovered from the combined aqueous phases by extraction with MTBE (1200 mL). The organic phase was washed with NaHCO$_3$ (400 mL), brine (400 mL), dried over Na$_2$SO$_4$, and concentrated. The combined material was dried in vacuo to give the title compound (104 g, 49% yield with a chiral purity of >99.5%) as a light yellow oil. LC-MS (ES, m/z): [M+H]$^+$=244.

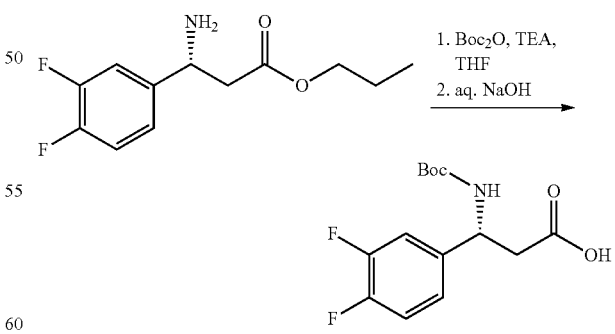

Compound 4.10. (R)-3-((tert-Butoxycarbonyl)amino)-3-(3,4-difluorophenyl)propanoic acid Propyl (R)-3-amino-3-(3,4-difluorophenyl)propanoate ((Compound 4.9), 135 g, 556 mmol) was dissolved in a mixture of THF (1000 mL) and triethylamine (80 mL, 573 mmol) and to this mixture was added di-tert-butyl dicarbonate (140 g, 641 mmol). The resulting reaction mixture was stirred at rt overnight. Next, THF was removed under reduced pressure and the residue was taken up in methanol (200 mL) and 2N NaOH$_{(aq)}$ (200 mL). The mixture was stirred at 60° C. for 1 h and then concentrated under reduced pressure. Subsequently, the aqueous residue was adjusted to pH 1 by the addition of 2N HCl$_{(aq)}$ at 0° C. The mixture was extracted with EtOAc (1000 mL), washed with water (250 mL) and brine (250 mL), and dried over anhydrous Na$_2$SO$_4$. The solvent was removed and the residue was dried in vacuo to give the title compound (161 g, 96% yield) as a white crystalline solid. LC-MS (ES, m/z): [M+H]$^+$=302.

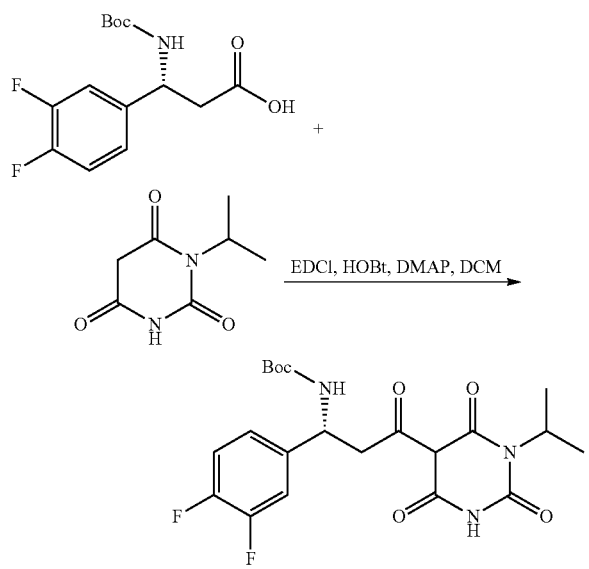

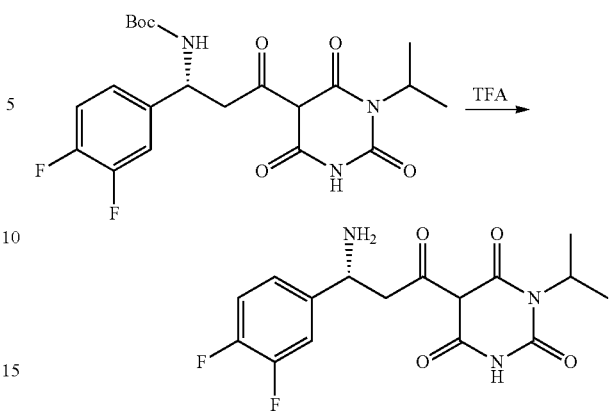

Compound 4.11. tert-Butyl ((1R)-1-(3,4-difluorophenyl)-3-(1-isopropyl-2,4,6-trioxohexahydropyrimidin-5-yl)-3-oxopropyl)carbamate A mixture of (R)-3-((tert-butoxycarbonyl)amino)-3-(3,4-difluorophenyl)propanoic acid ((Compound 4.10), 77 g, 256 mmol)) and 1-isopropylpyrimidine-2,4,6(1H,3H,5H)-trione ((Compound 1.2), 65 g, 382 mmol) in dichloromethane (800 mL) and triethylamine (108 mL, 753 mmol) was added EDCI (62 g, 327 mmol), HOBT (20 g, 151 mmol), and DMAP (15 g, 125 mmol). After stirring rt for 16 h, the reaction mixture was concentrated and residue was dissolved in EtOAc (1500 mL). The resulting mixture was washed with saturated NaHCO$_{3(aq)}$ (300 mL) and brine (300 mL), respectively. After removing most of EtOAc, the residue was poured into 0.5 N aq. HCl (1400 mL). The resulting suspension was filtered. The solid was washed with water (500 mL×3) and azeotroped with toluene to near dryness to afford a crude material of the title compound (175 g), which was used in the next reaction without further purification. LC-MS (ES, m/z): [M+H]$^+$=454.

Compound 4.12. 5-((R)-3-Amino-3-(3,4-difluorophenyl)propanoyl)-1-isopropylpyrimidine-2,4,6(1H,3H,5H)-trione The crude product (175 g) from the previous step was taken up in 25% (v/v) TFA in methylene chloride (500 mL). After stirring at rt for 3 h, the reaction mixture was concentrated and the residue was dried in vacuo to give a curde material of the title compound (180 g). LC-MS (ES, m/z): [M+H]$^+$=354.

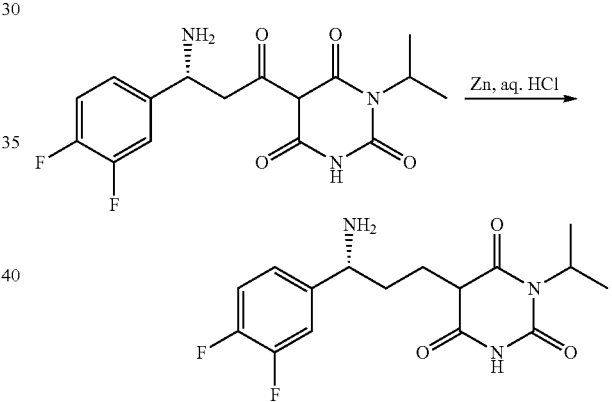

Compound 4.13. 5-((R)-3-Amino-3-(3,4-difluorophenyl)propyl)-1-isopropylpyrimidine-2,4,6(1H,3H,5H)-trione Crude 5-((R)-3-amino-3-(3,4-difluorophenyl)propanoyl)-1-isopropylpyrimidine-2,4,6-(1H,3H,5H)-trione ((Compound 4.12), 45 g, 128 mmol) in ethanol (500 mL) was treated with 2N HCl$_{(aq)}$ (360 mL) to form a suspension. To this suspension was added zinc dust over 10 minutes in portions. After the initial evolution of hydrogen gas subsided, the mixture was heated in an oil bath preheated to 51° C. Within 15 min, a homogeneous solution was obtained. LC/MS analysis showed about 86% conversion to product. Heating continued for an additional 90 min at which time the solution was cooled and the solid was filtered off. The solvent was removed under reduced pressure and the residue was partitioned between dichloromethane and NaHCO$_{3(aq)}$. After neutralization of the organic layer, the solvent was removed under reduced pressure to afford a crude material of the title compound (50 g). LC-MS (ES, m/z): [M+H]$^+$=340.

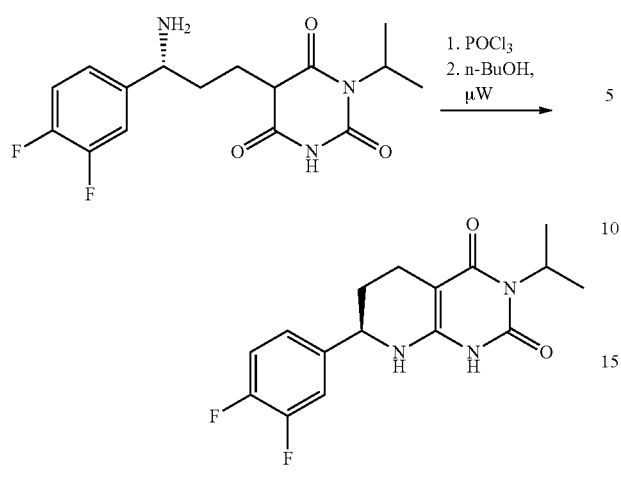

Compound 4. (R)-7-(3,4-Difluorophenyl)-3-isopropyl-5,6,7,8-tetrahydropyrido[2,3-d]pyrimidine-2,4(1H,3H)-dione To 5-((R)-3-amino-3-(3,4-difluorophenyl)propyl)-1-isopropylpyrimidine-2,4,6-(1H,3H,5H)-trione hydrochloride ((Compound 4.13), 0.376 g, 1.0 mmol) was added phosphorus oxychloride (3 mL). The mixture was heated to 80° C. until the starting material was consumed. Excess POCl₃ was removed in vacuo. The resulting mixture was suspended with dichloromethane (30 mL), cooled to 0° C., and treated with 10% aq. NaOH solution until the pH of the resulting aqueous phase was around 12. The aqueous phase was extracted with dichloromethane (5 mL×2). The combined organic phase was dried over anhydrous Na₂SO₄, and concentrated to give a viscous oil, which was immediately used in the following step. The residue was dissolved in n-butanol (2 mL) and transferred to a microwave vial. Solid potassium carbonate (450 mg, 3.3 mmol) was added to the vial. The mixture was heated in a microwave reactor at 140° C. for 15 minutes. After cooling, the liquid was decanted. The solid was washed with an additional quantity of n-butanol (5 mL). The combined organic phase was concentrated, and the residue was treated with acetonitrile (3 mL) and water (6 mL). The precipitated solid was collected by filtration, washed with water (5 mL), and dried in vacuo to afford the title compound (129 mg, 40% yield). The process was repeated iteratively to produce additional quantities of the desired product. LC-MS (ES, m/z): [M+H]⁺=322.

The following are representative compounds that were synthesized using the methodology outlined in example 4:

14

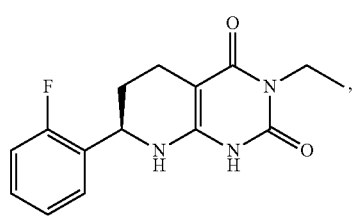

17

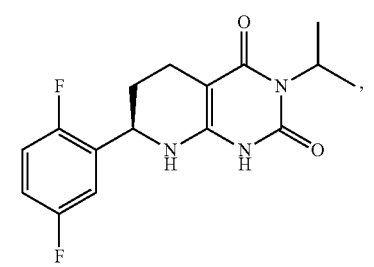

18

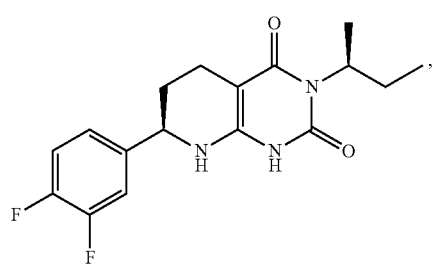

22

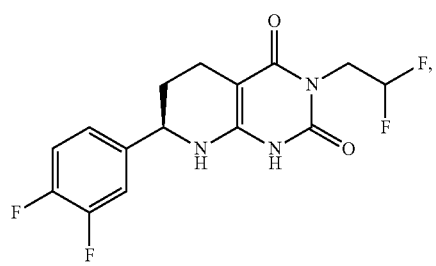

24

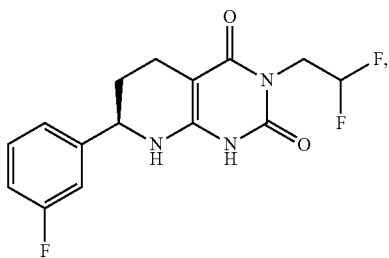

25

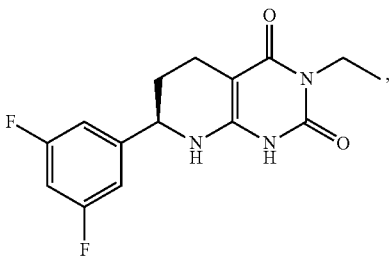

26

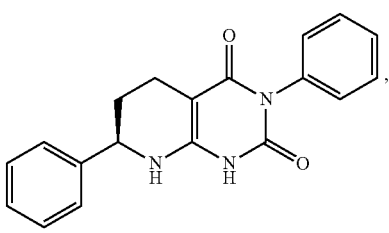

32
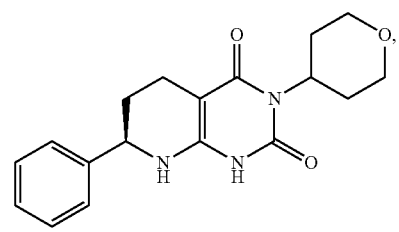
34
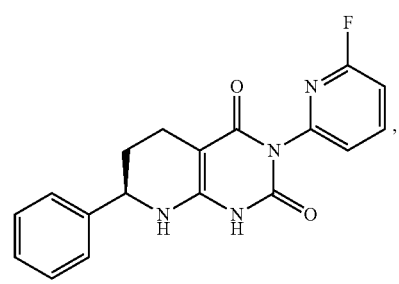
35
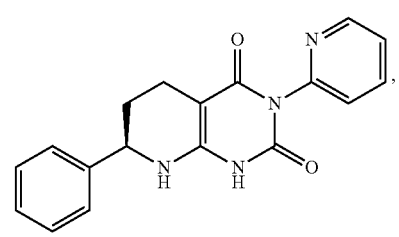
48
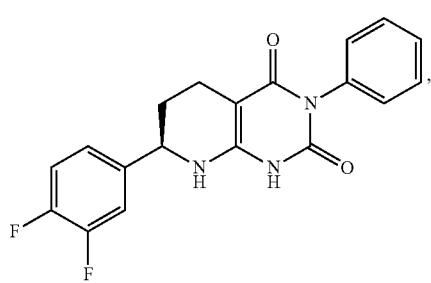
49
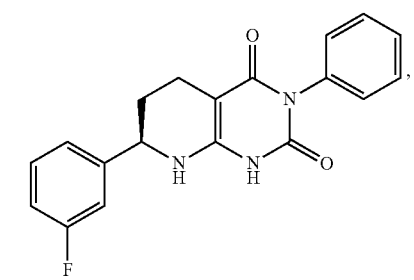
50
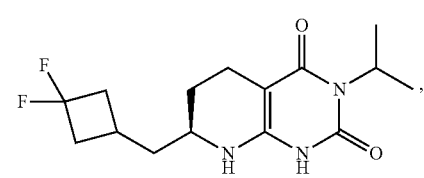
51
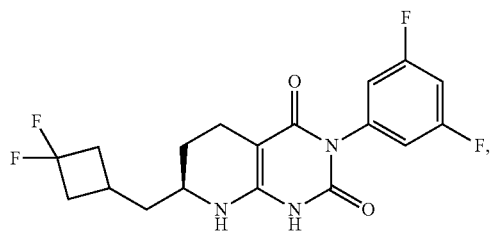
52
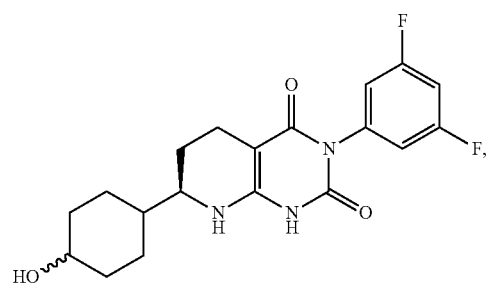
55
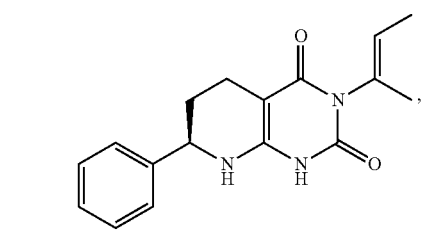
56
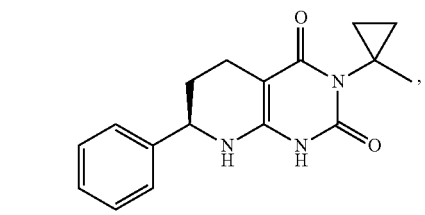
58
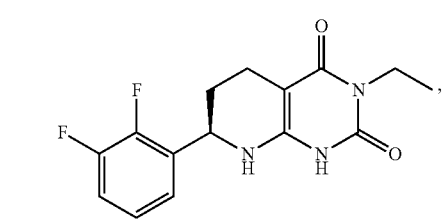
60
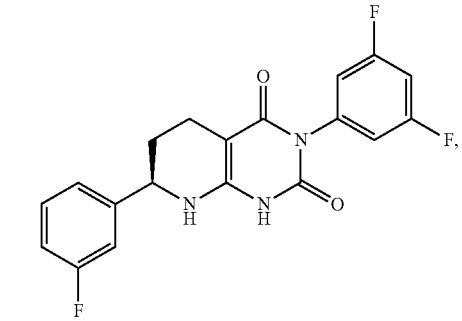

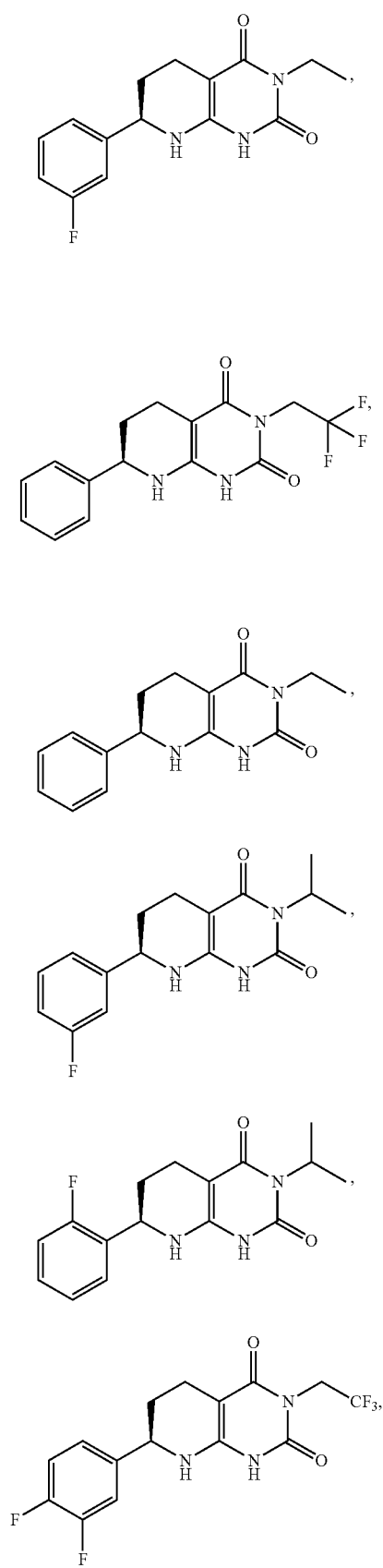
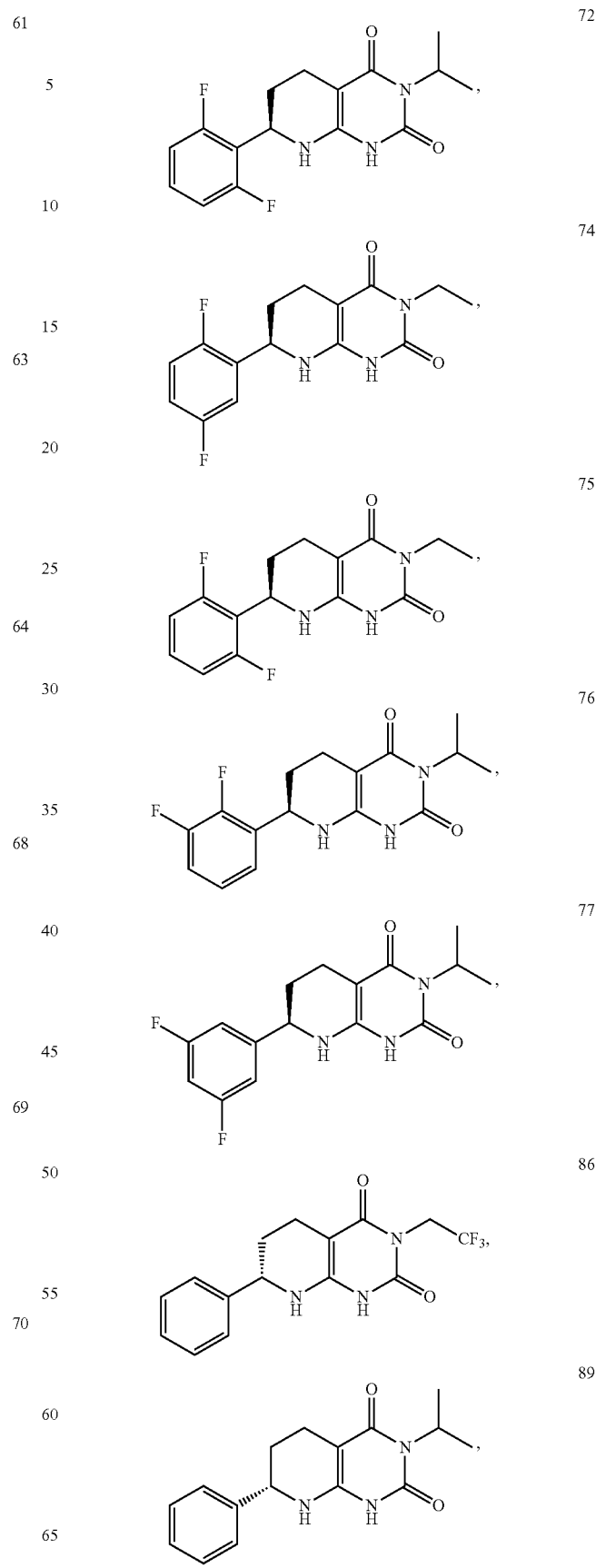

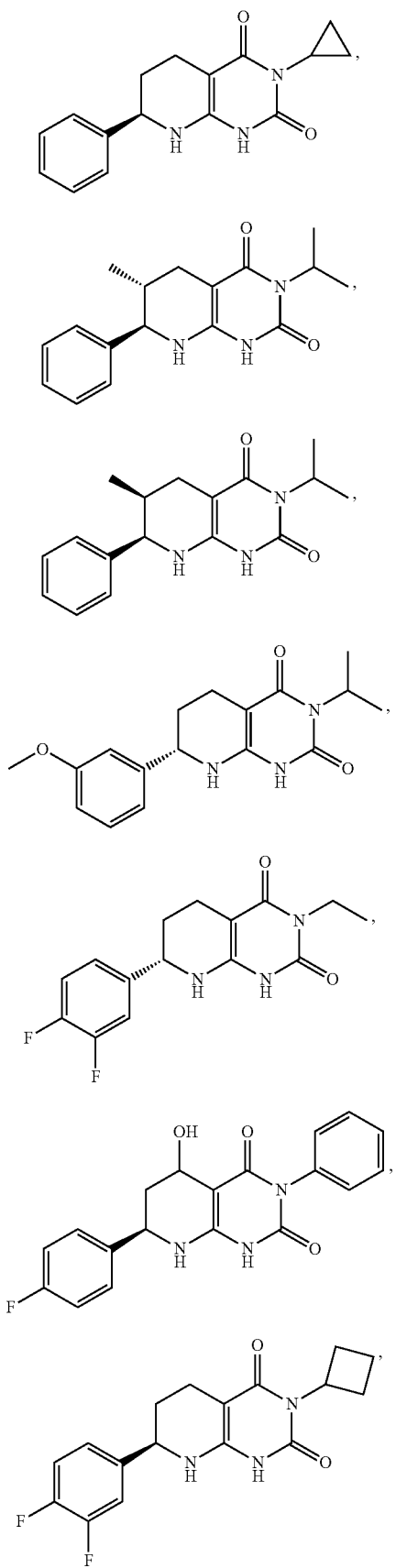
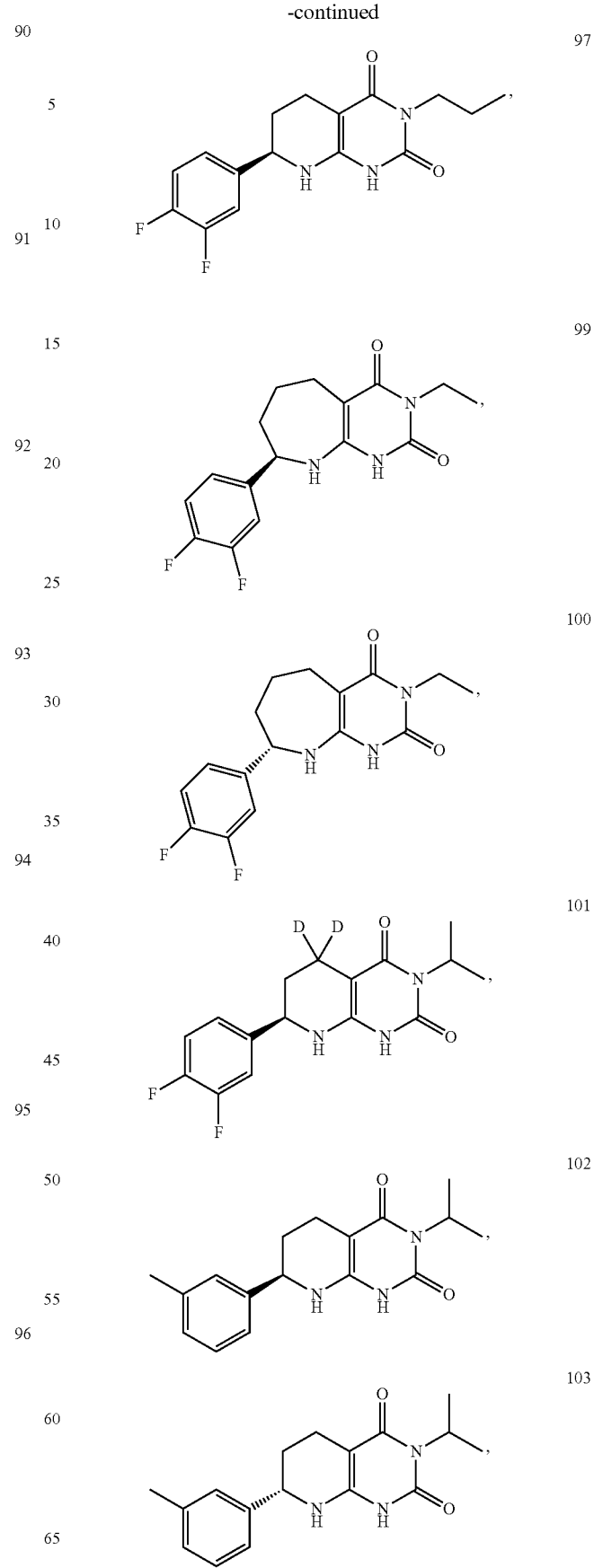

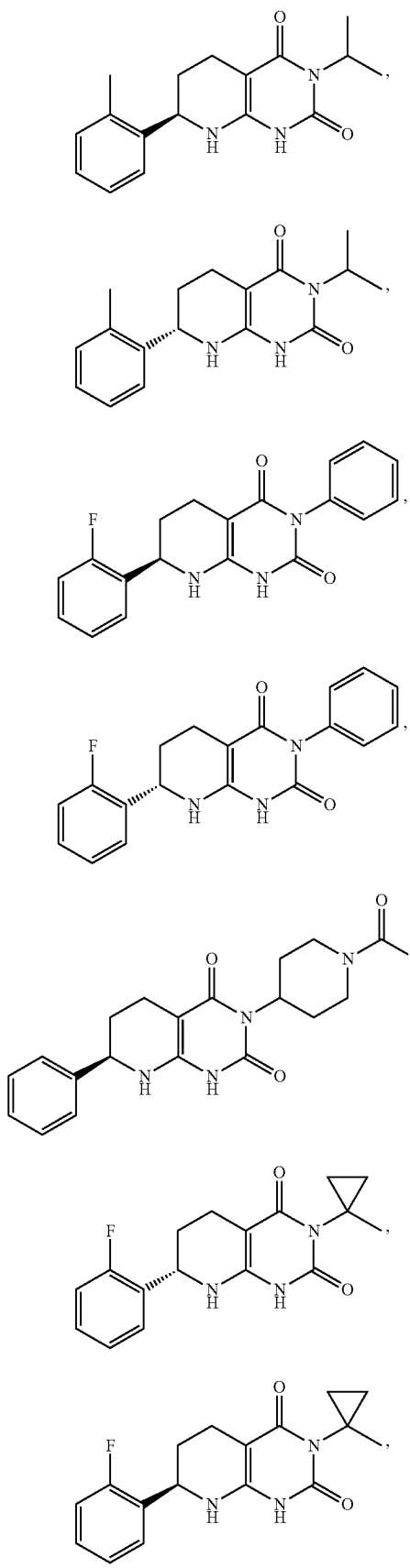
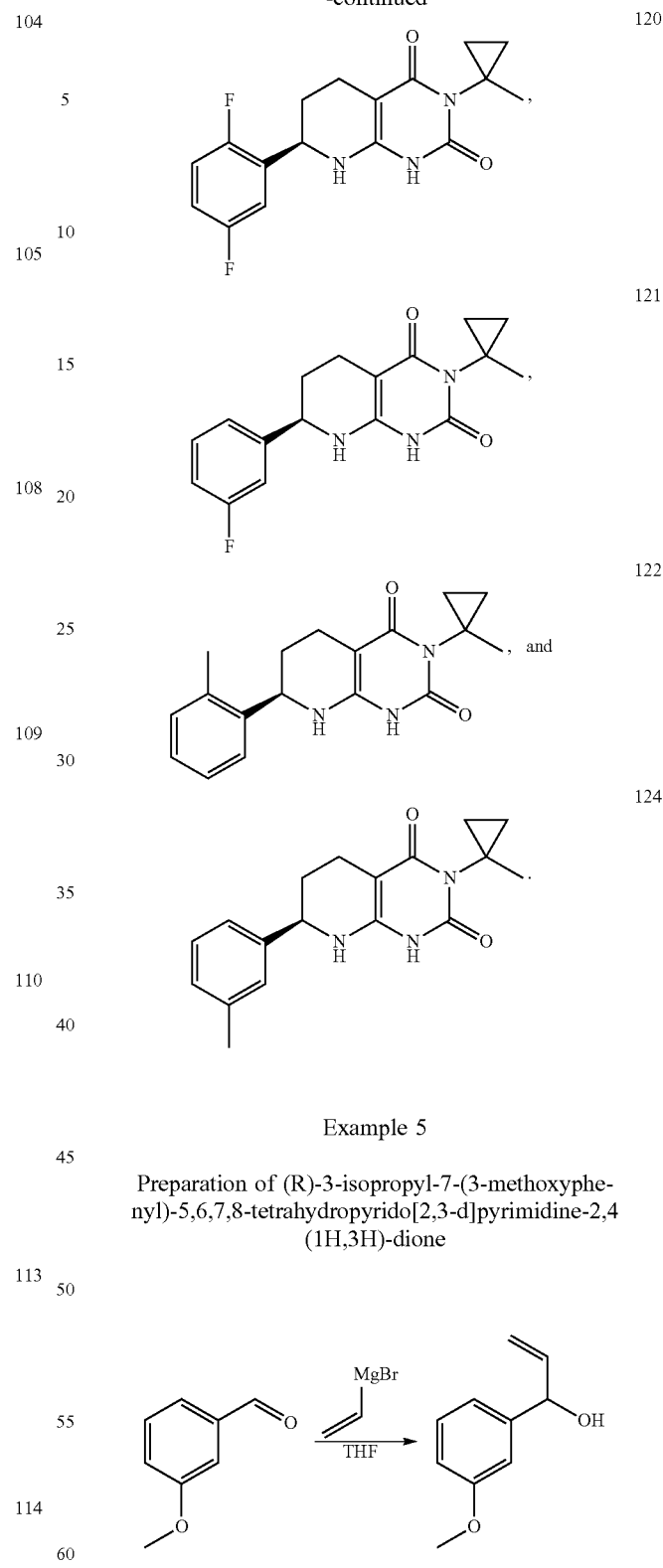
Example 5
Preparation of (R)-3-isopropyl-7-(3-methoxyphenyl)-5,6,7,8-tetrahydropyrido[2,3-d]pyrimidine-2,4 (1H,3H)-dione
Compound 5.1. 1-(3-Methoxyphenyl)prop-2-en-1-ol
To a stirring solution of 3-methoxybenzaldehyde (30 g, 220.35 mmol, 1.00 equiv) in THF (330 mL) under argon at 0° C. was added vinyl magnesium chloride (320 mL, 1.00 equiv, 0.7 M in THF) dropwise. The resulting solution was warmed to room temperature and stirred for 16 hours. The reaction was carefully quenched by the addition of ice water (600 mL). The resulting mixture was extracted with EtOAc (3×250 mL) and the organic layers combined. The organic layer was washed with brine (500 mL), dried over anhydrous Na₂SO₄ and concentrated in vacuo. The resulting residue was purified by silica gel column chromatography eluting with EtOAc/petroleum ether=1/3 (v/v). The fractions containing pure compound were combined and concentrated in vacuo to yield 30 g (83%) of the title compound as a yellow oil. ¹H-NMR (300 MHz, DMSO-d₆): δ 7.23 (m, 1H), 6.90 (m, 2H), 6.78 (m, 1H), 5.95 (m, 1H), 5.49 (m, 1H), 5.26 (m, 1H), 5.05 (m, 2H), 3.73 (s, 3H) ppm.

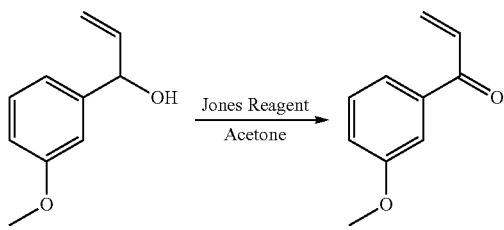

Compound 5.2. 1-(3-Methoxyphenyl)prop-2-en-1-one

To a stirring solution of 1-(3-methoxyphenyl)prop-2-en-1-ol ((compound 5.1), 26. g, 160 mmol, 1.0 equiv) in acetone (520 mL) at 0° C. was added Jones Reagent (130 mL, 2.10 equiv) dropwise. The resulting solution was stirred for 1 h at 0° C. and then diluted with Et₂O (500 mL). The solid was filtered and the filtrate was concentrated in vacuo. The resulting residue was treated with H₂O (200 mL) and extracted with EtOAc (150 mL×3). The organic layers were combined, washed with H₂O (150 mL), dried over anhydrous Na₂SO₄ and concentrated in vacuo. The crude product was purified by silica gel column chromatography eluting with EtOAc/petroleum ether=1/5 (v/v). The fractions containing pure compound were combined and concentrated in vacuo to yield 7.9 g (31%) of the title compound as a yellow oil. ¹H-NMR (400 MHz, CDCl₃): δ 7.53-7.41 (m, 2H), 7.38 (m, 1H), 7.15 (m, 2H), 6.44 (m, 1H), 5.92 (m, 1H), 3.87 (s, 3H) ppm.

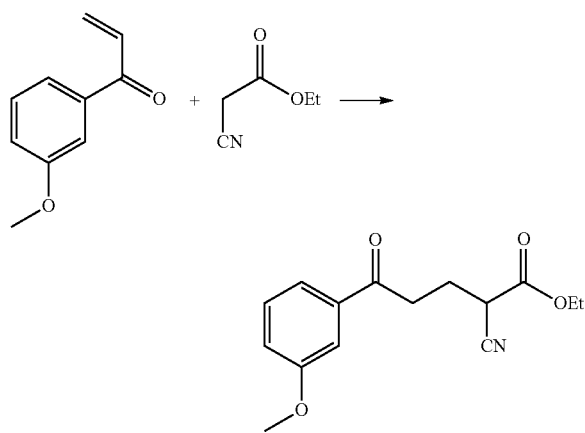

Compound 5.3. Ethyl 2-cyano-5-(3-methoxyphenyl)-5-oxopentanoate

To a stirring solution of ethyl 2-cyanoacetate (32.64 g, 288.56 mmol, 6.00 equiv) in THF (120 mL) at 0° C. was added K₂CO₃ (6.63 g, 47.97 mmol, 1.00 equiv). The reaction mixture was stirred for 30 min at 0° C. and then 1-(3-methoxyphenyl)prop-2-en-1-one ((compound 5.2), 7.8 g, 48 mmol, 1.0 equiv) was added. The resulting solution was stirred for 1 hour at 0° C. and was quenched by the addition of ice water (200 mL). The mixture was extracted with EtOAc (2×100 mL) and the organic layers were combined, dried over anhydrous Na₂SO₄, and concentrated in vacuo. The resulting residue was purified by preparative HPLC ((IntelFlash): Column, C18; mobile phase, H₂O and CH₃CN (5% CH₃CN up to 95% (v/v) over 45 min)). The fractions containing pure compound were combined and concentrated in vacuo to yield 7.9 g (60%) of the title compound as a yellow oil. ¹H-NMR (400 MHz, DMSO-d₆): δ 7.56 (m, 1H), 7.46 (m, 2H), 7.23 (m, 1H), 4.27-4.16 (m, 3H), 3.82 (s, 3H), 3.21 (m, 2H), 2.30-2.13 (m, 2H), 1.22 (m, 3H) ppm.

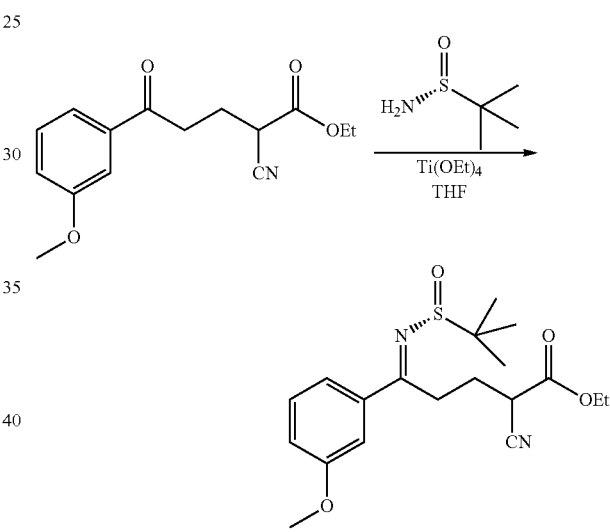

Compound 5.4. Ethyl (5E)-2-cyano-5-(3-methoxyphenyl)-5-[[(R)-2-methylpropane-2-sulfinyl]imino]pentanoate To a stirring solution of ethyl 2-cyano-5-(3-methoxyphenyl)-5-oxopentanoate ((compound 5.3), 7.8 g, 28 mmol, 1.0 equiv) and (R)-2-methylpropane-2-sulfinamide (6.86 g, 56.6 mmol, 2.00 equiv) in THF (400 mL) under argon was added titanium(IV) ethoxide (25.84 g, 113 mmol, 4.0 equiv). The resulting solution was stirred overnight at 65° C. The reaction was cooled, quenched with MeOH (10 mL) and diluted with H₂O (500 mL). The resulting solution was extracted with EtOAc (3×250 mL). The organic layers were combined, dried over anhydrous Na₂SO₄ and concentrated in vacuo. The resulting residue was purified by silica gel column chromatography eluting with EtOAc/petroleum ether=1/10 (v/v). The fractions containing pure compound were combined and concentrated in vacuo to yield 9.8 g (91%) of the title compound as a yellow oil. LC-MS (ES, m/z): [M+H]⁺=379.

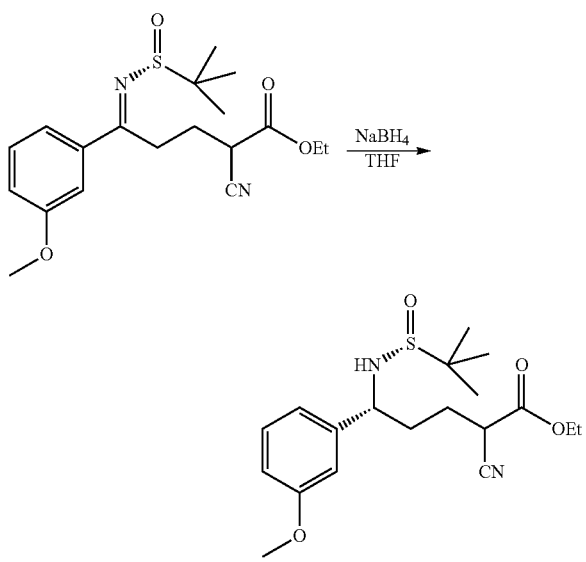

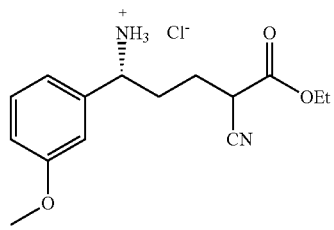

Compound 5.6. Ethyl (5R)-5-amino-2-cyano-5-(3-methoxyphenyl)pentanoate hydrochloride To a stirring solution of ethyl (5R)-2-cyano-5-(3-methoxyphenyl)-5-[[(R)-2-methylpropane-2-sulfinyl]amino]pentanoate ((compound 5.5), 1.0 g, 2.6 mmol, 1.0 equiv) in CH₃CN (10 mL) at 0° C. was added 4N HCl in 1,4-dioxane (2.5 mL) dropwise. The resulting solution was stirred for 1 h at 0° C. and was concentrated in vacuo. The resulting residue was precipitated with Et₂O (10 mL). The solid was isolated by filtration and dried under reduced pressure to yield 1 g (crude) of title compound as a white solid. LC-MS (ES, m/z): [M−HCl+H]⁺=277.

Compound 5.5. (5R)-2-Cyano-5-(3-methoxyphenyl)-5-[[(R)-2-methylpropane-2-sulfinyl]amino]pentanoate To a stirring solution of ethyl (5E)-2-cyano-5-(3-methoxyphenyl)-5-[[(R)-2-methylpropane-2-sulfinyl]imino]pentanoate ((compound 5.4), 9.8 g, 26 mmol, 1.0 equiv) in THF (200 mL) under argon at 0° C. was added sodium borohydride (1.96 g, 51.81 mmol, 2.00 equiv) portionwise. The resulting solution was stirred for 1 h at 0° C. The reaction was quenched by the careful addition of H₂O (200 mL). The resulting mixture was extracted with EtOAc (3×150 mL) and the organic layers were combined. The resulting solution was washed with brine (150 mL), dried over anhydrous Na₂SO₄ and concentrated in vacuo. The resulting residue was purified by silica gel column chromatography eluting with EtOAc/petroleum ether=1/1 (v/v). The fractions containing pure compound were combined and concentrated in vacuo to yield 2.2 g (22%) of the title compound as a clear oil. ¹H-NMR (300 MHz, DMSO-d₆): δ 7.24 (m, 1H), 6.95 (m, 2H), 6.81 (m, 1H), 5.72 (m, 1H), 4.21-4.09 (m, 4H), 3.73 (s, 3H), 2.00-1.67 (m, 4H), 1.20 (m, 3H), 1.16 (s, 9H) ppm.

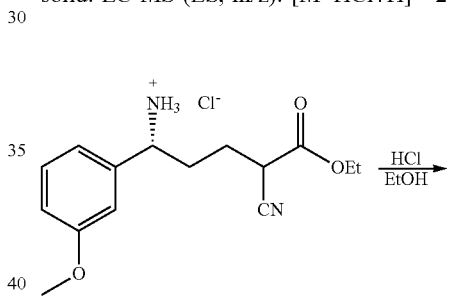

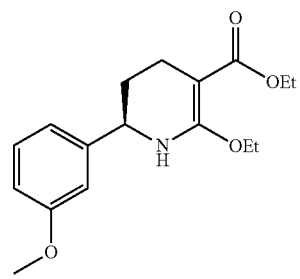

Compound 5.7. Ethyl (R)-2-ethoxy-6-(3-methoxyphenyl)-1,4,5,6-tetrahydropyridine-3-carboxylate To a stirring solution of ethyl (5R)-5-amino-2-cyano-5-(3-methoxyphenyl)pentanoate hydrochloride ((compound 5.6), 100 mg, 0.32 mmol, 1.00 equiv) in EtOH (10 mL) at 0° C. was bubbled HCl (g) for 5 minutes. The resulting solution was stirred for 5 h at 0° C. The resulting mixture was concentrated in vacuo to give 1.0 g (crude) of the title compound as a clear oil. LC-MS (ES, m/z): [M+H]⁺=306.

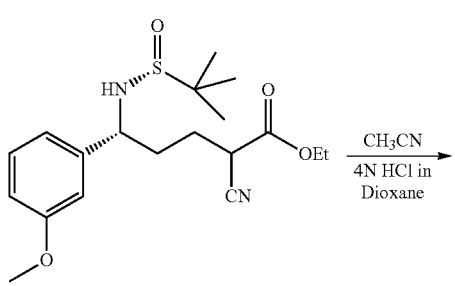

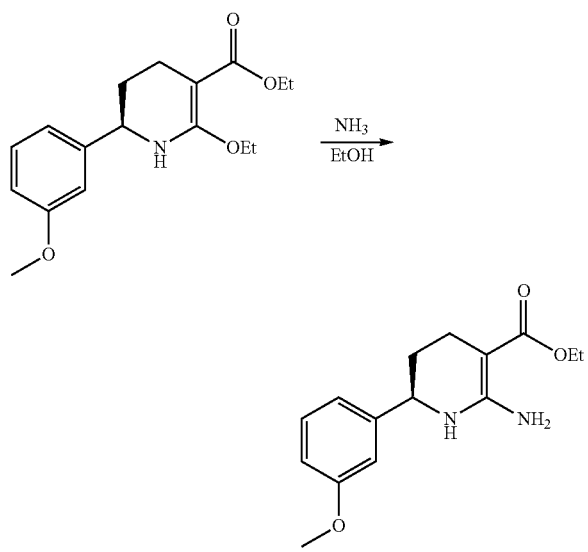

Compound 5.8. Ethyl (R)-2-amino-6-(3-methoxyphenyl)-1,4,5,6-tetrahydropyridine-3-carboxylate To EtOH (15 mL) at 0° C. was added NH$_3$(g). Upon saturation, ethyl (R)-2-ethoxy-6-(3-methoxyphenyl)-1,4,5,6-tetrahydropyridine-3-carboxylate ((compound 5.7), 1.0 g, 3.27 mmol, 1.00 equiv) was added. The resulting solution was stirred for 1 h at 0° C. and concentrated in vacuo. The crude residue was purified by silica gel column chromatography eluting with EtOAc/petroleum ether=1/1 (v/v). The fractions containing pure compound were combined and concentrated to yield 420 mg (46%) of the title compound as a clear oil. LC-MS (ES, m/z): [M+H]$^+$=277.

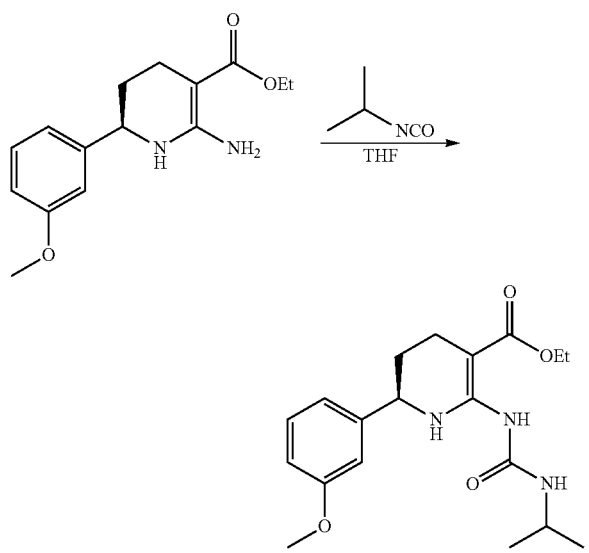

Compound 5.9. Ethyl (R)-2-(3-isopropylureido)-6-(3-methoxyphenyl)-1,4,5,6-tetrahydropyridine-3-carboxylate To a stirred solution of ethyl (6R)-2-amino-6-(3-methoxyphenyl)-1,4,5,6-tetrahydropyridine-3-carboxylate ((compound 5.8), 150 mg, 0.54 mmol, 1.00 equiv) and triethylamine (110 mg, 1.09 mmol, 2.00 equiv) in THF (3 mL) under argon at 0° C. was added 2-isocyanatopropane (116 mg, 1.36 mmol, 2.50 equiv) dropwise. The resulting solution was stirred for 5 h at 0° C. The reaction was then quenched by the addition of MeOH (1 mL) and concentrated in vacuo. The resulting residue was purified by silica gel column chromatography eluting with CH$_2$Cl$_2$/MeOH=50/1(v/v). The fractions containing pure compound were combined and concentrated in vacuo to yield 80 mg (41%) of the title compound as a yellow oil. LC-MS (ES, m/z): [M+H]$^-$=362. $^1$H-NMR (400 MHz, CD$_3$OD): δ 7.27 (m, 1H), 6.88 (m, 3H), 4.46 (m, 1H), 4.10 (m, 2H), 3.83 (m, 1H), 3.81 (s, 3H), 2.39 (m, 2H), 1.95 (m, 1H), 1.75 (m, 1H), 1.12-1.32 (m, 9H) ppm.

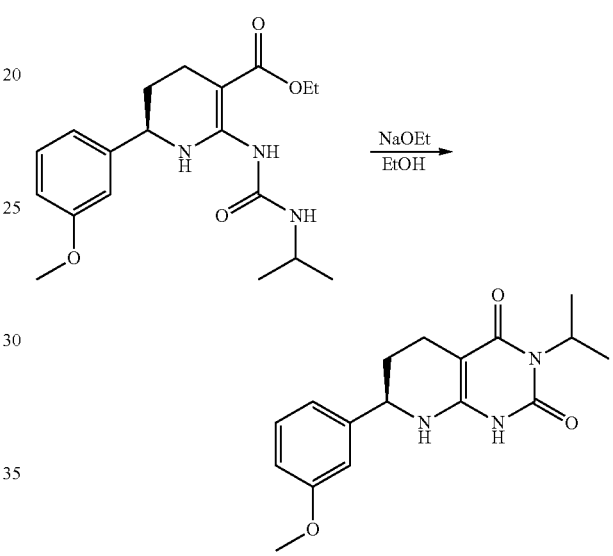

Compound 5. (R)-3-Isopropyl-7-(3-methoxyphenyl)-5,6,7,8-tetrahydropyrido[2,3-d]pyrimidine-2,4(1H,3H)-dione To a stirring solution of NaOEt (20 mg, 0.30 mmol, 1.00 equiv) in EtOH (5 mL) at 0° C. was added a solution of ethyl (R)-2-(3-isopropylureido)-6-(3-methoxyphenyl)-1,4,5,6-tetrahydropyridine-3-carboxylate ((compound 5.9), 110 mg, 0.30 mmol, 1.00 equiv) in EtOH (5 mL) dropwise. The resulting solution was stirred overnight at 0° C. and then was quenched with H$_2$O (20 mL). The reaction mixture was extracted with EtOAc (3×25 mL) and the organic layers were combined. The organic layer was washed with H$_2$O (10 mL), dried over anhydrous Na$_2$SO$_4$ and concentrated in vacuo. The resulting residue (110 mg) was purified by preparative HPLC (X Bridge RP18 Column, 19×150 mm, 5 um; Mobile Phase A: H$_2$O/0.05% NH$_4$HCO$_3$, Mobile Phase B: CH$_3$CN; Gradient: 30% B to 50% B over 8 min). The product was further purified by preparative chiral HPLC (Column, Chiralpak IA, 2×25 cm, 5 um; mobile phase, Hexanes (0.1% IPA) and EtOH (70.0% EtOH to 30.0% over 9 min)). The fractions containing pure compound were combined and lyophilized to yield 10.0 mg (21%) of the title compound as a white solid. LC-MS (ES, m/z): [M+H]$^+$=316. $^1$H-NMR (400 MHz, DMSO-d$_6$): δ 9.80 (br s, 1H), 7.28 (t, J=7.6 Hz, 1H), 6.88-6.84 (m, 3H), 6.27 (br s, 1H), 5.03-4.98 (m, 1H), 4.48-4.46 (m, 1H), 3.75 (s, 3H), 2.30-2.23 (m, 1H), 2.12-2.05 (m, 1H), 1.95-1.89 (m, 1H), 1.80-1.71 (m 1H), 1.49 (d, J=7.2 Hz, 6H) ppm.

The following are representative compounds that were synthesized using the methodology outlined in example 5:

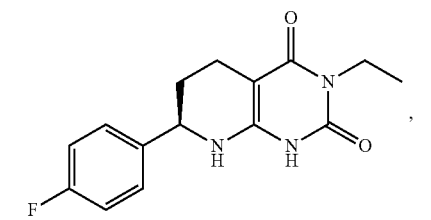
20

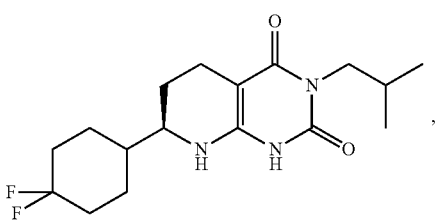
23

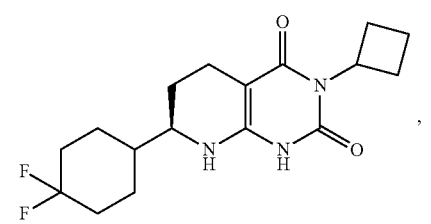
31

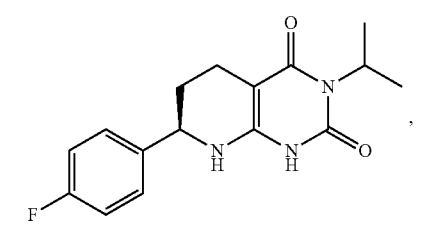
67

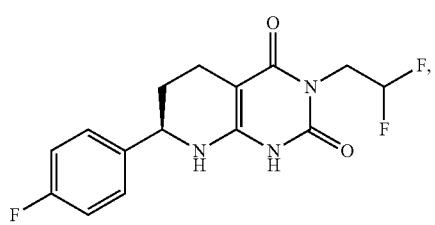
73

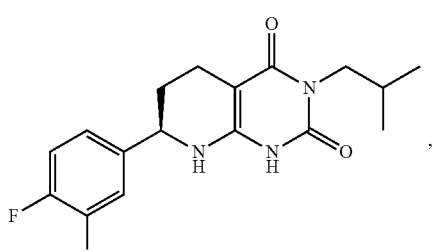
80

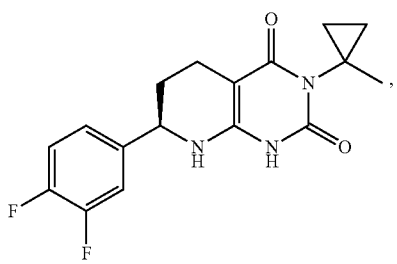
81

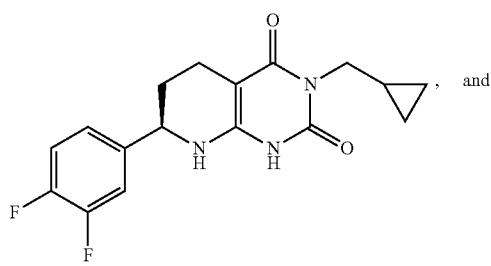
82
and

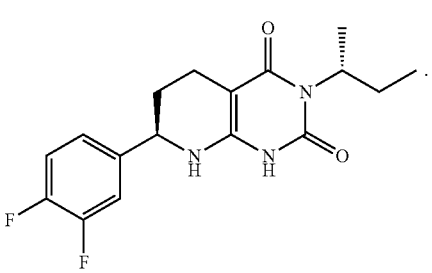
83

Example 6

Preparation of (R)-7-(2,4-difluorophenyl)-3-isopropyl-5,6,7,8-tetrahydropyrido[2,3-d]pyrimidine-2,4(1H,3H)-dione

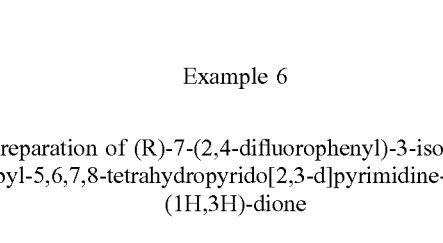

Compound 6.1. (R)-7-(2,4-Difluorophenyl)-3-isopropyl-7,8-dihydropyrido[2,3-d]pyrimidine-2,4,5(1H,3H,6H)-trione The title compound was synthesized according to procedures similar to that described in Example 4 (starting from 2,4-diflurobenzaldehye and tert-butyl 2-(diethoxyphosphoryl)acetate). LC-MS (ES, m/z): [M+H]$^+$=336.

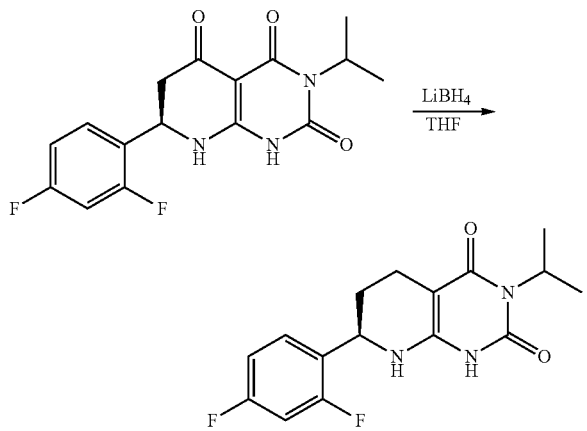

Compound 6. (R)-7-(2,4-Difluorophenyl)-3-isopropyl-5,6,7,8-tetrahydropyrido[2,3-d]pyrimidine-2,4(1H,3H)-dione The title compound was synthesized according to procedures similar to that described in Example 4 utilizing (R)-7-(2,4-difluorophenyl)-3-isopropyl-7,8-dihydropyrido[2,3-d]pyrimidine-2,4,5(1H,3H,6H)-trione in place of (R)-7-(3,4-difluorophenyl)-3-isopropyl-7,8-dihydropyrido[2,3-d]pyrimidine-2,4,5(1H,3H,6H)-trione. LC-MS (ES, m/z): [M+H]$^+$=322. $^1$H-NMR (300 MHz, DMSO-d$_6$): δ 10.26 (br s, 1H), 7.31-7.23 (m, 2H), 7.10 (td, J=8.4, 2.1 Hz, 1H), 6.31 (br s, 1H), 5.06-4.97 (m, 1H), 4.81-4.79 (m, 1H), 2.36-2.26 (m, 1H), 2.00-1.84 (m, 2H), 1.82-1.72 (m, 1H), 1.33 (dd, J=7.2, 1.5 Hz, 6H) ppm.

Example 7

Preparation of (R)-3-isopropyl-6-phenyl-1,5,6,7-tetrahydro-2H-pyrrolo[2,3-d]pyrimidine-2,4(3H)-dione

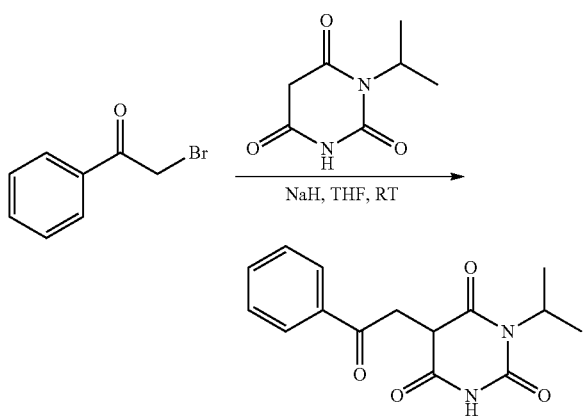

Compound 7.1. 1-Isopropyl-5-(2-oxo-2-phenylethyl)pyrimidine-2,4,6(1H,3H,5H)-trione To a stirring solution of 1-isopropylpyrimidine-2,4,6(1H,3H,5H)-trione ((compound 1.2), 2.0 g, 12 mmol, 1.0 equiv) in THF (30 mL) under an argon atmosphere at 0° C. was added 60% sodium hydride (494 mg, 17.6 mmol, 1.5 equiv) portionwise. The reaction mixture was stirred for 30 min at 0° C. and 2-bromo-1-phenylethan-1-one (2.34 g, 11.8 mmol, 1.00 equiv) was added. The resulting solution was stirred for 4 h at 25° C., diluted with H$_2$O (30 mL) and extracted with EtOAc (2×30 mL). The organic layer was discarded and the aqueous layer was adjusted to pH1 with 1N HCl$_{(aq)}$. The resulting precipitate was collected by filtration and dried under reduced pressure to yield 850 mg (25%) of the title compound as a yellow solid. LC-MS (ES, m/z): [M+H]$^-$=289. $^1$H-NMR (400 MHz, DMSO-d$_6$): δ 11.42 (s, 1H), 8.01 (m, 2H), 7.70 (t, J=7.2 Hz, 1H), 7.56 (t, J=7.6 Hz, 2H), 4.80-4.91 (m, 1H), 4.16 (t, J=4.0 Hz, 1H), 3.84 (t, J=4.0 Hz, 2H), 3.57 (s, 1H), 1.32 (m, 6H) ppm.

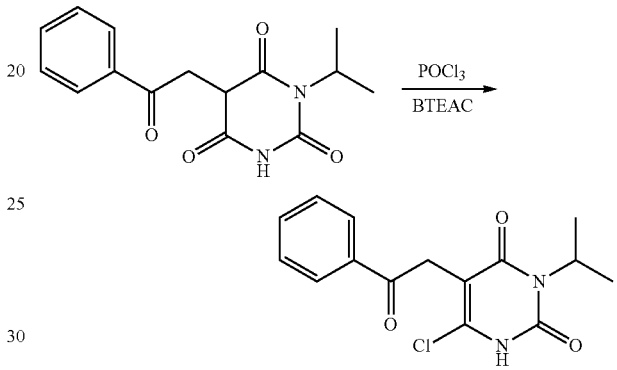

Compound 7.2. 6-Chloro-3-isopropyl-5-(2-oxo-2-phenylethyl)pyrimidine-2,4(1H,3H)-dione To a 50-mL round-bottom flask purged and maintained with an inert atmosphere of argon was added 1-isopropyl-5-(2-oxo-2-phenylethyl)pyrimidine-2,4,6(1H,3H,5H)-trione ((compound 7.1), 400 mg, 1.39 mmol, 1.00 equiv), BTEAC (441 mg, 1.94 mmol, 1.40 equiv) and phosphoryl trichloride (15 mL). The resulting solution was stirred for 2 days at 65° C., cooled and concentrated in vacuo. The reaction was slowly and carefully quenched by the addition of ice water (15 mL) and extracted with EtOAc (2×25 mL). The organic layers were combined, dried over anhydrous Na$_2$SO$_4$ and concentrated in vacuo. The resulting residue was purified by silica gel column chromatography eluting with EtOAc/petroleum ether=1/3 (v/v). The fractions containing pure compound were combined and lyophilized to yield 80 mg (19%) of the title compound as a yellow solid. LC-MS (ES, m/z): [M+H]$^+$=307. $^1$H-NMR (400 MHz, CDCl$_3$): δ 9.16 (s, 1H), 8.05 (m, 2H), 7.62 (t, J=7.6 Hz, 1H), 7.52 (t, J=7.2 Hz, 2H), 5.18-5.11 (m, 1H), 4.19 (s, 2H), 1.42 (m, 6H) ppm.

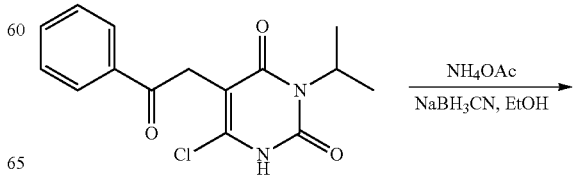

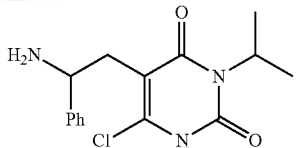

Compound 7.3. 5-(2-Amino-2-phenylethyl)-6-chloro-3-isopropylpyrimidine-2,4(1H,3H)-dione To a stirring solution of 6-chloro-3-isopropyl-5-(2-oxo-2-phenylethyl)pyrimidine-2,4(1H,3H)-dione ((compound 7.2), 180 mg, 0.59 mmol, 1.0 equiv) in EtOH (20 mL) were added ammonium acetate (1.76 g, 22.8 mmol, 39 equiv) and sodium cyanoborohydride (234 mg, 3.72 mmol, 6.4 equiv). The resulting solution was stirred for 1 h at 50° C. and then concentrated in vacuo. The crude product was purified by preparative HPLC ((IntelFlash): Column: C18; Mobile Phase A: H$_2$O, Mobile Phase B: CH$_3$CN; Gradient: 0-100% B over 25 min). The fractions containing pure compound were combined and concentrated in vacuo to yield 130 mg (72%) of the title compound as yellow oil. LC-MS (ES, m/z): [M+H]$^+$=308. $^1$H-NMR (400 MHz, CD$_3$OD): δ 7.43 (m, 5H), 5.10 (m, 1H), 4.58 (t, J=7.2 Hz, 1H), 3.63 (m, 2H), 3.18-3.02 (m, 2H), 1.44 (m, 6H) ppm.

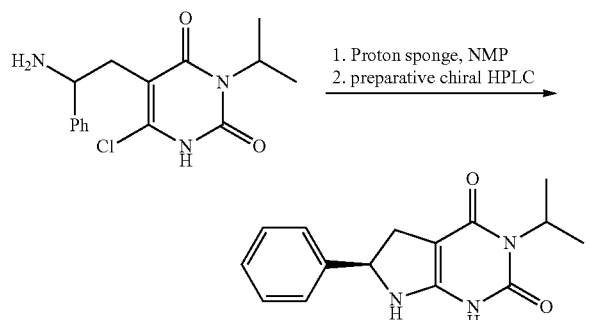

Compound 7. (R)-3-Isopropyl-6-phenyl-1,5,6,7-tetrahydro-2H-pyrrolo[2,3-d]pyrimidine-2,4(3H)-dione To a stirring solution of 5-(2-amino-2-phenylethyl)-6-chloro-3-isopropylpyrimidine-2,4(1H,3H)-dione ((compound 7.3), 50 mg, 0.16 mmol, 1.0 equiv) in NMP (1 mL) was added proton sponge (42 mg, 0.19 mmol, 1.2 equiv). The resulting solution was stirred for 1 h at 120° C., cooled and diluted with DMF (10 mL). The crude product was purified directly by preparative HPLC (Column: X Bridge RP C18, 19×150 mm, 5 um; Mobile Phase A: H$_2$O/10 mM NH$_4$HCO$_3$, Mobile Phase B: CH$_3$CN; Gradient: 20-60% B over 5 min). The fractions containing the racemic compound were combined and lyophilized to yield 20 mg. The racemate was separated by preparative chiral HPLC (Column, Phenomenex Lux 5u Cellulose-4, AXIA Packed, 250×21.2 mm, 1 um; mobile phase, hexanes and EtOH (isocratic mixture of 30.0% EtOH over 15 min)). The first peak was collected and lyophilized to yield 5.9 mg (27%) of the title compound as a white solid. LC-MS (ES, m/z): [M+H]$^+$=272. $^1$H-NMR (400 MHz, DMSO-d$_6$): δ 11.18 (br s, 1H), 7.39-7.26 (m, 5H), 7.10 (s, 1H), 5.05-4.92 (m, 2H), 3.21-3.15 (m, 1H), 2.41 (m, 1H), 1.33 (d, J=6.8 Hz, 6H) ppm.

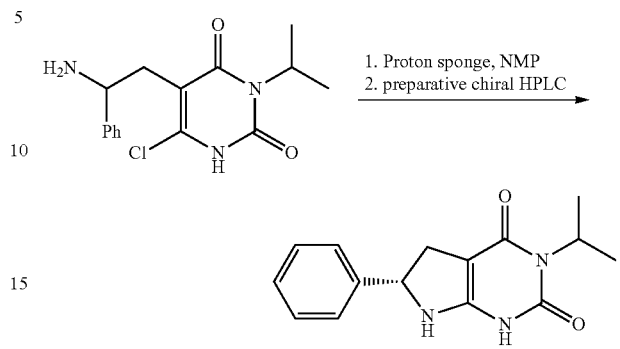

Example 8

Preparation of (S)-3-isopropyl-6-phenyl-1,5,6,7-tetrahydro-2H-pyrrolo[2,3-d]pyrimidine-2,4(3H)-dione Compound 8. (S)-3-Isopropyl-6-phenyl-1,5,6,7-tetrahydro-2H-pyrrolo[2,3-d]pyrimidine-2,4(3H)-dione The second peak eluted in the preparative chiral HPLC in the preparation of (R)-3-isopropyl-6-phenyl-1,5,6,7-tetrahydro-2H-pyrrolo[2,3-d]pyrimidine-2,4(3H)-dione (Compound 7) was collected and lyophilized to yield 5.4 mg (25%) of the title compound as a white solid. LC-MS (ES, m/z): [M+H]$^+$=272. $^1$H-NMR (400 MHz, DMSO-d$_6$): δ 11.19 (br s, 1H), 7.39-7.28 (m, 5H), 7.11 (br s, 1H), 5.04-4.92 (m, 2H), 3.21-3.15 (m, 1H), 2.42 (m, 1H), 1.33 (d, J=6.8 Hz, 6H) ppm.

The following are representative compounds that were synthesized using the methodology outlined in examples 7 and 8:

71

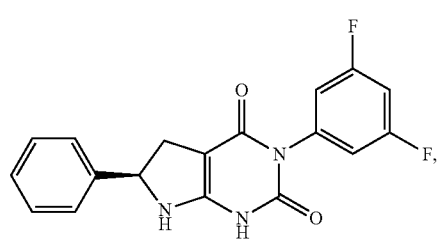

79

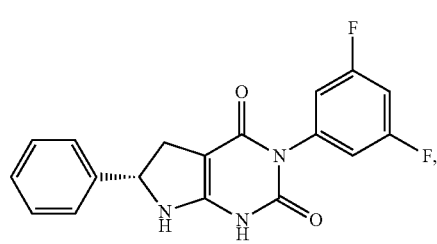

87

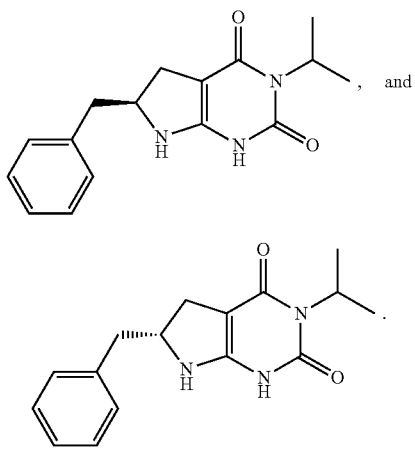

, and

88

Example 9

Preparation of (R)-7-(3,4-difluorophenyl)-3-ethyl-5,6,7,8-tetrahydropyrido[2,3-d]pyrimidine-2,4(1H,3H)-dione

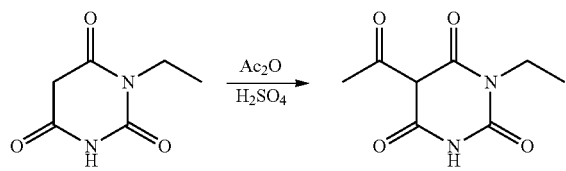

Compound 9.1. 5-Acetyl-1-ethylpyrimidine-2,4,6(1H,3H,5H)-trione

To a stirring solution of 1-ethylpyrimidine-2,4,6(1H,3H,5H)-trione (2.21 g, 14.2 mmol) in a microwave vial was added Ac$_2$O (4.0 mL) and H$_2$SO$_4$ (0.5 mL, dropwise) (CAUTION!). The reaction mixture was capped and heated in an oil bath at 100° C. for 1 h 50 min. The reaction mixture was cooled and carefully diluted with ice-cold H$_2$O (15 mL). Solid precipitated and was isolated by filtration. The solid was further washed with H$_2$O (30 mL), toluene (2×30 mL) and was dried under pressure to give 2.16 g (74%) of the title compound. LC-MS (ES, m/z): [M+H]$^+$=199.

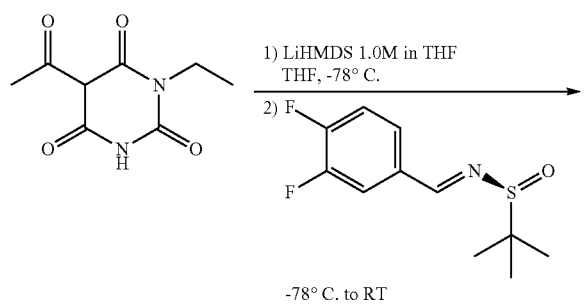

Compound 9.2. (S)—N-((1R)-1-(3,4-Difluorophenyl)-3-(1-ethyl-2,4,6-trioxohexahydropyrimidin-5-yl)-3-oxopropyl)-2-methylpropane-2-sulfinamide To a stirring solution of 5-acetyl-1-ethylpyrimidine-2,4,6(1H,3H,5H)-trione ((compound 9.1), 1.08 g, 5.45 mmol) in THF (40 mL) under an N$_2$ atmosphere at −78° C. was added LiHMDS (15 mL, 1M in toluene, dropwise, 2.75 equiv). The reaction was stirred at −78° C. for 5 minutes, warmed to 0° C. and stirred at 0° C. for 30 minutes. The reaction mixture cooled to −78° C. and then (S,E)-N-(3,4-difluorobenzylidene)-2-methylpropane-2-sulfinamide (2.15 g, 8.73 mmol, 1.6 eq) in THF (20 mL) was added dropwise. The reaction mixture was warmed to 0° C., stirred for 2 h and quenched with saturated NH$_4$Cl$_{(aq)}$ (20 mL). The mixture was diluted with EtOAc (50 mL) and the two layers were separated. The organic layer was washed with 5% NaHCO$_{3(aq)}$ (4×30 mL). The aqueous layers were combined and acidified to pH~3 with 1 N HCl$_{(aq)}$. The resulting solution was extracted with EtOAc (2×50 mL). The EtOAc extractions were combined and concentrated in vacuo. The resulting residue was purified by silica gel column chromatography eluting with a 0 to 4% (v/v) MeOH in CH$_2$Cl$_2$ gradient. The fractions containing pure compound were combined and concentrated in vacuo to yield 745 mg (31%) of the title compound. LC-MS (ES, m/z): [M+H]$^+$=444.

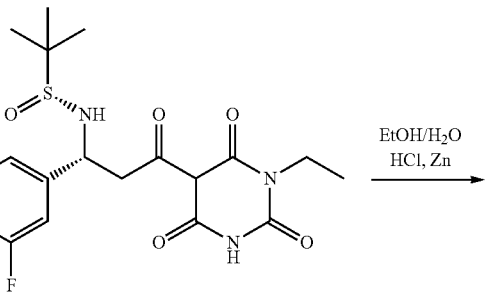

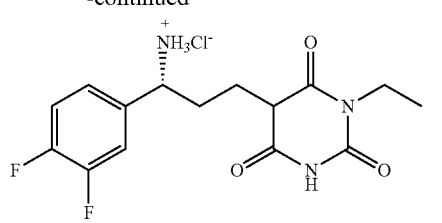

Compound 9.3. (1R)-1-(3,4-Difluorophenyl)-3-(1-ethyl-2,4,6-trioxohexahydropyrimidin-5-yl)propan-1-amine hydrochloride To a stirring solution of (S)—N-((1R)-1-(3,4-difluorophenyl)-3-(1-ethyl-2,4,6-trioxohexahydropyrimidin-5-yl)-3-oxopropyl)-2-methylpropane-2-sulfinamide ((compound 9.2), 745 mg, 1.68 mmol) in a a 1:1 mixture of EtOH/2N HCl$_{(aq)}$ (16 mL) was added Zn (300 mg, 4.59 mmol, 2.73 equiv). The reaction mixture was heated at 50° C. for 1 h and then cooled and filtered. The filtrate was concentrated in vacuo to give 410 mg (67%) of a crude residue, which was used in the next step without further purification. LC-MS (ES, m/z): [M+H]$^+$=326.

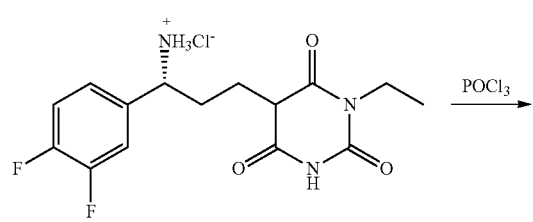

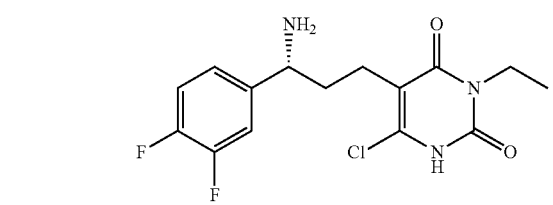

Compound 9.4. (R)-5-(3-Amino-3-(3,4-difluorophenyl)propyl)-6-chloro-3-ethylpyrimidine-2,4(1H,3H)-dione A solution of (1R)-1-(3,4-difluorophenyl)-3-(1-ethyl-2,4,6-trioxohexahydropyrimidin-5-yl)propan-1-amine hydrochloride ((compound 9.3), 410 mg, 1.13 mmol) in POCl$_3$ was heated to 80° C. for 2 hours. The reaction mixture was cooled and concentrated. The mixture was diluted with CH$_2$Cl$_2$ (50 mL) and then carefully basified to pH-8 (at 0° C.) with 3N NaOH$_{(aq)}$ and then to pH12 with 10% Na$_2$SO$_{4(aq)}$. The combined organics were concentrated to give 140 mg crude product (36%), which was used in the next reaction without further purification. LC-MS (ES, m/z): [M+H]$^+$=344.

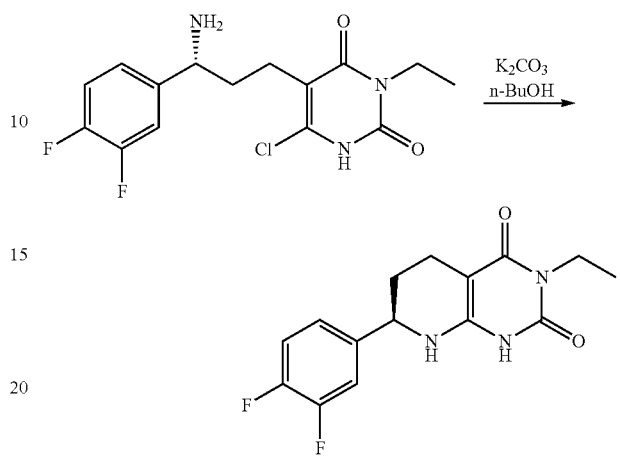

Compound 9. (R)-7-(3,4-Difluorophenyl)-3-ethyl-5,6,7,8-tetrahydropyrido[2,3-d]pyrimidine-2,4(1H,3H)-dione To a microwave vial containing (R)-5-(3-amino-3-(3,4-difluorophenyl)propyl)-6-chloro-3-ethylpyrimidine-2,4(1H,3H)-dione ((compound 9.4), 140 mg, 0.41 mmol) in n-BuOH (1.5 mL) was added K$_2$CO$_3$ (300 mg, 2.17 mmol, 5.3 equiv). The reaction mixture capped and heated in a microwave reactor at 140° C. for 10 min. The reaction mixture was cooled and filtered and the solid was further washed with n-BuOH (5 ml). The filtrate was concentrated and the crude residue was treated with 6 mL of 1:1 (v/v) mixture of H$_2$O/CH$_3$CN (0.1% (v/v) TFA). Solid precipitated and was isolated by filtration. The solid was further washed with H$_2$O (10 mL) and dried under reduced pressure to yield 52 mg (41%) of title compound as a white solid. LC-MS (ES, m/z): [M+H]$^+$=308. $^1$H-NMR (400 MHz, DMSO-d$_6$): δ 10.29 (br s, 1H), 7.47-7.35 (m, 2H), 7.15-7.10 (m, 1H) 6.40 (br s, 1H), 4.60-4.55 (m, 1H), 3.74 (q, J=6.8 Hz, 2H), 2.33-2.26 (m, 1H), 2.08-1.97 (m, 1H), 1.95-1.88 (m, 1H), 1.84-1.76 (m, 1H), 1.06 (t, J=6.8 Hz, 3H) ppm.

The following is a representative compound which was synthesized using the methodology outlined in example 9:

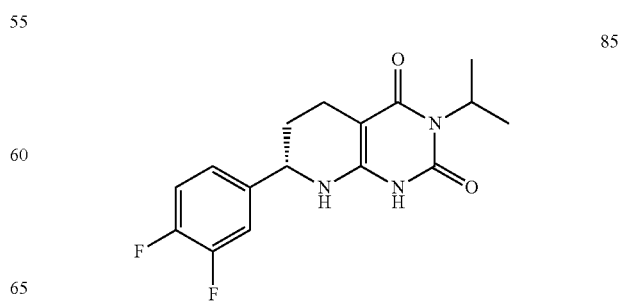

Example 10

Preparation of 3-isopropyl-5,6,7,8-tetrahydropyrido[2,3-d]pyrimidine-2,4(1H,3H)-dione

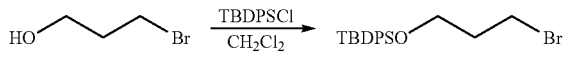

Compound 10.1. (3-Bromopropoxy)(tert-butyl)diphenylsilane

To a stirring solution of 3-bromopropan-1-ol (5.0 g, 36 mmol, 1.0 equiv) in $CH_2Cl_2$ (50 mL) under argon were added tert-butyl(chloro)diphenylsilane (14.9 g, 54.2 mmol, 1.5 equiv), 4-dimethylaminopyridine (2.2 g, 18 mmol, 0.50 equiv) and 1H-imidazole (4.9 g, 72 mmol, 2.0 equiv). The resulting solution was stirred overnight at room temperature and then was partitioned with $H_2O$ (2×100 mL). The organic layer was separated, dried over anhydrous $Na_2SO_4$ and concentrated in vacuo. The resulting residue was purified by silica gel column chromatography eluting with EtOAc/petroleum ether=80/1 (v/v). The fractions containing pure compound were combined and concentrated in vacuo to yield 9.0 g (66%) of the title compound as a yellow oil. $^1$H-NMR (400 MHz, $CDCl_3$): δ 7.70 (m, 4H), 7.45 (m, 6H), 3.83 (m, 2H), 3.63 (m, 2H), 2.13 (m, 2H), 1.10 (s, 9H) ppm.

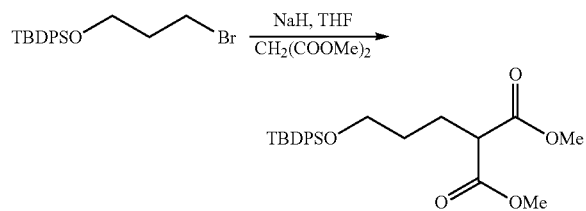

Compound 10.2. 1,3-Dimethyl 2-[3-[(tert-butyldiphenylsilyl)oxy]propyl]propanedioate To a stirring solution of 1,3-dimethyl propanedioate (800 mg, 6.06 mmol, 1.10 equiv) in THF (20 mL) at 0° C. under an argon atmosphere was added sodium hydride (130 mg, 5.40 mmol, 1.20 equiv), portion-wise. The resulting mixture was stirred for 1 h at 0° C. To this was added (3-bromopropoxy)(tert-butyl)diphenylsilane ((compound 10.1), 1.7 g, 4.5 mmol, 1.0 equiv). The resulting solution was stirred overnight at 60° C. Upon cooling, the mixture was diluted with $H_2O$ (50 mL) and extracted with EtOAc (2×50 mL). The organic layers were combined, dried over anhydrous $Na_2SO_4$ and concentrated in vacuo. The resulting residue was purified by silica gel column chromatography eluting with EtOAc/petroleum ether=1/9 (v/v). The fractions containing pure compound were combined and concentrated in vacuo to yield 1.5 g (78%) of the title compound as a light yellow oil. $^1$H-NMR (300 MHz, $CDCl_3$): δ 7.63 (m, 4H), 7.36 (m, 6H), 3.70 (s, 6H), 3.64 (t, J=6.3 Hz, 2H), 3.38 (t, J=7.5 Hz, 1H), 1.99 (m, 2H), 1.58-1.53 (m, 2H), 1.02 (s, 9H) ppm.

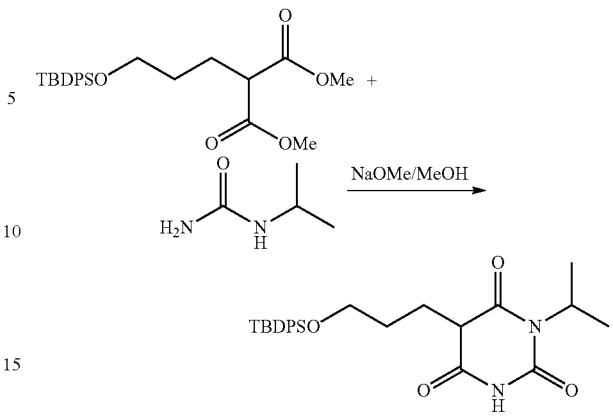

Compound 10.3. 5-(3-((tert-Butyldiphenylsilyl)oxy)propyl)-1-isopropylpyrimidine-2,4,6(1H,3H,5H)-trione To a stirring solution of sodium methoxide (160 mg, 1.00 equiv) in MeOH (10 mL) under argon was added 1,3-dimethyl 2-[3-[(tert-butyldiphenylsilyl)oxy]propyl]propanedioate ((compound 10.2), 1.0 g, 2.3 mmol, 1.0 equiv) and isopropylurea ((compound 1.1), 282 mg, 2.76 mmol, 1.20 equiv). The reaction mixture heated overnight at 65° C. The reaction was cooled and quenched by the addition of ice water (20 mL). The pH of the solution was adjusted to 1 with 2N $HCl_{(aq)}$ and the resulting solution was extracted with EtOAc (2×20 mL). The organic layers were combined, dried over anhydrous $Na_2SO_4$ and concentrated in vacuo. The resulting residue was purified by silica gel column chromatography eluting with EtOAc/petroleum ether=3/1 (v/v). The fractions containing pure compound were combined and concentrated in vacuo to yield 500 mg (46%) of the title compound as a yellow oil. LC-MS (ES, m/z): $[M+H]^+$=467. $^1$H-NMR (400 MHz, $CDCl_3$): δ 7.93 (s, 1H), 7.67 (m, 4H), 7.43 (m, 6H), 5.02 (m, 1H), 3.68 (m, 2H), 3.51 (m, 1H), 2.25 (m, 2H), 1.63 (m, 2H), 1.47 (d, J=4.0 Hz, 6H), 1.08 (s, 9H) ppm.

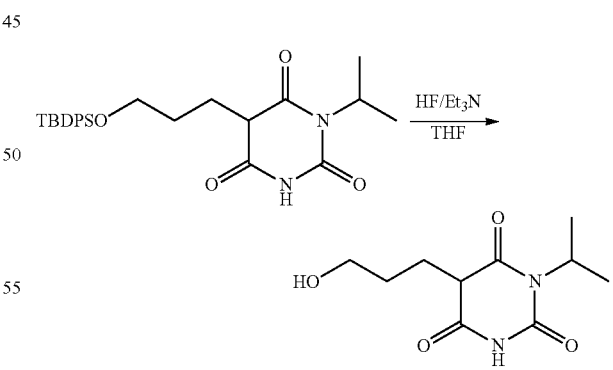

Compound 10.4. 5-(3-Hydroxypropyl)-1-isopropylpyrimidine-2,4,6(1H,3H,5H)-trione To a stirring solution of 5-(3-((tert-butyldiphenylsilyl)oxy)propyl)-1-isopropylpyrimidine-2,4,6(1H,3H,5H)-trione ((compound 10.3), 1 g, 2.14 mmol, 1.00 equiv) in THF (10 mL) under an argon atmosphere at 0° C. was added 3M hydrogen fluoride/triethylamine (2.5 mL, CAUTION!) dropwise. The resulting solution was stirred for 2 h at 20° C. The resulting mixture was concentrated in vacuo to yield 1.0 g (crude) of the title compound as a yellow oil. LC-MS (ES, m/z): [M+H]$^+$=229.

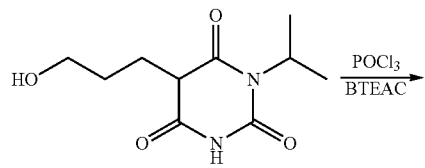

Compound 10.5. 6-Chloro-5-(3-chloropropyl)-3-isopropylpyrimidine-2,4(1H,3H)-dione To crude 5-(3-hydroxypropyl)-1-isopropylpyrimidine-2,4,6(1H,3H,5H)-trione ((compound 10.4), 489 mg, 2.14 mmol, 1.00 equiv) at 0° C. were added phosphoroyl trichloride (5 mL) and BTEAC (684 mg, 3.00 mmol, 1.40 equiv). The resulting solution was stirred overnight at 50° C. Upon cooling, the reaction was quenched by the addition of ice water (50 mL) (CAUTION!). The resulting solution was extracted with CH$_2$Cl$_2$ (5×100 mL) and the organic layers were combined. The organic solution was dried over anhydrous MgSO$_4$ and concentrated in vacuo. The resulting residue was purified by silica gel column chromatography eluting with EtOAc/petroleum ether=1/3 (v/v). The fractions containing pure compound were combined and concentrated in vacuo to yield 110 mg (19%) of the title compound as a yellow oil. $^1$H-NMR (300 MHz, CDCl$_3$): δ 10.68 (s, 1H), 5.11 (t, J=6.3 Hz, 1H), 3.54 (t, J=7.2 Hz, 2H), 2.58 (m, 2H), 1.97 (m, 2H), 1.44 (m, 6H) ppm.

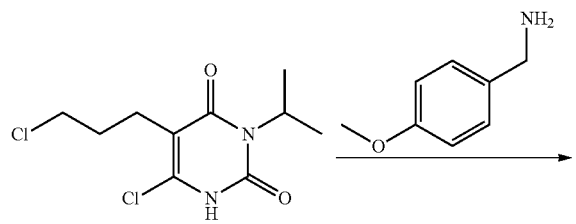

Compound 10.6. 3-Isopropyl-8-(4-methoxybenzyl)-5,6,7,8-tetrahydropyrido[2,3-d]pyrimidine-2,4(1H,3H)-dione Into a 10-mL round-bottom flask purged and maintained with an inert atmosphere of argon, was added 6-chloro-5-(3-chloropropyl)-3-isopropylpyrimidine-2,4(1H,3H)-dione ((compound 10.5), 10 mg, 0.04 mmol, 1.00 equiv) and (4-methoxyphenyl)methanamine (0.2 mL). The resulting mixture was stirred overnight at 100° C. The resulting mixture was concentrated in vacuo to yield 20 mg (crude) of the title compound as a yellow oil. LC-MS (ES, m/z): [M+H]$^+$=330.

Compound 10. 3-Isopropyl-5,6,7,8-tetrahydropyrido[2,3-d]pyrimidine-2,4(1H,3H)-dione To 3-isopropyl-8-(4-methoxybenzyl)-5,6,7,8-tetrahydropyrido[2,3-d]pyrimidine-2,4(1H,3H)-dione ((compound 10.6), 138.6 mg, 0.42 mmol, 1.00 equiv) under argon was added trifluoroacetic acid (5 mL). The resulting solution was stirred for 48 hours at 40° C. and then concentrated in vacuo. The resulting residue was purified by preparative HPLC (XBridge Prep C18 OBD Column, 5 um, 19*150 mm; mobile phase, H$_2$O (0.05% TFA) and CH$_3$CN (15.0% CH$_3$CN to 45.0% (v/v) over 10 min). The fractions containing pure compound were combined and lyophilized to yield 9.5 mg (11%) of the title compound as a white solid. LC-MS (ES, m/z): [M+H]$^+$=210. $^1$H-NMR (400 MHz, DMSO-d$_6$): δ 6.51 (m, 2H), 5.05-5.00 (m, 1H), 4.31 (t, J=4.8 Hz, 2H), 2.23 (t, J=4.4 Hz, 2H), 1.91 (t, J=5.2 Hz, 2H), 1.33 (d, J=6.8 Hz, 6H) ppm.

Example 11

Preparation of (R)-7-(3-chlorophenyl)-3-ethyl-5,6,7,8-tetrahydropyrido[2,3-d]pyrimidine-2,4(1H,3H)-dione

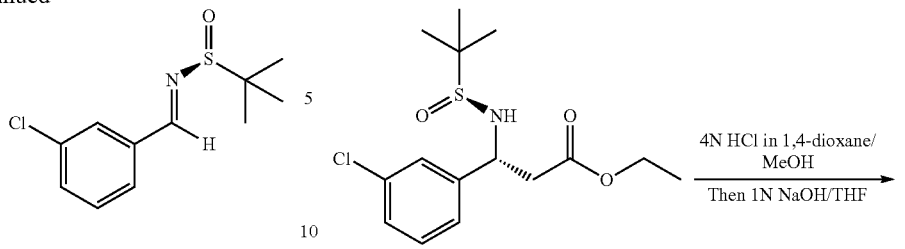

Compound 11.1. (S,E)-N-(3-Chlorobenzylidene)-2-methylpropane-2-sulfinamide

To 3-chlorobenzaldehyde (20 g, 142.28 mmol, 1.00 equiv) in in $CH_2Cl_2$ (500 mL) were added PPTS (1.8 g, 0.05 equiv), (S)-2-methylpropane-2-sulfinamide (26 g, 214.52 mmol, 1.50 equiv) and anhydrous $MgSO_4$ (85 g, 5.00 equiv). The resulting mixture was stirred overnight at 40° C. Upon cooling, the solid were removed by filtration and the filtrate was concentrated in vacuo. The resulting residue was purified by silica gel column chromatography eluting with EtOAc/petroleum ether=1/10 (v/v). The fractions containing pure compound were combined and concentrated in vacuo to yield 14 g (40%) of the title compound as yellow oil. LC-MS (ES, m/z): $[M+H]^+=244$. $^1$H-NMR (400 MHz, $CDCl_3$): 8.48 (s, 1H), 7.78 (m, 1H), 7.61 (m, 1H), 7.40 (m, 1H), 7.33 (m, 1H), 1.19 (s, 9H) ppm.

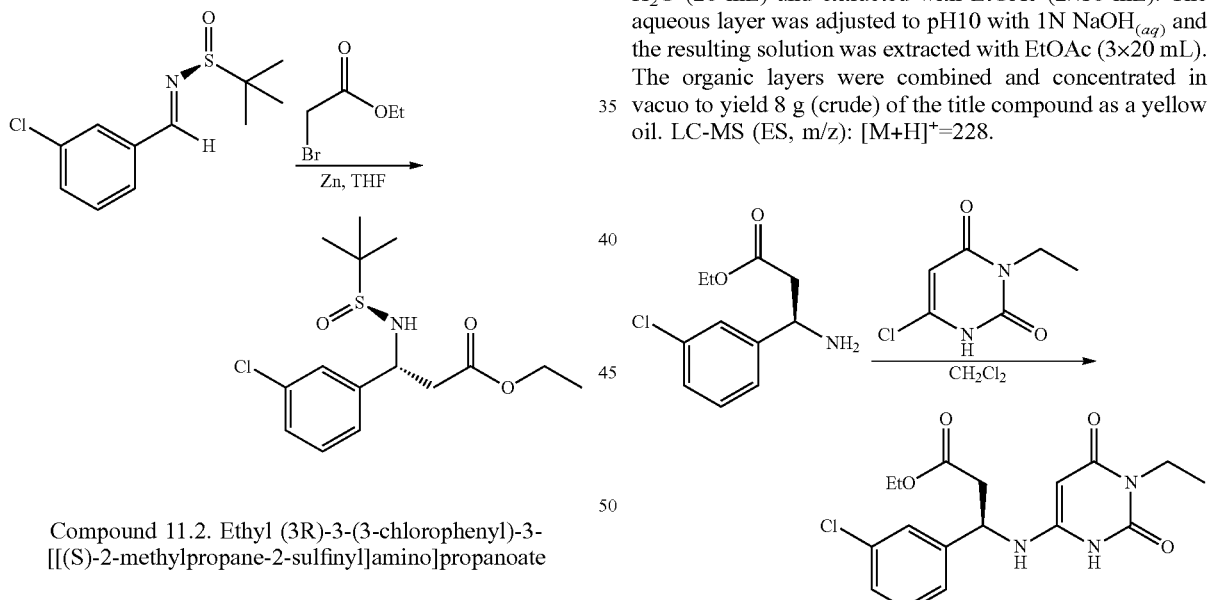

Compound 11.2. Ethyl (3R)-3-(3-chlorophenyl)-3-[[(S)-2-methylpropane-2-sulfinyl]amino]propanoate To a stirring solution of activated zinc powder (9.7 g, 3.00 equiv) in THF (200 mL) was added a solution of ethyl 2-bromoacetate (24.7 g, 147.90 mmol, 3.00 equiv) and (S,E)-N-(3-chlorobenzylidene)-2-methylpropane-2-sulfinamide ((11.1), 12 g, 49.23 mmol, 1.00 equiv) in THF (20 mL) dropwise. The resulting mixture was stirred for 1 h at 70° C. Upon cooling, the solid was removed by filtration and the filtrate was concentrated in vacuo. The resulting residue was purified by silica gel column chromatography eluting with EtOAc/petroleum ether=1/10 (v/v). This resulted in 11 g (67%) of the title compound as a yellow oil. LC-MS (ES, m/z): $[M+H]^+=332$. $^1$H-NMR (400 MHz, $CDCl_3$): δ 7.33-7.22 (m, 4H), 4.75 (m, 2H), 4.13 (m, 2H), 2.84 (m, 2H), 1.22 (m, 12H) ppm.

Compound 11.3. Ethyl (3R)-3-amino-3-(3-chlorophenyl)propanoate

To a stirring solution of ethyl (3R)-3-(3-chlorophenyl)-3-[[(S)-2-methylpropane-2-sulfinyl]amino]propanoate ((compound 11.2), 11 g, 33 mmol, 1.0 equiv) in MeOH (20 mL) was added 4N HCl in 1,4-dioxane (5 mL). The resulting mixture was stirred for 30 min at room temperature and then concentrated in vacuo. The crude residue was diluted with $H_2O$ (20 mL) and extracted with EtOAc (2×10 mL). The aqueous layer was adjusted to pH10 with 1N $NaOH_{(aq)}$ and the resulting solution was extracted with EtOAc (3×20 mL). The organic layers were combined and concentrated in vacuo to yield 8 g (crude) of the title compound as a yellow oil. LC-MS (ES, m/z): $[M+H]^+=228$.

Compound 11.4. Ethyl (3R)-3-(3-chlorophenyl)-3-[(1-ethyl-2,6-dioxo-1,2,3,6-tetrahydropyrimidin-4-yl)amino]propanoate To a stirring solution of ethyl (3R)-3-amino-3-(3-chlorophenyl)propanoate ((compound 11.3), 1.9 g, 8.3 mmol, 1.5 equiv) in $CH_2Cl_2$ (0.5 mL) was added 6-chloro-3-ethyl-1,2,3,4-tetrahydropyrimidine-2,4-dione (1 g, 5.73 mmol, 1.00 equiv). The resulting solution was stirred for 7 h at 120° C. The resulting solution was diluted with DMF (10 mL) and purified by preparative HPLC ((IntelFlash): Column, C18;

mobile phase, H₂O/CH₃CN=100/0 (v/v) increasing to H₂O/CH₃CN=0/100 (v/v) over 45 min). The fractions containing pure compound were combined and concentrated in vacuo to yield 1.7 g (81%) of the title compound as a yellow solid. LC-MS (ES, m/z): [M+H]⁺=366. ¹H-NMR (400 MHz, DMSO-d₆): 10.25 (s, 1H), 7.49 (m, 1H), 7.41-7.32 (m, 3H), 6.80 (m, 1H), 4.84 (m, 1H), 4.50 (s, 1H), 4.04 (m, 2H), 3.66 (m, 2H), 2.85 (m, 2H), 1.12 (m, 3H), 0.98 (m, 3H) ppm.

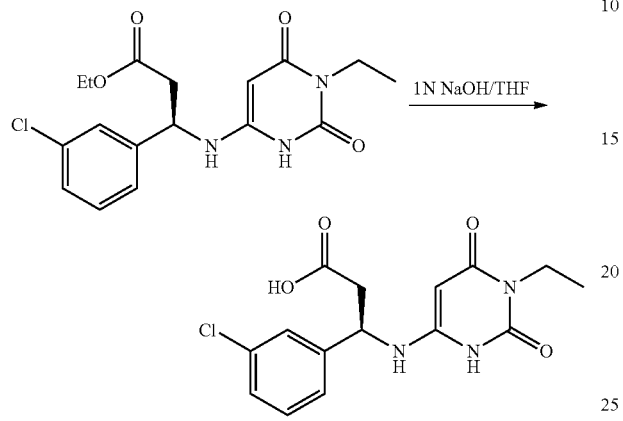

Compound 11.5. (3R)-3-(3-Chlorophenyl)-3-[(1-ethyl-2,6-dioxo-1,2,3,6-tetrahydropyrimidin-4-yl)amino]propanoic acid To a stirring solution of ethyl (3R)-3-(3-chlorophenyl)-3-[(1-ethyl-2,6-dioxo-1,2,3,6-tetrahydropyrimidin-4-yl)amino]propanoate ((compound 11.4), 1.7 g, 4.7 mmol, 1.0 equiv) in THF (4 mL) was added 1N aq. NaOH (5 mL). The resulting solution was stirred for 1 h at room temperature. The pH of the reaction mixture was adjusted to ~6 with an ion exchange resin (Dowex, 50WX8 (H) Fine Mesh Resin, 100-200 Mesh). The solid was removed by filtration and the filtrate was concentrated in vacuo to yield 1.4 g (89%) of the title compound as a white solid. LC-MS (ES, m/z): [M+H]⁺=338.

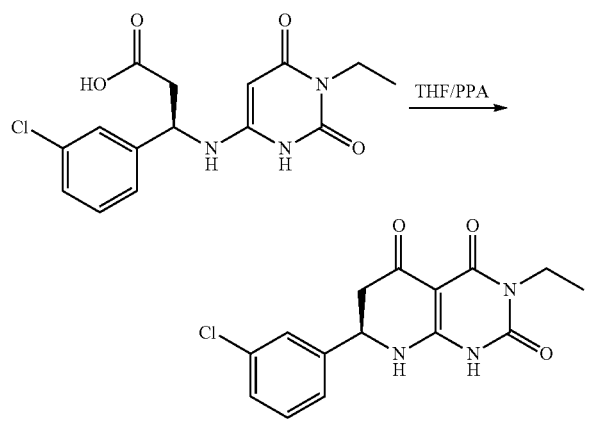

Compound 11.6. (R)-7-(3-Chlorophenyl)-3-ethyl-7,8-dihydropyrido[2,3-d]pyrimidine-2,4,5(1H,3H,6H)-trione To a 50-mL round-bottom flask purged and maintained with an inert atmosphere of argon, was added a solution of (3R)-3-(3-chlorophenyl)-3-[(1-ethyl-2,6-dioxo-1,2,3,6-tetrahydropyrimidin-4-yl)amino]propanoic acid ((compound 11.5), 900 mg, 2.66 mmol, 1.00 equiv) and THF (0.5 mL) in PPA (5 mL). The resulting solution was stirred for 2.5 h at 80° C. and then quenched with ice water (10 mL). The resulting solid was filtered and dried to afford 0.8 g (94%) of the title compound as a yellow solid. LC-MS (ES, m/z): [M+H]⁺=320.

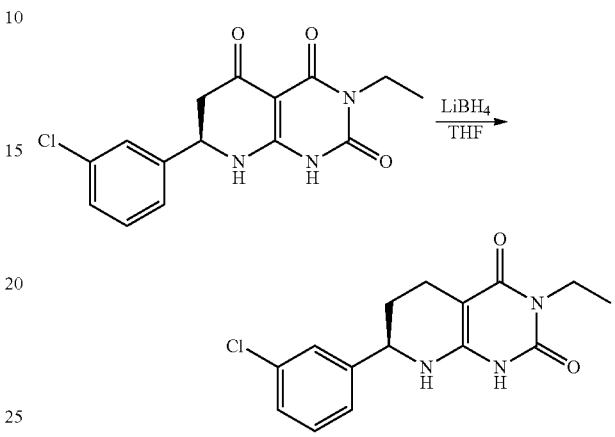

Compound 11. (R)-7-(3-Chlorophenyl)-3-ethyl-5,6,7,8-tetrahydropyrido[2,3-d]pyrimidine-2,4(1H,3H)-dione To a stirring solution of (R)-7-(3-chlorophenyl)-3-ethyl-7,8-dihydropyrido[2,3-d]pyrimidine-2,4,5(1H,3H,6H)-trione ((compound 11.6), 500 mg, 1.56 mmol, 1.00 equiv) in THF (5 mL) under argon at 0° C. was added LiBH₄ (4N in THF) (8 mL, 15.00 equiv) dropwise. The resulting solution was warmed to room temperature and stirred overnight. The reaction was quenched by the addition of saturated NH₄Cl$_{(aq)}$ (20 mL) and extracted with EtOAc (3×20 mL). The organic layers were combined, dried over anhydrous Na₂SO₄ and concentrated in vacuo. The resulting residue was purified by preparative HPLC (X Bridge RP Column, 19*150 mm, 5 um; Mobile Phase A: H₂O/10 mM NH₄HCO₃, Mobile Phase B: CH₃CN; Gradient: 30% B to 40% B over 9 min). The fractions containing pure compound were combined and lyophilized to yield 109.1 mg (23%) of the title compound as a white solid. LC-MS (ES, m/z): [M+H]⁺=306. ¹H-NMR (400 MHz, CD₃OD): δ 7.35-7.23 (m, 4H), 4.59-4.55 (m, 1H), 3.91 (q, J=7.2 Hz, 2H) 2.47-2.40 (m, 1H), 2.29-2.22 (m, 1H), 2.10-2.03 (m, 1H), 1.93-1.85 (m, 1H), 1.20 (t, J=7.2 Hz, 3H) ppm.

The following are representative compounds that were synthesized using the methodology outlined in example 11:

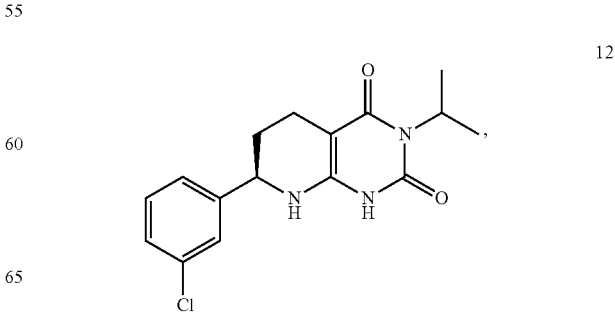

12

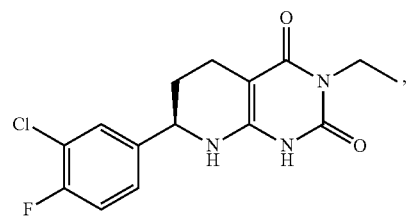
13
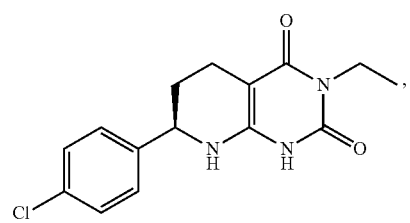
15
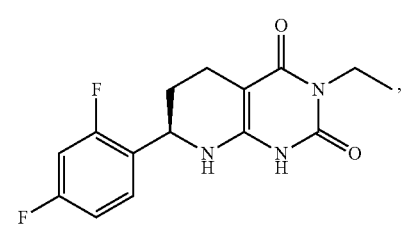
16
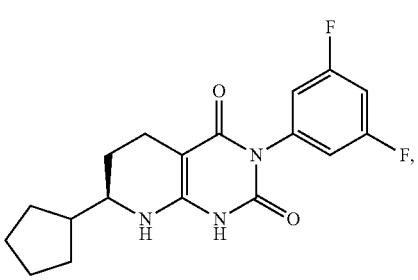
44
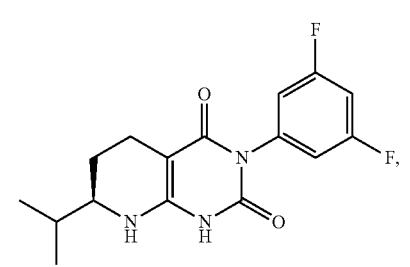
57
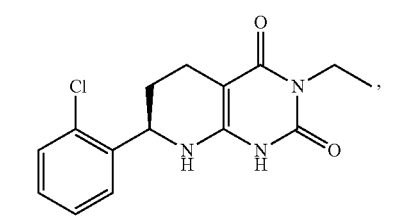
91
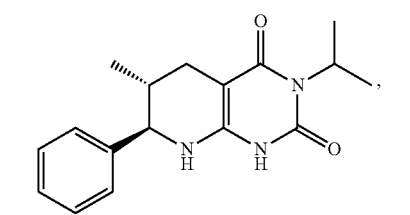
92
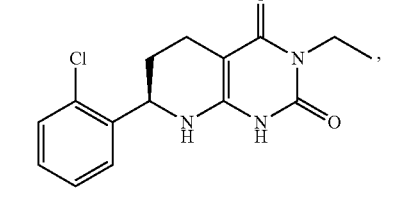
102
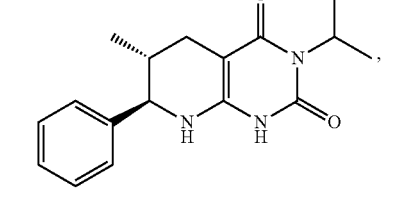
103
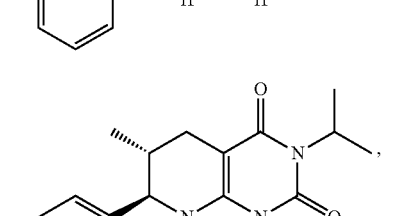
104
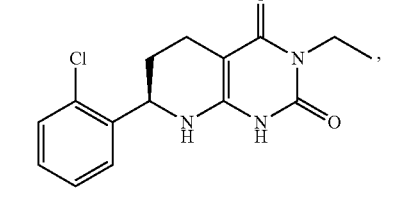
105
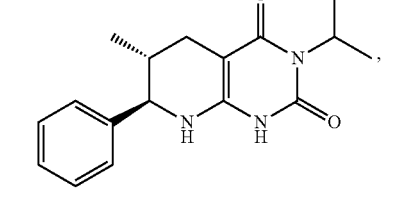
108
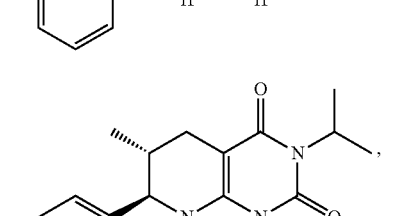
109

110

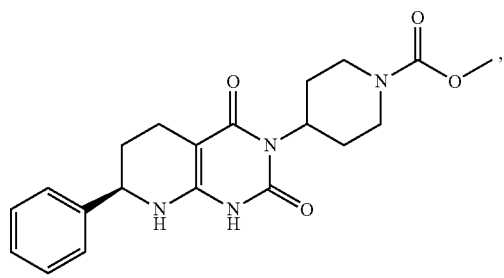

113

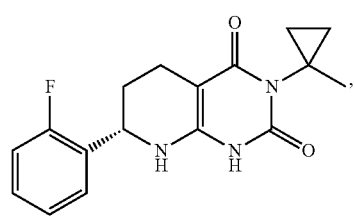

114

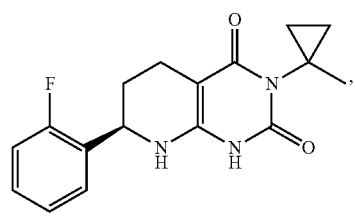

120

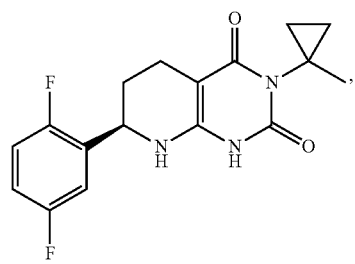

121

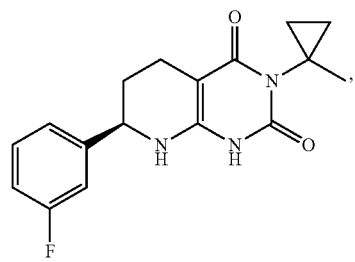

122

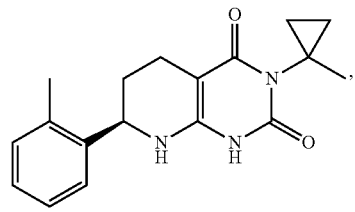

124

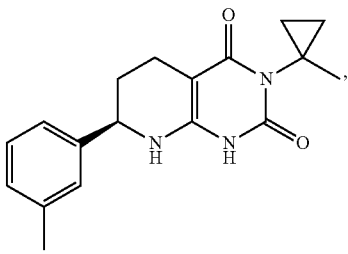

147

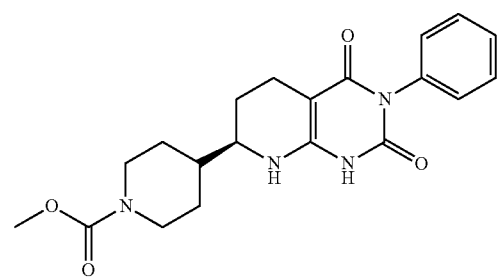

and

148

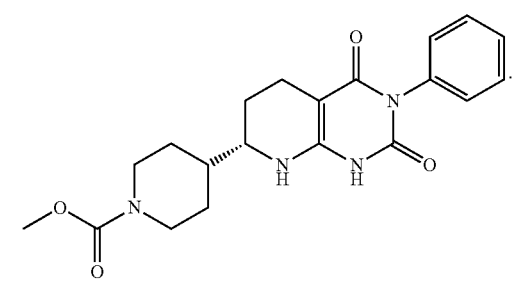

Example 12

Preparation of (R)-7-(3-fluorophenyl)-3-ethyl-5,6,7,8-tetrahydropyrido[2,3-d]pyrimidine-2,4(1H,3H)-dione

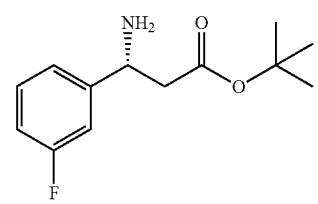 [SMILES: CC(C)(C)OC(=O)C[C@@H](N)c1cccc(F)c1]

Compound 68.1. tert-Butyl (R)-3-amino-3-(3-fluorophenyl)propanoate

Following the same procedure used to prepare tert-butyl (R)-3-amino-3-(3,4-difluorophenyl)propanoate (Compound 4.3) by replacing 3,4-difluorobenzaldehyde with 3-fluorobenzaldehyde, the title compound was prepared. LC-MS (ES, m/z): [M+H]$^+$=240.

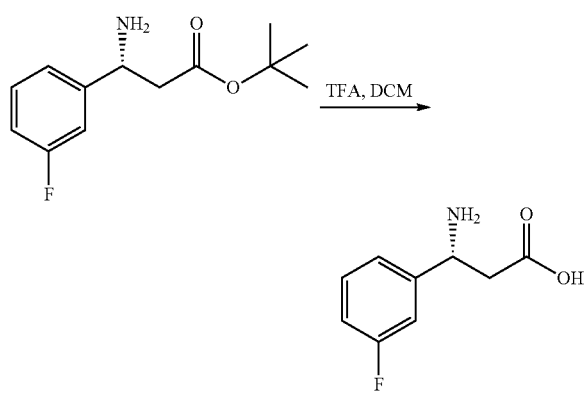

Compound 68.2.
(R)-3-Amino-3-(3-fluorophenyl)propanoic acid

Into a 250-mL round-bottom flask purged and maintained with an inert atmosphere of argon was placed tert-butyl (3R)-3-amino-3-(3-fluorophenyl)propanoate (13 g, 54.33 mmol, 1.00 equiv) in DCM (100 mL)/TFA (10 mL). After stirring at rt for 5 h, the reaction mixture was concentrated and the residue was adjusted to pH 7 with 1 N NaOH$_{(aq)}$. The resulting solution was extracted with EtOAc (100 mL×3) and the organic extracts were combined and dried over anhydrous sodium sulfate. The solvent was removed and the residue was dried in vacuo to give a crude material of the title compound (12 g) as a solid. LC-MS (ES, m/z): [M+H]$^+$=184.

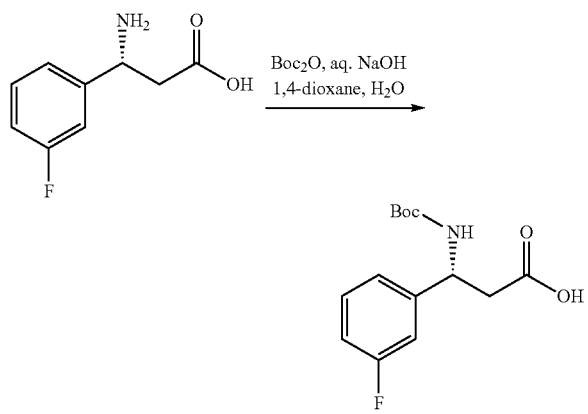

Compound 68.3. N-Boc-(R)-3-amino-3-(3-fluorophenyl)propanoic acid

Into a 250-mL round-bottom flask purged and maintained with an inert atmosphere of argon was placed (3R)-3-amino-3-(3-fluorophenyl)propanoic acid (11 g, 60.05 mmol, 1.00 equiv), sodium hydroxide (4.8 g, 120.00 mmol, 2.00 equiv), Boc$_2$O (19.6 g, 89.81 mmol, 1.50 equiv) in 1,4-dioxane (50 mL)/water (50 mL). The resulting solution was stirred for 3 h at room temperature. The pH value of the solution was adjusted to 6 with 1 M HCl$_{(aq)}$. The resulting solution was extracted with EtOAc (30 mL×3) and the organic layers were combined and dried over anhydrous sodium sulfate. The solvent was removed and the residue was dried in vacuo to give crude material of the title compound (10 g, 59% yield) as a yellow solid. LC-MS (ES, m/z): [M-Boc+H]$^+$=184.

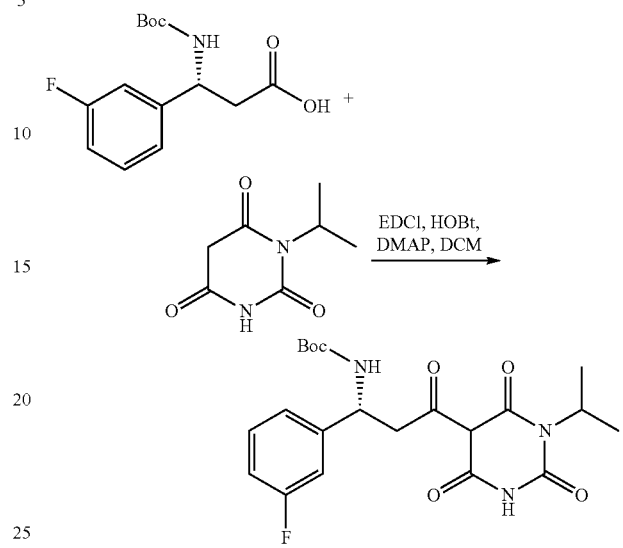

Compound 68.4. tert-Butyl ((1R)-1-(3-fluorophenyl)-3-(1-isopropyl-2,4,6-trioxohexahydropyrimidin-5-yl)-3-oxypropyl)carbamate Following the same procedure used to prepare tert-butyl ((1R)-1-(3,4-difluorophenyl)-3-(1-isopropyl-2,4,6-trioxohexahydropyrimidin-5-yl)-3-oxopropyl)carbamate (Compound 4.11) by replacing (R)-3-((tert-butoxycarbonyl)amino)-3-(3,4-difluorophenyl)propanoic acid (Compound 4.10) with N-Boc-(R)-3-amino-3-(3-fluorophenyl)propanoic acid (Compound 68.3), the title compound was prepared. LC-MS (ES, m/z): [M+H]$^+$=436.

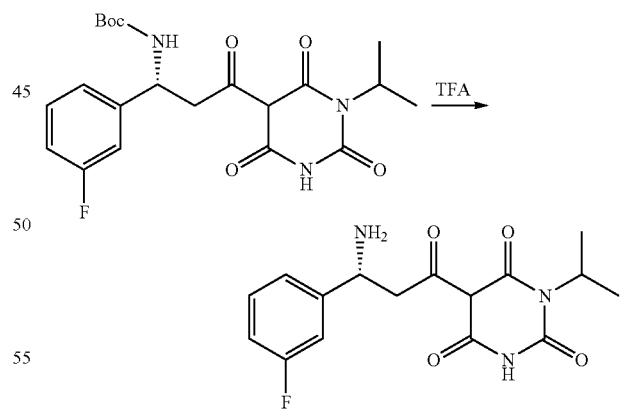

Compound 68.5. 5-((R)-3-Amino-3-(3-fluorophenyl)propanoyl)-1-isopropylpyrimidine-2,4,6(1H,3H,5H)-trione Following the same procedure used to prepare 5-((R)-3-amino-3-(3,4-difluorophenyl)-propanoyl)-1-isopropylpyrimidine-2,4,6(1H,3H,5H)-trione (Compound 4.12) by replacing tert-butyl ((1R)-1-(3,4-difluorophenyl)-3-(1-isopropyl-2,4,6-trioxohexahydropyrimidin-5-yl)-3-oxopropyl)carbamate (Compound 4.11) with tert-butyl ((1R)-1-(3-fluorophenyl)-3-(1-isopropyl-2,4,6-trioxohexahydropyrimidin-5-yl)-3-oxopropyl)carbamate (Compound 68.4), the title compound was prepared. LC-MS (ES, m/z): [M+H]$^+$=336.

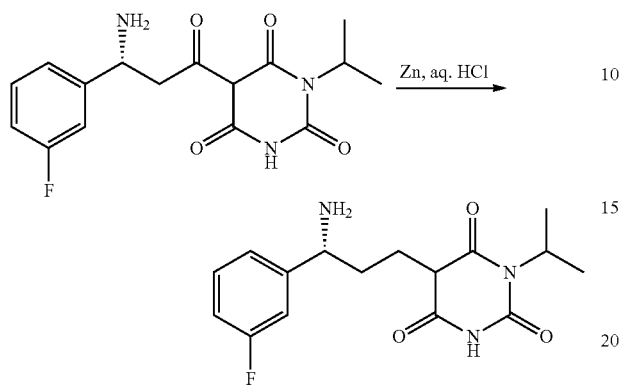

Compound 68.6. 5-((R)-3-Amino-3-(3-fluorophenyl)propyl)-1-isopropylpyrimidine-2,4,6(1H,3H,5H)-trione Following the same procedure used to prepare 5-((R)-3-amino-3-(3,4-difluorophenyl)propyl)-1-isopropylpyrimidine-2,4,6(1H,3H,5H)-trione (Compound 4.13) by replacing 5-((R)-3-amino-3-(3,4-difluorophenyl)propanoyl)-1-isopropylpyrimidine-2,4,6-(1H,3H,5H)-trione (Compound 4.12) with 5-((R)-3-amino-3-(3-fluorophenyl)propanoyl)-1-isopropylpyrimidine-2,4,6(1H,3H,5H)-trione (Compound 68.5), the title compound was prepared. LC-MS (ES, m/z): [M+H]$^+$=322.

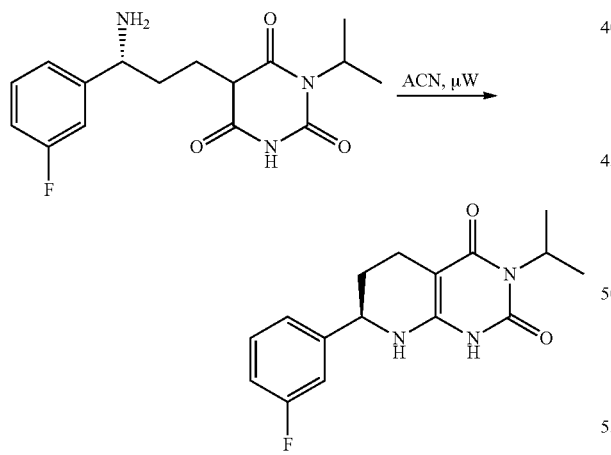

Compound 68. (R)-7-(3-Fluorophenyl)-3-isopropyl-5,6,7,8-tetrahydropyrido[2,3-d]pyrimidine-2,4(1H,3/H)-dione Into a 30-mL vial purged and maintained with an inert atmosphere of argon was placed 5-[(3R)-3-amino-3-(3-fluorophenyl)propyl]-1-(propan-2-yl)-1,3-diazinane-2,4,6-trione hydrochloride ((Compound 68.6), 1.5 g, 4.19 mmol, 1.00 equiv) in ACN (15 mL). The resulting solution was stirred for 2 h at 150° C. in a microwave bath. The resulting mixture was concentrated under vacuum. The resulting solution was diluted with DMF (3 mL). The crude product was purified by Flash-Prep-HPLC with the following conditions (IntelFlash-1): Column, C18 silica gel; mobile phase, CAN/H$_2$O=5:95 (v/v) increasing to CAN/H$_2$O=95:5 (v/v) within 40 min; Detector, UV at 254 nm to give 1.3 g crude product, which was further purified by Prep-SFC with the following conditions: Column: Chiralpak IC, 2*25 cm, 5 μm; Mobile Phase A: CO$_2$: 75%, Mobile Phase B: MeOH (0.1% (v/v) DEA) 25%; Flow rate: 45 mL/min; UV at 220 nm; S-isomer: t$_R$=4.83 min; R-siomer: t$_R$=5.98 min. This resulted in 1.07 g (84% yield) of the title compound as a white solid. LC-MS (ES, m/z): [M+H]$^+$=304.

Example 13

Preparation of (R)-7-(2-fluorophenyl)-3-ethyl-5,6,7,8-tetrahydropyrido[2,3-d]pyrimidine-2,4(1H,3H)-dione

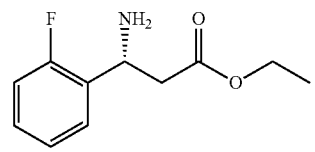

Compound 69.1. Ethyl (R)-3-amino-3-(2-fluorophenyl)propanoate

Following the same procedure used to prepare tert-butyl (R)-3-amino-3-(3,4-difluorophenyl)propanoate (Compound 4.3) by replacing 3,4-difluorobenzaldehyde with 2-fluorobenzaldehyde and tert-butyl 2-(diethoxyphosphoryl)acetate with ethyl 2-(diethoxyphosphoryl)acetate, the title compound was prepared. LC-MS (ES, m/z): [M+H]$^+$=240.

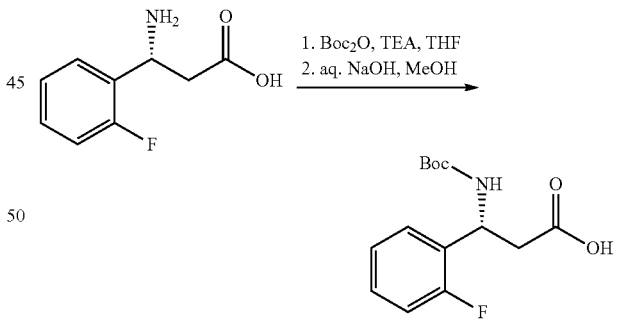

Compound 69.2. N-Boc-(R)-3-amino-3-(2-fluorophenyl)propanoic acid

Into a 250-mL round-bottom flask purged and maintained with an inert atmosphere of argon was placed a solution of ethyl (3R)-3-amino-3-(2-fluorophenyl)propanoate ((Compound 69.1), 3.4 g, 16.10 mmol, 1.00 equiv), TEA (4.88 g, 48.32 mmol, 3.00 equiv), Boc$_2$O (5.27 g, 24.17 mmol, 1.50 equiv) in THF (50 mL). After stirring at rt for 1 h, the reaction mixture was diluted with water (20 mL). The resulting mixture was extracted with EtOAc (300 mL×3)

and the organic extracts were combined, washed with brine (300 mL), dried over anhydrous Na$_2$SO$_4$. The solvent was removed and the residue was dried in vacuo. Subsequently, the residue was dissolved in MeOH (20 mL), followed by adding 2 N NaOH$_{(aq)}$ (5 mL). After stirring at rt for 2 h, the mixture was diluted with water (100 mL) and extracted with EtOAc (20 mL×3). The pH value of the aq. Layer was adjusted to around 6 with 1N HCl$_{(aq)}$. The resulting solution was extracted with EtOAc (100 mL×3) and the organic extracts were combined, dried over anhydrous Na$_2$SO$_4$. The solvent was removed and the residue was dried in vacuo to give 3.9 g (86% yield) of the title compound as a white solid. LC-MS (ES, m/z): [M-Boc+H]$^+$=184.

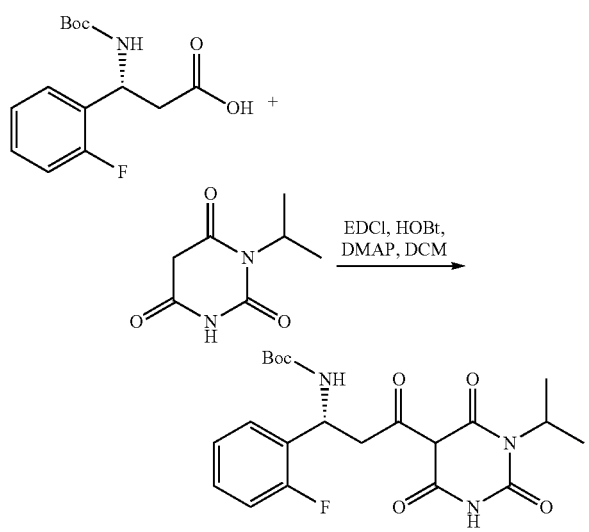

Compound 69.3. tert-Butyl ((1R)-1-(2-fluorophenyl)-3-(1-isopropyl-2,4,6-trioxohexahydropyrimidin-5-yl)-3-oxopropyl)carbamate Following the same procedure used to prepare tert-butyl ((1R)-1-(3,4-difluorophenyl)-3-(1-isopropyl-2,4,6-trioxohexahydropyrimidin-5-yl)-3-oxopropyl)carbamate (Compound 4.11) by replacing (R)-3-((tert-butoxycarbonyl)amino)-3-(3,4-difluorophenyl)propanoic acid (Compound 4.10) with N-Boc-(R)-3-amino-3-(3-fluorophenyl)propanoic acid (Compound 69.2), the title compound was prepared. LC-MS (ES, m/z): [M+H]$^+$=436.

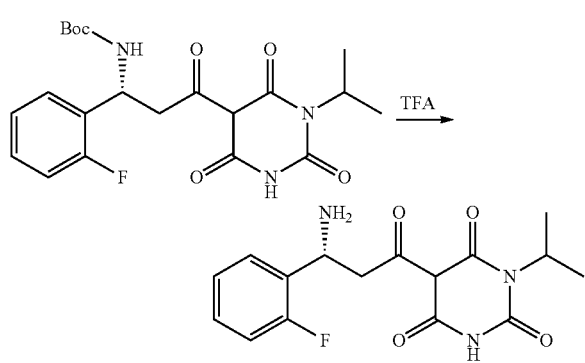

Compound 69.4. 5-((R)-3-Amino-3-(2-fluorophenyl)propanoyl)-1-isopropylpyrimidine-2,4,6(1H,3H,5H)-trione Following the same procedure used to prepare 5-((R)-3-amino-3-(3,4-difluorophenyl)-propanoyl)-1-isopropylpyrimidine-2,4,6(1H,3H,5H)-trione (Compound 4.12) by replacing tert-butyl ((1R)-1-(3,4-difluorophenyl)-3-(1-isopropyl-2,4,6-trioxohexahydropyrimidin-5-yl)-3-oxopropyl) carbamate (Compound 4.11) with tert-butyl ((1R)-1-(2-fluorophenyl)-3-(1-isopropyl-2,4,6-trioxohexahydropyrimidin-5-yl)-3-oxopropyl)carbamate (Compound 69.3), the title compound was prepared. LC-MS (ES, m/z): [M+H]$^+$=336.

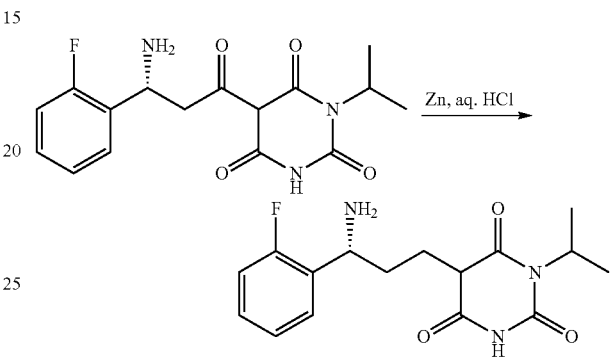

Compound 69.5. 5-((R)-3-Amino-3-(2-fluorophenyl)propyl)-1-isopropylpyrimidine-2,4,6(1H,3H, 5H)-trione Following the same procedure used to prepare 5-((R)-3-amino-3-(3,4-difluorophenyl)propyl)-1-isopropylpyrimidine-2,4,6(1H,3H,5H)-trione (Compound 4.13) by replacing 5-((R)-3-amino-3-(3,4-difluorophenyl)propanoyl)-1-isopropylpyrimidine-2,4,6-(1H,3H,5H)-trione (Compound 4.12) with 5-((R)-3-amino-3-(2-fluorophenyl)propanoyl)-1-isopropylpyrimidine-2,4,6(1H,3H,5H)-trione (Compound 69.4), the title compound was prepared. LC-MS (ES, m/z): [M+H]$^+$=322.

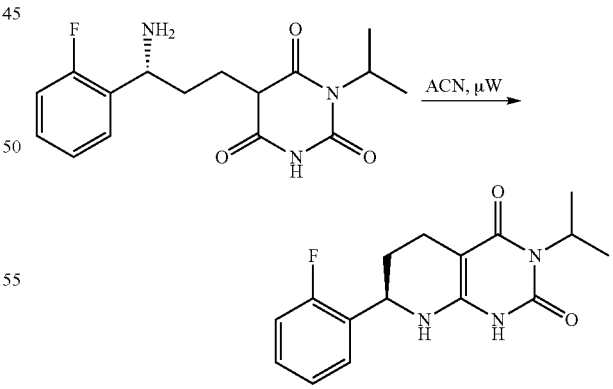

Compound 69. (R)-7-(2-Fluorophenyl)-3-isopropyl-5,6,7,8-tetrahydropyrido[2,3-d]pyrimidine-2,4(1H, 3H)-dione Following the same procedure used to prepare (R)-7-(2-fluorophenyl)-3-isopropyl-5,6,7,8-tetrahydropyrido[2,3-d]

pyrimidine-2,4(1H,3H)-dione (Compound 68) by replacing 5-[(3R)-3-amino-3-(3-fluorophenyl)propyl]-1-(propan-2-yl)-1,3-diazinane-2,4,6-trione hydrochloride (Compound 68.6) with 5-((R)-3-amino-3-(2-fluorophenyl)propyl)-1-isopropylpyrimidine-2,4,6(1H,3H,5H)-trione (Compound 69.5), the title compound was prepared. LC-MS (ES, m/z): [M+H]$^+$=304.

Example 14

Preparation of (7R)-7-(4-fluorophenyl)-5-hydroxy-3-phenyl-5,6,7,8-tetrahydropyrido[2,3-d]pyrimidine-2,4(1H,3H)-dione

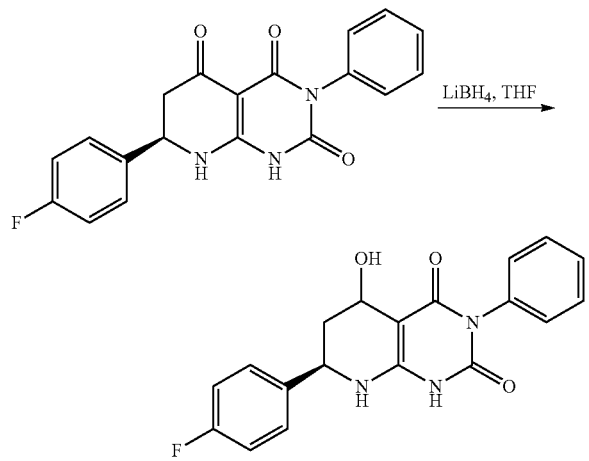

Compound 95. (7R)-7-(4-Fluorophenyl)-5-hydroxy-3-phenyl-5,6,7,8-tetrahydropyrido[2,3-d]pyrimidine-2,4(1H,3H)-dione A mixture of (R)-7-(4-fluorophenyl)-3-phenyl-7,8-dihydropyrido[2,3-d]pyrimidine-2,4,5(1H,3H,6H)-trione (35 mg, 1 mmol, 1.0 eq) in THF (4 mL, 0.1 M) was added LiBH$_4$ (21 mg, 1 mmol, 10.0 eq.). After stirring at rt overnight, the reaction was quenched by adding several milliliters of acetone. The solvent was removed and the residue was purified by preparative HPLC to give the title compound (26.5 mg, 75% yield) as a white solid. LC-MS (ES, m/z): [M+H]$^+$=354.

Example 15

Preparation of (7R)-7-(3,4-difluorophenyl)-3-isopropyl-5,6,7,8-tetrahydropyrido[2,3-d]pyrimidine-2,4(1H,3H)-dione-5,5-d$_2$

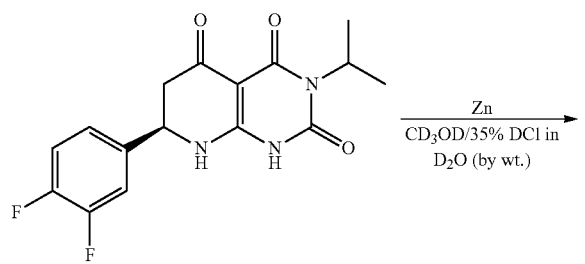

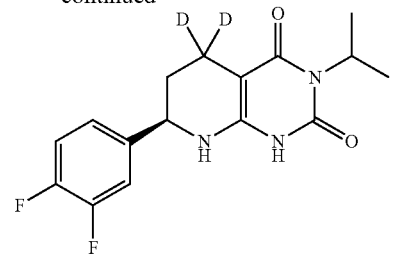

Compound 101. (7R)-7-(3,4-Difluorophenyl)-3-isopropyl-5,6,7,8-tetrahydropyrido[2,3-d]pyrimidine-2,4(1H,3H)-dione-5,5-d$_2$ To a stirring solution of (R)-7-(3,4-difluorophenyl)-3-isopropyl-7,8-dihydropyrido[2,3-d] pyrimidine-2,4,5(1H,3H,6H)-trione ((Compound 4.6), 28 mg, 84 μmol) in CD$_3$OD (5 mL) with 35% DCl in D$_2$O by weight (5 mL, Sigma Aldrich) was added Zinc (100 mg). The reaction mixture was heated at 65° C. for 1 h. The reaction mixture was cooled, filtered, and concentrated. The resulting material was dissolved in ACN/H$_2$O (0.1% TFA) (5 mL) and purified by preparative HPLC utilizing 30% of ACN (0.1% TFA) up to 75% of ACN (0.1% TFA) in H$_2$O (0.1% TFA) (v/v) as eluent over 23 min. The fractions containing the product were combined, frozen, and lyophilized to dryness, giving 8 mg (29% yield) of the title compound as a white solid. LC-MS (ES, m/z): [M+H]$^+$=324.

Example 16

Preparation of (R)- and (S)-6,6-difluoro-3-isopropyl-7-phenyl-5,6,7,8-tetrahydropyrido[2,3-d]pyrimidine-2,4(1H,3H)-dione

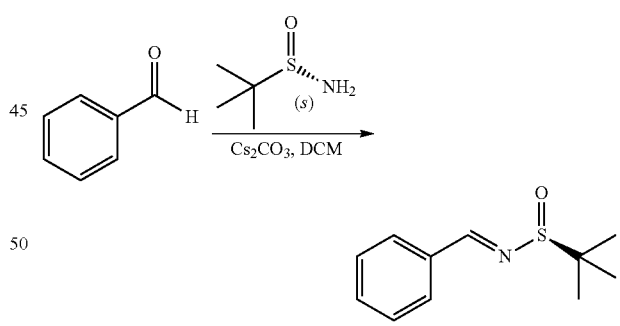

Compound 116.1. (S,E)-N-Benzylidene-2-methylpropane-2-sulfinamide

A mixture of benzaodehyde (10.0 g, 94.3 mmol), (S)-2-methylpropane-2-sulfinamide (11.4 g, 94.3 mmol) and Cs$_2$CO$_3$ (36.5 g, 113.2 mmol) in DCM (500 mL) was stirred at room temperature overnight. The reaction mixture was filtered and the filtrate was concentrated. The residue was purified by silica gel column chromatography using Petroleum ether/EtOAc=2:1 (v/v) as the eluent to give the title compound (17.1 g, 86%) as colorless oil. LC-MS (ES, m/z): [M+H]$^+$=210.

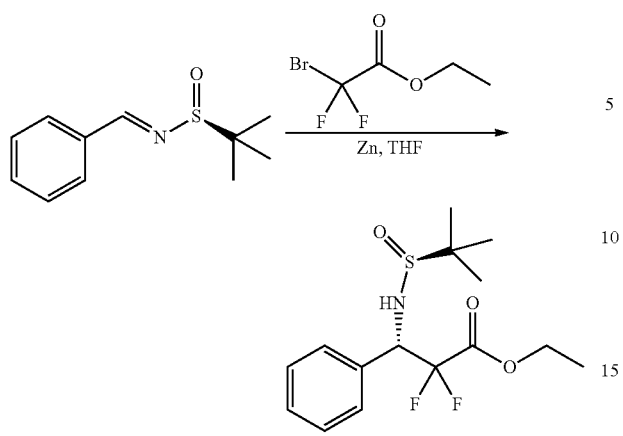

Compound 116.2. Ethyl (S)-3-(((S)-tert-butylsulfi-nyl)amino)-2,2-difluoro-3-phenylpropanoate A solution of Zn (7.8 g, 120.5 mmol) and ethyl 2-bromo-2,2-difluoroacetate (15.2 g, 75.6 mmol) in dry THF (200 mL) was stirred at refluxing for 30 mins. Then (S,E)-N-benzylidene-2-methylpropane-2-sulfinamide ((Compound 116.1), 7.2 g, 34.4 mmol) in dry THF (100 mL) was added to the mixture slowly at that temperature. After stirring at reflux for 1.5 h, the reaction mixture was filtered and the filtrate was concentrated. The residue was purified by silica gel column chromatography using Petroleum ether/EtOAc=1:2 (v/v) as the eluent to give the title compound (5.0 g, 43% yield) as colorless oil. LC-MS (ES, m/z): [M+H]$^+$=334.

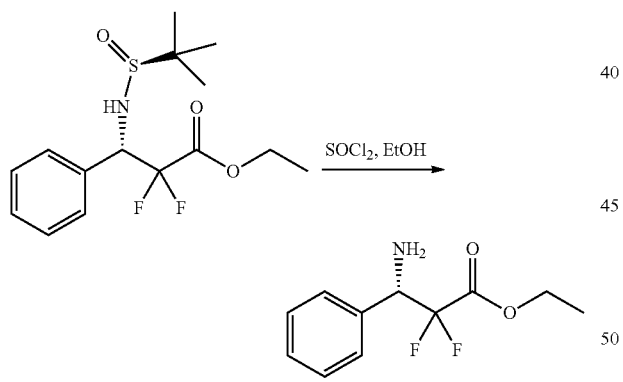

Compound 116.3. Ethyl (S)-3-amino-2,2-difluoro-3-phenylpropanoate

To a mixture of ethyl (S)-3-(((S)-tert-butylsulfinyl)amino)-2,2-difluoro-3-phenylpropanoate ((Compound 116.2), 5.0 g, 15.0 mmol) in EtOH (150 mL) was added SOCl$_2$ (2.3 g, 19.5 mmol) slowly at room temperature for 5 min. After stirring at rt for 2 h, the reaction mixture was concentrated and the residue was dried in vacuo to give a crude material of the title compound (3.3 g, purity 92%) as a white solid, which was used directly in the next step without further purification. LC-MS (ES, m/z): [M+H]$^+$=230.

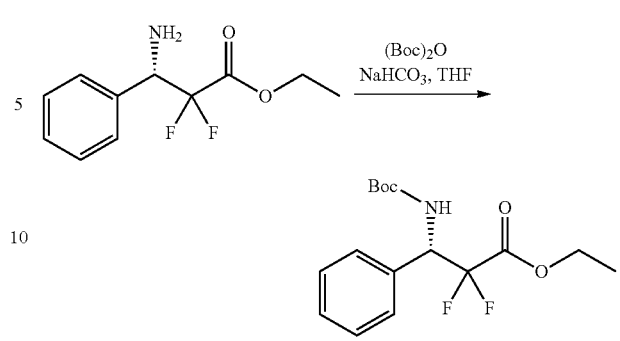

Compound 116.4. Ethyl (S)-3-((tert-butoxycarbonyl)amino)-2,2-difluoro-3-phenylpropanoate A mixture of ethyl (S)-3-amino-2,2-difluoro-3-phenylpropanoate ((Compound 116.3), 3.0 g, 13.1 mmol), (Boc)$_2$O (5.7 g, 26.2 mmol) and NaHCO$_3$ (3.3 g, 39.3 mmol) in THF (150 mL) was stirred at reflux overnight. The reaction mixture was diluted with water (500 mL) and the mixture was extracted with EtOAc (100 mL×3). The organic extracts were combined, washed with brian, and dried over anhydrous Na$_2$SO$_4$. The solvent was removed and the residue was purified by silica gel column chromatography using Petroleum ether/EtOAc=20:1 (v/v) as the eluent to give the title compound (4.1 g, 93% yield) as a white solid. LC-MS (ES, m/z): [M+H]$^+$=330.

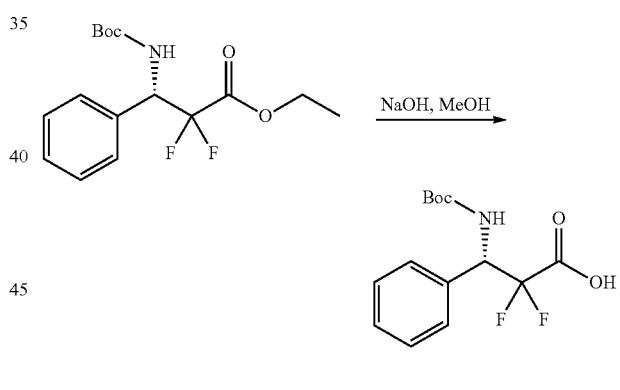

Compound 116.5. (S)-3-((tert-Butoxycarbonyl)amino)-2,2-difluoro-3-phenylpropanoic acid A mixture of ethyl (S)-3-((tert-butoxycarbonyl)amino)-2,2-difluoro-3-phenylpropanoate ((Compound 116.4), 4.1 g, 12.4 mmol), 2 N NaOH (5 eq.) in MeOH was stirred at room temperature overnight. The mixture was concentrated and the residue was diluted with water and adjusted pH to 4-5 using 6N HCl$_{(aq)}$. Subsequently, the mixture was extracted with EtOAc (80 mL×3) and the combined organic extracts were washed with brine (50 mL×3) and dried over anhydrous sodium sulfate. The solvent was removed and the residue was dried in vacuo to give a crude material of the title compound (3.5 g, purity 91%) as a white solid, which was used in the next step without further purification. LC-MS (ES, m/z): [M+Na]$^+$=302.

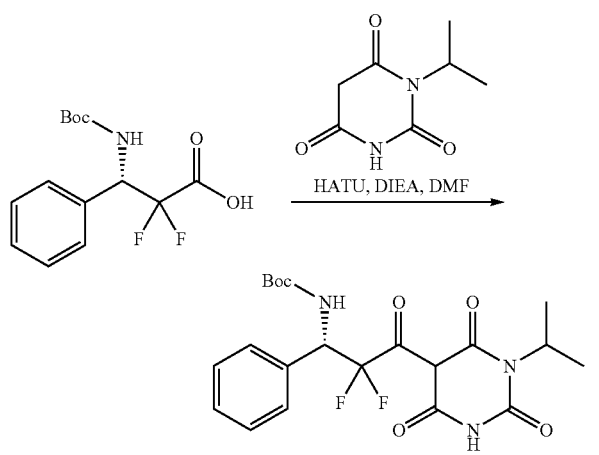

Compound 116.6. tert-Butyl ((1S)-2,2-difluoro-3-(1-isopropyl-2,4,6-trioxohexahydropyrimidin-5-yl)-3-oxo-1-phenylpropyl)carbamate A mixture of (S)-3-((tert-butoxycarbonyl)amino)-2,2-difluoro-3-phenylpropanoic acid ((Compound 116.5), 1.7 g, 5.6 mmol), HATU (2.5 g, 6.7 mmol) and DIPEA (2.1 g, 16.8 mmol) in DMF (40 mL) was stirred at room temperature for 30 min. Subsequently, 1-isopropylpyrimidine-2,4,6(1H,3H,5H)-trione ((Compound 1.2), 1.4 g, 8.4 mmol, 1.5 eq.) was added and the mixture was stirred at room temperature overnight. The reaction mixture was concentrated and the residue was diluted with EtOAc (100 mL). The resulting mixture was washed with water and dried over anhydrous $Na_2SO_4$. The solvent was removed and the residue was purified by silica gel column chromatography using DCM/MeOH=10:1 (v/v) as the eluent to give the title compound (810 mg, 31% yield) as a yellow oil. LC-MS (ES, m/z): $[M+H]^+$=454.

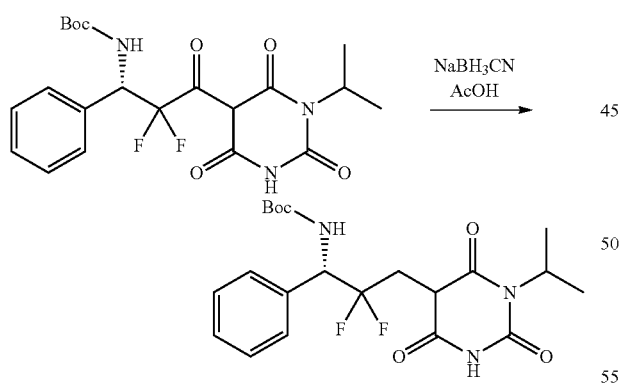

Compound 116.7. tert-Butyl ((1S)-2,2-difluoro-3-(1-isopropyl-2,4,6-trioxohexahydropyrimidin-5-yl)-1-phenylpropyl)carbamate To a solution of tert-butyl ((1S)-2,2-difluoro-3-(1-isopropyl-2,4,6-trioxohexahydropyrimidin-5-yl)-3-oxo-1-phenylpropyl)carbamate ((Compound 116.6), 810 mg, 1.7 mmol) in AcOH (20 mL) was added $NaBH_3CN$ (3.2 g, 5.1 mmol). After stirring at rt for 2 h, the reaction mixture was concentrated and the residue was dried in vacuo to give a crude material of the title compound (750 mg, purity 96%), which was used directly in the next step without further purification. LC-MS (ES, m/z): $[M+H]^+$=440.

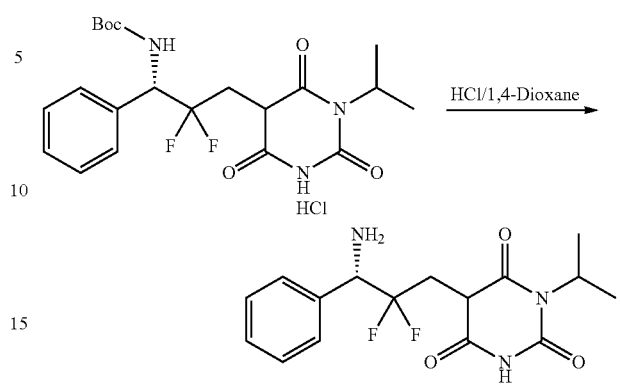

Compound 116.8. 5-((S)-3-Amino-2,2-difluoro-3-phenylpropyl)-1-isopropylpyrimidine-2,4,6(1H,3H,5H)-trione hydrochloride To a solution of crude tert-Butyl ((1S)-2,2-difluoro-3-(1-isopropyl-2,4,6-trioxohexahydropyrimidin-5-yl)-1-phenylpropyl)carbamate ((Compound 116.7), 750 mg, 1.7 mmol) in DCM (15 mL) was added 4M HCl in dioxane (5 mL). After stirring at rt for 4 h, the reaction mixture was concentrated and the residue was dried in vacuo to give a crude material of the title compound (500 mg, purity 92%), which was used directly in the next step without further purification. LC-MS (ES, m/z): $[M+H]^+$=340.

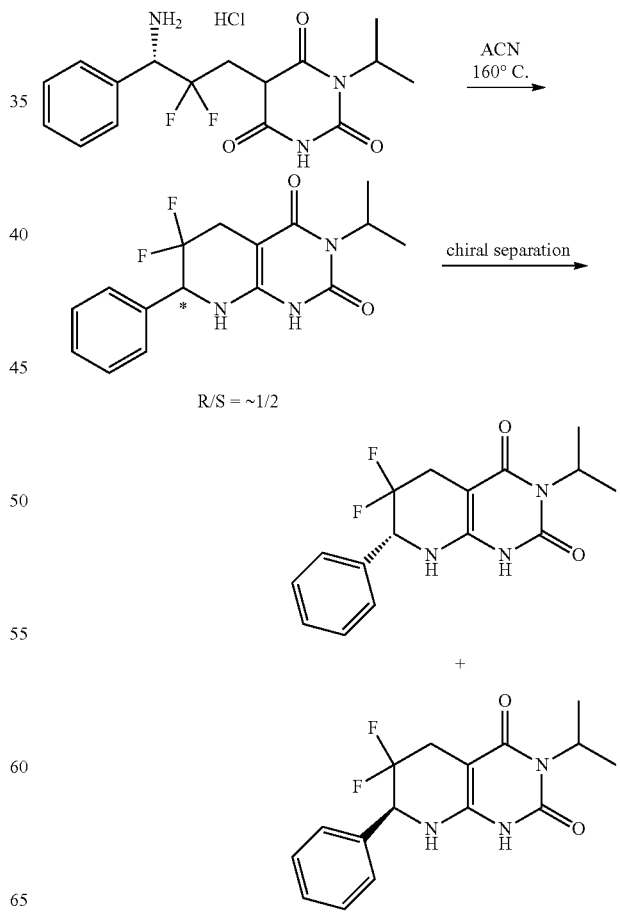

R/S = ~1/2

Compound 116. (S)-6,6-Difluoro-3-isopropyl-7-phenyl-5,6,7,8-tetrahydropyrido[2,3-d]pyrimidine-2,4(1H,3H)-dione A reaction mixture of 5-((S)-3-amino-2,2-difluoro-3-phenylpropyl)-1-isopropylpyrimidine-2,4,6(1H,3H,5H)-trione hydrochloride ((Compound 116.8), 500 mg, 1.5 mmol) in $CH_3CN$ was heated at 160° C. in a microwave device for 2 h. The solid was filtered, washed with $CH_3CN$, and then purified by prep-HPLC to afford a crude material (250 mg) as a white solid, which was further purified by chiral HPLC (Column: AS-H (4.6×250 mm, 5 μm); Co-solvent: MeOH (0.2% Methanol Ammonia); Column Temperature: 32.6° C.; $CO_2$ Flow Rate: 2.55 mL/min; Co-Solvent Flow Rate: 0.45 mL/min; Co-Solvent %: 15; Back Pressure: 122 par; Total Flow: 3 mL/min; PDA Start Wavelength: 214 nm; PDA Stop Wavelength: 359 nm) to give the title compound ($t_R$=4.9 min, 89.8 mg, 19% yield) as a white solid. LC-MS (ES, m/z): $[M+H]^+$=322.

Compound 117. (R)-6,6-Difluoro-3-isopropyl-7-phenyl-5,6,7,8-tetrahydropyrido[2,3-d]pyrimidine-2,4(1H,3H)-dione The fractions at $t_R$=4.09 min were collected and dried in vacuo to give the title compound (36.7 mg, 7.7% yield) as a white solid. LC-MS (ES, m/z): $[M+H]^+$=322.

The following are representative compounds that were synthesized using the methodology outlined in example 16:

116
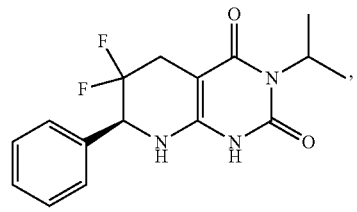

117
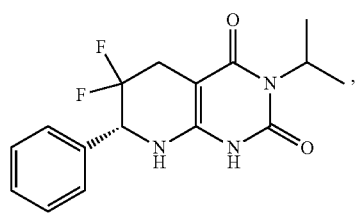

129
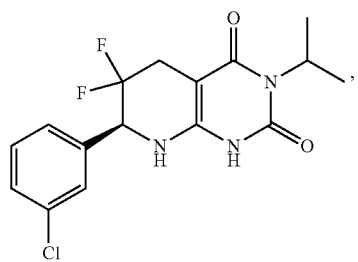

130
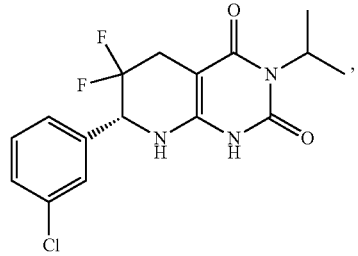

140
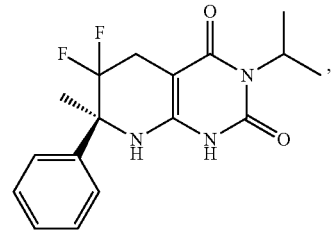

149
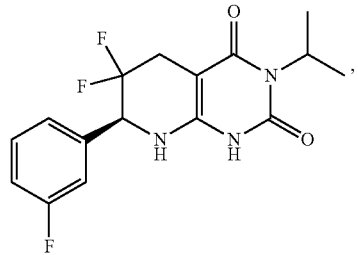

150
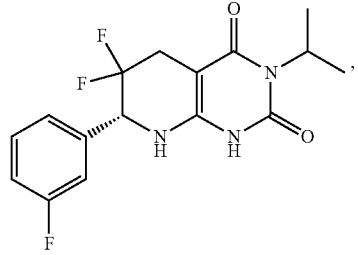

151
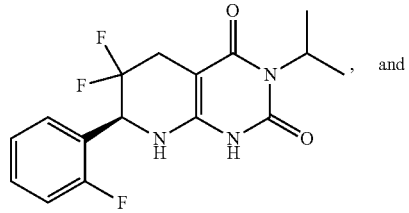
and

152
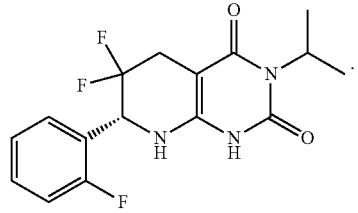

Example 17

Preparation of (R)-7-(3-fluorophenyl)-3,7-dimethyl-5,6,7,8-tetrahydropyrido[2,3-d]pyrimidine-2,4(1H,3H)-dione

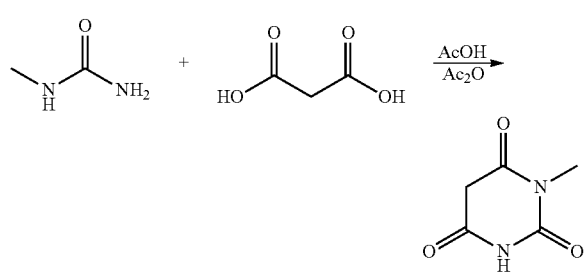

Compound 126.1.
1-Methylpyrimidine-2,4,6(1H,3H,5H)-trione

To a solution of 1-methylurea (14 g, 189 mmol, 1.0 eq.) and malonic acid (23.6 g, 226.8 mmol, 1.2 eq.) in acetic acid (60 mL), acetic anhydride (36 mL, 378 mmol, 2.0 eq.) was added slowly at 70° C. After the completion of the addition, the reaction mixture was stirred at 90° C. for 3 h and then cooled to rt. The reaction mixture was concentrated and the residue was diluted with EtOH (100 mL). The solid was collected and re-crystalized in EtOH to give the title compound (17.0 g, 64% yield) as a light yellow solid. LC-MS (ES, m/z): [M+H]$^+$=143; $^1$H NMR (400 MHz, DMSO-d$_6$): δ 11.32 (s, 1H), 3.58 (s, 2H), 2.50 (s, 3H) ppm.

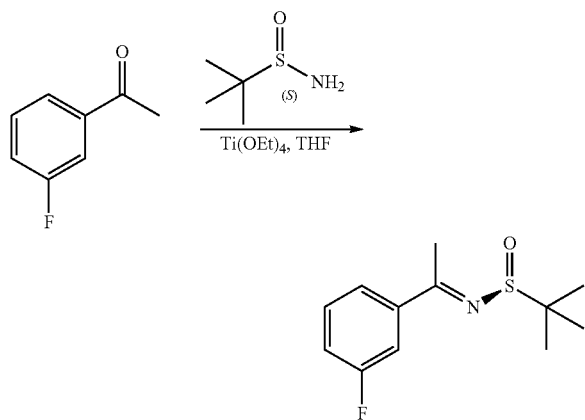

Compound 126.2. (S,E)-N-(1-(3-Fluorophenyl)ethylidene)-2-methylpropane-2-sulfinamide To a solution of (S)-2-methylpropane-2-sulfinamide (21.0 g, 173.8 mmol, 2.0 eq.) and 1-(3-fluorophenyl)ethan-1-one (12.0 g, 86.9 mmol, 1.0 eq.) in THF (200 mL) was added Ti(OEt)$_4$ (79.3 g, 347.6 mmol, 4.0 eq.). The reaction mixture was stirred at 85° C. for 2 hours and then poured into EA (100 mL). Water (20 mL) was added dropwise and the resultant slurry was stirred for 15 min and then filtered through a pad of Celite®545. The filtered cake was washed with EtOAc and the filtrate was washed with water (50 mL×3), dried over anhydrous Na$_2$SO$_4$, filtered and concentrated. The residue was purified by silica gel column chromatography using Petroleum ether/EtOAc=50:1 to 5:1 (v/v) as the eluent to give the title compound (19.0 g, 91% yield) as light yellow oil. LC-MS (ES, m/z): [M+H]$^+$=242.

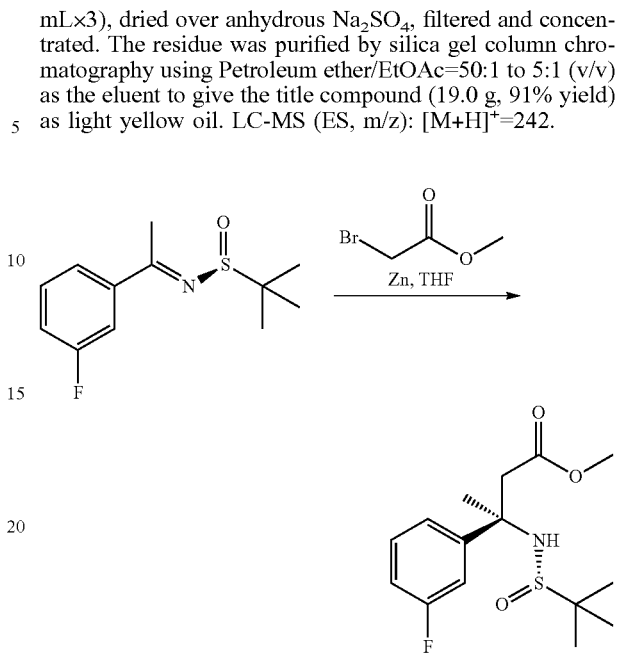

Compound 126.3. Methyl (R)-3-(((S)-tert-butylsulfinyl)amino)-3-(3-fluorophenyl)butanoate Following the same procedure used to prepare ethyl (S)-3-(((S)-tert-butylsulfinyl)amino)-2,2-difluoro-3-phenylpropanoate (Compound 116.2) by replacing ethyl 2-bromo-2,2-difluoroacetate with methyl 2-bromoacetate and (S,E)-N-benzylidene-2-methylpropane-2-sulfinamide (Compound 116.1) with (S,E)-N-(1-(3-fluorophenyl)ethylidene)-2-methylpropane-2-sulfinamide (Compound 126.3), the title compound was prepared (17.6 g, 71.5% yield) as a light yellow oil. LC-MS (ES, m/z): [M+Na]$^+$=338.

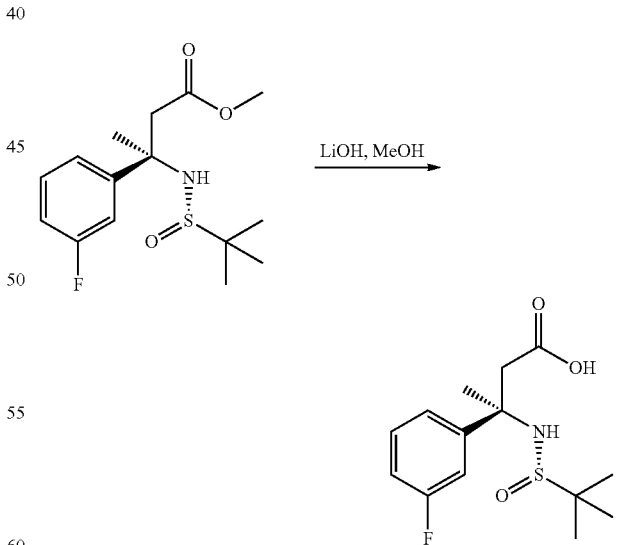

Compound 126.4. (R)-3-(((S)-tert-Butylsulfinyl)amino)-3-(3-fluorophenyl)butanoic acid To a stirring solution of methyl (R)-3-(((S)-tert-butylsulfinyl)amino)-3-(3-fluorophenyl)butanoate ((Compound 126.3), 17.6 g, 55.8 mmol, 1.0 eq.) in MeOH (100 mL) was added 5 N aq. LiOH solution (5.0 eq.). After stirring at rt for 1 h, the reaction mixture was concentrated and adjusted pH to 4-5 with 6NHCl$_{(aq)}$. The mixture was filtered and the solid was dried in vacuo to give a crude material of the title compound (9.9 g) as a light yellow solid, which was used in the next reaction without further purification. LC-MS (ES, m/z): [M+Na]$^+$=302.

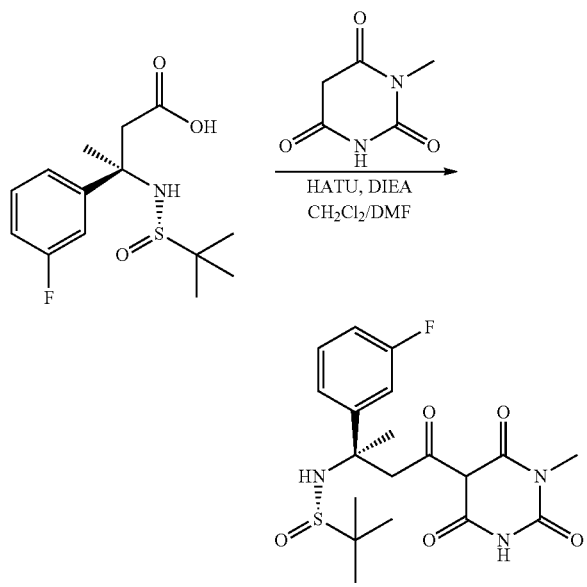

Compound 126.5. (S)—N-((2R)-2-(3-Fluorophenyl)-4-(1-methyl-2,4,6-trioxohexahydropyrimidin-5-yl)-4-oxobutan-2-yl)-2-methylpropane-2-sulfinamide A reaction mixture of (R)-3-(((S)-tert-butylsulfinyl)amino)-3-(3-fluorophenyl)butanoic acid ((Compound 126.4), 3.1 g, 10.2 mmol, 1.0 eq.), 1-methylpyrimidine-2,4,6(1H,3H,5H)-trione ((Compound 126.1), 2.2 g, 15.3 mmol, 1.5 eq.), HATU (5.8 g, 15.3 mmol, 1.5 eq.) and DIPEA (4.0 g, 30.6 mmol, 3.0 eq.) in DMF (25 mL) was stirred at rt for 3 h. The mixture was concentrated and the residue was diluted with EtOAc (100 mL). The resulting mixture was washed with water (50 mL), dried with anhydrous Na$_2$SO$_4$, and concentrated. The residue was purified by silica gel column chromatography using EtOAc/MeOH=15:1 (v/v) as the eluent to give the title compound (2.0 g, 46%) as a light yellow solid. LC-MS (ES, m/z): [M+H]$^+$=426.

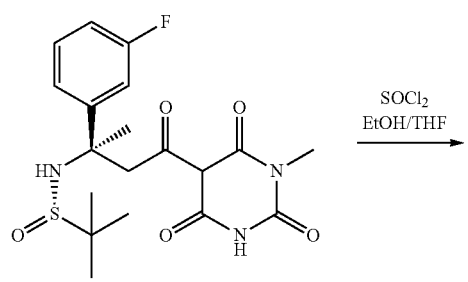

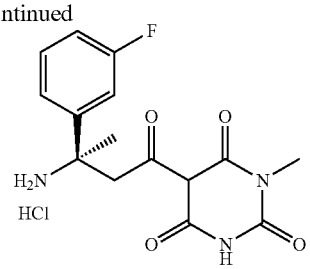

Compound 126.6. 5-((R)-3-Amino-3-(3-fluorophenyl)butanoyl)-1-methylpyrimidine-2,4,6(1H,3H,5H)-trione hydrochloride To a reaction mixture of (S)—N-((2R)-2-(3-fluorophenyl)-4-(1-methyl-2,4,6-trioxohexahydropyrimidin-5-yl)-4-oxobutan-2-yl)-2-methylpropane-2-sulfinamide ((Compound 126.5), 1.2 g, 2.8 mmol, 1.0 eq.) in EtOH/THF=5/1 (v/v) (10 mL) was added SOCl$_2$ (1 mL). After stirring at rt for 2 h, the reaction mixture was concentrated. The residue was washed with ether (10 mL×3) and dried in vacuo to give the title compound (900 mg, 90% yield) as a light yellow solid, which was used in the next step without further purification. LC-MS (ES, m/z): [M+H]$^+$=322; $^1$HNMR (400 MHz, DMSO-d$_6$): δ 8.83 (br, 1H), 7.46-7.34 (m, 3H), 7.18 (t, 1H), 4.00-3.82 (m, 2H), 3.39-3.37 (m, 1H), 3.09 (s, 3H), 1.71 (s, 3H) ppm.

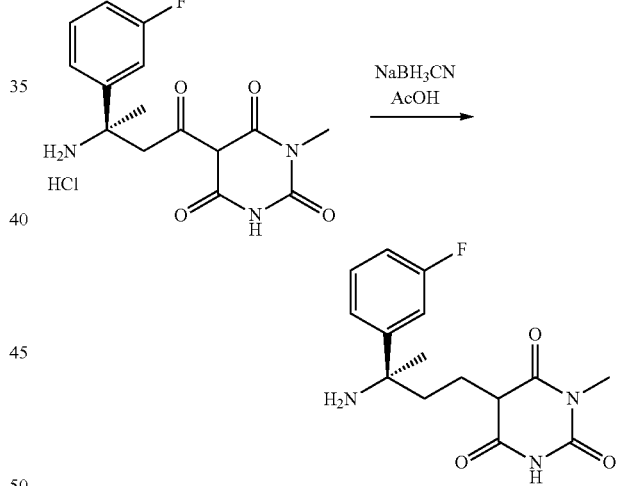

Compound 126.7. 5-((R)-3-Amino-3-(3-fluorophenyl)butyl)-1-methylpyrimidine-2,4,6(1H,3H,5H)-trione Following the same procedure used to prepare tert-butyl ((1S)-2,2-difluoro-3-(1-isopropyl-2,4,6-trioxohexahydropyrimidin-5-yl)-1-phenylpropyl)carbamate (Compound 116.7) by replacing ((1S)-2,2-difluoro-3-(1-isopropyl-2,4,6-trioxohexahydropyrimidin-5-yl)-3-oxo-1-phenylpropyl)carbamate (Compound 116.6) with 5-((R)-3-Amino-3-(3-fluorophenyl)butanoyl)-1-methylpyrimidine-2,4,6(1H,3H,5H)-trione hydrochloride (Compound 126.6), the title compound was prepared (500 mg, purity 86%) as yellow oil, which was used in the next step without further purification. LC-MS (ES, m/z): [M+H]$^+$=308.

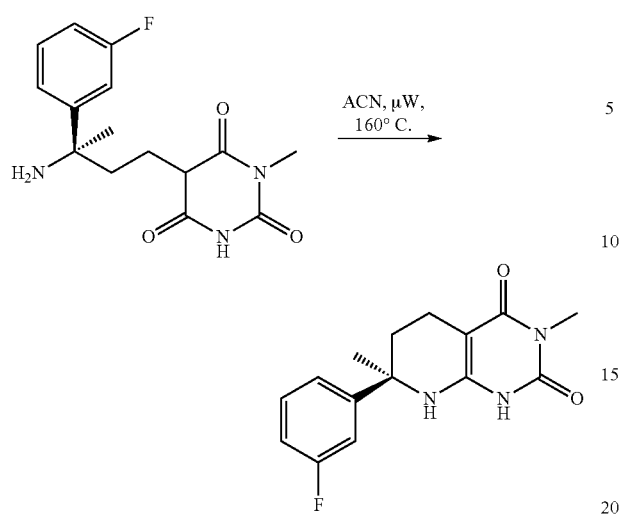

Compound 126. (R)-7-(3-Fluorophenyl)-3,7-dimethyl-5,6,7,8-tetrahydropyrido[2,3-d]pyrimidine-2,4(1H,3H)-dione Following the same procedure used to prepare (R)-7-(2-fluorophenyl)-3-isopropyl-5,6,7,8-tetrahydropyrido[2,3-d]pyrimidine-2,4(1H,3H)-dione (Compound 68) by replacing 5-[(3R)-3-amino-3-(3-fluorophenyl)propyl]-1-(propan-2-yl)-1,3-diazinane-2,4,6-trione hydrochloride (Compound 68.6) with 5-((R)-3-amino-3-(3-fluorophenyl)butyl)-1-methylpyrimidine-2,4,6(1H,3H,5H)-trione (Compound 126.7), the title compound was prepared as a pale grey solid. LC-MS (ES, m/z): [M+H]$^+$=290.

The following are representative compounds that were synthesized using the methodology outlined in example 17:

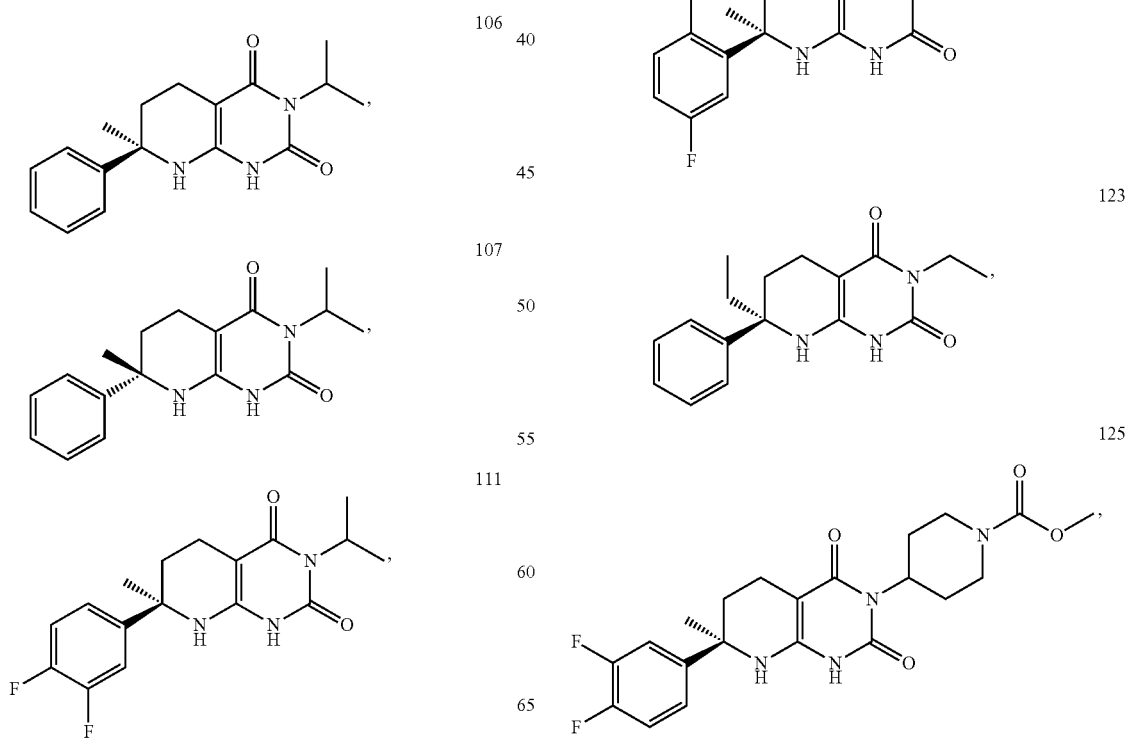

126
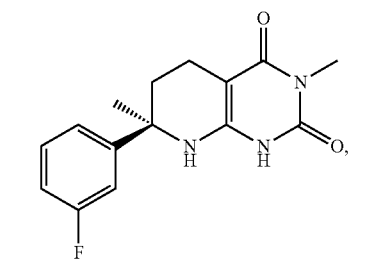
127
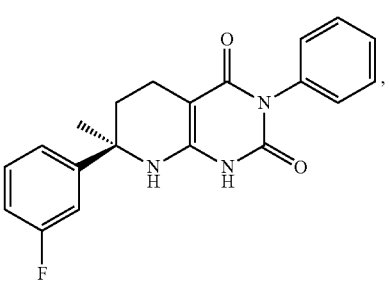
128
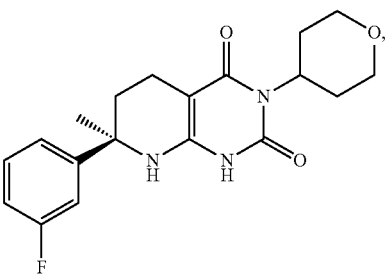
131
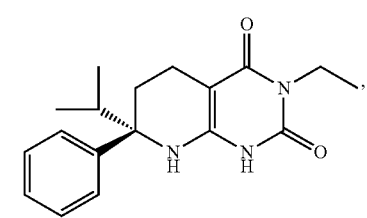
132
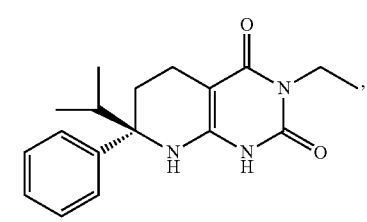
133
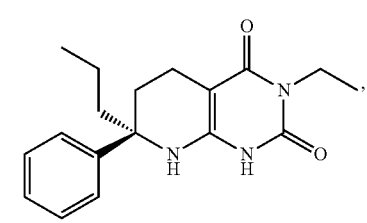
134
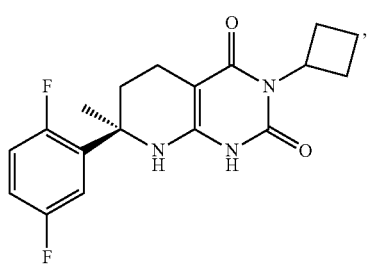
135
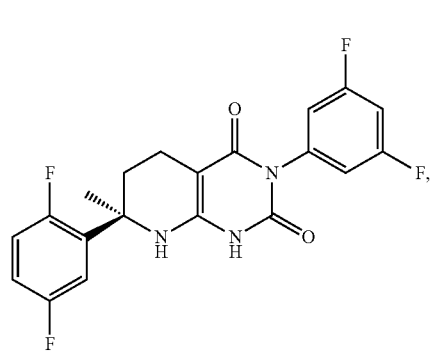
136
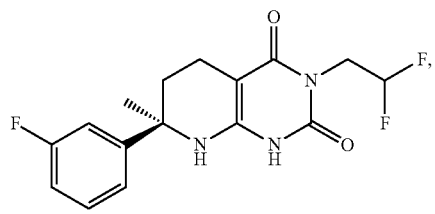
137
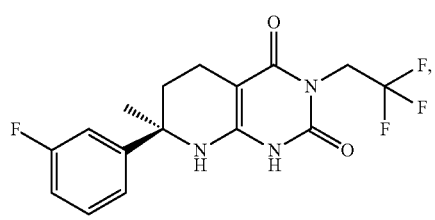
138
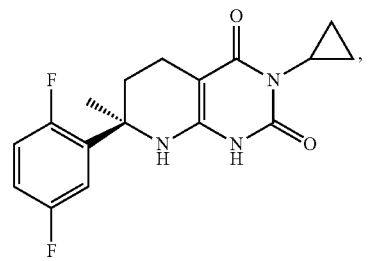
139
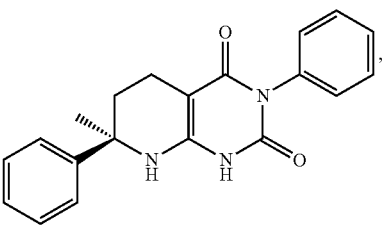

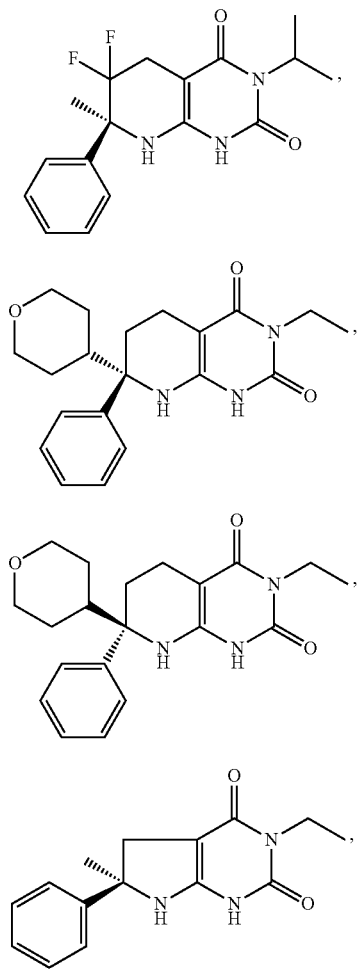

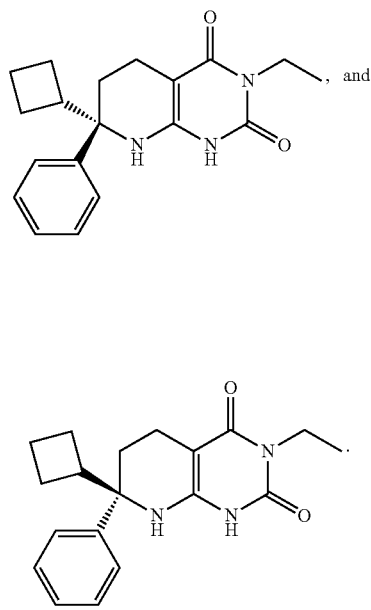

Example 18

Preparation of Additional Bicyclic Pyrimidinedione Compounds

The compounds in Table 1 were prepared according to the examples as described above.

TABLE 1

Representative compounds of the Invention and Analytical Data

| Structure | Compd. No. | Ref. Example | Observed Mass | $^1$H NMR |
|---|---|---|---|---|
| 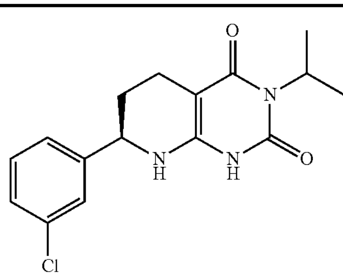 | 12 | 11 | 320 [M + H]$^+$ | $^1$H-NMR (400 MHz, CD$_3$OD): δ 7.44-7.20 (m, 4H), 5.19-5.10 (m, 1H), 4.52-4.48 (m, 1H), 2.45-2.38 (m, 1H), 2.27-2.20 (m, 1H), 2.10-2.01 (m, 1H), 1.92-1.86 (m, 1H), 1.46-1.44 (m, 6H) ppm |
| 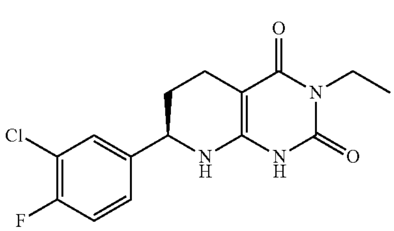 [SMILES: CCn1c(=O)[nH]c2c(c1=O)CC[C@H](c1ccc(F)c(Cl)c1)N2] | 13 | 11 | 324 [M + H]$^+$ | $^1$H-NMR (400 MHz, DMSO-d$_6$): δ 10.30 (br s, 1H), 7.52-7.49 (m, 1H), 7.43-7.39 (m, 1H), 7.31-7.27 (m, 1H), 6.41 (br s, 1H), 4.59-4.55 (m, 1H), 3.74 (q, J = 6.8 Hz, 2H), 2.33-2.26 (m, 1H), 2.04-1.97 (m, 1H), 1.94-1.88 (m, 1H), 1.82-1.77 (m, 1H), 1.05 (t, J = 6.8 Hz, 3H) ppm |

TABLE 1-continued

Representative compounds of the Invention and Analytical Data

| Structure | Compd. No. | Ref. Example | Observed Mass | $^1$H NMR |
|---|---|---|---|---|
| 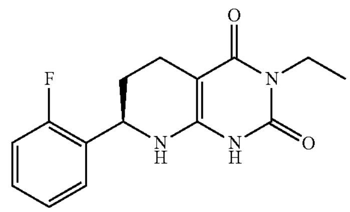 [SMILES: CCn1c(=O)[nH]c2c(c1=O)CC[C@H](c1ccccc1F)N2] | 14 | 4 | 290 [M + H]$^+$ | $^1$H-NMR (400 MHz, DMSO-d$_6$): δ 10.39 (br s, 1H), 7.38-7.33 (m, 1H), 7.27-7.19 (m, 3H), 6.38 (br s, 1H), 4.86-4.84 (m, 1H), 3.75 (q, J = 6.8 Hz, 2H) 2.38-2.30 (m, 1H), 2.01-1.89 (m, 2H), 1.85-1.79 (m, 1H), 1.05 (t, J = 6.8 Hz, 3H) ppm |
| 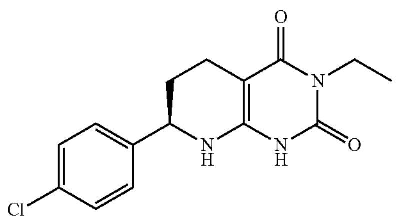 [SMILES: CCn1c(=O)[nH]c2c(c1=O)CC[C@H](c1ccc(Cl)cc1)N2] | 15 | 11 | 306 [M + H]$^+$ | $^1$H-NMR (400 MHz, CD$_3$OD): δ 7.37 (d, J = 8.4 Hz, 2H), 7.30 (d, J = 8.4 Hz, 2H), 4.57 (dd, J = 7.6, 3.6 Hz, 1H), 3.91 (q, J = 7.2 Hz, 2H), 2.46-2.40 (m, 1H), 2.29-2.22 (m, 1H), 2.09-2.02 (m, 1H), 1.91-1.83 (m, 1H), 1.17 (t, J = 7.2 Hz, 3H) ppm |
| 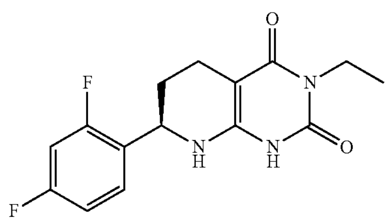 [SMILES: CCn1c(=O)[nH]c2c(c1=O)CC[C@H](c1ccc(F)cc1F)N2] | 16 | 11 | 308 [M + H]$^+$ | $^1$H-NMR (300 MHz, DMSO-d$_6$): δ 10.42 (br s, 1H), 7.31-7.23 (m, 2H), 7.13-7.07 (m, 1H), 6.42 (br s, 1H), 4.84-4.79 (m, 1H), 3.74 (q, J = 7.2 Hz, 2H), 2.38-2.27 (m, 1H), 2.01-1.76 (m, 3H), 1.07 (t, J = 7.2 Hz, 3H) ppm |
| 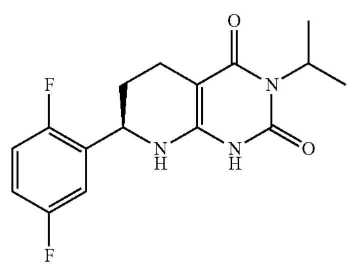 [SMILES: CC(C)n1c(=O)[nH]c2c(c1=O)CC[C@H](c1cc(F)ccc1F)N2] | 17 | 4 | 322 [M + H]$^+$ | $^1$H-NMR (300 MHz, DMSO-d$_6$): δ 10.22 (br s, 1H), 7.33-7.17 (m, 2H), 7.07-7.01 (m, 1H), 6.35 (br s, 1H), 5.06-4.97 (m, 1H), 4.82-4.78 (m, 1H), 2.37-2.27 (m, 1H), 2.03-1.90 (m, 2H), 1.85-1.77 (m, 1H), 1.33 (dd, J = 6.6, 1.8 Hz, 6H) ppm |
| 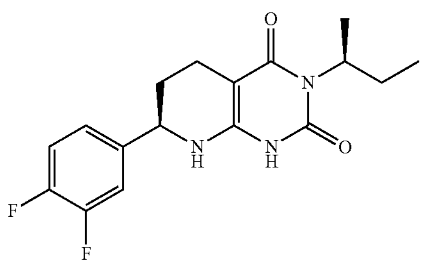 [SMILES: CC[C@H](C)n1c(=O)[nH]c2c(c1=O)CC[C@H](c1ccc(F)c(F)c1)N2] | 18 | 4 | 336 [M + H]$^+$ | $^1$H-NMR (300 MHz, CD$_3$OD): δ 7.31-7.22 (m, 2H), 7.17-7.12 (m, 1H), 4.92 (obscured m, 1H), 4.58-4.55 (m, 1H), 2.48-2.38 (m, 1H), 2.30-2.04 (m, 3H), 1.94-1.68 (m, 2H), 1.42 (d, J = 7.2 Hz, 3H), 0.86 (t, J = 7.2 Hz, 3H) ppm |
| 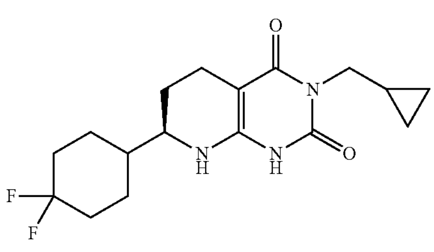 [SMILES: O=c1[nH]c2c(c(=O)n1CC1CC1)CC[C@H](C1CCC(F)(F)CC1)N2] | 19 | 2 | 340 [M + H]$^+$ | $^1$H-NMR (400 MHz, CD$_3$OD): δ 3.73 (d, J = 6.8 Hz, 2H), 3.23 (m, 1H), 2.48-2.43 (m, 1H), 2.38-2.32 (m, 1H), 2.12 (m, 2H), 1.94-1.71 (m, 6H), 1.63-1.54 (m, 1H), 1.45-1.38 (m, 2H), 1.24-1.20 (m, 1H), 0.48-0.35 (m, 4H) ppm |

TABLE 1-continued

Representative compounds of the Invention and Analytical Data

| Structure | Compd. No. | Ref. Example | Observed Mass | ¹H NMR |
|---|---|---|---|---|
| 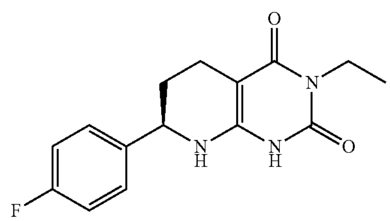 [SMILES: CCn1c(=O)[nH]c2c(c1=O)CC[C@H](c1ccc(F)cc1)N2] | 20 | 5 | 290 [M + H]⁺ | ¹H-NMR (300 MHz, DMSO-d₆): δ 10.21 (br s, 1H), 7.32 (dd, J = 8.4, 5.4 Hz, 2H), 7.19 (t, J = 9.0 Hz, 2H), 6.35 (br s, 1H), 4.52 (m, 1H), 3.74 (q, J = 6.9 Hz, 2H) 2.33-2.25 (m, 1H), 2.08-1.99 (m, 1H), 1.96-1.86 (m, 1H), 1.82-1.72 (m, 1H), 1.05 (t, J = 6.9 Hz, 3H) ppm |
| 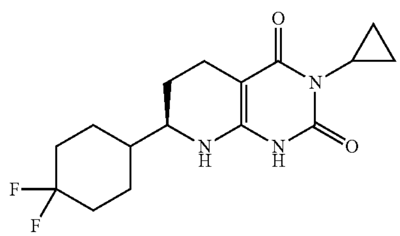 [SMILES: O=c1[nH]c2c(c(=O)n1C1CC1)CC[C@H](C1CCC(F)(F)CC1)N2] | 21 | 2 | 326 [M + H]⁺ | ¹H-NMR (400 MHz, DMSO-d₆): δ 9.72 (br s, 1H), 5.95 (br s, 1H), 3.11 (m, 1H), 2.44-2.40 (m, 1H), 2.26-2.13 (m, 2H) 2.07-1.99 (m, 2H), 1.83-1.65 (m, 5H), 1.59-1.49 (m, 2H), 1.27-1.19 (m, 2H), 0.89-0.84 (m, 2H), 0.63-0.59 (m, 2H) ppm |
| 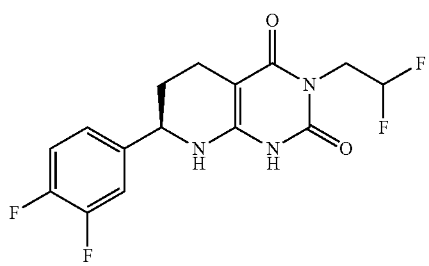 [SMILES: O=c1[nH]c2c(c(=O)n1CC(F)F)CC[C@H](c1ccc(F)c(F)c1)N2] | 22 | 4 | 344 [M + H]⁺ | ¹H-NMR (300 MHz, DMSO-d₆): δ 10.59 (br s, 1H), 7.47-7.33 (m, 2H), 7.15-7.10 (m, 2H), 6.60 (br s, 1H), 6.15 (tt, J = 56.7, 4.5 Hz, 1H), 4.63-4.59 (m, 1H), 4.12 (td, 14.1, 4.5 Hz, 2H), 2.36-2.28 (m, 1H), 2.07-1.80 (m, 3H) ppm. |
| 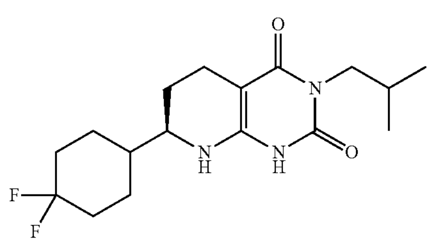 [SMILES: CC(C)Cn1c(=O)[nH]c2c(c1=O)CC[C@H](C1CCC(F)(F)CC1)N2] | 23 | 5 | 342 [M + H]⁺ | ¹H-NMR (400 MHz, DMSO-d₆): δ 9.86 (br s, 1H), 5.97 (br s, 1H), 3.49 (d, J = 7.4 Hz, 2H), 3.14-3.10 (m, 1H), 2.33-2.10 (m, 2H), 2.09-1.64 (m, 8H), 1.62-1.45 (m, 2H) 1.32-1.15 (m, 2H), 0.78 (d, J = 6.7 Hz, 6H) ppm |
| 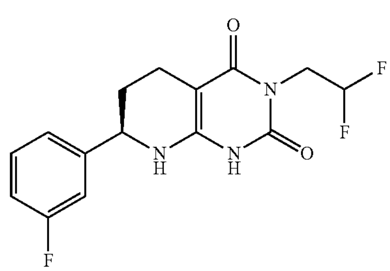 [SMILES: O=c1[nH]c2c(c(=O)n1CC(F)F)CC[C@H](c1cccc(F)c1)N2] | 24 | 4 | 326 [M + H]⁺ | ¹H-NMR (300 MHz, DMSO-d₆): δ 10.16 (br s, 1H), 7.43-7.38 (m, 1H), 7.14-7.08 (m, 3H), 6.75 (br s, 1H), 6.14 (tt, J = 56.7, 4.5 Hz, 1H), 4.63-4.59 (m, 1H), 4.12 (td, 14.1, 4.5 Hz, 2H), 2.36-2.28 (m, 1H), 2.07-1.80 (m, 3H) ppm. |
| 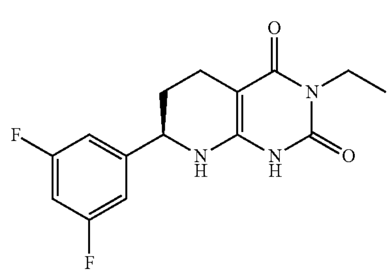 [SMILES: CCn1c(=O)[nH]c2c(c1=O)CC[C@H](c1cc(F)cc(F)c1)N2] | 25 | 4 | 308 [M + H]⁺ | ¹H-NMR (400 MHz, DMSO-d₆): δ 10.32 (br s, 1H), 7.18-7.12 (m, 1H), 7.01 (d, J = 7.2 Hz, 2H), 6.45 (br s, 1H), 4.65-4.61 (m, 1H), 3.74 (q, J = 6.8 Hz, 2H), 2.32-2.26 (m, 1H), 2.02-1.80 (m, 3H), 1.06 (t, J = 6.8 Hz, 3H) ppm |

TABLE 1-continued

Representative compounds of the Invention and Analytical Data

| Structure | Compd. No. | Ref. Example | Observed Mass | $^1$H NMR |
|---|---|---|---|---|
| 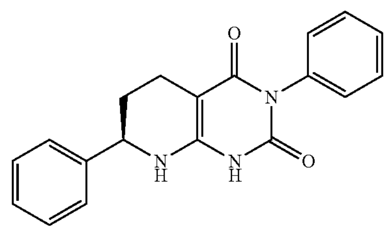 [SMILES: O=c1[nH]c2c(c(=O)n1-c1ccccc1)CC[C@H](c1ccccc1)N2] | 26 | 4 | 320 [M + H]$^+$ | $^1$H-NMR (400 MHz, CD$_3$OD): δ 7.51-7.47 (m, 2H), 7.45-7.31 (m, 6H), 7.26-7.24 (m, 2H), 4.65 (dd, J = 7.2, 4.0 Hz, 1H), 2.51-2.45 (m, 1H), 2.38-2.31 (m, 1H), 2.16-2.11 (m, 1H), 1.99-1.93 (m, 1H) ppm |
| 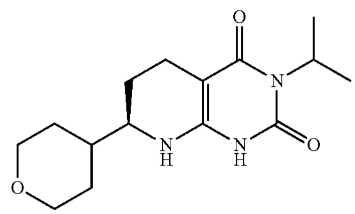 [SMILES: CC(C)n1c(=O)[nH]c2c(c1=O)CC[C@H](C1CCOCC1)N2] | 27 | 2 | 294 [M + H]$^+$ | $^1$H-NMR (400 MHz, CD$_3$OD): δ 5.15-5.08 (m, 1H), 4.03-3.98 (m, 2H), 3.43 (t, J = 12.0 Hz, 2H), 3.16-3.11 (m, 1H), 2.46-2.39 (m, 1H), 2.36-2.28 (m, 1H), 1.90-1.84 (m, 1H), 1.77-1.67 (m 4H), 1.44-1.37 (m, 8H) ppm |
| 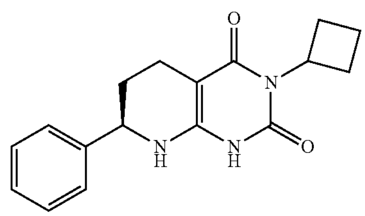 [SMILES: O=c1[nH]c2c(c(=O)n1C1CCC1)CC[C@H](c1ccccc1)N2] | 28 | 1 | 298 [M + H]$^+$ | $^1$H NMR (400 MHz, DMSO-d$_6$): δ 10.10 (br s, 1H), 7.36-7.33 (m, 2H), 7.30-7.23 (m, 3H), 6.31 (br s, 1H), 5.22 (quint, J = 9.2 Hz, 1H), 4.54-4.49 (m, 1H), 2.99-2.84 (m, 2H), 2.30-2.21 (m, 1H), 2.06-1.85 (m, 4H), 1.81-1.55 (m, 3H) ppm |
| 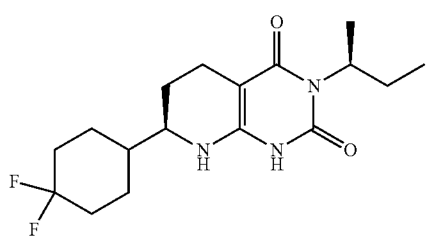 [SMILES: CC[C@H](C)n1c(=O)[nH]c2c(c1=O)CC[C@H](C1CCC(F)(F)CC1)N2] | 29 | 2 | 342 [M + H]$^+$ | $^1$H-NMR (300 MHz, DMSO-d$_6$): δ 9.78 (m, 1H), 6.18 (m, 1H), 4.80-4.69 (m, 1H), 3.15-3.09 (m, 1H), 2.31-1.45 (m, 13H), 1.33-1.19 (m, 5H), 0.72 (t, J = 7.2 Hz, 3H) ppm. |
| 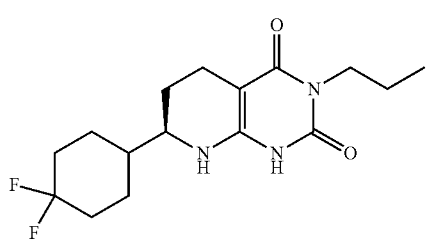 [SMILES: CCCn1c(=O)[nH]c2c(c1=O)CC[C@H](C1CCC(F)(F)CC1)N2] | 30 | 2 | 328 [M + H]$^+$ | $^1$H-NMR (300 MHz, DMSO-d$_6$): δ 9.83 (br s, 1H), 6.01 (br s, 1H), 3.65-3.60 (m, 2H), 3.16-3.11 (m, 1H), 2.31-2.14 (m, 2H), 2.13-1.99 (m, 2H), 1.91-1.66 (m, 5H), 1.64-1.39 (m, 4H), 1.35-1.18 (m, 2H), 0.82 (t, J = 7.2 Hz, 3H) ppm |
| 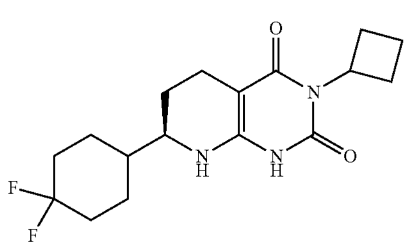 [SMILES: O=c1[nH]c2c(c(=O)n1C1CCC1)CC[C@H](C1CCC(F)(F)CC1)N2] | 31 | 5 | 340 [M + H]$^+$ | $^1$H-NMR (400 MHz, DMSO-d$_6$): δ 9.82 (br s, 1H), 6.01 (br s, 1H), 5.23-5.15 (m, 1H), 3.14-3.09 (m, 1H), 2.93-2.83 (m, 2H), 2.26-2.09 (m, 2H), 2.07-1.92 (m, 4H), 1.87-1.42 (m, 9H), 1.31-1.18 (m, 2H) ppm |

TABLE 1-continued

Representative compounds of the Invention and Analytical Data

| Structure | Compd. No. | Ref. Example | Observed Mass | ¹H NMR |
|---|---|---|---|---|
| 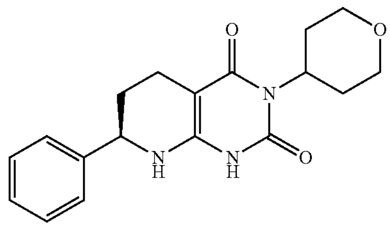 [SMILES: O=c1[nH]c2c(c(=O)n1C1CCOCC1)CC[C@H](c1ccccc1)N2] | 32 | 4 | 328 [M + H]⁺ | ¹H-NMR (400 MHz, CD₃OD): δ 7.38-7.29 (m, 5H), 5.05-4.98 (m, 1H), 4.57 (dd, J = 7.6, 4.0 Hz, 1H), 4.06-4.02 (m, 2H), 3.53-3.46 (m, 2H), 2.84-2.76 (m, 2H), 2.47-2.39 (m, 1H), 2.33-2.26 (m, 1H), 2.13-2.04 (m, 1H), 1.94-1.86 (m, 1H), 1.53 (d, J = 12.8 Hz, 2H) ppm |
| 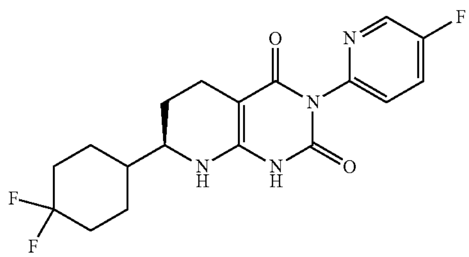 [SMILES: O=c1[nH]c2c(c(=O)n1-c1ccc(F)cn1)CC[C@H](C1CCC(F)(F)CC1)N2] | 33 | 2 | 381 [M + H]⁺ | ¹H-NMR (400 MHz, CD₃OD): δ 8.48 (d, J = 1.2 Hz, 1H), 7.82-7.76 (m, 1H), 7.44 (dd, J = 8.8, 4.0 Hz, 1H), 3.32 (obscured m, 1H), 2.52-2.42 (m, 1H), 2.40-2.34 (m, 1H), 2.18-2.07 (m, 2H), 1.99-1.73 (m, 6H), 1.66-1.63 (m, 1H), 1.50-1.39 (m, 2H) ppm |
| 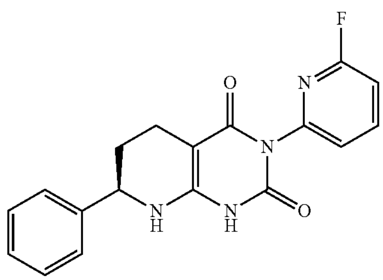 [SMILES: O=c1[nH]c2c(c(=O)n1-c1cccc(F)n1)CC[C@H](c1ccccc1)N2] | 34 | 4 | 339 [M + H]⁺ | ¹H-NMR (300 MHz, CD₃OD): δ 8.09-8.03 (m, 1H), 7.39-7.25 (m, 6H), 7.14 (dd, J = 2.4, 8.1 Hz, 1H), 4.84-4.80 (m, 1H), 2.48-2.38 (m, 1H), 2.32-2.23 (m, 1H), 2.14-2.05 (m, 1H), 1.96-1.87 (m, 1H) ppm |
| 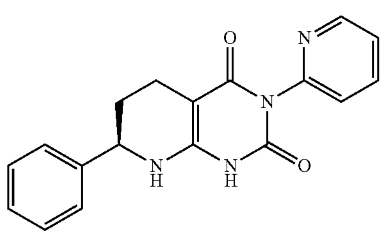 [SMILES: O=c1[nH]c2c(c(=O)n1-c1ccccn1)CC[C@H](c1ccccc1)N2] | 35 | 4 | 321 [M + H]⁺ | ¹H-NMR (400 MHz, CD₃OD): δ 8.60-8.58 (m, 1H), 8.05-8.01 (m, 1H), 7.54-7.51 (m, 1H), 7.45-7.31 (m, 6H), 4.68-4.65 (m, 1H), 2.51-2.45 (m, 1H), 2.36-2.29 (m, 1H), 2.18-2.12 (m, 1H), 2.01-1.95 (m, 1H) ppm |
| 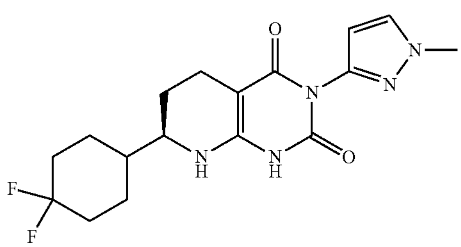 [SMILES: Cn1ccc(-n2c(=O)[nH]c3c(c2=O)CC[C@H](C2CCC(F)(F)CC2)N3)n1] | 36 | 2 | 366 [M + H]⁺ | ¹H NMR (400 MHz, CD₃OD): δ 7.66 (d, J = 2.0 Hz, 1H), 6.20 (d, J = 2.4 Hz, 1H), 3.91 (s, 3H), 3.33-3.27 (obscured m, 1H), 2.52-2.45 (m, 1H), 2.40-2.33 (m, 1H), 2.18-2.08 (m, 2H), 1.99-1.71 (m, 6H), 1.69-1.59 (m, 1H), 1.51-1.38 (m, 2H) ppm |
| 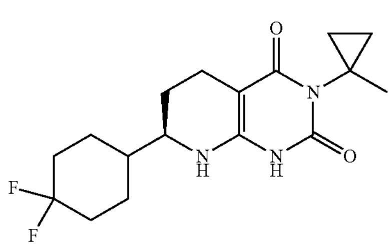 [SMILES: CC1(n2c(=O)[nH]c3c(c2=O)CC[C@H](C2CCC(F)(F)CC2)N3)CC1] | 37 | 2 | 340 [M + H]⁺ | ¹H-NMR (400 MHz, CD₃OD): δ 3.22-3.18 (m, 1H), 2.55-2.25 (m, 2H), 2.16-2.04 (m, 2H), 1.97-1.75 (m, 6H), 1.65-1.53 (m, 1H), 1.42-1.35 (m, 5H), 0.98-0.82 (m, 4H) ppm |

TABLE 1-continued

Representative compounds of the Invention and Analytical Data

| Structure | Compd. No. | Ref. Example | Observed Mass | ¹H NMR |
|---|---|---|---|---|
| 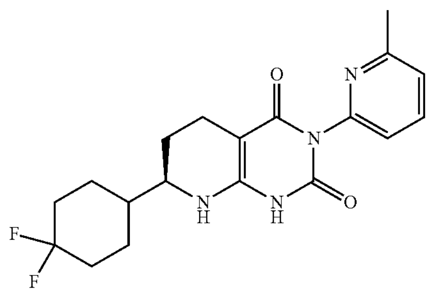 [SMILES: Cc1cccc(-n2c(=O)[nH]c3c(c2=O)CC[C@H](C2CCC(F)(F)CC2)N3)n1] | 38 | 2 | 377 [M + H]⁺ | ¹H-NMR (400 MHz, CD₃OD): δ 7.88 (t, J = 7.6 Hz, 1H), 7.37 (d, J = 7.6 Hz, 1H), 7.18 (d, J = 7.6 Hz, 1H), 3.33-3.29 (obscured m, 1H), 2.57 (s, 3H), 2.52-2.45 (m, 1H), 2.42-2.34 (m, 1H), 2.19-2.05 (m, 2H), 1.99-1.70 (m, 6H), 1.69-1.59 (m, 1H), 1.51-1.36 (m, 2H) ppm |
| 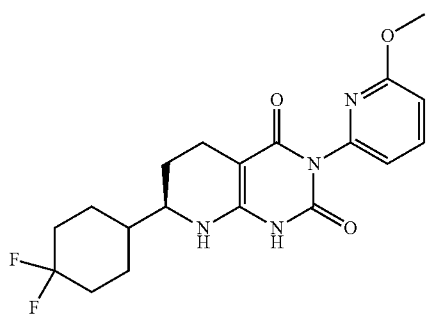 [SMILES: COc1cccc(-n2c(=O)[nH]c3c(c2=O)CC[C@H](C2CCC(F)(F)CC2)N3)n1] | 39 | 1 | 393 [M + H]⁺ | ¹H-NMR (400 MHz, DMSO-d₆): δ 10.11 (br s, 1H), 7.78 (t, J = 7.8 Hz, 1H), 6.84 (dd, J = 10.6, 7.8 Hz, 2H), 6.22 (br s, 1H), 3.75 (s, 3H), 3.23-3.18 (m, 1H), 2.35-2.13 (m, 2H), 2.11-1.96 (m, 2H), 1.92-1.47 (m, 7H), 1.37-1.18 (m, 2H) ppm |
| 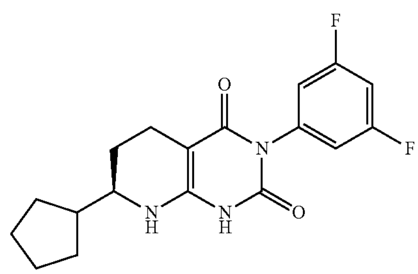 [SMILES: O=c1[nH]c2c(c(=O)n1-c1cc(F)cc(F)c1)CC[C@H](C1CCCC1)N2] | 40 | 11 | 348 [M + H]⁺ | ¹H-NMR (400 MHz, DMSO-d₆): δ 10.25 (br s, 1H), 7.31-7.25 (m, 1H), 7.06-7.03 (m, 2H), 6.09 (br s, 1H), 3.12-3.07 (m, 1H), 2.38-2.30 (m, 1H), 2.25-2.15 (m, 1H), 1.94-1.72 (m, 4H), 1.69-1.46 (m, 5H), 1.35-1.15 (m, 2H) ppm |
| 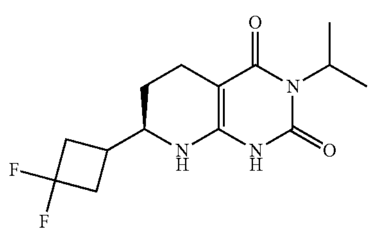 [SMILES: CC(C)n1c(=O)[nH]c2c(c1=O)CC[C@H](C1CC(F)(F)C1)N2] | 41 | 2 | 300 [M + H]⁺ | ¹H-NMR (400 MHz, CDCl₃): δ 10.59 (br s, 1H), 5.23-5.16 (m, 1H), 4.72-4.61 (m, 1H), 3.39-3.30 (m, 1H), 2.82-2.64 (m, 2H), 2.55-2.25 (m, 5H), 1.98-1.87 (m, 1H), 1.63-1.53 (m, 1H), 1.45 (d, J = 7.2 Hz, 6H) ppm |
| 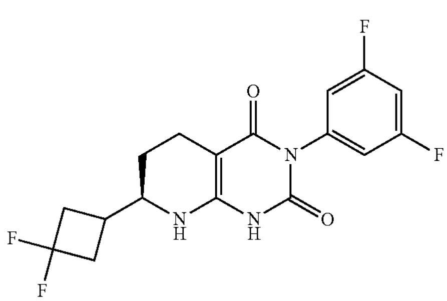 [SMILES: O=c1[nH]c2c(c(=O)n1-c1cc(F)cc(F)c1)CC[C@H](C1CC(F)(F)C1)N2] | 42 | 2 | 370 [M + H]⁺ | ¹H-NMR (400 MHz CD₃Cl₃): δ 10.02 (br s, 1H), 6.94-6.90 (m, 1H), 6.83 (d, J = 5.2 Hz, 2H), 5.40 (br s, 1H), 3.28-3.23 (m, 1H), 2.77-2.35 (m, 4H), 2.26-2.12 (m, 3H), 1.97-1.80 (m, 1H), 1.61-1.53 (m, 1H) ppm |

TABLE 1-continued

Representative compounds of the Invention and Analytical Data

| Structure | Compd. No. | Ref. Example | Observed Mass | ¹H NMR |
|---|---|---|---|---|
| 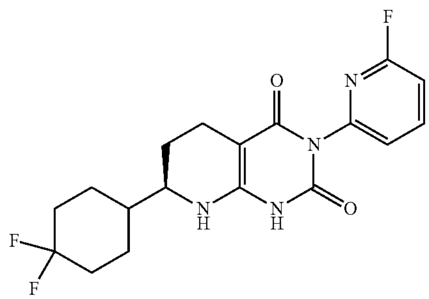 [SMILES: O=c1[nH]c2c(c(=O)n1-c1cccc(F)n1)CC[C@H](C1CCC(F)(F)CC1)N2] | 43 | 2 | 381 [M + H]⁺ | ¹H-NMR (400 MHz, CD$_3$OD): δ 8.12-8.08 (m, 1H), 7.30 (dd, J = 7.2, 0.8 Hz, 1H), 7.18 (dd, J = 8.0, 2.0 Hz, 1H), 2.52-2.43 (m, 1H), 2.41-2.34 (m, 1H), 2.16-2.03 (m, 2H), 1.98-1.70 (m, 6H), 1.68-1.56 (m, 1H), 1.47-1.35 (m, 2H) ppm |
| 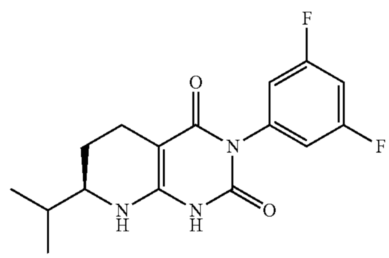 [SMILES: CC(C)[C@H]1CCc2c([nH]c(=O)n(-c3cc(F)cc(F)c3)c2=O)N1] | 44 | 11 | 322 [M + H]⁺ | ¹H-NMR (400 MHz, DMSO-d$_6$): δ 10.21 (br s, 1H), 7.30-7.25 (m, 1H), 7.07-7.03 (m, 2H) 6.10 (br s, 1H), 3.11-3.07 (m, 1H), 2.38-2.31 (m, 1H), 2.22-2.14 (m, 1H), 1.82-1.70 (m, 2H), 1.58-1.45 (m, 1H). 0.97-0.92 (m, 6H) ppm |
| 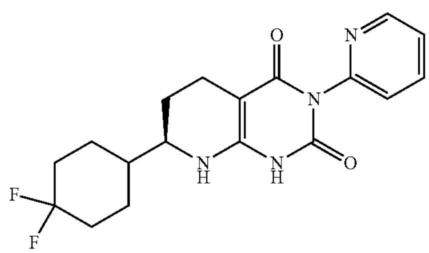 [SMILES: O=c1[nH]c2c(c(=O)n1-c1ccccn1)CC[C@H](C1CCC(F)(F)CC1)N2] | 45 | 2 | 363 [M + H]⁺ | ¹H-NMR (400 MHz, CD$_3$OD): δ 8.58-8.57 (m, 1H), 8.03-7.98 (m, 1H), 7.52-7.49 (m, 1H), 7.39 (d, J = 8.0 Hz, 1H), 3.30-3.25 (m, 1H), 2.52-2.46 (m, 1H), 2.44-2.34 (m, 1H), 2.16-2.04 (m, 2H), 1.95-1.54 (m, 7H), 1.47-1.33 (m, 2H) ppm |
| 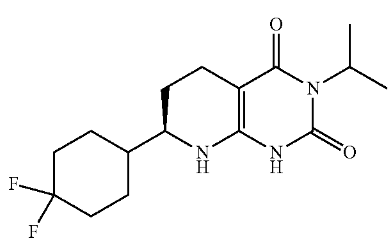 [SMILES: CC(C)n1c(=O)[nH]c2c(c1=O)CC[C@H](C1CCC(F)(F)CC1)N2] | 46 | 2 | 328 [M + H]⁺ | ¹H-NMR (400 MHz, CD$_3$OD): δ 5.16-5.08 (m, 1H), 3.23-3.19 (m, 1H), 2.49-2.40 (m, 1H), 2.35-2.27 (m, 1H), 2.16-2.03 (m, 2H), 1.95-1.70 (m, 6H), 1.64-1.54 (m, 1H), 1.47-1.32 (m, 8H) ppm |
| 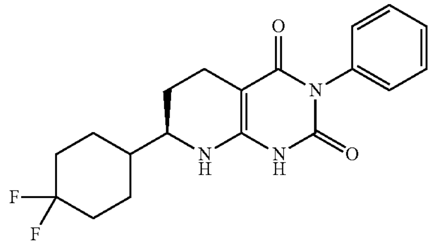 [SMILES: O=c1[nH]c2c(c(=O)n1-c1ccccc1)CC[C@H](C1CCC(F)(F)CC1)N2] | 47 | 2 | 362 [M + H]⁺ | ¹H-NMR (400 MHz, DMSO-d$_6$): δ 7.43-7.32 (m, 3H), 7.15-7.13 (m, 2H), 6.18 (br s, 1H), 3.22-3.18 (m, 1H), 2.36-2.22 (m, 2H), 2.16-2.03 (m, 2H), 1.95-1.71 (m, 5H) 1.70-1.51 (m, 2H), 1.35-1.22 (m, 2H) ppm |

TABLE 1-continued

Representative compounds of the Invention and Analytical Data

| Structure | Compd. No. | Ref. Example | Observed Mass | ¹H NMR |
|---|---|---|---|---|
| 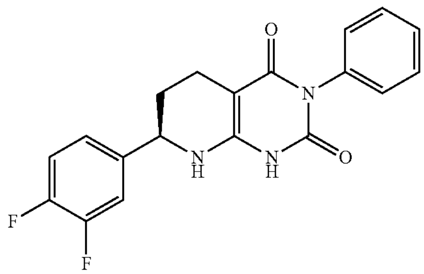 [SMILES: O=c1[nH]c2c(c(=O)n1-c1ccccc1)CC[C@H](c1ccc(F)c(F)c1)N2] | 48 | 4 | 356 [M + H]⁺ | ¹H-NMR (300 MHz, DMSO-d₆): δ 10.51 (br s, 1H), 7.51-7.33 (m, 5H), 7.21-7.15 (m, 3H), 6.61 (br s, 1H), 4.65-4.61 (m, 1H), 2.38-2.26 (m, 1H), 2.10-1.82 (m, 3H) ppm |
| 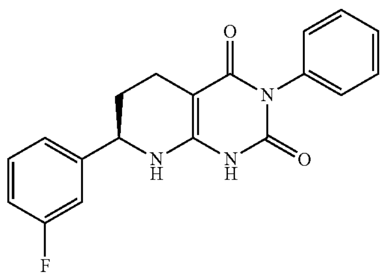 [SMILES: O=c1[nH]c2c(c(=O)n1-c1ccccc1)CC[C@H](c1cccc(F)c1)N2] | 49 | 4 | 338 [M + H]⁺ | ¹H-NMR (400 MHz, DMSO-d₆): δ 10.50 (br s, 1H), 7.48-7.32 (m, 4H), 7.21-7.11 (m, 5H), 6.57 (br s, 1H), 4.66-4.62 (m, 1H), 2.38-2.26 (m, 1H), 2.12-1.94 (m, 2H), 1.88-1.81 (m, 1H) ppm |
| 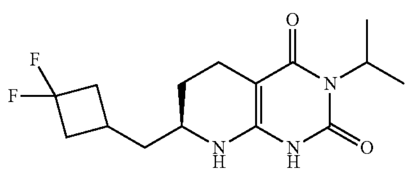 [SMILES: CC(C)n1c(=O)[nH]c2c(c1=O)CC[C@H](CC1CC(F)(F)C1)N2] | 50 | 4 | 314 [M + H]⁺ | ¹H-NMR (400 MHz, DMSO-d₆): δ 9.90 (br s, 1H), 5.87 (br s, 1H), 5.03-4.97(m, 1H), 3.27-3.24 (m, 1H), 2.73-2.66 (m, 2H), 2.32-2.14 (m, 5H), 1.78-1.64 (m, 2H), 1.62-1.55 (m 1H), 1.47-1.40 (m, 1H), 1.31 (d, J = 6.8 Hz, 6H) ppm |
| 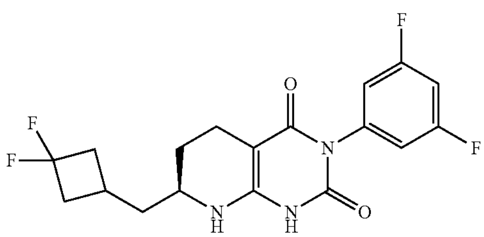 [SMILES: O=c1[nH]c2c(c(=O)n1-c1cc(F)cc(F)c1)CC[C@H](CC1CC(F)(F)C1)N2] | 51 | 4 | 384 [M + H]⁺ | ¹H-NMR (400 MHz, DMSO-d₆): δ 10.45 (br s, 1H), 7.29-7.24 (m, 1H), 7.05-7.02 (m, 2H) 6.19 (br s, 1H), 3.32-3.29 (obscured m, 1H), 2.78-2.65 (m, 2H), 2.34-2.20 (m, 5H), 1.81-1.70 (m, 2H), 1.68-1.45 (m, 2H) ppm |
| 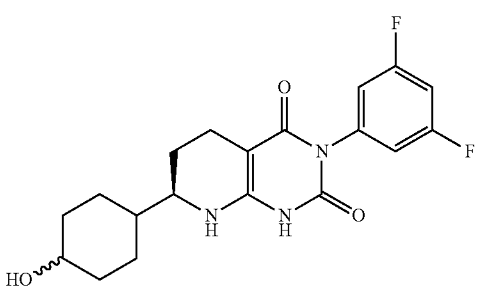 [SMILES: O=c1[nH]c2c(c(=O)n1-c1cc(F)cc(F)c1)CC[C@H](C1CCC(O)CC1)N2] | 52 | 4 | 378 [M + H]⁺ | ¹H-NMR (400 MHz, DMSO-d₆): δ 10.15 (br, s, 1H), 7.24 (tt, J = 9.4, 2.4 Hz, 1H), 7.06-6.99 (m, 2H) 6.12 (br s, 1H), 4.01 (m, 1H), 3.38-3.25 (m, 1H), 3.10-3.05 (m, 1H), 2.34-2.26 (m, 1H), 2.22-2.09 (m, 1H), 1.92-1.81 (m, 2H), 1.79-1.65 (m, 3H) 1.61-1.49 (m, 1H), 1.36-1.24 (m, 1H), 1.18-0.94 (m, 4H) ppm |
| 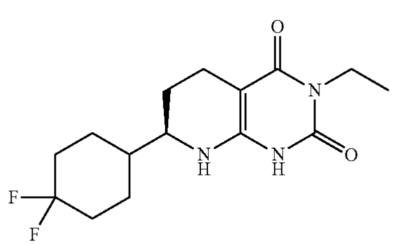 [SMILES: CCn1c(=O)[nH]c2c(c1=O)CC[C@H](C1CCC(F)(F)CC1)N2] | 53 | 2 | 314 [M + H]⁺ | ¹H-NMR (400 MHz, CD₃OD): δ 3.90 (q, J = 7.2 Hz, 2H), 3.25-3.20 (m, 1H), 2.49-2.43 (m, 1H), 2.38-2.30 (m, 1H), 2.16-2.06 (m, 2H), 1.94-1.72 (m 6H), 1.65-1.57 (m, 1H), 1.47-1.33 (m, 2H), 1.17 (t, J = 7.2 Hz, 3H) ppm |

TABLE 1-continued

Representative compounds of the Invention and Analytical Data

| Structure | Compd. No. | Ref. Example | Observed Mass | $^1$H NMR |
|---|---|---|---|---|
| 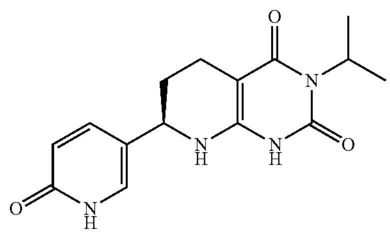 [SMILES: CC(C)n1c(=O)[nH]c2c(c1=O)CC[C@H](c1ccc(=O)[nH]c1)N2] | 54 | 1 | 303 [M + H]$^+$ | $^1$H-NMR (400 MHz, DMSO-d$_6$): δ 11.54 (m, 1H), 9.95 (br s, 1H), 7.40 (dd, J = 9.6, 2.5 Hz, 1H), 7.19 (d, J = 9.6 Hz, 1H), 6.33 (d, J = 9.4 Hz, 1H), 6.09 (br s, 1H), 5.02-4.94 (m, 1H), 4.26-4.23 (m, 1H), 2.24-2.06 (m, 2H), 1.89-1.65 (m, 2H), 1.30 (d, J = 7.0 Hz, 6H) ppm |
| 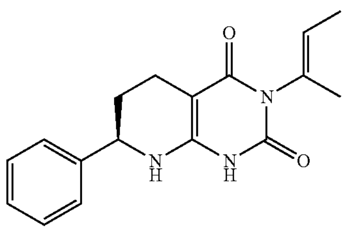 [SMILES: C/C=C(\C)n1c(=O)[nH]c2c(c1=O)CC[C@H](c1ccccc1)N2] | 55 | 4 | 298 [M + H]$^+$ | $^1$H-NMR (300 MHz, CD$_3$OD): δ 7.35-7.23 (m, 5H), 5.42-5.37 (m, 1H), 4.57-4.52 (m, 1H), 2.45-2.35 (m, 1H), 2.31-2.26 (m, 1H), 2.13-2.02 (m, 1H), 1.92-1.82 (m, 4H), 1.73 (d, J = 6.9 Hz, 3H) ppm |
| 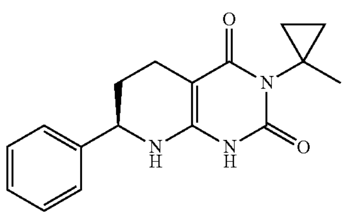 [SMILES: CC1(n2c(=O)[nH]c3c(c2=O)CC[C@H](c2ccccc2)N3)CC1] | 56 | 4 | 298 [M + H]$^+$ | $^1$H-NMR (400 MHz, CD$_3$OD): δ 7.40-7.28 (m, 5H), 4.57-4.52 (m, 1H), 2.49-2.15 (m, 2H), 2.13-2.05 (m, 1H), 1.93-1.84 (m, 1H), 1.41 (s, 3H), 0.98-0.86 (m, 4H) ppm |
| 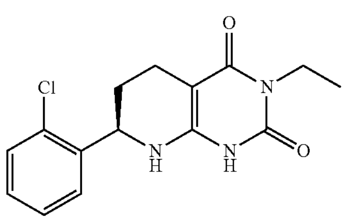 [SMILES: CCn1c(=O)[nH]c2c(c1=O)CC[C@H](c1ccccc1Cl)N2] | 57 | 11 | 306 [M + H]$^+$ | $^1$H-NMR (300 MHz, DMSO-d$_6$): δ 10.48 (br s, 1H), 7.47 (dd, J = 7.5, 1.5 Hz, 1H), 7.38-7.25 (m, 3H), 6.44 (br s, 1H), 4.92-4.88 (m, 1H), 3.75 (q, J = 6.9 Hz, 2H), 2.37-2.27 (m, 1H), 1.94-1.78 (m, 3H), 1.06 (t, J = 6.9 Hz, 3H) ppm |
| 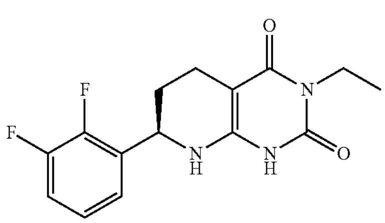 [SMILES: CCn1c(=O)[nH]c2c(c1=O)CC[C@H](c1cccc(F)c1F)N2] | 58 | 4 | 308 [M + H]$^+$ | $^1$H-NMR (400 MHz, DMSO-d$_6$): δ 10.48 (br s, 1H), 7.40-7.34 (m, 1H), 7.24-7.15 (m, 1H), 7.06-7.03 (m, 1H), 6.43 (br s, 1H), 4.90 (br s, 1H), 4.90 (br s, 1H), 3.74 (q, J = 6.8 Hz, 2H), 2.30-2.26 (m, 1H), 2.00-1.80 (m, 3H), 1.06 (t, J = 6.8 Hz, 3H) ppm |
| 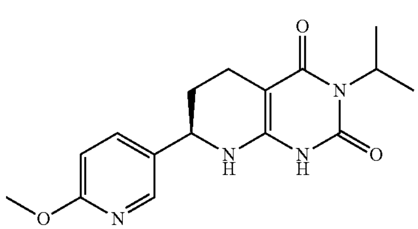 [SMILES: COc1ccc([C@H]2CCc3c([nH]c(=O)n(C(C)C)c3=O)N2)cn1] | 59 | 1 | 317 [M + H]$^+$ | $^1$H-NMR (400 MHz, DMSO-d$_6$): δ 10.02 (br s, 1H), 8.06 (d, J = 2.7 Hz, 1H), 7.61 (dd, J = 8.6, 2.7 Hz, 1H), 6.81 (d, J = 8.6 Hz, 1H), 6.22 (br s, 1H), 5.03-4.96 (m, 1H), 4.49-4.45 (m, 1H), 3.82 (s, 3H), 2.26-2.20 (m, 1H), 2.08 (dt, J = 16.0, 5.7 Hz, 1H), 1.94-1.84 (m, 1H), 1.82-1.69 (m, 1H), 1.31 (dd, J = 7.0, 0.8 Hz, 6H) ppm |

TABLE 1-continued

Representative compounds of the Invention and Analytical Data

| Structure | Compd. No. | Ref. Example | Observed Mass | ¹H NMR |
|---|---|---|---|---|
| 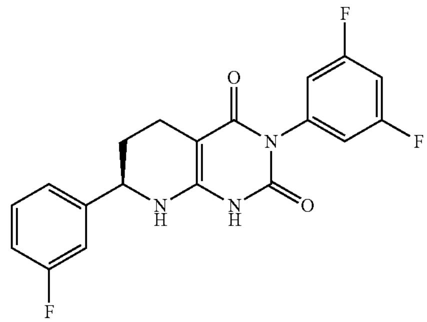 [SMILES: O=c1[nH]c2c(c(=O)n1-c1cc(F)cc(F)c1)CC[C@H](c1cccc(F)c1)N2] | 60 | 4 | 374 [M + H]⁺ | ¹H-NMR (400 MHz, DMSO-d₆): δ 10.69 (br s, 1H), 7.48-7.42 (m, 1H), 7.33-7.26 (m, 1H), 7.21-7.08 (m, 5H), 6.67 (br s, 1H), 4.69-4.64 (m, 1H), 2.37-2.31 (m, 1H), 2.05-1.94 (m, 2H), 1.90-1.85 (m, 1H) ppm |
| 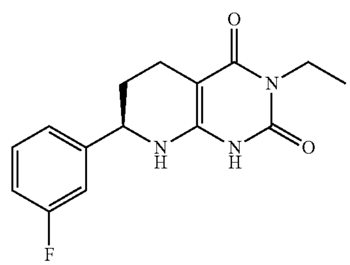 [SMILES: CCn1c(=O)[nH]c2c(c1=O)CC[C@H](c1cccc(F)c1)N2] | 61 | 4 | 290 [M + H]⁺ | 1H-NMR (400 MHz, DMSO-d6): δ 10.28 (br s, 1H), 7.45-7.39 (m, 1H), 7.14-7.10 (m, 3H), 6.42 (br s, 1H), 4.61-4.55 (m, 1H), 3.75 (q, J = 6.8 Hz, 2H), 2.34-2.27 (m, 1H), 2.08-1.89 (m, 2H), 1.84-1.76 (m, 1H), 1.06 (t, J = 6.8 Hz, 3H) ppm |
| 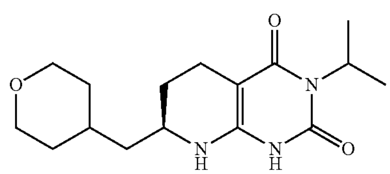 [SMILES: CC(C)n1c(=O)[nH]c2c(c1=O)CC[C@H](CC1CCOCC1)N2] | 62 | 2 | 308 [M + H]⁺ | 1H-NMR (300 MHz, DMSO-d6): δ 9.82 (br s, 1H), 5.90 (br s, 1H), 5.03-4.94 (m, 1H), 3.86-3.81 (m, 2H), 3.39-3.24 (m, 2H), 2.27-2.12 (m, 3H), 1.80-1.73 (m, 1H), 1.68-1.53 (m, 4H), 1.47-1.10 (m, 10H) ppm |
| 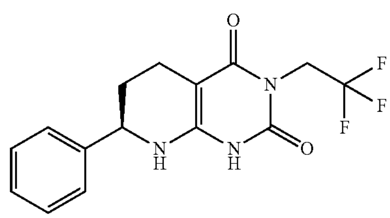 [SMILES: O=c1[nH]c2c(c(=O)n1CC(F)(F)F)CC[C@H](c1ccccc1)N2] | 63 | 4 | 326 [M + H]⁺ | ¹H-NMR (400 MHz, CD₃OD): δ 7.42-7.28 (m, 5H), 4.73-4.60 (m, 3H), 2.49-2.43 (m, 1H), 2.37-2.30 (m, 1H), 2.17-2.06 (m, 1H), 1.98-1.89 (m, 1H) ppm |
| 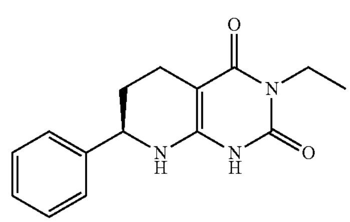 [SMILES: CCn1c(=O)[nH]c2c(c1=O)CC[C@H](c1ccccc1)N2] | 64 | 4 | 272 [M + H]⁺ | ¹H-NMR (400 MHz, DMSO-d₆): δ 9.99 (br s, 1H), 7.40-7.28 (m, 5H), 6.36 (br s, 1H), 4.55-4.51 (m, 1H), 3.75 (q, J = 6.8 Hz, 2H), 2.34-2.27 (m, 1H), 2.11-2.04 (m, 1H), 1.96-1.89 (m, 1H), 1.82-1.75 (m, 1H), 1.06 (t, J = 6.8 Hz, 3H) ppm |
| 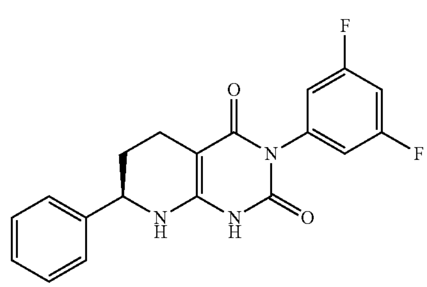 [SMILES: O=c1[nH]c2c(c(=O)n1-c1cc(F)cc(F)c1)CC[C@H](c1ccccc1)N2] | 65 | 1 | 356 [M + H]⁺ | ¹H-NMR (400 MHz, DMSO-d₆): δ 10.55 (br s, 1H), 7.40-7.35 (m, 2H), 7.32-7.26 (m, 4H), 7.11-7.02 (m, 2H), 6.57 (br s, 1H), 2.33-2.28 (m, 1H), 2.10-1.94 (m, 2H), 1.85-1.75 (m 1H) ppm |

TABLE 1-continued

Representative compounds of the Invention and Analytical Data

| Structure | Compd. No. | Ref. Example | Observed Mass | ¹H NMR |
|---|---|---|---|---|
| 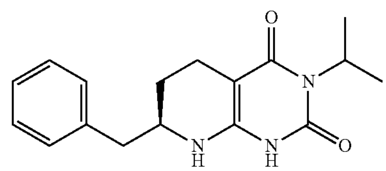 [SMILES: CC(C)n1c(=O)[nH]c2c(c1=O)CC[C@H](Cc1ccccc1)N2] | 66 | 1 | 300 [M + H]⁺ | ¹H-NMR (400 MHz, DMSO-d₆): δ 9.89 (br s, 1H), 7.34-7.30 (m, 2H), 7.25-7.21 (m, 3H), 5.69 (br s, 1H), 5.02-4.94 (m, 1H), 4.55-4.51 (m, 1H), 2.74-2.67 (m, 2H), 2.32-2.24 (m, 1H), 2.18-2.10 (m, 1H), 1.74-1.70 (m, 1H), 1.46-1.42 (m, 1H), 1.28 (d, J = 7.0 Hz, 6H) ppm |
| 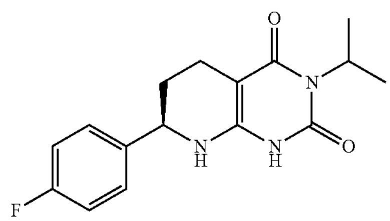 [SMILES: CC(C)n1c(=O)[nH]c2c(c1=O)CC[C@H](c1ccc(F)cc1)N2] | 67 | 5 | 304 [M + H]⁺ | ¹H-NMR (300 MHz, DMSO-d₆): δ 10.04 (br s, 1H), 7.35-7.29 (m, 2H), 7.22-7.16 (m, 2H), 6.28 (br s, 1H), 5.05-4.96 (m, 1H), 4.54-4.50 (m, 1H), 2.33-2.23 (m, 1H), 2.09-2.00 (m, 1H), 1.95-1.87 (m, 1H), 1.80-1.74 (m, 1H), 1.33 (d, J = 7.2 Hz, 6H) ppm |
| 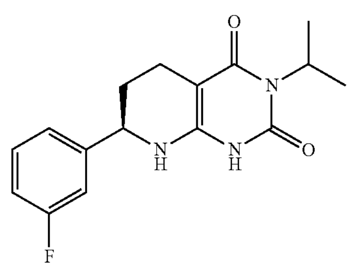 [SMILES: CC(C)n1c(=O)[nH]c2c(c1=O)CC[C@H](c1cccc(F)c1)N2] | 68 | 4 | 304 [M + H]⁺ | ¹H-NMR (400 MHz, CD₃OD): δ 7.39-7.35 (m, 1H), 7.13 (d, J = 8.0 Hz, 1H), 7.07-6.99 (m, 2H), 5.17-5.10 (m, 1H), 4.57 (dd, J = 7.2, 4.0 Hz, 1H), 2.44-2.38 (m, 1H), 2.27-2.20 (m, 1H), 2.12-2.04 (m, 1H), 1.94-1.85 (m, 1H), 1.43 (dd, J = 7.2, 1.2 Hz, 6H) ppm |
| 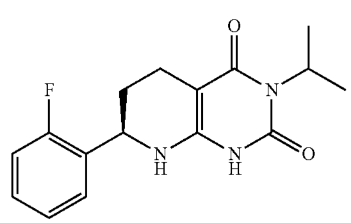 [SMILES: CC(C)n1c(=O)[nH]c2c(c1=O)CC[C@H](c1ccccc1F)N2] | 69 | 4 | 304 [M + H]⁺ | ¹H-NMR (300 MHz, DMSO-d₆): δ 10.21 (br s, 1H), 7.38-7.31 (m, 1H), 7.27-7.18 (m, 3H) 6.32 (br s, 1H), 5.03-4.97 (m, 1H), 4.84-4.80 (m, 1H), 2.36-2.27 (m, 1H), 2.02-1.88 (m, 2H), 1.83-1.75 (m, 1H), 1.33 (dd, J = 6.9, 1.5 Hz, 6H) ppm |
| 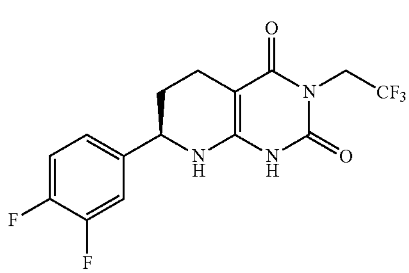 [SMILES: O=c1[nH]c2c(c(=O)n1CC(F)(F)F)CC[C@H](c1ccc(F)c(F)c1)N2] | 70 | 4 | 362 [M + H]⁺ | ¹H-NMR (400 MHz, DMSO-d₆): δ 10.66 (br s, 1H), 7.48-7.34 (m, 2H), 7.15-7.10 (m, 1H), 6.66 (br s, 1H), 4.64-4.59 (m, 1H), 4.52 (q, J = 12.4 Hz, 2H), 2.37-2.27 (m, 1H), 2.09-1.80 (m, 3H) ppm |
| 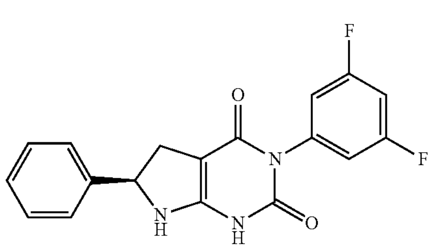 [SMILES: O=c1[nH]c2c(c(=O)n1-c1cc(F)cc(F)c1)C[C@H](c1ccccc1)N2] | 71 | 7 | 342 [M + H]⁺ | ¹H-NMR (400 MHz, CD₃OD): δ 7.42-7.40 (m, 4H), 7.36-7.30 (m, 1H), 7.08-7.03 (m, 1H), 6.98-6.93 (m, 2H), 5.18-5.12 (m, 1H), 3.38 (obscured m, 1H), 2.75-2.71 (m, 1H) ppm |

TABLE 1-continued

Representative compounds of the Invention and Analytical Data

| Structure | Compd. No. | Ref. Example | Observed Mass | 1H NMR |
|---|---|---|---|---|
| 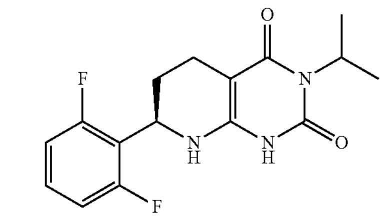 [SMILES: CC(C)n1c(=O)[nH]c2c(c1=O)CC[C@H](c1c(F)cccc1F)N2] | 72 | 4 | 322 [M + H]+ | 1H-NMR (400 MHz, DMSO-d6): δ 10.06 (br s, 1H) 7.46-7.38 (m, 1H), 7.14-7.09 (m, 2H), 6.35 (br s, 1H), 5.05-4.98 (m, 1H), 4.85-4.80 (m, 1H), 2.33-2.28 (m, 2H), 1.97-1.94 (m, 2H), 1.33 (d, J = 6.8 Hz, 6H) ppm |
| 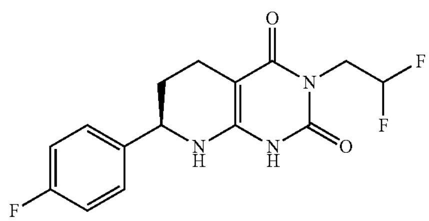 [SMILES: O=c1[nH]c2c(c(=O)n1CC(F)F)CC[C@H](c1ccc(F)cc1)N2] | 73 | 5 | 326 [M + H]+ | 1H-NMR (400 MHz, DMSO-d6): δ 10.53 (br s, 1H), 7.47-7.33 (dd, J = 5.2, 8.8 Hz, 2H), 7.23-7.18 (m, 2H), 6.54 (br s, 1H), 6.16 (tt, J = 56.8, 4.4 Hz), 4.62-4.58 (m, 1H), 4.13 (td, 14.4, 4.4 Hz, 2H), 2.36-2.28 (m, 1H), 2.09-2.02 (m, 1H), 1.96-1.89 (m, 1H), 1.83-1.76 (m, 1H) ppm |
| 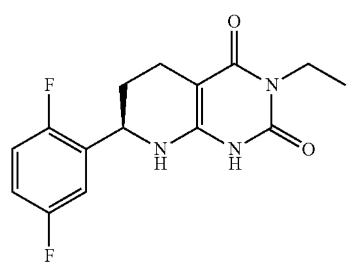 [SMILES: CCn1c(=O)[nH]c2c(c1=O)CC[C@H](c1cc(F)ccc1F)N2] | 74 | 4 | 308 [M + H]+ | 1H-NMR (400 MHz, DMSO-d6): δ 10.40 (br s, 1H), 7.32-7.26 (m, 1H), 7.22-7.17 (m, 1H), 7.06-7.01 (m, 1H), 6.41 (br s, 1H), 4.84-4.80 (m, 1H), 3.75 (q, J = 6.8 Hz, 2H), 2.38-2.31 (m, 1H), 2.02-1.89 (m, 2H), 1.84-1.76 (m, 1H), 1.06 (t, J = 6.8 Hz, 3H) ppm |
| 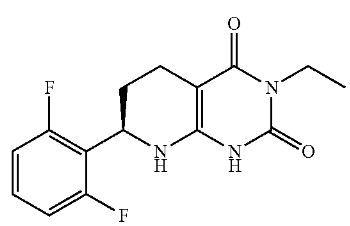 [SMILES: CCn1c(=O)[nH]c2c(c1=O)CC[C@H](c1c(F)cccc1F)N2] | 75 | 4 | 308 [M + H]+ | 1H-NMR (400 MHz, DMSO-d6): δ 10.22 (br s, 1H), 7.45-7.39 (m, 1H), 7.14-7.10 (m, 2H), 6.41 (br s, 1H), 4.87-4.83 (m, 1H), 3.75 (q, J = 6.8 Hz, 2H), 2.33-2.26 (m, 2H), 1.98-1.95 (m, 2H), 1.06 (t, J = 6.8 Hz, 3H) ppm |
| 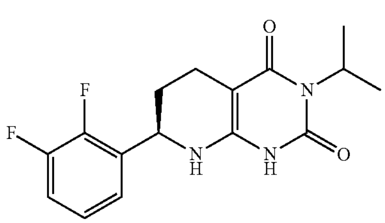 [SMILES: CC(C)n1c(=O)[nH]c2c(c1=O)CC[C@H](c1cccc(F)c1F)N2] | 76 | 4 | 322 [M + H]+ | 1H-NMR (300 MHz, DMSO-d6): δ 10.29 (br s, 1H), 7.39-7.33 (m, 1H), 7.39-7.33 (m, 1H), 7.23 (dd, J = 7.2, 12.6 Hz, 1H), 7.08-7.03 (m, 1H), 6.38 (br s, 1H), 5.05-4.99 (m, 1H), 4.92-4.88 (m, 1H), 2.37-2.31 (m, 1H), 2.01-1.78 (m, 3H), 1.34 (d, J = 6.9 Hz, 6H) ppm |
| 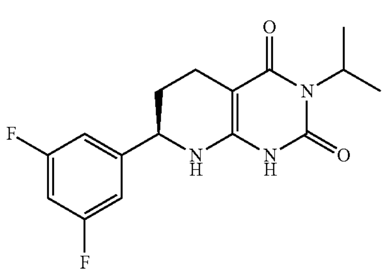 [SMILES: CC(C)n1c(=O)[nH]c2c(c1=O)CC[C@H](c1cc(F)cc(F)c1)N2] | 77 | 4 | 322 [M + H]+ | 1H-NMR (400 MHz, CD3OD): δ 6.94-6.92, (m, 2H), 6.90-6.85 (m, 1H), 5.17-5.10 (m, 1H), 4.59 (dd, J = 7.2, 4.0 Hz, 1H), 2.46-2.39 (m, 1H), 2.24-2.17 (m, 1H), 2.12-2.03 (m, 1H), 1.92-1.86 (m, 1H), 1.43 (dd, J = 6.8, 1.6 Hz, 6H) ppm. |

TABLE 1-continued

Representative compounds of the Invention and Analytical Data

| Structure | Compd. No. | Ref. Example | Observed Mass | ¹H NMR |
|---|---|---|---|---|
| 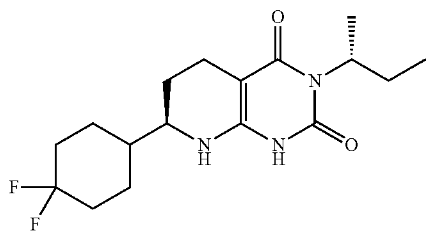 [SMILES: CC[C@@H](C)n1c(=O)[nH]c2c(c1=O)CC[C@H](C1CCC(F)(F)CC1)N2] | 78 | 2 | 342 [M + H]⁺ | ¹H-NMR (300 MHz, DMSO-d₆): δ 9.72 (br s, 1H), 5.96 (br s, 1H), 4.76-4.71 (m, 1H), 3.17-3.07 (m, 1H), 2.31-1.45 (m, 13H), 1.34-1.18 (m, 5H), 0.74 (t, J = 7.2 Hz, 3H) ppm |
| 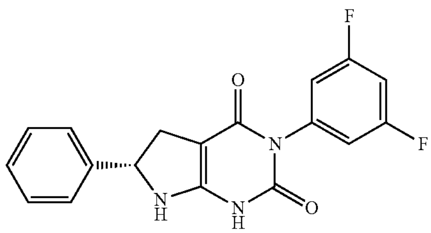 [SMILES: O=c1[nH]c2c(c(=O)n1-c1cc(F)cc(F)c1)C[C@@H](c1ccccc1)N2] | 79 | 7 | 342 [M + H]⁺ | ¹H-NMR (400 MHz, CD₃OD): δ 7.42-7.40 (m, 4H), 7.36-7.30 (m, 1H), 7.08-7.03 (m, 1H), 6.98-6.93 (m, 2H), 5.18-5.12 (m, 1H), 3.38 (obscured m, 1H), 2.75-2.71 (m, 1H) ppm |
| 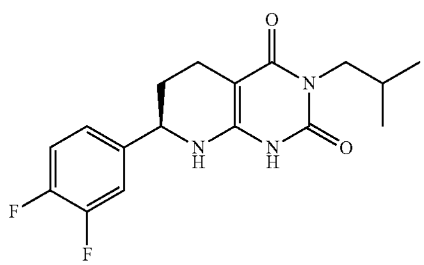 [SMILES: CC(C)Cn1c(=O)[nH]c2c(c1=O)CC[C@H](c1ccc(F)c(F)c1)N2] | 80 | 5 | 336 [M + H]⁺ | ¹H-NMR (300 MHz, DMSO-d₆): δ 10.33 (br s, 1H), 7.48-7.34 (m, 2H), 7.15-7.10 (m, 1H), 6.62 (br s, 1H), 4.58-4.53 (m, 1H), 3.54 (d, J = 7.2 Hz, 2H), 2.34-2.24 (m, 1H), 2.06-1.73 (m, 4H), 0.81 (d, J = 6.6 Hz, 6H) ppm |
| 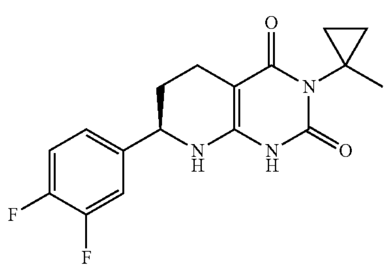 [SMILES: CC1(n2c(=O)[nH]c3c(c2=O)CC[C@H](c2ccc(F)c(F)c2)N3)CC1] | 81 | 5 | 334 [M + H]⁺ | ¹H-NMR (400 MHz, DMSO-d₆): δ 10.08 (br s, 1H), 7.46-7.34 (m, 2H), 7.15-7.10 (m, 1H), 6.30 (br s, 1H), 4.55-4.50 (m, 1H), 2.33-2.24 (m, 1H), 2.09-1.87 (m, 2H), 1.84-1.78 (m, 1H), 1.26 (s, 3H), 0.75 (m, 4H) ppm |
| 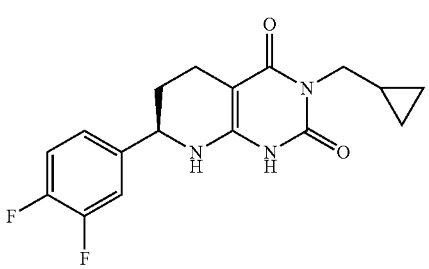 [SMILES: O=c1[nH]c2c(c(=O)n1CC1CC1)CC[C@H](c1ccc(F)c(F)c1)N2] | 82 | 5 | 334 [M + H]⁺ | 1H-NMR (300 MHz, DMSO-d6): δ 10.29 (br s, 1H), 7.45-7.38 (m, 2H), 7.16-7.12 (m, 1H), 6.43 (br s, 1H), 4.59-4.55 (m, 1H), 3.58 (d, J = 7.2 Hz, 2H), 2.35-2.24 (m, 1H), 2.10-1.78 (m, 3H), 1.05-1.01 (m, 1H), 0.39-0.29 (m, 4H) ppm |
| 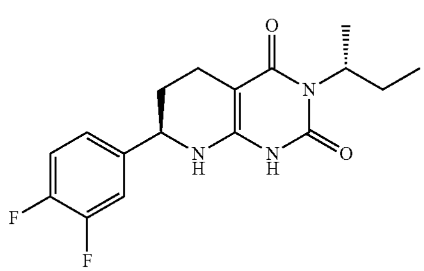 [SMILES: CC[C@@H](C)n1c(=O)[nH]c2c(c1=O)CC[C@H](c1ccc(F)c(F)c1)N2] | 83 | 5 | 336 [M + H]⁺ | ¹H-NMR (300 MHz, DMSO-d₆): δ 10.10 (br s, 1H), 7.46-7.39 (m, 2H), 7.16-7.12 (m, 1H), 6.35 (br s, 1H), 4.78-4.71 (m, 1H), 4.56-4.52 (m, 1H), 2.31-2.24 (m, 1H), 2.12-1.89 (m, 3H), 1.87-1.64 (m, 2H), 1.30 (d, J = 6.9 Hz, 3H), 0.75 (t, J = 7.5 Hz, 3H) ppm |

TABLE 1-continued

Representative compounds of the Invention and Analytical Data

| Structure | Compd. No. | Ref. Example | Observed Mass | ¹H NMR |
|---|---|---|---|---|
| 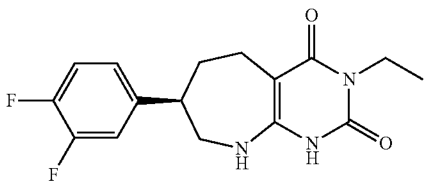 [SMILES: CCn1c(=O)[nH]c2c(c1=O)CC[C@H](c1ccc(F)c(F)c1)CN2] | 84 | 1 | 322 [M + H]⁺ | 1H-NMR (300 MHz, DMSO-d6): δ 10.42 (br s, 1H), 7.46-7.35 (m, 2H), 7.18-7.13 (m, 1H), 4.52 (s, 1H), 3.78-3.70 (m, 3H), 3.54-3.23 (m, 4H), 2.37-2.27 (m 1H), 2.07-1.97 (m, 1H), 1.03 (t, 3H) ppm |
| 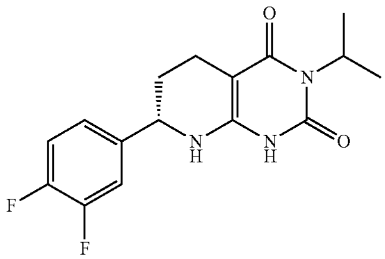 [SMILES: CC(C)n1c(=O)[nH]c2c(c1=O)CC[C@@H](c1ccc(F)c(F)c1)N2] | 85 | 9 | 322 [M + H]⁺ | ¹H-NMR (400 MHz, DMSO-d$_6$): δ 10.11 (br s, 1H), 7.48-7.33 (m, 2H), 7.14-7.10 (m, 1H), 6.33 (br s 1H), 5.05-4.96 (m, 1H), 4.54-4.52 (m, 1H), 2.32-2.22 (m, 1 H), 2.04-1.74 (m, 3H), 1.33-1.30 (m, 6H) ppm |
| 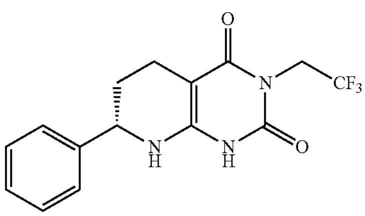 [SMILES: O=c1[nH]c2c(c(=O)n1CC(F)(F)F)CC[C@@H](c1ccccc1)N2] | 86 | 4 | 326 [M + H]⁺ | ¹H-NMR (400 MHz, CD$_3$OD): δ 7.42-7.28 (m, 5H), 4.73-4.60 (m, 3H), 2.49-2.43 (m, 1H), 2.37-2.30 (m, 1H), 2.17-2.06 (m, 1H), 1.98-1.89 (m, 1H) ppm |
| 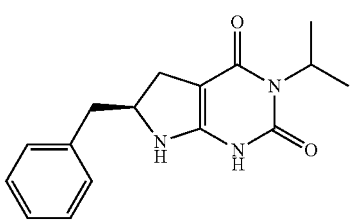 [SMILES: CC(C)n1c(=O)[nH]c2c(c1=O)C[C@H](Cc1ccccc1)N2] | 87 | 7, 8 | 286 [M + H]⁺ | ¹H-NMR (400 MHz, CD$_3$OD): δ 7.34-7.30 (m, 2H), 7.27-7.22 (m, 3H), 5.14-5.07 (m, 1H), 4.28-4.21 (m, 1H), 2.94-2.83 (m, 3H), 2.57 (dd, J = 14.0, 6.0 Hz, 1H), 1.41 (d, J = 6.8 Hz, 6H) ppm |
| 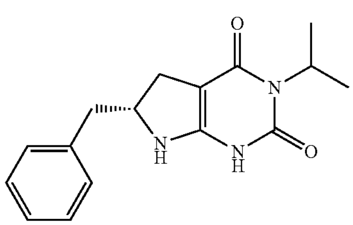 [SMILES: CC(C)n1c(=O)[nH]c2c(c1=O)C[C@@H](Cc1ccccc1)N2] | 88 | 7, 8 | 286 [M + H]⁺ | ¹H-NMR (400 MHz, CD$_3$OD): δ 7.34-7.30 (m, 2H), 7.27-7.22 (m, 3H), 5.14-5.07 (m, 1H), 4.28-4.21 (m, 1H), 2.94-2.83 (m, 3H), 2.57 (dd, J = 14.0, 6.0 Hz, 1H), 1.41 (d, J = 6.8 Hz, 6H) ppm |
| 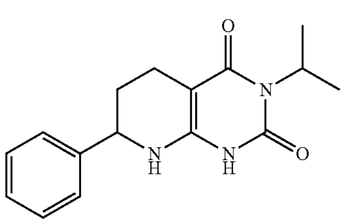 [SMILES: CC(C)n1c(=O)[nH]c2c(c1=O)CCC(c1ccccc1)N2] | 89 | 1, 4 | 286 [M + H]⁺ | ¹H NMR (400 MHz, DMSO-d$_6$) δ 10.00 (s, 1H), 7.41-7.19 (m, 5H), 6.25 (d, J = 1.6 Hz, 1H), 4.99 (dt, J = 13.9, 6.8 Hz, 1H), 4.49 (dt, J = 6.2, 3.4 Hz, 1H), 2.32-2.21 (m, 1H), 2.09-2.01 (m, 1H), 1.96-1.86 (m, 1H), 1.74 (dtd, J = 12.9, 7.6, 7.6, 5.1 Hz, 1H), 1.31 (dd, J = 7.0, 1.6 Hz, 6H) ppm |

TABLE 1-continued

Representative compounds of the Invention and Analytical Data

| Structure | Compd. No. | Ref. Example | Observed Mass | $^1$H NMR |
|---|---|---|---|---|
| 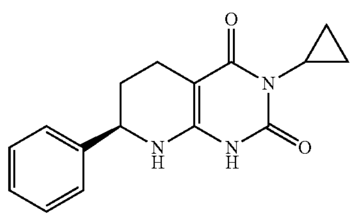 [SMILES: O=c1[nH]c2c(c(=O)n1C1CC1)CC[C@H](c1ccccc1)N2] | 90 | 1, 4 | 284 [M + H]$^+$ | $^1$H NMR (400 MHz, DMSO-d$_6$) δ 9.93 (br s, 1H), 7.40-7.12 (m, 5H), 6.24 (d, J = 2.0 Hz, 1H), 4.49 (dt, J = 6.40, 3.3 Hz, 1H), 2.46-2.40 (m, 1H), 2.32-2.19 (m, 1H), 2.08-2.01 (m, 1H), 1.95-1.85 (m, 1H), 1.78-1.69 (m, 1H), 0.95-0.80 (m, 2H), 0.71-0.58 (m, 2H) ppm |
| 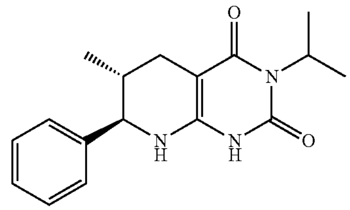 [SMILES: CC(C)n1c(=O)[nH]c2c(c1=O)C[C@@H](C)[C@H](c1ccccc1)N2] | 91 | 4, 11 | 300 [M + H]$^+$ | $^1$H NMR (400 MHz, CDCl$_3$) δ 9.86 (br s, 1H), 7.46-7.35 (m, 3H), 7.34-7.28 (m, 2H), 5.14-5.07 (m, 1H), 4.70 (br s, 1H), 3.99 (d, J = 8.8 Hz, 1H), 2.66 (dd, J = 15.6, 4.8 Hz, 1H), 2.16-2.09 (m, 1H), 1.99-1.90 (m, 1H), 1.37 (dd, J = 6.8, 4.4 Hz, 6H), 0.89 (d, J = 6.4 Hz, 3H) ppm |
| 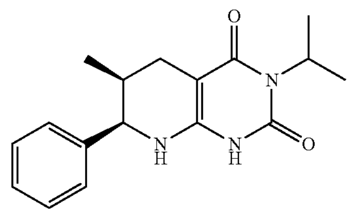 [SMILES: CC(C)n1c(=O)[nH]c2c(c1=O)C[C@H](C)[C@H](c1ccccc1)N2] | 92 | 4, 11 | 300 [M + H]$^+$ | $^1$H NMR (400 MHz, DMSO-d6) δ 9.88 (s, 1H), 7.41-7.37 (m, 2H), 7.34-7.28 (m, 3H), 6.21 (d, J = 4.8 Hz, 1H), 5.05-5.00 (m, 1H), 4.03 (d, J = 7.6 Hz, 1H), 2.31 (dd J = 15.2, 4.8 Hz, 1H), 2.00-1.85 (m, 2H), 1.33 (dd, J = 6.8 Hz, 6H), 0.79 (d, J = 6.4 Hz, 3H) ppm |
| 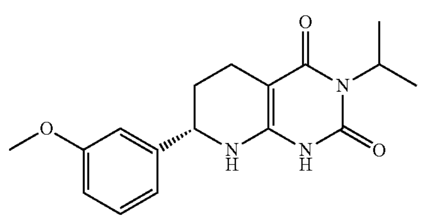 [SMILES: COc1cccc([C@@H]2CCc3c([nH]c(=O)n(C(C)C)c3=O)N2)c1] | 93 | 1, 4 | 316 [M + H]$^+$ | $^1$H-NMR (300 MHz, DMSO-d$_6$): δ 7.32-7.26 (m, 1H), 6.88-6.84 (m, 3H), 6.26 (br s, 1H), 5.03-4.98 (m, 1H), 4.48-4.45 (m, 1H), 3.75 (s, 3H), 2.30-2.23 (m, 1H), 2.12-2.05 (m, 1H), 1.95-1.89 (m, 1H), 1.80-1.71 (m 1H), 1.33 (d, J = 6.6 Hz, 6H) ppm |
| 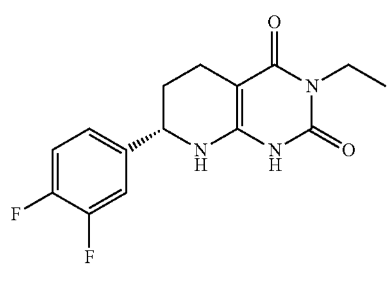 [SMILES: CCn1c(=O)[nH]c2c(c1=O)CC[C@@H](c1ccc(F)c(F)c1)N2] | 94 | 1, 4 | 308 [M + H]$^+$ | $^1$H-NMR (400 MHz, DMSO-d$_6$): δ 10.25 (br s, 1H), 7.48-7.28 (m, 2H), 7.15-7.10 (m, 1H) 6.36 (br s, 1H), 4.57-4.53 (m, 1H), 3.72 (q, J = 6.7 Hz, 2H), 2.33-2.26 (m, 1H), 2.08-1.97 (m, 1H), 1.95-1.88 (m, 1H), 1.84-1.76 (m, 1H), 1.03 (t, J = 6.9 Hz, 3H) ppm |
| 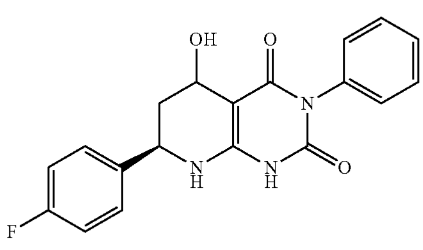 [SMILES: O=c1[nH]c2c(c(=O)n1-c1ccccc1)C(O)C[C@H](c1ccc(F)cc1)N2] | 95 | 1, 4, 14 | 354 [M + H]$^+$ | |

TABLE 1-continued

Representative compounds of the Invention and Analytical Data

| Structure | Compd. No. | Ref. Example | Observed Mass | ¹H NMR |
|---|---|---|---|---|
| 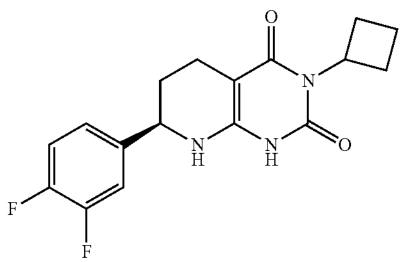 [SMILES: O=c1[nH]c2c(c(=O)n1C1CCC1)CC[C@H](c1ccc(F)c(F)c1)N2] | 96 | 1, 4 | 334 [M + H]⁺ | ¹H NMR (400 MHz, DMSO-$d_6$) δ 10.19 (s, 1H), 7.48-7.29 (m, 2H), 7.15-7.04 (m, 1H), 6.38 (d, J = 2.4 Hz, 1H), 5.21 (quin, J = 9.0 Hz, 1H), 4.56-4.54 (m, 1H), 2.99-2.80 (m, 2H), 2.33-2.19 (m, 1H), 2.04-1.93 (m, 3H), 1.92-1.83 (m, 1H), 1.82-1.70 (m, 2H), 1.68-1.59 (m, 1H) ppm |
| 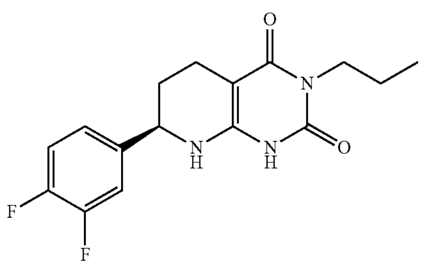 [SMILES: CCCn1c(=O)[nH]c2c(c1=O)CC[C@H](c1ccc(F)c(F)c1)N2] | 97 | 1, 4 | 322 [M + H]⁺ | ¹H NMR (400 MHz, DMSO-$d_6$) δ 10.29 (s, 1H), 7.44-7.36 (m, 2H), 7.13-7.11 (m, 1H), 6.41 (d, J = 2.0 Hz, 1H), 4.56-4.54 (m, 1H), 3.65-3.62 (m, 2H), 2.32-2.22 (m, 1H), 2.04-1.95 (m, 1H), 1.93-1.84 (m, 1H), 1.81-1.73 (m, 1H), 1.53-1.42 (m, 2H), 0.81 (t, J = 7.4 Hz, 3H) ppm |
| 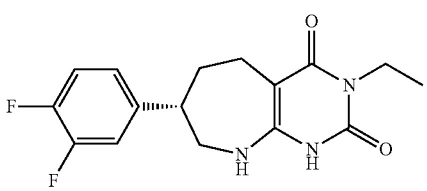 [SMILES: CCn1c(=O)[nH]c2c(c1=O)CC[C@@H](c1ccc(F)c(F)c1)CN2] | 98 | 1 | 322 [M + H]⁺ | ¹H NMR (300 MHz, DMSO-$d_6$): δ 10.41 (br s, 1H), 7.46-7.35 (m, 2H), 7.18-7.13 (m, 1H), 4.49 (s, 1H), 3.78-3.70 (m, 3H), 3.54-3.23 (m, 4H), 2.37-2.27 (m 1H), 2.07-1.97 (m, 1H), 1.03 (t, J = 6.9 Hz, 3H) ppm |
| 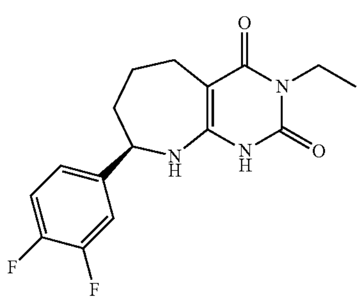 [SMILES: CCn1c(=O)[nH]c2c(c1=O)CCC[C@H](c1ccc(F)c(F)c1)N2] | 99 | 1, 4 | 322 [M + H]⁺ | ¹H NMR (400 MHz, DMSO-$d_6$): δ 10.39 (br s, 1H), 7.44-7.36 (m, 1H), 7.32-7.26 (m, 1H), 7.05-7.02 (m, 1H), 4.95-4.91 (m, 1H) 4.25 (s, 1H), 3.81-3.76 (m, 1H), 3.69 (q, J = 7.2 Hz, 2H), 3.47-3.42 (m, 1H), 2.34-2.28 (m 1H), 1.93-1.74 (m, 3H), 1.00 (t, J = 7.2 Hz, 3H) ppm |
| 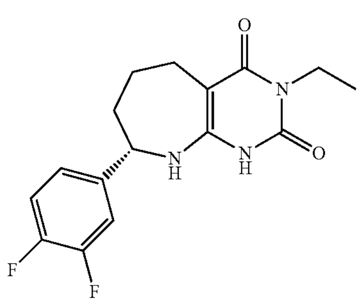 [SMILES: CCn1c(=O)[nH]c2c(c1=O)CCC[C@@H](c1ccc(F)c(F)c1)N2] | 100 | 1, 4 | 322 [M + H]⁺ | ¹H NMR (400 MHz, DMSO-$d_6$): δ 10.39 (br s, 1H), 7.45-7.39 (m, 1H), 7.32-7.26 (m, 1H), 7.05-7.02 (m, 1H), 4.95-4.91 (m, 1H) 4.25 (s, 1H), 3.81-3.76 (m, 1H), 3.69 (q, J = 7.6 Hz, 2H), 3.47-3.42 (m, 1H), 2.34-2.28 (m, 1H), 1.93-1.74 (m, 3H), 1.00 (t, J = 7.2 Hz, 3H) ppm |

TABLE 1-continued

Representative compounds of the Invention and Analytical Data

| Structure | Compd. No. | Ref. Example | Observed Mass | ¹H NMR |
|---|---|---|---|---|
| (structure with D,D and 3,4-difluorophenyl) | 101 | 1, 4, 15 | 324 [M + H]⁺ | |
| (structure with m-tolyl) | 102 | 1, 4, 11 | 300 [M + H]⁺ | ¹H NMR (400 MHz, DMSO-d$_6$) δ 9.97 (br s, 1H), 7.27-7.23 (m, 1H), 7.11-7.05 (m, 3H), 6.23 (s, 1H), 5.05-4.98 (m, 1H), 4.46-4.44 (m, 1H), 2.31-2.24 (m, 4H), 2.14-2.08 (m, 1H) 1.94-1.88 (m, 1H), 1.77-1.71 (m, 1H), 1.33 (d, J = 6.4 Hz, 6H) ppm |
| (structure with m-tolyl) | 103 | 1, 4, 11 | 300 [M + H]⁺ | ¹H NMR (500 MHz, DMSO-d$_6$) δ 9.58 (br, 1H), 7.27-7.23 (m, 1H), 7.11-7.05 (m, 3H), 6.25 (s, 1H), 5.04-4.98 (m, 1H), 4.46-4.44 (m, 1H), 2.31-2.24 (m, 4H), 2.14-2.07 (m, 1H), 1.93-1.88 (m, 1H), 1.77-1.71 (m, 1H), 1.33 (d, J = 6.0 Hz, 6H) ppm |
| (structure with o-tolyl) | 104 | 1, 4, 11 | 300 [M + H]⁺ | ¹H NMR (400 MHz, DMSO-d$_6$) δ 10.06 (br s, 1H), 7.21-7.17 (m, 4H), 6.16 (s, 1H), 5.50-5.00 (m, 1H), 4.70-4.68 (m, 1H), 2.32-2.26 (m, 4H), 2.15-2.07 (m, 1H), 1.94-1.88 (m, 1H), 1.67-1.61 (m, 1H), 1.34 (dd, J = 7.0, 2.5 Hz, 6H) ppm |
| (structure with o-tolyl) | 105 | 1, 4, 11 | 300 [M + H]⁺ | ¹H NMR (500 MHz, DMSO-d$_6$) δ 10.05 (br s, 1H), 7.21-7.17 (m, 4H), 6.16 (s, 1H), 5.05-5.00 (m, 1H), 4.70-4.68 (m, 1H), 2.32-2.26 (m, 4H), 2.14-2.07 (m, 1H), 1.93-1.87 (m, 1H), 1.67-1.61 (m, 1H), 1.34 (dd, J = 7.0, 2.5 Hz, 6H) ppm |
| (structure with methyl and phenyl) | 106 | 17 | 300 [M + H]⁺ | ¹H NMR (400 MHz, DMSO-d$_6$) δ 9.85 (br s, 1H), 7.38-7.30 (m, 4H), 7.26-7.22 (m, 1H), 6.44 (s, 1H), 5.01-4.94 (m, 1H), 2.28-2.14 (m, 2H), 1.73-1.64 (m, 1H), 1.61-1.52 (m, 1H), 1.50 (s, 3H), 1.31 (d, J = 7.0 Hz, 6H) ppm. |

TABLE 1-continued

Representative compounds of the Invention and Analytical Data

| Structure | Compd. No. | Ref. Example | Observed Mass | ¹H NMR |
|---|---|---|---|---|
| 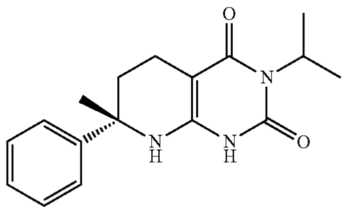 | 107 | 17 | 300 [M + H]⁺ | ¹H NMR (500 MHz, DMSO-d₆) δ 9.83 (br s, 1H), 7.37-7.30 (m, 4H), 7.25-7.23 (m, 1H), 6.43 (s, 1H), 5.00-4.93 (m, 1H), 2.25-2.14 (m, 2H), 1.69-1.63 (m, 1H), 1.59-1.51 (m, 1H), 1.49 (s, 3H), 1.29 (d, J = 7.0 Hz, 6H) ppm |
| 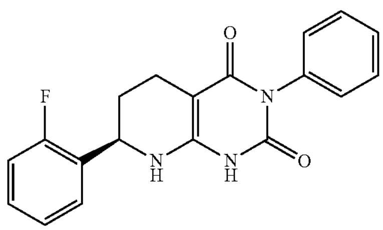 [SMILES: O=c1[nH]c2c(c(=O)n1-c1ccccc1)CC[C@H](c1ccccc1F)N2] | 108 | 1, 4, 11 | 338 [M + H]⁺ | ¹H NMR (500 MHz, DMSO-d₆) δ 10.76-10.67 (m, 1H), 7.45-7.34 (m, 5H), 7.33-7.14 (m, 4H), 6.77 (br s, 1H), 4.89 (s, 1H), 2.38-2.32 (m, 1H), 2.03-1.95 (m, 2H), 1.92-1.83 (m, 1H) ppm |
| 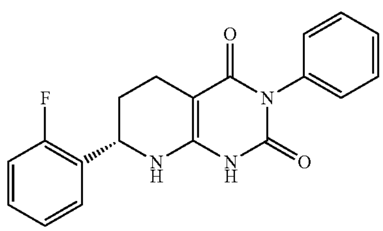 [SMILES: O=c1[nH]c2c(c(=O)n1-c1ccccc1)CC[C@@H](c1ccccc1F)N2] | 109 | 1, 4, 11 | 338 [M + H]⁺ | ¹H NMR (500 MHz, DMSO-d₆) δ 10.89-10.79 (m, 1H), 7.48-7.36 (m, 5H), 7.35-7.16 (m, 4H), 6.77 (br s, 1H), 4.89 (s, 1H), 2.38-2.32 (m, 1H), 2.03-1.95 (m, 2H), 1.92-1.83 (m, 1H) ppm |
| 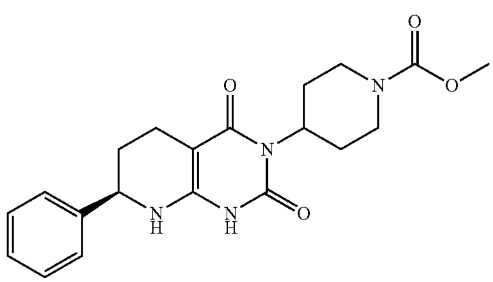 [SMILES: COC(=O)N1CCC(n2c(=O)[nH]c3c(c2=O)CC[C@H](c2ccccc2)N3)CC1] | 110 | 1, 4, 11 | 385 [M + H]⁺ | ¹H NMR (500 MHz, DMSO-d₆) δ 10.19 (br s, 1H), 7.39-7.36 (m, 2H), 7.30-7.27 (m, 3H), 6.36 (br s, 1H), 4.85-4.79 (m, 1H), 4.55-4.49 (m, 1H), 4.05-4.00 (m, 2H), 3.60 (s, 3H), 2.83-2.75 (m, 2H), 2.48-2.37 (m, 2H), 2.31-2.25 (m, 1H), 2.08-2.02 (m, 1H), 1.96-1.89 (m, 1H), 1.80-1.73 (m, 1H), 1.45 (d, J = 11.5 Hz, 2H) ppm |
| 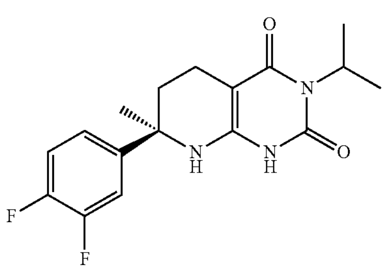 [SMILES: CC(C)n1c(=O)[nH]c2c(c1=O)CC[C@](C)(c1ccc(F)c(F)c1)N2] | 111 | 17 | 336 [M + H]⁺ | ¹H NMR (400 MHz, DMSO-d₆) δ 9.85 (br s, 1H), 7.46-7.38 (m, 2H), 7.16-7.12 (m, 1H), 6.50 (s, 1H), 5.04-4.93 (m, 1H), 2.28-2.15 (m, 2H), 1.73-1.48 (m, 5H), 1.31 (d, J = 6.7 Hz, 6H) ppm |
| 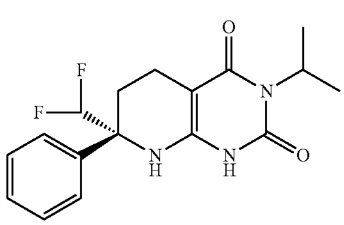 [SMILES: CC(C)n1c(=O)[nH]c2c(c1=O)CC[C@@](c1ccccc1)(C(F)F)N2] | 112 | 17 | 336 [M + H]⁺ | ¹H NMR (400 MHz, DMSO-d₆) δ 9.74 (s, 1H), 7.41-7.27 (m, 5H), 6.89 (s, 1H), 6.36 (t, J = 56.0 Hz, 1H), 4.93-4.84 (m, 1H), 2.37-2.24 (m, 2H), 1.82 (td, J = 12.4, 5.0 Hz, 1H), 1.52-1.42 (m, 1H), 1.23 (d, J = 7.0 Hz, 6H) ppm |

TABLE 1-continued

Representative compounds of the Invention and Analytical Data

| Structure | Compd. No. | Ref. Example | Observed Mass | ¹H NMR |
|---|---|---|---|---|
| 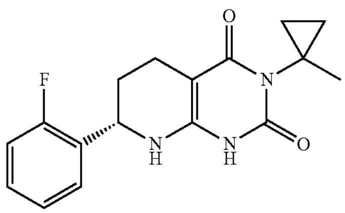 | 113 | 1, 4, 11 | 304 [M + H]⁺ | ¹H NMR (500 MHz, DMSO-d₆) δ 10.18 (br s, 1H), 7.35-7.33 (m, 1H), 7.25-7.19 (m, 3H), 6.31 (s, 1H), 4.82-4.80 (m, 1H), 2.30-2.21 (m, 1H), 2.03-1.90 (m, 2H), 1.80-1.73 (m, 1H), 1.27 (s, 3H), 0.78-0.74 (m, 4H) ppm |
| 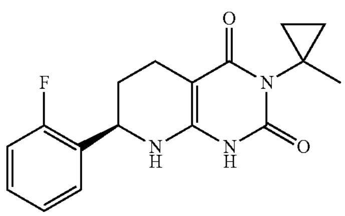 [SMILES: CC1(n2c(=O)[nH]c3c(c2=O)CC[C@H](c2ccccc2F)N3)CC1] | 114 | 1, 4, 11 | 316 [M + H]⁺ | ¹H NMR (500 MHz, DMSO-d₆) δ 10.21 (br s, 1H), 7.35-7.33 (m, 1H), 7.25-7.19 (m, 3H), 6.33 (s, 1H), 4.82-4.80 (m, 1H), 2.30-2.21 (m, 1H), 2.03-1.90 (m, 2H), 1.80-1.73 (m, 1H), 1.27 (s, 3H), 0.78-0.74 (m, 4H) ppm |
| 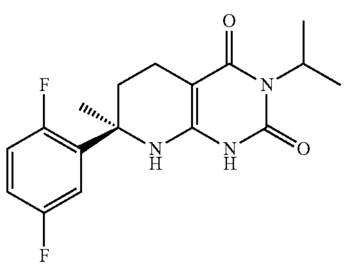 [SMILES: CC(C)n1c(=O)[nH]c2c(c1=O)CC[C@](C)(c1cc(F)ccc1F)N2] | 115 | 17 | 336 [M + H]⁺ | ¹H NMR (400 MHz, DMSO-d₆) δ 9.98-9.86 (m, 1H), 7.31-7.25 (m, 1H), 7.22-7.19 (m, 1H), 7.00-6.93 (m, 1H), 6.57 (s, 1H), 5.02-4.93 (m, 1H), 2.42-2.22 (m, 2H), 1.72-1.64 (m, 1H), 1.58-1.50 (m, 4H), 1.32 (dd, J = 6.9, 2.0 Hz, 6H) ppm |
| 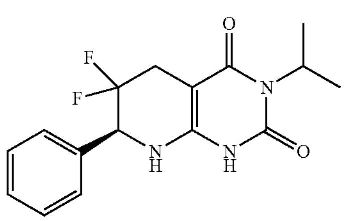 [SMILES: CC(C)n1c(=O)[nH]c2c(c1=O)CC(F)(F)[C@H](c1ccccc1)N2] | 116 | 16 | 322 [M + H]⁺ | ¹H NMR (500 MHz, CD₃OD) δ 7.44-7.40 (m, 5H), 5.17-5.13 (m, 1H), 4.81-4.77 (m, 1H), 2.91-2.84 (m, 1H), 2.73-2.63 (m, 1H), 1.47 (dd, J = 7.0, 2.0 Hz, 6H) ppm |
| 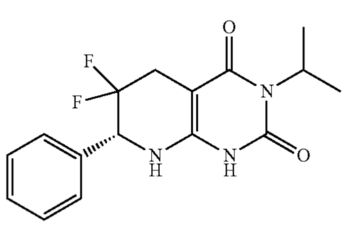 [SMILES: CC(C)n1c(=O)[nH]c2c(c1=O)CC(F)(F)[C@@H](c1ccccc1)N2] | 117 | 16 | 322 [M + H]⁺ | ¹H NMR (500 MHz, CD₃OD) δ 7.43-7.40 (m, 5H), 5.17-5.13 (m, 1H), 4.81-4.77 (m, 1H), 2.91-2.84 (m, 1H), 2.73-2.63 (m, 1H), 1.47 (dd, J = 7.0, 2.0 Hz, 6H) ppm |
| 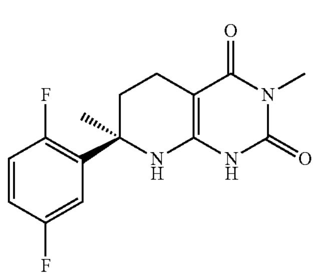 [SMILES: Cn1c(=O)[nH]c2c(c1=O)CC[C@](C)(c1cc(F)ccc1F)N2] | 118 | 17 | 308 [M + H]⁺ | ¹H NMR (500 MHz, DMSO-d₆) δ 10.06 (br s, 1H), 7.26-7.18 (m, 1H), 7.16-7.09 (m, 1H), 6.92-6.86 (m, 1H), 6.53 (s, 1H), 2.98 (s, 3H), 2.36-2.21 (m, 2H), 1.65-1.58 (m, 1H), 1.54-1.46 (m, 4H) ppm |

TABLE 1-continued

Representative compounds of the Invention and Analytical Data

| Structure | Compd. No. | Ref. Example | Observed Mass | ¹H NMR |
|---|---|---|---|---|
| 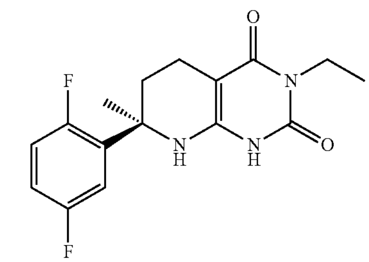 [SMILES: CCn1c(=O)[nH]c2c(c1=O)CC[C@](C)(c1cc(F)ccc1F)N2] | 119 | 17 | 322 [M + H]⁺ | ¹H NMR (400 MHz, DMSO-d₆) δ 10.00 (br s, 1H), 7.26-7.18 (m, 1H), 7.16-7.10 (m, 1H), 6.94-6.85 (m, 1H), 6.53 (s, 1H), 3.65 (q, J = 7.0 Hz, 2H), 2.36-2.21 (m, 2H), 1.65-1.58 (m, 1H), 1.54-1.46 (m, 4H), 0.96 (t, J = 7.0 Hz, 3H) ppm |
| 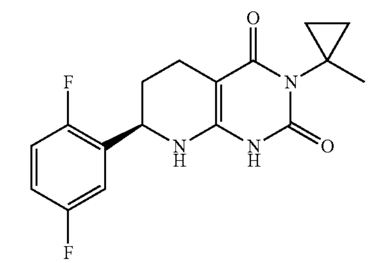 [SMILES: CC1(n2c(=O)[nH]c3c(c2=O)CC[C@H](c2cc(F)ccc2F)N3)CC1] | 120 | 1, 4, 11 | 334 [M + H]⁺ | ¹H NMR (400 MHz, DMSO-d₆) δ 10.18 (br s, 1H), 7.30-7.24 (m, 1H), 7.21-7.14 (m, 1H), 7.04-6.98 (m, 1H), 6.29 (br s, 1H), 4.79-4.75 (m, 1H), 2.33-2.25 (m, 1H), 2.03-1.86 (m, 2H), 1.81-1.72 (m, 1H), 1.25 (s, 3H), 0.77-0.73 (m, 4H) ppm |
| 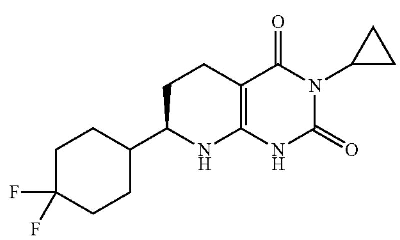 [SMILES: O=c1[nH]c2c(c(=O)n1C1CC1)CC[C@H](C1CCC(F)(F)CC1)N2] | 121 | 1, 4, 11 | 316 [M + H]⁺ | ¹H-NMR (400 MHz, CD₃OD): δ 7.39-7.34 (m, 1H), 7.12 (d, J = 6.8 Hz, 1H), 7.06-6.99 (m, 2H), 4.57-4.52 (m, 1H), 2.41-2.34 (m, 1H), 2.32-2.18 (m, 1H), 2.09-2.03 (m, 1H), 1.91-1.83 (m, 1H), 1.38 (s, 3H), 0.92-0.85 (m, 4H) ppm |
| 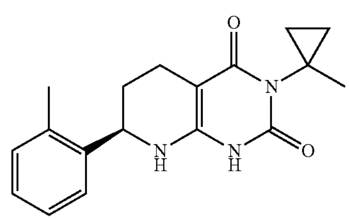 [SMILES: Cc1ccccc1[C@H]1CCc2c([nH]c(=O)n(C3(C)CC3)c2=O)N1] | 122 | 1, 4, 11 | 312 [M + H]⁺ | ¹H-NMR (400 MHz, DMSO-d₆): δ 10.03 (s, 1H), 7.19-7.15 (m, 4H), 6.11 (s, 1H), 4.69-4.65 (m, 1H), 2.33-2.28 (m, 4H), 2.18-2.04 (m, 1H), 1.94-1.83 (m, 1H), 1.71-1.58 (m, 1H), 1.21 (s, 3H), 0.82-0.74 (m, 4H) ppm |
| 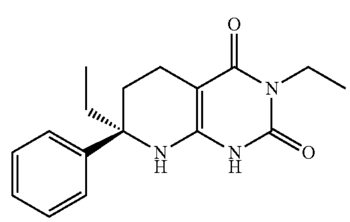 | 123 | 17 | 300 [M + H]⁺ | ¹H NMR (400 MHz, DMSO-d₆) δ 9.87 (s, 1H), 7.33-7.28 (m, 2H), 7.21-7.16 (m, 3H), 6.40 (s, 1H), 3.66-3.62 (m, 2H), 2.22-2.08 (m, 2H), 1.91-1.80 (m, 1H), 1.76-1.59 (m, 2H), 1.48-1.38 (m, 1H), 0.95 (t, J = 7.0 Hz, 3H), 0.61 (t, J = 7.4 Hz, 3H) ppm |
| 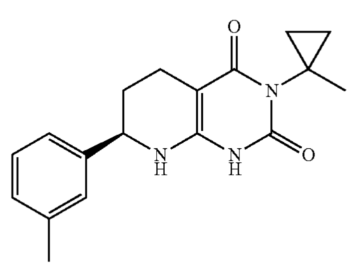 [SMILES: Cc1cccc([C@H]2CCc3c([nH]c(=O)n(C4(C)CC4)c3=O)N2)c1] | 124 | 1, 4, 11 | 312 [M + H]⁺ | ¹H-NMR (400 MHz, DMSO-d₆): δ 9.90 (s, 1H), 7.24-7.19 (m, 1H), 7.08-7.00 (m, 3H), 6.15 (s, 1H), 4.40-4.38 (m, 1H), 2.46 (s, 3H), 2.27-2.08 (m, 2H), 1.89-1.82 (m, 1H), 1.72-1.65 (m, 1H), 1.22 (s, 3H), 0.74-0.70 (m, 4H) ppm |

TABLE 1-continued

Representative compounds of the Invention and Analytical Data

| Structure | Compd. No. | Ref. Example | Observed Mass | ¹H NMR |
|---|---|---|---|---|
| 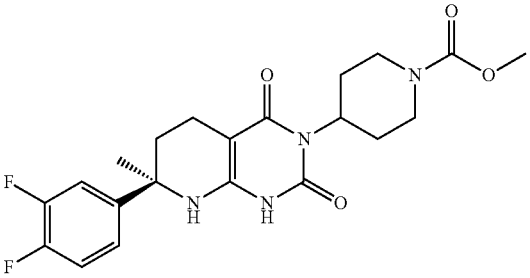 [SMILES: COC(=O)N1CCC(n2c(=O)[nH]c3c(c2=O)CC[C@](C)(c2ccc(F)c(F)c2)N3)CC1] | 125 | 17 | 435 [M + H]⁺ | ¹H NMR (500 MHz, DMSO-d₆) δ 10.01 (s, 1H), 7.46-7.38 (m, 2H), 7.16-7.11 (m, 1H), 6.67 (br s, 1H), 4.87-4.77 (m, 1H), 4.05-4.00 (m, 2H), 3.60 (s, 3H), 2.83-2.75 (m, 2H), 2.48-2.37 (m, 2H), 2.31-2.25 (m, 2H), 2.22-2.12 (m, 1H), 1.69-1.55 (m, 1H), 1.50 (s, 3H), 1.46-1.42 (m, 2H) ppm |
| 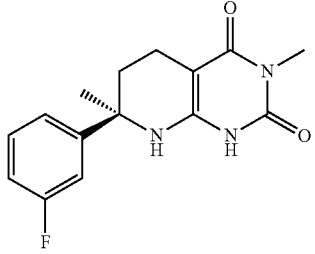 [SMILES: Cn1c(=O)[nH]c2c(c1=O)CC[C@](C)(c1cccc(F)c1)N2] | 126 | 17 | 290 [M + H]⁺ | ¹H NMR (400 MHz, DMSO-d₆) δ 10.07 (br s, 1H), 7.42-7.37 (m, 1H), 7.16-7.06 (m, 3H), 6.54 (s, 1H), 3.03 (s, 3H), 2.28-2.18 (m, 2H), 1.70-1.64 (m, 1H), 1.54-1.52 (m, 1H), 1.51 (s, 3H) ppm |
| 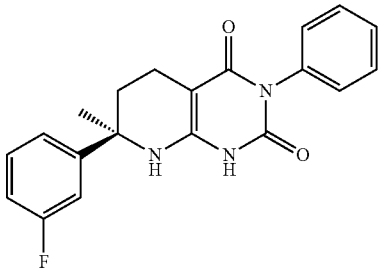 [SMILES: C[C@]1(c2cccc(F)c2)CCc2c([nH]c(=O)n(-c3ccccc3)c2=O)N1] | 127 | 17 | 352 [M + H]⁺ | ¹H NMR (500 MHz, DMSO-d₆) δ 7.44-7.33 (m, 4H), 7.22-7.10 (m, 5H), 6.83 (br s, 1H), 2.27-2.21 (m, 2H), 1.72-1.65, 1.62-1.56 (m, 2H), 1.54 (s, 3H) ppm |
| 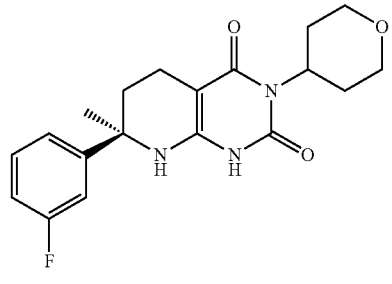 [SMILES: C[C@]1(c2cccc(F)c2)CCc2c([nH]c(=O)n(C3CCOCC3)c2=O)N1] | 128 | 17 | 360 [M + H]⁺ | ¹H NMR (500 MHz, DMSO-d₆) δ 9.95 (br s, 1H), 7.43-7.38 (m, 1H), 7.17-7.06 (m, 3H), 6.55 (br s, 1H), 4.83-4.82 (m, 1H), 3.89-3.87 (m, 2H), 3.32-3.27 (m, 2H), 2.60-2.56 (m, 2H), 2.23-2.18 (m, 2H), 1.69-1.50 (m, 5H), 1.36-1.34 (m, 2H) ppm |
| 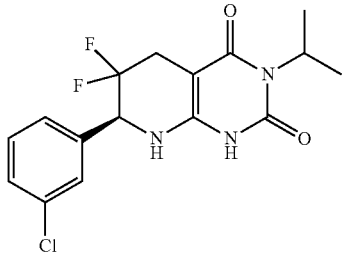 | 129 | 16 | 356 [M + H]⁺ | ¹H NMR (500 MHz, DMSO-d₆) δ 11.15-10.95 (m, 1H), 7.48-7.41 (m, 4H), 7.33 (d, J = 7.0 Hz, 1H), 5.02-4.88 (m, 2H), 2.84-2.79 (m, 1H), 2.64-2.52 (m, 1H), 1.32 (dd, J = 7.0, 3.0 Hz, 6H) ppm |

TABLE 1-continued

Representative compounds of the Invention and Analytical Data

| Structure | Compd. No. | Ref. Example | Observed Mass | $^1$H NMR |
|---|---|---|---|---|
| 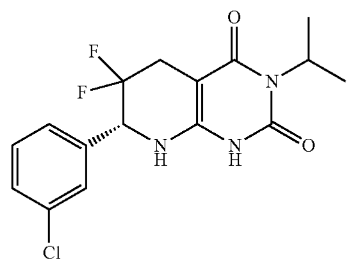 [SMILES: CC(C)n1c(=O)[nH]c2c(c1=O)CC(F)(F)[C@@H](c1cccc(Cl)c1)N2] | 130 | 16 | 356 [M + H]$^+$ | $^1$H NMR (500 MHz, DMSO-d$_6$) δ 10.90-10.70 (m, 1H), 7.48-7.41 (m, 4H), 7.33 (d, J = 6.5 Hz, 1H), 5.02-4.88 (m, 2H), 2.84-2.79 (m, 1H), 2.64-2.52 (m, 1H), 1.32 (dd, J$_1$ = 6.5, J$_2$ = 3.0 Hz, 6H) ppm |
| 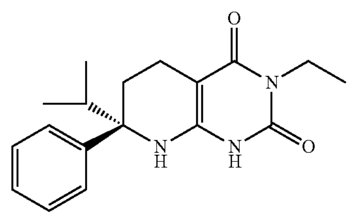 [SMILES: CCn1c(=O)[nH]c2c(c1=O)CC[C@@](c1ccccc1)(C(C)C)N2] | 131 | 17 | 314 [M + H]$^+$ | $^1$H NMR (400 MHz, DMSO-d$_6$) δ 9.96 (s, 1H), 7.38-7.34 (m, 2H), 7.25-7.21 (m, 3H), 6.38 (s, 1H), 3.69 (q, J = 6.9 Hz, 2H), 2.30-2.24 (m, 2H), 2.12 (quin, J = 6.8 Hz, 1H), 1.78 (td, J = 13.0, 5.1 Hz, 1H), 1.36 (ddd, J = 15.4, 12.8, 5.1 Hz, 1H), 1.01 (t, J = 7.0 Hz, 3H), 0.93 (d, J = 6.6 Hz, 3H), 0.66 (d, J = 7.0 Hz, 3H) ppm |
| 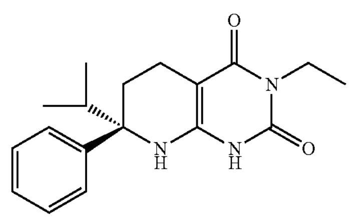 [SMILES: CCn1c(=O)[nH]c2c(c1=O)CC[C@@](c1ccccc1)(C(C)C)N2] | 132 | 17 | 314 [M + H]$^+$ | $^1$H NMR (400 MHz, DMSO-d$_6$) δ 9.95 (s, 1H), 7.38-7.32 (m, 2H), 7.25-7.20 (m, 3H), 6.37 (s, 1H), 3.67 (q, J = 7.0 Hz, 2H), 2.30-2.20 (m, 2H), 2.11 (quin, J = 6.8 Hz, 1H), 1.77 (td, J = 13.0, 5.2 Hz, 1H), 1.35 (ddd, J = 15.4, 12.8, 5.1 Hz, 1H), 1.00 (t, J = 7.0 Hz, 3H), 0.91 (d, J = 6.6 Hz, 3H), 0.65 (d, J = 7.0 Hz, 3H) ppm |
| 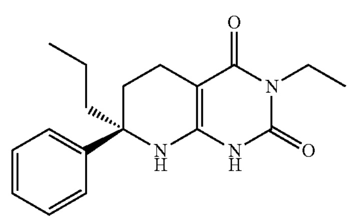 [SMILES: CCC[C@]1(c2ccccc2)CCc2c([nH]c(=O)n(CC)c2=O)N1] | 133 | 17 | 314 [M + H]$^+$ | $^1$H NMR (400 MHz, DMSO-d$_6$) δ ppm 9.84 (br s, 1H), 7.32-7.28 (m, 2H), 7.16-7.12 (m, 3H), 6.43 (s, 1H), 3.63 (q, J = 6.9 Hz, 2H), 2.20-2.10 (m, 2H), 1.83-1.74 (m, 1H), 1.71-1.58 (m, 2H), 1.47-1.36 (m, 1H), 1.20-1.09 (m, 1H), 0.95 (t, J = 6.9 Hz, 3H), 0.88-0.80 (m, 1H), 0.74 (t, J = 8.0 Hz, 3H) ppm |
| 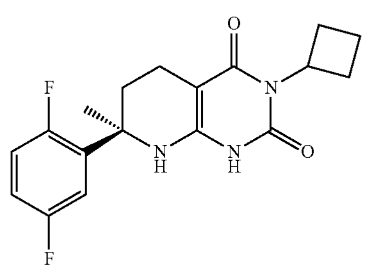 [SMILES: C[C@]1(c2cc(F)ccc2F)CCc2c([nH]c(=O)n(C3CCC3)c2=O)N1] | 134 | 17 | 348 [M + H]$^+$ | $^1$H NMR (300 MHz, CD$_3$OD) δ 7.13-7.07 (m, 1H), 7.04-6.99 (m, 1H), 6.93-6.86 (m, 1H), 5.26-5.19 (m, 1H), 2.99-2.89 (m, 2H), 2.55-2.48 (m, 1H), 2.42-2.35 (m, 1H), 2.17-2.08 (m, 2H), 1.88-1.62 (m, 7H) ppm |
| 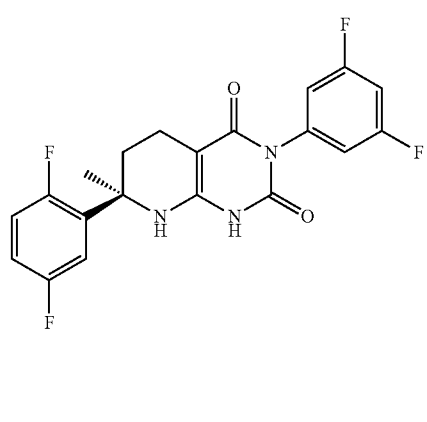 [SMILES: C[C@]1(c2cc(F)ccc2F)CCc2c([nH]c(=O)n(-c3cc(F)cc(F)c3)c2=O)N1] | 135 | 17 | 406 [M + H]$^+$ | $^1$H NMR (300 MHz, CD$_3$OD) δ 7.17-6.90 (m, 6H), 2.62-2.56 (m, 1H), 2.52-2.43 (m, 1H), 1.83-1.72 (m, 2H), 1.68 (s, 3H) ppm |

TABLE 1-continued

Representative compounds of the Invention and Analytical Data

| Structure | Compd. No. | Ref. Example | Observed Mass | ¹H NMR |
|---|---|---|---|---|
| 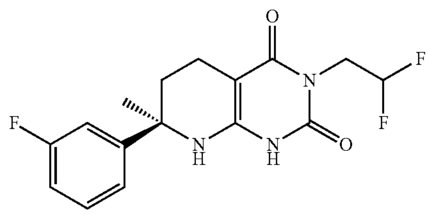 [SMILES: C[C@]1(c2cccc(F)c2)CCc2c([nH]c(=O)n(CC(F)F)c2=O)N1] | 136 | 17 | 340 [M + H]⁺ | ¹H NMR (500 MHz, DMSO-d₆): δ ppm 10.48-10.41 (m, 1H), 7.42-7.38 (m, 1H), 7.18-7.15 (m, 2H), 7.12-7.07 (m, 1H), 6.92 (br s, 1H), 6.13 (tt, J = 57.0, 4.5 Hz, 1H), 4.10 (td, 14.0, 4.5 Hz, 2H), 2.26-2.20 (m, 2H), 1.71-1.65 (m, 1H), 1.60-1.52 (m, 4H) ppm |
| 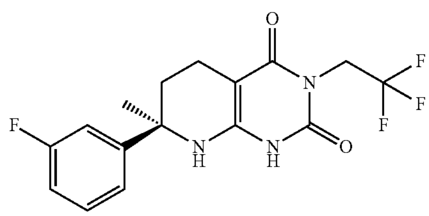 [SMILES: C[C@]1(c2cccc(F)c2)CCc2c([nH]c(=O)n(CC(F)(F)F)c2=O)N1] | 137 | 17 | 358 [M + H]⁺ | ¹H NMR (500 MHz, DMSO-d₆): δ 10.45-10.40 (m, 1H), 7.42-7.38 (m, 1H), 7.18-7.15 (m, 2H), 7.11-7.07 (m, 1H), 6.79 (br s, 1H), 6.79 (br s, 1H), 4.52-4.46 (m, 2H), 2.30-2.20 (m, 2H), 1.71-1.57 (m, 2H), 1.53 (s, 3H) ppm |
| 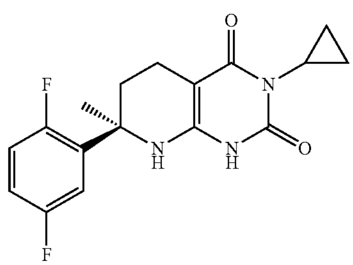 [SMILES: C[C@]1(c2cc(F)ccc2F)CCc2c([nH]c(=O)n(C3CC3)c2=O)N1] | 138 | 17 | 334 [M + H]⁺ | ¹H NMR (400 MHz, CD₃OD): δ 7.17-7.11 (m, 1H), 7.06-7.03 (m, 1H), 6.95-6.91 (m, 1H) 2.54-2.51 (m, 2H), 2.46-2.42 (m, 1H), 1.73-1.70 (m, 2H), 1.65 (s, 3H), 1.03-1.00 (m, 2H), 0.75-0.72 (m, 2H) ppm |
| 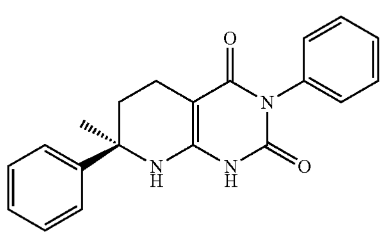 [SMILES: C[C@]1(c2ccccc2)CCc2c([nH]c(=O)n(-c3ccccc3)c2=O)N1] | 139 | 17 | 334 [M + H]⁺ | ¹H NMR (500 MHz, DMSO-d₆): δ 10.18-10.03 (m, 1H), 7.41-7.33 (m, 7H), 7.28-7.27 (m, 1H), 7.14 (d, J = 7.5 Hz, 2H), 6.64 (br s, 1H), 2.28-2.19 (m, 2H), 1.71-1.57 (m, 2H), 1.55 (s, 3H) ppm |
| 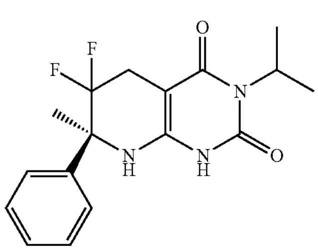 [SMILES: CC(C)n1c(=O)[nH]c2c(c1=O)CC(F)(F)[C@](C)(c1ccccc1)N2] | 140 | 16, 17 | 336 [M + H]⁺ | ¹H NMR (400 MHz, DMSO-d₆): δ 7.45-7.36 (m, 5H), 6.99 (br s, 1H), 4.99 (m, 1H), 2.77 (m, 1H), 2.32 (m, 1H), 1.33 (dd, J₁ = 6.4 Hz, J₂ = 2.4 Hz, 6H) ppm |
| 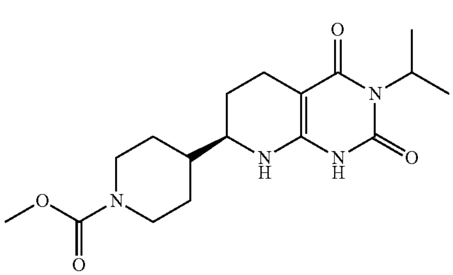 [SMILES: COC(=O)N1CCC([C@H]2CCc3c([nH]c(=O)n(C(C)C)c3=O)N2)CC1] | 141 | 1, 4, 11 | 351 [M + H]⁺ | ¹H NMR (400 MHz, DMSO-d₆): δ 9.50 (br s, 1H), 5.99 (br s, 1H), 5.02-4.94 (m, 1H), 4.02 (m, 2H), 3.58 (s, 3H), 3.08-3.02 (m, 1H), 2.78-2.67 (m, 2H), 2.25-2.11 (m, 2H), 1.70-1.51 (m, 5H), 1.31-1.29 (m, 6H), 1.16-1.08 (m, 2H) ppm |

TABLE 1-continued

Representative compounds of the Invention and Analytical Data

| Structure | Compd. No. | Ref. Example | Observed Mass | ¹H NMR |
|---|---|---|---|---|
| 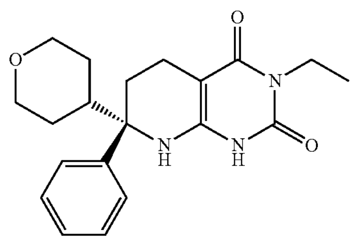 [SMILES: CCn1c(=O)[nH]c2c(c1=O)CC[C@@](c1ccccc1)(C1CCOCC1)N2] | 142 | 17 | 356 [M + H]⁺ | ¹H NMR (500 MHz, DMSO-d₆): δ 9.83 (s, 1H), 7.38-7.34 (m, 2H), 7.26-7.22 (m, 3H), 6.51 (s, 1H), 3.91 (dd, J = 3.5 Hz, 11.0 Hz, 1H), 3.82-3.78 (m, 1H), 3.68 (q, J = 7.0 Hz, 2H), 3.30-3.26 (m, 1H), 3.17-3.12 (m, 1H), 2.27-2.23 (m, 2H), 2.04-2.02 (m, 1H), 1.82-1.80 (m, 1H), 1.71-1.67 (m, 1H), 1.38-1.30 (m, 2H), 1.18-1.16 (m, 1H), 1.02-0.96 (m, 4H) ppm |
| 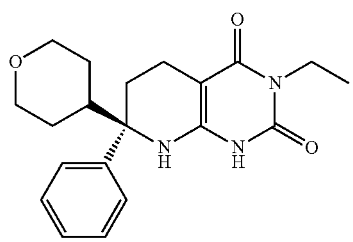 [SMILES: CCn1c(=O)[nH]c2c(c1=O)CC[C@](c1ccccc1)(C1CCOCC1)N2] | 143 | 17 | 356 [M + H]⁺ | ¹H NMR (500 MHz, DMSO-d₆): δ 9.83 (s, 1H), 7.38-7.34 (m, 2H), 7.26-7.22 (m, 3H), 6.51 (s, 1H), 3.91 (dd, J = 3.5 Hz, 11.0 Hz, 1H), 3.82-3.78 (m, 1H), 3.68 (q, J = 7.0 Hz, 2H), 3.30-3.26 (m, 1H), 3.17-3.12 (m, 1H), 2.27-2.23 (m, 2H), 2.04-2.02 (m, 1H), 1.82-1.80 (m, 1H), 1.71-1.67 (m, 1H), 1.38-1.30 (m, 2H), 1.18-1.16 (m, 1H), 1.02-0.96 (m, 4H) ppm |
| 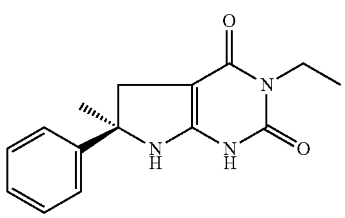 [SMILES: CCn1c(=O)[nH]c2c(c1=O)C[C@](C)(c1ccccc1)N2] | 144 | 17 | 272 [M + H]⁺ | ¹H NMR (400 MHz, DMSO-d₆): δ 11.32 (s, 1H), 7.40-7.26 (m, 4H), 7.19-7.15 (m, 1H), 6.49 (br s, 1H), 3.65 (q, J = 8.0 Hz, 2H), 2.82 (d, J = 13.7 Hz, 1H), 2.63 (d, J = 13.7 Hz, 1H), 1.50 (s, 3H), 0.96 (t, J = 7.0 Hz, 3H) ppm |
| 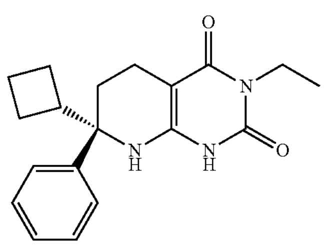 [SMILES: CCn1c(=O)[nH]c2c(c1=O)CC[C@@](c1ccccc1)(C1CCC1)N2] | 145 | 17 | 326 [M + H]⁺ | ¹H NMR (400 MHz, DMSO-d₆): δ 7.35-7.33 (m, 2H), 7.26-7.21 (m, 3H), 6.58 (br s, 1H), 3.69 (q, J = 5.6 Hz, 2H), 2.87 (m, 1H), 2.23 (m, 1H), 2.14 (m, 1H), 1.93-1.86 (m, 2H), 1.78-1.55 (m, 4H), 1.49 (m, 2H), 1.01 (t, J = 5.6 Hz, 3H) ppm |
| 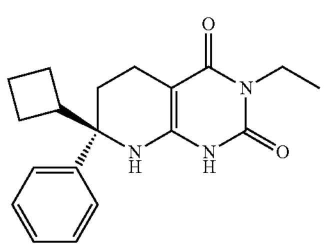 [SMILES: CCn1c(=O)[nH]c2c(c1=O)CC[C@](c1ccccc1)(C1CCC1)N2] | 146 | 17 | 326 [M + H]⁺ | ¹H NMR (400 MHz, DMSO-d₆): δ 7.35-7.33 (m, 2H), 7.26-7.21 (m, 3H), 6.58 (br s, 1H), 3.69 (q, J = 5.6 Hz, 2H), 2.87 (m, 1H), 2.23 (m, 1H), 2.14 (m, 1H), 1.93-1.86 (m, 2H), 1.78-1.55 (m, 4H), 1.49 (m, 2H), 1.01 (t, J = 5.6 Hz, 3H) ppm |
| 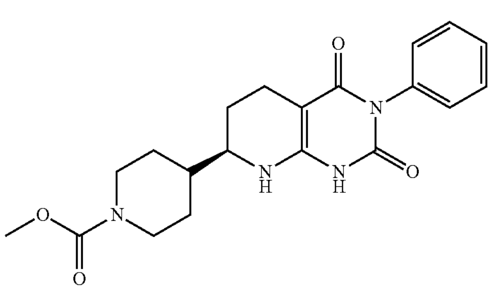 [SMILES: COC(=O)N1CCC([C@H]2CCc3c([nH]c(=O)n(-c4ccccc4)c3=O)N2)CC1] | 147 | 1, 4, 11 | 385 [M + H]⁺ | ¹H NMR (400 MHz, DMSO-d₆): δ 7.36-7.32 (m, 2H), 7.24 (m, 1H), 7.04 (m, 2H), 3.97 (br s, 2H), 3.59 (s, 3H), 2.99 (br s, 1H), 2.63 (br s, 2H), 2.26 (m, 1H), 2.17 (m, 1H), 1.64-1.61 (m, 1H), 1.53-1.49 (m, 2H), 1.36 (m, 2H), 1.08-1.01 (m, 2H) ppm |

TABLE 1-continued

Representative compounds of the Invention and Analytical Data

| Structure | Compd. No. | Ref. Example | Observed Mass | $^1$H NMR |
|---|---|---|---|---|
| [structure] | 148 | 1, 4, 11 | 385 [M + H]$^+$ | $^1$H NMR (400 MHz, CD$_3$OD): δ 7.46-7.42 (m, 2H), 7.36 (m, 1H), 7.18 (m, 2H), 4.22 (m, 2H), 3.70 (s, 3H), 3.19 (m, 1H), 2.82 (m, 2H), 2.54-2.45 (m, 2H), 1.91-1.80 (m, 5H), 1.31-1.26 (m, 2H) ppm |
| [structure] | 149 | 16 | 340 [M + H]$^+$ | $^1$H NMR (400 MHz, DMSO-d$_6$): δ 10.57 (br s, 1H), 7.48 (m, 1H), 7.27-7.19 (m, 3H), 6.99 (s, 1H), 5.00 (m, 1H), 4.92 (m, 1H), 2.82 (m, 1H), 2.57 (m, 1H), 1.35 (dd, J$_1$ = 6.5 Hz, J$_2$ = 3.5 Hz, 6H) ppm |
| [structure] | 150 | 16 | 340 [M + H]$^+$ | $^1$H NMR (400 MHz, DMSO-d$_6$): δ 10.57 (br s, 1H), 7.48 (m, 1H), 7.27-7.19 (m, 3H), 7.02 (s, 1H), 5.01 (m, 1H), 4.92 (m, 1H), 2.82 (m, 1H), 2.57 (m, 1H), 1.35 (dd, J$_1$ = 6.5 Hz, J$_2$ = 3.5 Hz, 6H) ppm |
| [structure] | 151 | 16 | 340 [M + H]$^+$ | $^1$H NMR (400 MHz, DMSO-d$_6$): δ 7.45 (m, 1H), 7.38 (m, 1H), 7.27 (m, 2H), 6.94 (br s, 1H), 5.15 (m, 1H), 5.02 (m, 1H), 2.86 (m, 1H), 2.57 (, 1H), 1.35 (d, J = 2.8 Hz, 6H) ppm |
| [structure] | 152 | 16 | 340 [M + H]$^+$ | $^1$H NMR (400 MHz, DMSO-d$_6$): δ 7.45 (m, 1H), 7.38 (m, 1H), 7.27 (m, 2H), 6.94 (br s, 1H), 5.15 (m, 1H), 5.02 (m, 1H), 2.86 (m, 1H), 2.57 (, 1H), 1.35 (d, J = 2.4 Hz, 6H) ppm |

Example 19

Myosin Inhibition Assay

Small molecule agents were assessed for their ability to inhibit the enzymatic activity of bovine cardiac myosin using a biochemical assay that couples the release of ADP (adenosine diphosphate) from cardiac myosin to an enzymatic coupling system consisting of pyruvate kinase and lactate dehydrogenase (PK/LDH) and monitoring the absorbance decrease of NADH (at 340 nm) as a function of time. PK converts ADP to ATP (adenosine triphosphate) by converting PEP (phosphoenolpyruvate) to pyruvate. Pyruvate is then converted to lactate by LDH by converting NADH (nicotinamide adenine dinucleotide) to NAD (oxidized nicotinamide adenine dinucleotide). The source of cardiac myosin was from bovine heart in the form of skinned myofibrils. Prior to testing small molecule agents, the bovine myofibrils were assessed for their calcium responsiveness and the calcium concentration that achieves a 50% activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM12 buffer). Final assay conditions were 1 mg/mL of bovine cardiac myofibrils, 0.4 mM PK/LDH, 50 uM ATP, 0.1 mg/mL BSA (bovine serum albumin), 10 ppm antifoam, 2 mM BME, 0.5 mM NADH, 1.5 mM PEP at the desired free calcium concentration required to achieve 50% activation of the myofibrils.

A dilution series of compound was created in DMSO such that the final desired concentration of compound would be achieved in a volume of 30 μL with a fixed DMSO concentration of 3.3% (v/v). Typically 1 μL of the dilution series were added to 384 well plate to achieve an 10 point dose response. Following the addition of 14 μL of a solution containing bovine cardiac myofibrils, PK/LDH and a solution of calcium (that achieved 50% activation), the enzymatic reaction was started with the addition of 15 μL of a solution containing ATP, PEP and NADH. The reaction progress was followed in a PerkinElmer Envision plate reader at ambient temperature using clear bottom plates. The plate reader was configured to read absorbance at 340 nm in kinetics mode for 15 minutes. Data were recorded as the slope of the absorbance response to time. The slopes of the absorbance response as a function of time were normalized to slopes on the plate containing DMSO. This normalized rate was then plotted as a function of small molecule concentration and the data was fitted to a four-parameter fit using EXCEL XLfit. The $IC_{50}$ is the concentration at which fifty percent of the total response is inhibited. Any agent that failed to achieve a fifty percent inhibition at the highest concentration tested was reported as an $IC_{50}$ greater than the highest concentration tested (ie. $IC_{50}$>50 μM).

TABLE 2

Myosin Inhibition Activity of Selected Compounds[a]

| Compound No. | bcMF pCa_6 $IC_{50}$ |
|---|---|
| 1 | ++ |
| 2 | +++ |
| 3 | ++ |
| 4 | ++ |
| 5 | ++ |
| 6 | +++ |
| 7 | ++ |
| 8 | + |
| 9 | ++ |
| 10 | + |
| 11 | ++ |
| 12 | +++ |
| 13 | ++ |
| 14 | ++ |
| 15 | ++ |
| 16 | ++ |
| 17 | ++ |
| 18 | ++ |
| 19 | ++ |
| 20 | ++ |
| 21 | ++ |
| 22 | ++ |
| 23 | +++ |
| 24 | ++ |
| 25 | + |
| 26 | ++ |
| 27 | ++ |
| 28 | ++ |
| 29 | ++ |
| 30 | +++ |
| 31 | +++ |
| 32 | ++ |
| 33 | +++ |
| 34 | ++ |
| 35 | ++ |
| 36 | +++ |
| 37 | +++ |
| 38 | ++ |
| 39 | ++ |
| 40 | ++ |
| 41 | ++ |
| 42 | + |
| 43 | +++ |
| 44 | + |
| 45 | +++ |
| 46 | +++ |
| 47 | +++ |
| 48 | ++ |
| 49 | ++ |
| 50 | ++ |
| 51 | ++ |
| 52 | ++ |
| 53 | ++ |
| 54 | + |
| 55 | ++ |
| 56 | ++ |
| 57 | ++ |
| 58 | + |
| 59 | ++ |
| 60 | ++ |
| 61 | ++ |
| 62 | + |
| 63 | ++ |
| 64 | + |
| 65 | ++ |
| 66 | +++ |
| 67 | ++ |
| 68 | ++ |
| 69 | ++ |
| 70 | ++ |
| 71 | + |
| 72 | ++ |
| 73 | ++ |
| 74 | ++ |
| 75 | + |
| 76 | ++ |
| 77 | ++ |
| 78 | +++ |
| 79 | + |
| 80 | ++ |
| 81 | ++ |
| 82 | ++ |
| 83 | +++ |
| 84 | + |
| 85 | + |
| 86 | + |
| 87 | + |
| 88 | + |
| 89 | ++ |
| 90 | ++ |
| 91 | + |
| 92 | + |
| 93 | + |
| 94 | ++ |
| 95 | + |
| 96 | ++ |
| 97 | ++ |
| 98 | + |
| 99 | + |
| 100 | + |
| 101 | ++ |
| 102 | +++ |
| 103 | + |
| 104 | ++ |
| 105 | + |

TABLE 2-continued

Myosin Inhibition Activity of Selected Compounds[a]

| Compound No. | bcMF pCa_6 IC$_{50}$ |
|---|---|
| 106 | +++ |
| 107 | + |
| 108 | ++ |
| 109 | + |
| 110 | ++ |
| 111 | +++ |
| 112 | +++ |
| 113 | + |
| 114 | ++ |
| 115 | +++ |
| 116 | ++ |
| 117 | + |
| 118 | ++ |
| 119 | ++ |
| 120 | ++ |
| 121 | ++ |
| 122 | ++ |
| 123 | ++ |
| 124 | ++ |
| 125 | ++ |
| 126 | ++ |
| 127 | +++ |
| 128 | +++ |
| 129 | +++ |
| 130 | + |
| 131 | ++ |
| 132 | + |
| 133 | ++ |
| 134 | +++ |
| 135 | +++ |
| 136 | +++ |
| 137 | +++ |
| 138 | +++ |
| 139 | +++ |
| 140 | ++ |
| 141 | ++ |
| 142 | +++ |
| 143 | ++ |
| 144 | + |
| 145 | +++ |
| 146 | + |

[a] +++ corresponds to IC$_{50}$ values below 1 µM. ++ corresponds to IC$_{50}$ values from 1 to 15 µM. + corresponds to IC$_{50}$ values above 15 µM.

Example 20

Cardiomyocyte Contractility Assay

Contractility of adult rat ventricular myocytes is determined by edge detection with an IonOptix contractility system. Aliquots of myocytes in Tyrode buffer (137 mM NaCl, 3.7 mM KCL, 0.5 mM MgCl$_2$, 1.5 mM CaCl$_2$, 4 mM HEPES, 11 mM glucose) are placed in a perfusion chamber (Series 20 RC-27NE; Warner Instruments), allowed to adhere to the coverslip, and then perfused with 37° C. Tyrode buffer. Myocytes are filed stimulated at 1 Hz and 10V. Only myocytes with clear striations, quiescent prior to pacing, with a cell length of 120-180 microns, a basal fractional shortening equal to 3-8% of the cell length, and a contraction velocity greater than 100 microns per second are used for contractility experiments. To determine the response to compounds, myocytes are first perfused for 60 seconds with Tyrodes buffer followed by 5 minutes of compound and a 140 second washout with Tyrodes buffer. Data is continuously recorded using IonOptix software. Contractility data is analyzed using Ionwizard software (IonOptix). For each cell, 10-20 contractility transients were averaged and compared under basal (no compound) and compound-treated conditions. Compound activity is measured by effects on fractional shortening (FS), where fractional shortening is the ratio of the peak length of the cell at contraction divided by the basal cell length normalized to 100% for an untreated cell.

TABLE 3

Inhibition of Cardiomyocyte Contraction by Selected Compounds[a]

| Compound No. | Activity at 0.1 µM | Activity at 0.3 µM | Activity at 1.0 µM |
|---|---|---|---|
| 1 | n.d | ++ | n.d |
| 2 | n.d | + | +++ |
| 4 | + | ++ | n.d. |
| 6 | n.d | ++ | +++ |
| 9 | n.d | n.d | ++ |
| 14 | n.d | + | +++ |
| 18 | n.d | ++ | n.d |
| 20 | n.d | n.d | ++ |
| 22 | n.d | n.d | ++ |
| 31 | n.d | ++ | n.d |
| 46 | n.d | n.d | +++ |
| 48 | n.d | + | + |
| 53 | n.d | n.d | ++ |
| 67 | n.d | ++ | n.d |
| 68 | +++ | n.d | n.d |
| 69 | +++ | n.d | n.d |
| 70 | n.d | n.d | ++ |
| 81 | n.d | n.d | ++ |
| 83 | n.d | ++ | n.d |
| 106 | +++ | n.d | n.d |
| 116 | n.d | ++ | +++ |

[a] n.d represents not determined; + represents fractional shorting inhibition values less than 33%; ++ represents fractional shorting inhibition values from 33% to 66%; and +++ represents fractional shortening inhibition values greater than 66%.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extert as if each reference was individually incorporated by reference. Where a conflict exists between the instant application and a reference provided herein, the instant application shall dominate.

What is claimed is:

1. A compound having the formula:

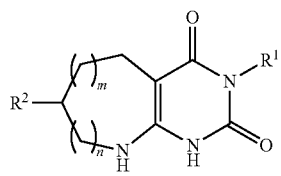

or a pharmaceutically acceptable salt thereof, wherein
the subscript m is an integer of from 0 to 2;
the subscript n is 0 or 1; and the sum of n+m is no more than 2;
R$^1$ is a member selected from the group consisting of C$_1$-C$_8$ alkyl, C$_3$-C$_8$ cycloalkyl, C$_3$-C$_8$ cycloalkyl-C$_1$-C$_3$ alkyl, 4- to 7-membered heterocycloalkyl, 4- to 7-membered heterocycloalkyl-C$_1$-C$_3$ alkyl, phenyl, phenyl-C$_1$-C$_3$ alkyl, 5- to 6-membered heteroaryl and 5- to 6-membered heteroaryl-C$_1$-C$_3$ alkyl, wherein each R$^1$ is optionally substituted with from 1-5 R$^a$;

$R^2$ is a member selected from the group consisting of $C_2$-$C_8$ alkyl, $C_3$-$C_8$ cycloalkyl, $C_3$-$C_8$ cycloalkyl-$C_1$-$C_3$ alkyl, phenyl, phenyl-$C_1$-$C_3$ alkyl, 4- to 7-membered heterocycloalkyl, 4- to 7-membered heterocycloalkyl-$C_1$-$C_3$ alkyl, 5- to 6-membered heteroaryl and 5- to 6-membered heteroaryl-$C_1$-$C_3$ alkyl, wherein each $R^2$ is optionally substituted with from 1-5 $R^b$;

each $R^a$ is independently selected from the group consisting of halo, CN, hydroxyl, $C_1$-$C_4$ alkyl, $C_1$-$C_4$ haloalkyl, $C_1$-$C_4$ alkoxy and —$CO_2$—$C_1$-$C_8$ alkyl;

each $R^b$ is independently selected from the group consisting of halo, CN, hydroxyl, $C_1$-$C_4$ alkyl, $C_1$-$C_4$ haloalkyl, $C_1$-$C_4$ alkoxy, —$COR^{b1}$, —$CO_2R^{b1}$, —$SO_2R^{b1}$, —$SO_2NR^{b1}R^{b2}$, and —$CONR^{b1}R^{b2}$, wherein each $R^{b1}$ and $R^{b2}$ is independently selected from the group consisting of H and $C_1$-$C_4$ alkyl or optionally two $R^b$ groups on the same carbon atom are combined to form oxo;

wherein the ring bearing $R^2$ is optionally further substituted with from one to five $R^c$, each of which is independently selected from the group consisting of halo, CN, hydroxyl, $C_1$-$C_4$ alkyl, $C_1$-$C_4$ haloalkyl and $C_1$-$C_4$ alkoxy, or optionally two $R^c$ groups on the same carbon atom are combined to form oxo, and wherein
the 5- to 6-membered heteroaryl of $R^1$ and $R^2$ comprises from 1 to 5 heteroatoms independently selected from the group consisting of N, O, and S, and
the 4- to 7-membered heterocycloalkyl of $R^1$ and $R^2$ comprises from 1 to 4 heteroatoms independently selected from the group consisting of N, O, and S.

2. A compound of claim 1, having the formula:

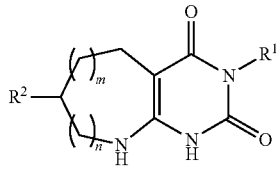

or a pharmaceutically acceptable salt thereof, wherein
the subscript m is an integer of from 0 to 2;
the subscript n is 0 or 1; and the sum of n+m is no more than 2;

$R^1$ is a member selected from the group consisting of $C_1$-$C_8$ alkyl, $C_3$-$C_8$ cycloalkyl, $C_3$-$C_8$ cycloalkyl-$C_1$-$C_3$ alkyl, 4- to 7-membered heterocycloalkyl, 4- to 7-membered heterocycloalkyl-$C_1$-$C_3$ alkyl, phenyl, phenyl-$C_1$-$C_3$ alkyl, 5- to 6-membered heteroaryl and 5- to 6-membered heteroaryl-$C_1$-$C_3$ alkyl, wherein each $R^1$ is optionally substituted with from 1-5 $R^a$;

$R^2$ is a member selected from the group consisting of $C_2$-$C_8$ alkyl, $C_3$-$C_8$ cycloalkyl, $C_3$-$C_8$ cycloalkyl-$C_1$-$C_3$ alkyl, phenyl, phenyl-$C_1$-$C_3$ alkyl, 4- to 7-membered heterocycloalkyl, 4- to 7-membered heterocycloalkyl-$C_1$-$C_3$ alkyl, 5- to 6-membered heteroaryl and 5- to 6-membered heteroaryl-$C_1$-$C_3$ alkyl, wherein each $R^2$ is optionally substituted with from 1-5 $R^b$;

each $R^a$ is independently selected from the group consisting of halo, CN, hydroxyl, $C_1$-$C_4$ alkyl, $C_1$-$C_4$ haloalkyl and $C_1$-$C_4$ alkoxy;

each $R^b$ is independently selected from the group consisting of halo, CN, hydroxyl, $C_1$-$C_4$ alkyl, $C_1$-$C_4$ haloalkyl, $C_1$-$C_4$ alkoxy, —$COR^{b1}$, —$CO_2R^{b1}$, —$SO_2R^{b1}$, —$SO_2NR^{b1}R^{b2}$, and —$CONR^{b1}R^{b2}$, wherein each $R^{b1}$ and $R^{b2}$ is independently selected from the group consisting of H and $C_1$-$C_4$ alkyl or optionally two $R^b$ groups on the same carbon atom are combined to form oxo;

and wherein the ring bearing $R^2$ is optionally further substituted with from one to four $R^c$, each of which is independently selected from the group consisting of halo, CN, hydroxyl, $C_1$-$C_4$ alkyl, $C_1$-$C_4$ haloalkyl and $C_1$-$C_4$ alkoxy, or optionally two $R^c$ groups on the same carbon atom are combined to form oxo.

3. A compound of claim 1, or a pharmaceutically acceptable salt thereof, wherein $R^1$ is a member selected from the group consisting of $C_1$-$C_8$ alkyl, $C_3$-$C_8$ cycloalkyl and $C_3$-$C_8$ cycloalkyl-$C_1$-$C_3$ alkyl, each of which is optionally substituted with from 1-3 $R^a$.

4. A compound of claim 1, or a pharmaceutically acceptable salt thereof, wherein $R^2$ is $C_3$-$C_8$ cycloalkyl, which is optionally substituted with from 1-3 $R^b$.

5. A compound of claim 1, or a pharmaceutically acceptable salt thereof, wherein $R^2$ is phenyl, which is optionally substituted with from 1-3 $R^b$.

6. A compound of claim 1, or a pharmaceutically acceptable salt thereof, wherein n is 0.

7. A compound of claim 1, or a pharmaceutically acceptable salt thereof, wherein m is 1 or 2.

8. A compound of claim 1, or a pharmaceutically acceptable salt thereof, wherein n is 0 and m is 1.

9. A compound of claim 1, or a pharmaceutically acceptable salt thereof, having the formula:

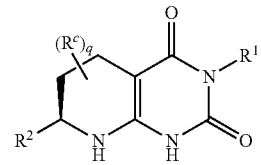

(Ia)

wherein
$R^1$ is a member selected from the group consisting of $C_1$-$C_8$ alkyl, $C_3$-$C_8$ cycloalkyl and $C_3$-$C_8$ cycloalkyl-$C_1$-$C_3$ alkyl, each of which is optionally substituted with from 1-3 $R^a$;

$R^2$ is a member selected from the group consisting of $C_5$-$C_6$ cycloalkyl and phenyl, each of which is optionally substituted with from 1-3 $R^b$;

each $R^a$ is independently selected from the group consisting of halo, CN, $C_1$-$C_4$ alkyl, $C_1$-$C_4$ and haloalkyl;

each $R^b$ is independently selected from the group consisting of halo, CN, hydroxyl, $C_1$-$C_4$ alkyl, $C_1$-$C_4$ haloalkyl and $C_1$-$C_4$ alkoxy;

the subscript q is 0 to 2;

each $R^c$ is independently selected from the group consisting of halo, $C_1$-$C_4$ alkyl and $C_1$-$C_4$ haloalkyl; and wherein the compound is substantially free of other isomers at the carbon atom bearing $R^2$.

10. A compound of claim 9, or a pharmaceutically acceptable salt thereof, wherein $R^2$ is phenyl, which is optionally substituted with from 1-2 $R^b$.

11. A compound of claim 9, or a pharmaceutically acceptable salt thereof, wherein $R^2$ is $C_5$-$C_6$ cycloalkyl, which is optionally substituted with from 1-2 $R^b$.

12. A compound of claim 9, or a pharmaceutically acceptable salt thereof, wherein q is 0.

13. A compound of claim 9, or a pharmaceutically acceptable salt thereof, wherein $R^1$ is $C_2$-$C_6$ alkyl, and is optionally substituted with from 1-4 halo.

14. A compound of claim 9, or a pharmaceutically acceptable salt thereof, wherein $R^1$ is $C_2$-$C_6$ alkyl.

15. A compound of claim 9, or a pharmaceutically acceptable salt thereof, having the formula:

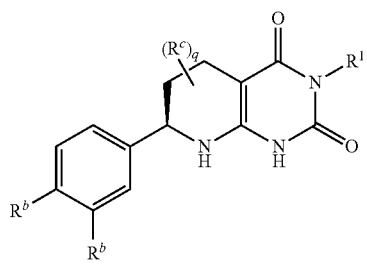

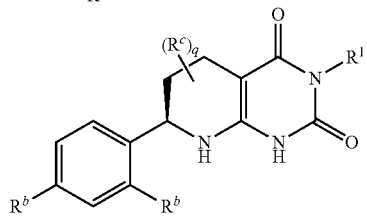

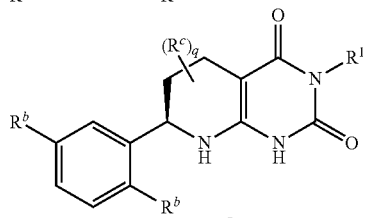

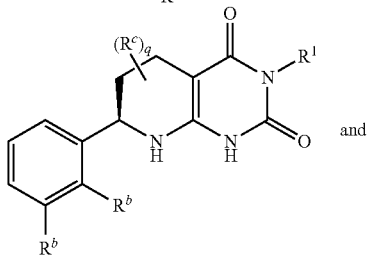

and

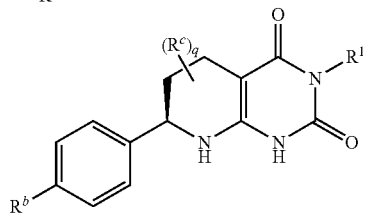

wherein
$R^1$ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl and 2,2-difluoroethyl;
each $R^b$ is independently selected from the group consisting of halo, $C_1$-$C_4$ alkyl, and $C_1$-$C_4$ haloalkyl;
q is an integer of from 0 to 2; and
each $R^c$ is independently selected from the group consisting of halo, $C_1$-$C_4$ alkyl and $C_1$-$C_4$ haloalkyl.

16. A compound of claim 9, or a pharmaceutically acceptable salt thereof, having a formula selected from the group consisting of:

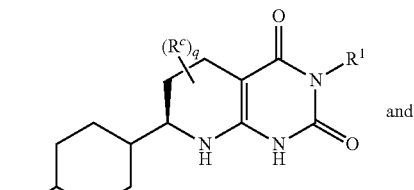 and

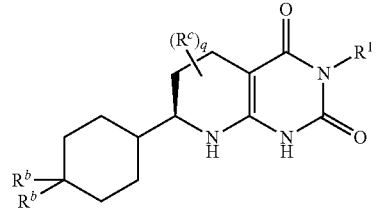

wherein
$R^1$ is selected from the group consisting of ethyl, isopropyl, isobutyl, t-butyl, cyclopropylmethyl, 1-methylcyclopropyl, (S)-2-butyl, (R)-2-butyl, 2,2,2-trifluoroethyl and 2,2-difluoroethyl;
each $R^b$ is independently selected from the group consisting of halo, $C_1$-$C_4$ alkyl, and $C_1$-$C_4$ haloalkyl;
q is an integer of from 0 to 2; and
each $R^c$ is independently selected from the group consisting of halo, $C_1$-$C_4$ alkyl and $C_1$-$C_4$ haloalkyl.

17. A pharmaceutical composition comprising a compound of claim 1, and a pharmaceutically acceptable excipient.

18. A compound of claim 1, selected from the group consisting of

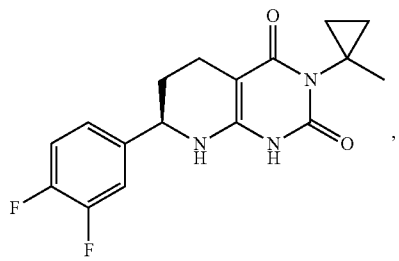

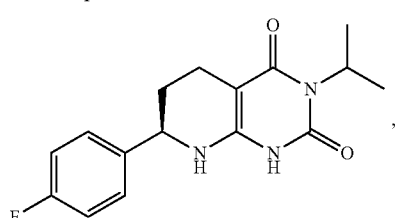

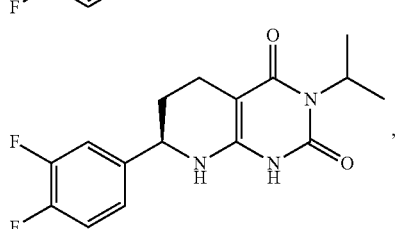

-continued
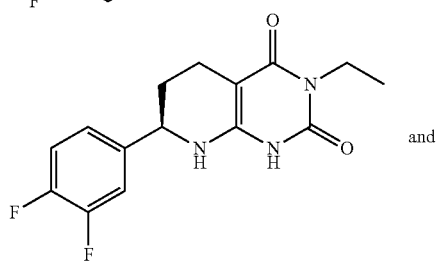
,
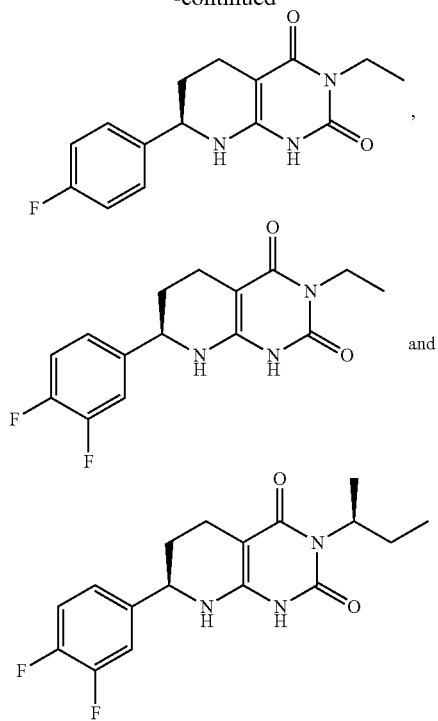
and
or a pharmaceutically acceptable salt thereof.
19. A compound of claim 1, selected from the group consisting of
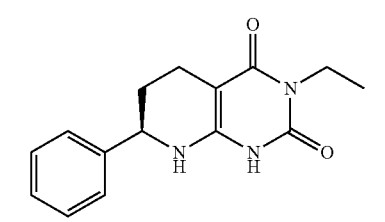
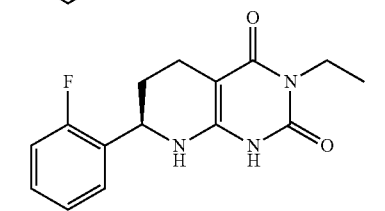
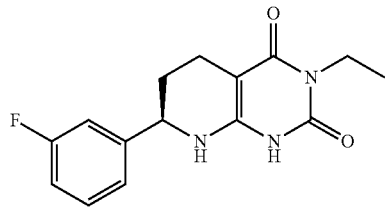
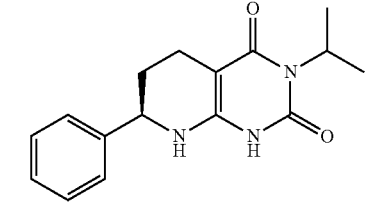
-continued
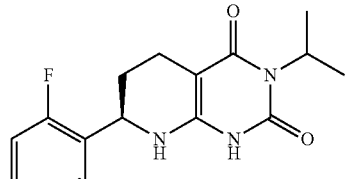
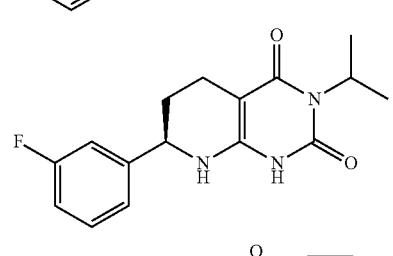
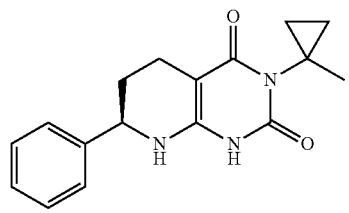
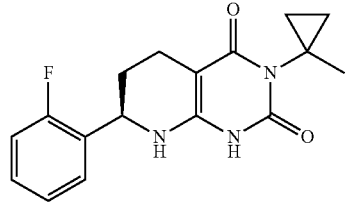
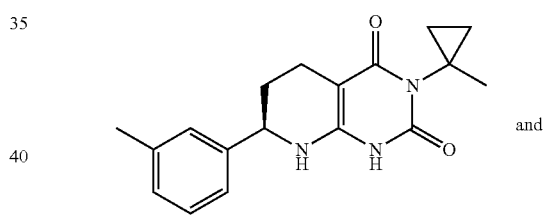
and
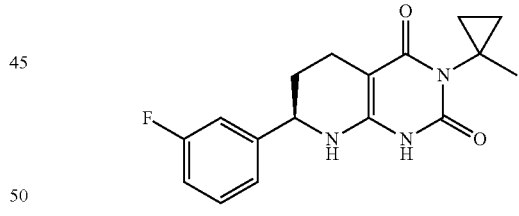
or a pharmaceutically acceptable salt thereof.
20. A compound of claim 1, selected from the group consisting of:
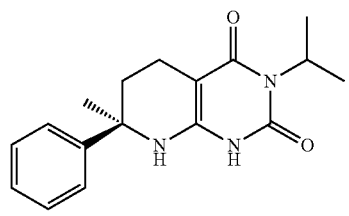

-continued

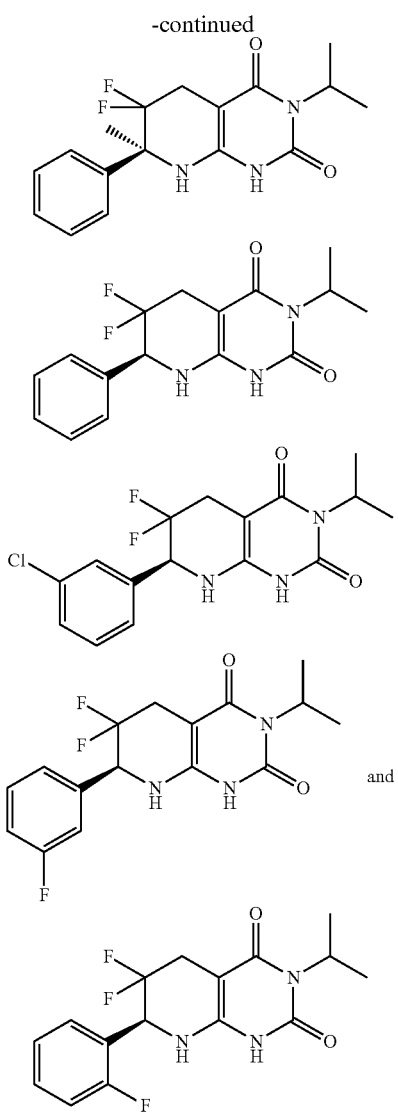

or a pharmaceutically acceptable salt thereof.

21. A compound of claim 1, having the formula:

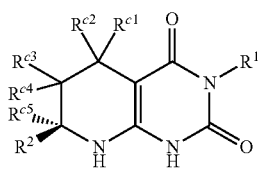

(II)

or a pharmaceutically acceptable salt thereof, wherein

R$^1$ is selected from the group consisting of methyl, ethyl, 2,2,2-trifluoroethyl, 2,2-difluoroethyl, propyl, isopropyl, cyclopropyl, n-butyl, isobutyl, (S)-2-butyl, (R)-2-butyl, cyclopropylmethyl, 1-methylcyclopropyl, cyclobutyl, 3,3-difluorocyclobut-1-yl, oxetan-3-yl, N-methoxycarbonylazetidin-3-yl, cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, pyrid-2-yl, 3-fluoropyrid-2-yl, 4-fluoropyrid-2-yl, 5-fluoropyrid-2-yl, 6-fluoropyrid-2-yl, and 6-methylpyrid-2-yl;

R$^2$ is selected from the group consisting of cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 3-methylphenyl, 4-methylphenyl, 2-chlorophenyl, 3-chlorophenyl, 4-chlorophenyl, 2-trifluoromethylphenyl, 3-trifluoromethylphenyl, 4-trifluoromethylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, 3-chloro-2-fluorophenyl, 5-chloro-2-fluorophenyl, 3-chloro-5-fluorophenyl, 2-fluoro-3-trifluoromethylphenyl, 2-fluoro-4-trifluoromethylphenyl, 2-fluoro-5-trifluoromethylphenyl, 3-fluoro-4-trifluoromethylphenyl, 3-fluoro-5-trifluoromethylphenyl, pyrid-2-yl, 3-fluoropyrid-2-yl, 4-fluoropyrid-2-yl, 5-fluoropyrid-2-yl, 6-fluoropyrid-2-yl, 6-methylpyrid-2-yl, phenylmethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, (S)-1-phenylethyl, (R)-1-phenylethyl, and phenyldifluoromethyl;

R$^{c5}$ is selected from the group consisting of hydrogen, deuterium, methyl, difluoromethyl, trifluoromethyl, ethyl, 2,2,2-trifluoroethyl, 2,2-difluoroethyl, propyl, isopropyl, n-butyl, isobutyl, (S)-2-butyl, (R)-2-butyl, and tert-butyl; and R$^{c1}$, R$^{c2}$, R$^{c3}$, R$^{c4}$ are independently selected from the group consisting of hydrogen, deuterium, fluoro, methyl, difluoromethyl, and trifluoromethyl.

22. A compound of claim 1, having the formula:

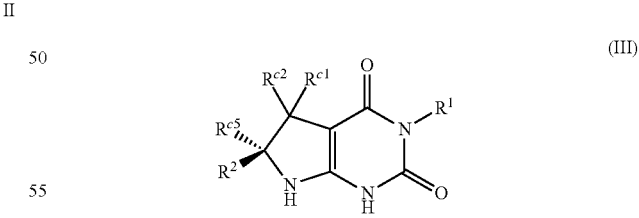

(III)

or a pharmaceutically acceptable salt thereof, wherein

R$^1$ is selected from the group consisting of methyl, ethyl, 2,2,2-trifluoroethyl, 2,2-difluoroethyl, propyl, isopropyl, cyclopropyl, n-butyl, isobutyl, (S)-2-butyl, (R)-2-butyl, cyclopropylmethyl, 1-methylcyclopropyl, cyclobutyl, 3,3-difluorocyclobut-1-yl, oxetan-3-yl, N-methoxycarbonylazetidin-3-yl, cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, pyrid-2-yl, 3-fluoropyrid-2-yl, 4-fluoropyrid-2-yl, 5-fluoropyrid-2-yl, 6-fluoropyrid-2-yl, and 6-methylpyrid-2-yl;

$R^2$ is selected from the group consisting of cyclopentyl, (S)-3,3-difluorocyclopent-1-yl, (R)-3,3-difluorocyclopent-1-yl, (S)-tetrahydrofur-3-yl, (R)-tetrahydrofur-3-yl, (R)—N-methoxycarbonylpyrrolidin-3-yl, (S)—N-methoxycarbonylpyrrolidin-3-yl, cyclohexyl, 4,4-difluorocyclohex-1-yl, tetrahydro-2H-pyran-4-yl, N-methoxycarbonylpiperidin-4-yl, 1-methylpyrazol-3-yl, 1-methylpyrazol-4-yl, isoxazol-3-yl, 4-methylisoxazol-3-yl, 5-methylisoxazol-3-yl, phenyl, 2-methylphenyl, 3-methylphenyl, 4-methylphenyl, 2-chlorophenyl, 3-chlorophenyl, 4-chlorophenyl, 2-trifluoromethylphenyl, 3-trifluoromethylphenyl, 4-trifluoromethylphenyl, 2-fluorophenyl, 3-fluorophenyl, 4-fluorophenyl, 2,3-difluorophenyl, 2,4-difluorophenyl, 2,5-difluorophenyl, 3,5-difluorophenyl, 3-chloro-2-fluorophenyl, 5-chloro-2-fluorophenyl, 3-chloro-5-fluorophenyl, 2-fluoro-3-trifluoromethylphenyl, 2-fluoro-4-trifluoromethylphenyl, 2-fluoro-5-trifluoromethylphenyl, 3-fluoro-4-trifluoromethylphenyl, 3-fluoro-5-trifluoromethylphenyl, pyrid-2-yl, 3-fluoropyrid-2-yl, 4-fluoropyrid-2-yl, 5-fluoropyrid-2-yl, 6-fluoropyrid-2-yl, 6-methylpyrid-2-yl, phenylmethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, (S)-1-phenylethyl, (R)-1-phenylethyl, and phenyldifluoromethyl;

$R^{c5}$ is selected from the group consisting of hydrogen, deuterium, methyl, difluoromethyl, trifluoromethyl, ethyl, 2,2,2-trifluoroethyl, 2,2-difluoroethyl, propyl, isopropyl, n-butyl, isobutyl, (S)-2-butyl, (R)-2-butyl, and tert-butyl;

$R^{c1}$ and $R^{c2}$ are independently selected from the group consisting of hydrogen, deuterium, fluoro, methyl, difluoromethyl, and trifluoromethyl.

23. A method of treating hypertrophic cardiomyopathy (HCM), or a cardiac disorder having a pathophysiological feature of HCM, comprising administering to a subject in need thereof an effective amount of a compound of claim 1.

24. A method of treating a disease or disorder selected from the group consisting of diastolic heart failure with preserved ejection fraction, ischemic heart disease, angina pectoris, and restrictive cardiomyopathy, comprising administering to a subject in need thereof an effective amount of a compound of claim 1 or a pharmaceutically acceptable salt thereof.

25. A method of treating a disease or disorder characterized by left ventricular hypertrophy due to volume or pressure overload, said disease or disorder selected from the group consisting of chronic mitral regurgitation, chronic aortic stenosis, and chronic systemic hypertension; in conjunction with therapies aimed at correcting or alleviating the primary cause of volume or pressure overload said therapies selected from the group consisting of valve repair/replacement and effective antihypertensive therapy, comprising administering to a subject in need thereof an effective amount of a compound of claim 1 or a pharmaceutically acceptable salt thereof.

26. A method of treating hypertrophic cardiomyopathy (HCM), or a cardiac disorder having a pathophysiological feature associated with HCM, comprising administering to a subject in need thereof an effective amount of a compound of claim 1 or a pharmaceutically acceptable salt thereof, combined with therapies that retard the progression of heart failure by down-regulating neurohormonal stimulation of the heart and attempt to prevent cardiac remodeling, said therapies selected from the group consisting of ACE inhibitors, angiotensin receptor blockers (ARBs), β-blockers, aldosterone receptor antagonists, and neural endopeptidase inhibitors.

27. A method of treating hypertrophic cardiomyopathy (HCM), or a cardiac disorder having a pathophysiological feature associated with HCM, comprising administering to a subject in need thereof an effective amount of a compound of claim 1 or a pharmaceutically acceptable salt thereof, combined with therapies that improve cardiac function by stimulating cardiac contractility, said therapy being one or more positive inotropic agents.

28. The method of claim 27, where in the positive inotropic agent is the β-adrenergic agonist dobutamine or the phosphodiesterase inhibitor milrinone.

29. A method of treating hypertrophic cardiomyopathy (HCM), or a cardiac disorder having a pathophysiological feature associated with HCM, comprising administering to a subject in need thereof an effective amount of a compound of claim 1 or a pharmaceutically acceptable salt thereof, combined with therapies that reduce cardiac preload or afterload, wherein the therapies that reduce cardiac preload are diuretics, and
the therapies that reduce cardiac afterload are vasodilators.

30. A method of claim 29, wherein the diuretic is furosemide.

31. A method of claim 29, wherein the vasodilators are selected from the group consisting of calcium channel blockers, phosphodiesterase inhibitors, endothelin receptor antagonists, renin inhibitors, and smooth muscle myosin modulators.

\* \* \* \* \*